(12) United States Patent
Akselrod

(10) Patent No.: US 10,758,153 B2
(45) Date of Patent: Sep. 1, 2020

(54) MATERIAL PROPERTY MONITORING AND DETECTION USING WIRELESS DEVICES

(71) Applicant: David Akselrod, Burlington (CA)

(72) Inventor: David Akselrod, Burlington (CA)

(*) Notice: Subject to any disclaimer, the term of this patent is extended or adjusted under 35 U.S.C. 154(b) by 0 days.

(21) Appl. No.: 15/653,461

(22) Filed: Jul. 18, 2017

(65) Prior Publication Data

US 2018/0014747 A1 Jan. 18, 2018

Related U.S. Application Data

(63) Continuation-in-part of application No. 15/607,673, filed on May 29, 2017, and a continuation-in-part of application No. 15/418,414, filed on Jan. 27, 2017.
(Continued)

(51) Int. Cl.
*A61B 5/053* (2006.01)
*A61B 5/145* (2006.01)
(Continued)

(52) U.S. Cl.
CPC ............ *A61B 5/0531* (2013.01); *A61B 5/053* (2013.01); *A61B 5/14507* (2013.01); *A61B 90/98* (2016.02); *A61C 5/35* (2017.02); *A61C 5/50* (2017.02); *A61C 5/70* (2017.02); *A61C 7/002* (2013.01); *A61C 7/10* (2013.01); *A61C 7/303* (2013.01); *A61C 8/0093* (2013.01); *A61C 19/04* (2013.01); *H04Q 9/00* (2013.01);
(Continued)

(58) Field of Classification Search
CPC .... A61B 5/0531; A61B 5/053; A61B 5/14507

USPC ......................................................... 600/547
See application file for complete search history.

(56) References Cited

U.S. PATENT DOCUMENTS 5,251,635 A 10/1993 Dumoulin
5,791,350 A 8/1998 Morton
(Continued)

OTHER PUBLICATIONS

J.J. More, "The Levenberg-Marquardt Algorithm: Implementation and Theory," Numerical Analysis, Springer Berlin Heidelberg, pp. 105 through 116, published 1978.
(Continued)

*Primary Examiner* — Daniel L Cerioni
(74) *Attorney, Agent, or Firm* — Eric Kelly

(57) ABSTRACT

Embodiments of the present invention provide devices (tags with sensors), systems, and methods to determine states (such as, but not limited to, complex impedance) of materials-of-interest, such as tissue-of-interest, implants, and construction members, to name a few, in a non-invasive and contactless way; and using comparatively safe and/or low energy electromagnetic radiation, such as radio waves. Negligible-sized wireless-tags with sensors are implanted in such materials-of-interest. Using wireless communication and imaging technology, the states of the materials-of-interest may be monitored; which may allow non-invasive and contactless detection of problems such as cracking, bending, excessive pressure, improper temperature, and/or the like. Additionally, initially unknown locations of the implanted negligible-sized wireless-tags with sensors may be readily determined upon a given scanning (reading) session; and thus mapped to provide an effective image of the material-of-interest.

19 Claims, 56 Drawing Sheets

Related U.S. Application Data

(60) Provisional application No. 62/363,392, filed on Jul. 18, 2016, provisional application No. 62/363,481, filed on Jul. 18, 2016.

(51) Int. Cl.

| | | |
|---|---|---|
| *A61C 7/30* | (2006.01) | |
| *A61C 7/00* | (2006.01) | |
| *A61C 7/10* | (2006.01) | |
| *A61C 5/35* | (2017.01) | |
| *A61C 5/70* | (2017.01) | |
| *A61C 19/04* | (2006.01) | |
| *H04Q 9/00* | (2006.01) | |
| *A61C 8/00* | (2006.01) | |
| *A61C 5/50* | (2017.01) | |
| *A61B 90/98* | (2016.01) | |

(52) U.S. Cl.
CPC .. *A61C 2204/005* (2013.01); *A61C 2204/007* (2013.01); *H04Q 2209/47* (2013.01)

(56) References Cited

U.S. PATENT DOCUMENTS

| | | |
|---|---|---|
| 2005/0201450 A1 | 9/2005 | Volpi |
| 2006/0134580 A1 | 6/2006 | Raby |
| 2008/0204240 A1* | 8/2008 | Hilgers ............... G01D 21/00 340/572.1 |
| 2009/0286195 A1 | 11/2009 | Sears |
| 2010/0097194 A1 | 4/2010 | Killian |
| 2011/0034912 A1* | 2/2011 | de Graff ........... H01L 27/14687 606/21 |
| 2013/0274563 A1* | 10/2013 | Duesterhoft ......... A61B 5/4848 600/301 |
| 2013/0328578 A1 | 12/2013 | Shah |
| 2014/0062717 A1* | 3/2014 | Mudumbai .......... A61B 5/0031 340/870.01 |
| 2015/0053575 A1 | 2/2015 | Bridges |
| 2015/0141268 A1* | 5/2015 | Rothberg ............. C12Q 1/6869 506/2 |
| 2015/0260498 A1* | 9/2015 | Soohoo .................. G01S 17/87 73/1.79 |
| 2016/0084894 A1* | 3/2016 | Govindaraj ........... G01R 25/00 307/104 |
| 2016/0220330 A1 | 8/2016 | Lemchen |
| 2016/0354012 A1* | 12/2016 | Zeng .................... A61B 5/1072 |
| 2017/0286820 A1 | 10/2017 | Nikunen |
| 2018/0008378 A1 | 1/2018 | Raghavan |
| 2019/0117339 A1 | 4/2019 | Bolzan |

OTHER PUBLICATIONS

A. Ben-Israel, "A Newton-Raphson Method for the Solution of Systems of Equations," Journal of Mathematical Analysis and Applications, vol. 15.2, pp. 243 through 252, published 1966.

S.Y. Lee, "The Gauss-Newton Algorithm for the Weighted Least Squares Factor Analysis," The Statistician, pp. 103 through 114, published 1978.

H. So, "Source Localization: Algorithms and Analysis," in Handbook of Position Location: Theory, Practice, and Advances, John Wiley & Sons, Inc. (publisher), pp. 25 through 66, published 2012.

P.V. Nikitin, R. Martinez, S. Ramamurthy, H. Leland, G. Spiess, and K.V.S. Rao, "Phase Based Spatial Identification of UHF RFID Tags," in 2010 IEEE International Conference on RFID, Orlando, FL, published 2010.

C. Hekimian-Williams, B. Grant, X.Z. Zhang, and P. Kumar, "Accurate Localization of RFID Tags Using Phase Difference," in 2010 IEEE International Conference on RFID, Orlando, FL, published 2010.

M. Bouet and A.L.D. Santos, "RFID Tags: Positioning Principles and Localization Techniques," in 2008 First IFIP Wireless Days, Dubai, UAE, published 2008.

* cited by examiner

MATERIAL PROPERTY MONITORING AND DETECTION USING WIRELESS DEVICES

PRIORITY NOTICE

The present application claims priority under 35 U.S.C. § 119(e) to U.S. Provisional Patent Application Ser. No. 62/363,392 filed on Jul. 18, 2016; and the present application claims priority under 35 U.S.C. § 119(e) to U.S. Provisional Patent Application Ser. No. 62/363,413 filed on Jul. 18, 2016, the disclosures of which are both incorporated herein by reference in their entirety.

The present application claims priority under 35 U.S.C. § 119(e) to U.S. Provisional Patent Application Ser. No. 62/363,481 filed on Jul. 18, 2016; and the present application claims priority under 35 U.S.C. § 119(e) to U.S. Provisional Patent Application Ser. No. 62/363,551 filed on Jul. 18, 2016, the disclosures of which are both incorporated herein by reference in their entirety.

The present patent application is a continuation-in-part (CIP) of U.S. non-provisional patent application Ser. No. 15/418,414 filed on Jan. 27, 2017; wherein this present patent application claims priority to said U.S. non-provisional patent application under 35 U.S.C. § 120. The above-identified parent U.S. non-provisional patent application is incorporated herein by reference in their entirety as if fully set forth below.

The present patent application is a continuation-in-part (CIP) of U.S. non-provisional patent application Ser. No. 15/607,673 filed on May 29, 2017; wherein this present patent application claims priority to said U.S. non-provisional patent application under 35 U.S.C. § 120. The above-identified parent U.S. non-provisional patent application is incorporated herein by reference in their entirety as if fully set forth below.

TECHNICAL FIELD OF THE INVENTION

The present invention relates in general to monitoring states of materials of interest and, more specifically, to monitoring states of materials of interest using wireless sensor tags and where the materials of interest may have uses in dental, medical, and/or construction fields.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

Prior art imaging techniques, such as, X-ray, CT-scan, MRI, ultrasound, radar, and/or the like generally involve expensive (expensive to buy, lease, use, train, maintain, etc.), specialized, complicated equipment, and/or equipment that may occupy a relatively large footprint. And in many applications the electromagnetic energy emitted for imaging purposes from some prior art imaging systems may be dangerous or destructive to the object being imaged and thus such imaging must be minimized to prevent problems from overexposure. A prime example of this is the use of X-rays to image hard (dense) structures in biologic samples, such as teeth and bones in vertebrates; where overexposure to X-rays may lead to undesirable mutations and cancers. And even in the case of inanimate objects, such objects may also still be prone to deterioration (e.g., becoming brittle) resulting from overexposure to emitted high energy imaging electromagnetic radiation, such as X-rays. In many instances, if overexposure was not a problem, practitioners would then prefer to utilize such imaging techniques more frequently thus significantly increasing probability of discovering issues earlier in time. In some instances, such as with cancer patients or with pregnant women, use of X-rays is necessarily restricted.

There is a need in the art for imaging techniques that in comparison to preexisting imaging techniques of X-ray, CT-scan, MRI, ultrasound, radar, and/or the like would be comparatively less expensive to implement; and/or would require a smaller equipment footprint to utilize. Additionally, there is a need in the art for a non-invasive, contactless, imaging techniques that may utilize comparatively less energetic electromagnetic spectra, such as radio waves to communicate information that upon analysis may yield imaging results and other state information of a given material-of-interest to be imaged.

It is to these ends that the present invention has been developed. Embodiments of the present invention may provide novel ways of analyzing (monitoring and/or tracking) current states, structural integrity, and various qualities of various materials-of-interest; with applications in medical care, dentistry, and construction and engineering without use of preexisting imaging techniques that may use X-ray, CT-scan, MRI, ultrasound, and/or a reliance upon dangerous imaging techniques utilizing ionizing radiation. Examples of materials-of-interest may include, but may not be limited to: dental fillings, root canals, dental crowns, dental sealants and resins, dental and other medical implants, and other structures used in medicine, dentistry and/or construction and/or engineering.

Using minimization advances in microelectronics and process manufacturing techniques, negligibly-sized micro-sensors may be implanted in the material-of-interest to be analyzed (monitored and/or tracked). In some applications, implantation of such negligibly-sized micro-sensors may be done prior to the given material-of-interest curing and/or hardening, e.g., a dental filling. Using the disclosed imaging technology, subsequent to the completion of such curing or hardening, the current state, e.g., the structural integrity, may be scanned (imaged) to determine possible problems in the material-of-interest such as, but not limited to, possible fracturing, cracking, bending, twisting, excessive pressure, abnormal temperature, foreign materials or liquids penetration, and the like. And such analysis may be done non-invasively, without use of ionizing radiation in some applications, and reading of the implanted negligibly-sized micro-sensors may be remotely measured. Thus, such scanning (i.e., reading or imaging) may be done comparatively much more frequently that would be permitted if the practitioner had to rely upon using X-ray imaging.

The present invention has also been developed in order to detect specific problems, conditions, and/or substances, such as, but not limited to, biological cells (e.g., foreign cells, abnormal cells, cancerous cells, etc.), infection, fever, inflammation, antigens, antibodies, foreign substances, tissue conditions, ailments, and/or the like. Detection may be a subset of monitoring; wherein devices disclosed herein, as well, as in the accompanying drawings, are capable of monitoring and detection in materials of interest.

The disclosed imaging techniques may not require a power source in the implanted negligibly-sized micro-sensors. Energy required for the operation of the implanted negligibly-sized micro-sensors may be harvested from external electromagnetic energy sources during the reading (scanning) process.

Embodiments of the present invention may also establish locations (e.g., positions or coordinates) of wireless-devices with the implanted negligibly-sized micro-sensors. Such location determination may utilize well-known LPS (local positioning systems) techniques, that may involve use of triangulation, trilateration, multilateration, combinations thereof, and the like; as well as involve solving various nonlinear equations using various well-known techniques. Embodiments of the present invention may provide contactless ways of determining real-time locations as well as real-time sensor readings of and from these implanted negligibly-sized wireless-devices with sensors, which over time and over differently placed implanted negligibly-sized wireless-devices with sensors may yield information as to the various current states and changes in state of the given material-of-interest that is being monitored.

Embodiments of the present invention may also establish locations (e.g., positions or coordinates) of wireless-devices with the implanted negligibly-sized micro-sensors without utilizing LPS (local positioning systems) techniques.

These wireless-devices (with sensors or without sensors) may be referred to as RFID tags or Near-Field Communication (NFC) devices. Distances (ranges) between these wireless-devices (with sensors or without sensors) and various readers may readily be determined. The reader may emit various electromagnetic (EM) signals and may receive back wireless (returned) electromagnetic signals (e.g., "backscattered") from the wireless-devices (with sensors or without sensors). And from such returning wireless electromagnetic (EM) signals (such as, but not limited to backscatter electromagnetic signals), distances (ranges) as well as location determination and readings from sensors may then be utilized to analyze various states of the material-of-interest being monitored.

Localization (location determination) of wireless-devices using well-known LPS (local positioning systems) techniques, that may involve use of triangulation, trilateration, multilateration, combinations thereof, and/or the like is well understood in the relevant art. For example, range measurements between readers and wireless-devices may be based on a number of prior art techniques, among them determining ranges based on phase differences between transmitted and wireless (returned) signals (e.g., "backscattered"), Returned Signal Strength (RSSI), and/or other means. For example, trilateration may be a well-known technique of determining three-dimensional (3D) coordinates of an object using the measured ranges (distances) from that object to three or more other objects with known three-dimensional (3D) coordinates. Triangulation may another well-known technique in this context.

BRIEF SUMMARY OF THE INVENTION

To minimize the limitations in the prior art, and to minimize other limitations that will be apparent upon reading and understanding the present specification, embodiments of the present invention describe devices (tags), systems, and methods to determine structural integrity and other states of materials-of-interest, such as dental fillings, implants, and root canal posts, to name a few, in a non-invasive and contactless way; and using comparatively safe and/or low energy electromagnetic (EM) radiation, such as, but not limited to, radio waves and/or magnetic fields for coupled magnetic induction communication.

For example, and without limiting the scope of the present invention, in some embodiments, such a system may comprise one or more monitoring-sensor-tags and one or more readers. The one or more monitoring-sensor-tags may be attached to the material-of-interest. The material-of-interest may be selected from a dental-filling, a root-canal-post, a dental-crown, an article implantable within a body of an organism, the article attachable to the body of the organism, specific tissue of the organism, a construction member, and/or the like. The one or more monitoring-sensor-tags may comprise at least one electric circuit, at least one antenna (a first-antenna), and at least one sensor. The at least one electric circuit may be in communication with the at least one antenna (the first-antenna) and the at least one sensor. The one or more readers may comprise one or more second-antennas. The one or more readers using the one or more second-antennas may transmit electromagnetic (EM) radiation of a predetermined characteristic. The first-antenna may receive this electromagnetic (EM) radiation of the predetermined characteristic as an input. This input may cause the at least one electric circuit to take one or more readings from the at least one sensor; and may then transmit the one or more readings using the first-antenna back to the one or more second-antennas. At least one of the second-antennas selected from the one or more second-antennas may then receive the one or more readings. The one or more readers or a device (e.g., a computer) in communication with the one or more readers may then use the one or more readings to determine the current state of the material-of-interest.

It is an objective of the present invention to provide an imaging system and an imaging method that may be comparatively less expensive to use and implement as compared against traditional X-ray, CT-scan, MRI, ultrasound, radar, or the like imaging systems.

It is another objective of the present invention to provide an imaging system and an imaging method that may be comparatively easy and simple to use and implement as compared against traditional X-ray, CT-scan, MRI, ultrasound, radar, or the like imaging systems.

It is another objective of the present invention to provide an imaging system and imaging method that comparatively utilizes as smaller equipment footprint as compared against traditional X-ray, CT-scan, MRI, ultrasound, radar, or the like imaging systems.

It is another objective of the present invention to provide devices (tags), systems, and methods to determine structural integrity and other states of a given materials-of-interest in a non-invasive and contactless way.

It is another objective of the present invention to provide devices (tags), systems, and methods to determine structural integrity and other states of a given materials-of-interest using comparatively safe and/or low energy electromagnetic (EM) radiation, such as radio waves, and/or magnetic fields for magnetic induction communication.

It is another objective of the present invention to provide wireless-tags with sensors (monitoring-sensor-tags) that may be implantable into a given type of material-of-interest as discussed herein.

It is another objective of the present invention to provide wireless-tags with sensors wherein the sensors may be of different types for measuring different qualities, properties, and/or characteristics.

It is yet another objective of the present invention to determine locations of wireless-tags with sensors (monitoring-sensor-tags), that may be implantable into a given type of material-of-interest, over time in the same monitoring-sensor-tag and/or as compared against different implanted monitoring-sensor-tags.

These and other advantages and features of the present invention are described herein with specificity so as to make the present invention understandable to one of ordinary skill in the art, both with respect to how to practice the present invention and how to make the present invention.

BRIEF DESCRIPTION OF THE SEVERAL VIEWS OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention.

Figure 1A:
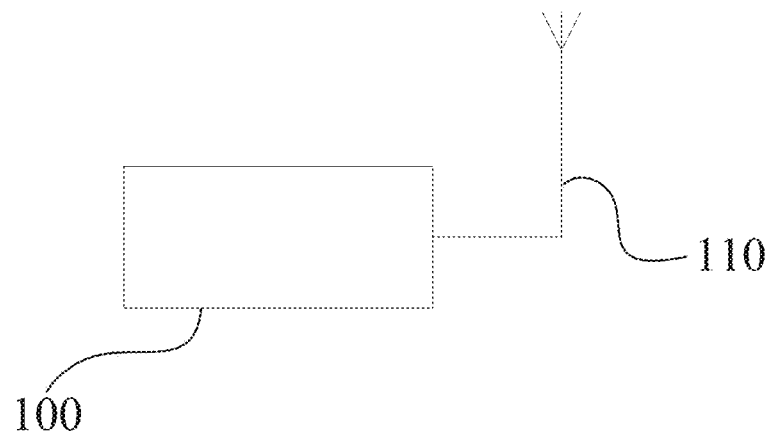
FIG. 1A may depict a schematic block diagram of a reader.

REFERENCE NUMERAL SCHEDULE 100 reader 100
110 antenna 110 (second-antenna 110)

120 monitoring-sensor-tag 120
130 antenna 130 (first-antenna 130)
140 electric circuit 140
202 capacitive-based sensor 202
203 resistance-based sensor 203
204 processing circuitry 204
205 capacitance measurement circuit 205
206 resistance measurement circuit 206
207 wireless-receiver-and-transmitter 207
208 inductance-based-sensor 208
209 inductance measurement circuit 209
300 load capacitor 300
310 digital inventor 310 (e.g., a C-MOS pair 310)
340 capacitive-based sensor 340
350 ring oscillator 350
400 plate 400
401 dielectric material 401
402 conductive surface type "A" 402
403 substrate 403
404 conductive surface type "B" 404
405 conductive surface type "C" 405
406 conductive surface type "D" 406
407 conductive surface type "E" 407
408 conductive surface type "F" 408
500 ring oscillator 500
501 switch 501
502 P-MOS transistor 502
503 N-MOS transistor 503
600 ring oscillator 600
601 load resistor 601
602 strain-influenced resistor 602
700 strain-influenced resistor 700
701 thin-film-coating 701
702 substrate 702
703 spiral-formed-electric-conductor 703
801 sensor-portion 801
802 processing-portion 802
930 CLOCK 930
931 RESTART_COUNT signal 931
932 COUNTER 932
933 COUNTER_OVERFLOW signal 933
934 zero value 934
935 0-to-1 transition of Pulse of Counter Overflow signal 935
936 1-to-0 transition of Pulse of Counter Overflow signal 936
937 maximal value 937
938 Pulse of RESTART_COUNT signal 938
1000 tooth 1000
1001 dental-filling 1001
1002 gum 1002
1003 root-canal-cavity 1003
1004 root-canal-post 1004
1005 dental-crown 1005
1006 standalone-strain-sensor 1006
1007 dental-implant 1007
1008 implant-post 1008
1020 first-sensor-tag 1020
1021 second-sensor-tag 1021
1023 lattice-of-sensors 1023
1025 initial predetermined spacing 1025
1026 sensor-spacing 1026
1028 material-of-interest 1028
1102 reference-sensor-tags 1102
1107 reference-housing-member 1107
1108 reader-housing-member 1108
1109 reader-and-calibration-member 1109
1110 member-separation-distance 1110
1111 reader-tag-separation-distance 1111
1112 reader-antenna-tag-separation-distance 1112
1113 reader-antenna-tag-separation-distance 1113
1115 antenna-interface 1115
1203 position-reference-tag 1203
1204 position-reference-member 1204
1320 Imaginary x-axis 1320
1321 Imaginary y-axis 1321
1322 Imaginary z-axis 1322
1325 origin 1325
1326 translating-scan-member 1326
1327 patient-fixation-member 1327
1328 patient 1328
1329 support 1329
1400 direction-of-motion 1400
1500 method 1500
1530 calibrate readers step 1530
1531 determine location of readers step 1531
1532 reader interrogation of monitoring-sensor-tags step 1532
1533 authentication step 1533
1534 determine location of monitoring-sensor-tags step 1534
1535 reader instructs monitoring-sensor-tags step 1535
1535a reader instructs monitoring-sensor-tags step 1535a
1536 reader transmit "restart counting" command step 1536
1537 determine if additional measurements to be taken step 1537
1538 determine if reader location to be re-determined step 1538
1539 determine if different measurement types to be taken step 1539
1540 transmit received monitoring-sensor-tag transmission step 1540
1600 method 1600
1680 choose set of calibration reference-sensor-tags step 1680
1681 select particular calibration method and settings step 1681
1682 perform calibration reference-sensor-tags measurements step 1682
1683 process calibration reference-sensor-tags measurements step 1683
1700 method 1700
1772 measuring ranges of monitoring-sensor tags step 1772
1773 applying calibration-based corrections step 1773
1777 process results step 1777
1800 system 1800
1801 processor 1801
1803 memory 1803
1805 display 1805
1807 device 1807
1828 material-of-interest 1828
1901 real part of complex permittivity 1901
1902 imaginary part of complex permittivity 1902
1905 capacitor 1905
1906 voltage source 1906
1907 resistor 1907
1908 capacitor 1908
1909 representative circuit 1909
1910 current 1910
1911 graph of real part of complex permittivity 1911
1912 graph of imaginary part of complex permittivity 1912
1913 graph real part of complex permittivity 1913
1914 graph of imaginary part of complex permittivity 1914
1915 graph of real part of complex permittivity 1915

1916 graph of imaginary part of complex permittivity 1916
1917 infrared (IR) light source 1917
1918 LED light source 1918
1919 ultraviolet (UV) light source 1919
1920 sonic or ultrasonic sound source 1920
1921 array-of-excitation-sources 1921
2010 complex-impedance-sensor 2010
2011 complex-impedance-measurement-circuit 2011
2020 complex-monitoring-sensor-tag 2020
2101 load 2101
2103 resistor 2103
2104 point 2104
2105 point 2105
2106 current source 2106
2201 material-of-interest 2201
2203 electrode 2203
2204 electrode 2204
2205 voltage meter 2205
2309 conductive surface type "G" 2309
2310 conductive surface type "G" 2310
2311 conductive surface of type "H" 2311
2312 conductive surface of type "H" 2312
2313 conductive surface of type "I" 2313
2314 conductive surface of type "I" 2314
2315 conductive surface of type "J" 2315
2316 conductive surface of type "J" 2316
2317 conductive surface of type "K" 2317
2318 infrared (IR) light source of type "A" 2318
2319 infrared (IR) light source of type "B" 2319
2401 cast-or-bandage 2401
2402 interior-surface 2402
2406 first-sensor-type 2406
2407 second-sensor-type 2407
2420 first-sensor-tag 2420
2421 second-sensor-tag 2421
2423 lattice-of-sensors 2423
2426 sensor-spacing 2426
2430 article-in-lattice-contact 2430
2431 implant 2431
2511 analyzer 2511
2512 variable-frequency-AC-source 2512
2513 frequency-divider 2513
2514 variable resistor 2514
2687 material-of-interest 2687
2688 section 2688
2709 reader-assembly 2709
2711 frame-member 2711
2712 imaging-device 2712
2720 wheel 2720
2722 axle 2722
2724 frame 2724
2726 handle 2726
2728 spring 2728
2730 base 2730
2820 x-axis 2820
2821 y-axis 2821
2822 z-axis 2822
2825 origin 2825
2904 position-reference-member 2904
2926 transmitter 2926
3101 internet-or-WAN-or-LAN 3101
3103 server 3103
3105 remote-computing-device 3105
3201 step of selecting frequency point to measure complex impedance 3201
3202 step of determining if one or more excitation-sources are to be enabled 3202
3203 step of choosing and enabling one or more excitation-sources 3203
3204 step of obtaining measurement of complex impedance of material-of-interest 3204
3205 step of determining if more measurements of material-of-interest to be taken 3205

DETAILED DESCRIPTION OF THE INVENTION

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized and changes may be made without departing from the scope of the invention.

FIG. 1A may depict a schematic block diagram of a reader 100. In some embodiments, reader 100 may comprise antenna 110. In some embodiments, reader 100 may comprise at least one antenna 110. In some embodiments, reader 100 may comprise one or more antennas 110.

Figure 1B:
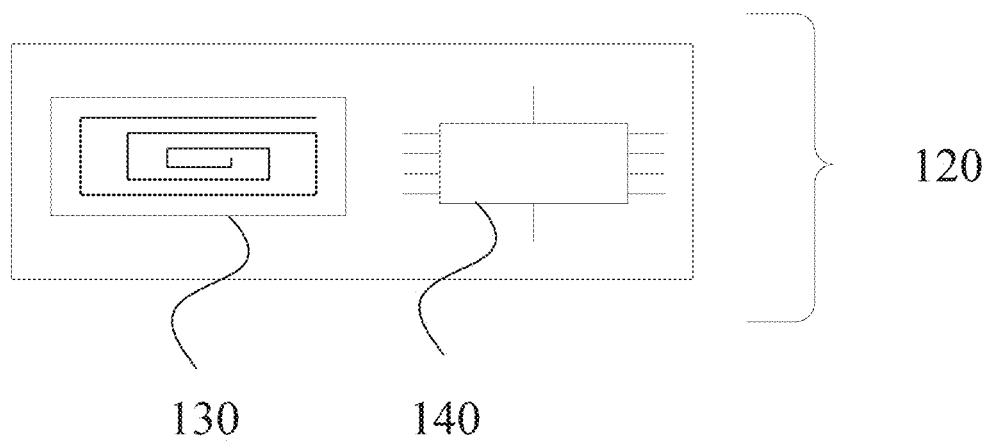
FIG. 1B may depict a schematic block diagram of a monitoring-sensor-tag.

FIG. 1B may depict a schematic block diagram of a monitoring-sensor-tag 120. In some embodiments, monitoring-sensor-tag 120 may comprise at least one electric circuit 140. In some embodiments, monitoring-sensor-tag 120 may comprise at least one antenna 130 in communication with the at least one electric circuit 140. In some embodiments, at least one electric circuit 140 may be in communication with at least one sensor. In some embodiments, monitoring-sensor-tag 120 may comprise the at least one sensor. In some embodiments, at least one electric circuit 140 may comprise the at least one sensor.

In some embodiments, at least one electric circuit 140 may be an integrated circuit. In some embodiments, the at least one sensor (e.g., 202, 203, and/or other sensors discussed herein) may be located inside of and integral with such an integrated circuit and in electrical communication with the integrated circuit. In some embodiments, the at least one sensor (e.g., 202, 203, 1006, and/or other sensors discussed herein) may be located outside of such an integrated circuit and in electrical communication with the integrated circuit.

In some embodiments, a given monitoring-sensor-tag 120 may be a wireless sensor tag. In some embodiments, a given monitoring-sensor-tag 120 may be one or more of: a RFID (radio frequency identification) sensor tag; a NFC (near field communication) sensor tag; a backscatter sensor tag; and/or magnetic inductive activated sensor tag.

In some embodiments, a given monitoring-sensor-tag 120 may communicate with a given reader 100. In some embodiments, such communication may be wireless. In some embodiments, such wireless communication may be via a predetermined wavelength or via predetermined wavelengths of electromagnetic (EM) radiation. For example, and without limiting the scope of the present invention, such a wavelength may be wavelengths associated with radio waves. For example, and without limiting the scope of the present invention, a given reader 100 may "interrogate" monitoring-sensor-tags 120 at a number of predetermined frequencies.

In some embodiments, upon at least one antenna 130 receiving electromagnetic (EM) radiation of a predetermined characteristic as an input from at least one antenna 110, this input may cause at least one electric circuit 140 to take one or more readings from the at least one sensor and to then transmit such one or more readings using at least one antenna 130. Then, at least one antenna 110 may receive these one or more readings being broadcast from at least one antenna 130. Hence, reader 100 may be "reading" from (i.e., scanning for) signals broadcast from a given monitoring-sensor-tag 120.

In some embodiments, when the at least one electric circuit 140 may cause the at least one antenna 130 to transmit the one or more readings, the at least one electric circuit 140 may also cause the at least one antenna 130 to transmit "additional information." In some embodiments, this "additional information" may comprise one or more of: identification information for a given monitoring-sensor-tag 120 that is transmitting (e.g., an ID for each monitoring-sensor-tag 120 that is transmitting); model number for the given monitoring-sensor-tag 120 that is transmitting; serial number for the given monitoring-sensor-tag 120 that is transmitting; manufacturer of the given monitoring-sensor-tag 120 that is transmitting; year of manufacture of the given monitoring-sensor-tag 120 that is transmitting; or a request for a security code associated with that given monitoring-sensor-tag 120 that is transmitting; a cyclic redundancy check code for the information that the given monitoring-sensor-tag 120 that is transmitting; a parity check code for information that the given monitoring-sensor-tag 120 that is transmitting; and receipt of a disable instruction for the given monitoring-sensor-tag 120 that is transmitting; wherein the given monitoring-sensor-tag 120 that is transmitting is selected from the one or more monitoring-sensor-tags 120.

In some embodiments, monitoring-sensor-tag 120 may be passive and receive power wirelessly transmitted from a given reader 100. That is, electrical power required to operate a given monitoring-sensor-tag 120 may be provided wirelessly from at least one antenna 110 from a given reader 100 that may be broadcasting and sufficiently close to at least one antenna 130 of given monitoring-sensor-tag 120.

In some embodiments, at least one of the one or more monitoring-sensor-tags 120 may be from substantially six inches to substantially 1.0 micrometer in a largest dimension of the at least one of the one or more monitoring-sensor-tags 120. In some embodiments, "substantially" in this context may mean plus or minus 10% of the given unit of measurement; i.e., plus or minus 10% of an inch and plus or minus 10% of a micrometer. In application, the size of a given monitoring-sensor-tag 120 may be negligible with respect to any impact the given monitoring-sensor-tag 120 may have on the associated material-of-interest; i.e., the sizes of the utilized monitoring-sensor-tags 120 may not negatively affect the associated material-of-interest.

In some embodiments, each monitoring-sensor-tag 120 may be attached to a given material-of-interest. Note, such materials-of-interest are not shown in FIG. 1A and in FIG. 1B. In some embodiments, a given material-of-interest may be selected from: a dental-filling 1001 (see e.g., FIG. 10A), a root-canal-post 1004 (see e.g., FIG. 10B), a root-canal-cavity 1003 (see e.g., FIG. 10B), a dental-crown 1005 (see e.g., FIG. 10B), a dental-implant 1007 (see e.g., FIG. 10C), an article implantable within a body of an organism, the article attachable to the body of the organism, specific tissue of the organism, a construction member, and/or the like. See also FIG. 10D for material-of-interest 1028, which in some embodiments may be any of the above identified given materials-of-interest. See also FIG. 13C showing monitoring-sensor-tag 120 located within a leg of a patient 1328; wherein in that example a portion of the leg (e.g., tissue, bone, an implant, or the like) may be given material-of-interest. See also FIG. 18 for material-of-interest 1828, which in some embodiments may be any of the above identified given materials-of-interest.

In some embodiments, the given material-of-interest may be an article. In some embodiments, the article may be selected from: a medical device; a tissue graft; a bone graft; an artificial tissue; a bolus with time-release medication; a medication; and/or the like. In some embodiments, the medical device may be selected from one or more of: a dental-implant 1007, an implantable device, an implantable organ (e.g., may include from a cadaver), implantable tissue (e.g., may include from a cadaver), an artificial organ, artificial tissue, an artificial joint, an artificial limb, an artificial valve, a suture, and/or the like.

In some embodiments, the construction member (of the given material-of-interest) may be selected from one or more of: concrete; cement; plaster; mortar; resin; brick; block; drywall; particle board; plywood; wood framing member (e.g., a stud); posts; beams; girders; engineered structural members; and/or the like.

In some embodiments, one or more monitoring-sensor-tags 120 being "attached to" the given material-of-interest, at an initial time of "attachment," may comprise one or more of the following locations: on a surface of the given material-of-interest; within the given material-of-interest; partially on the surface of the given material-of-interest and partially within the given material-of-interest; and/or the like. In some embodiments, the one or more monitoring-sensor-tags 120 may be immersed entirely within the material-of-interest. In some embodiments, the one or more monitoring-sensor-tags 120 may be immersed at least partially within the material-of-interest. That is, in some embodiments, "attached to" may comprise "immersion." In some embodiments, one or more monitoring-sensor-tags 120 may associate with the given material-of-interest; such as, but not limited to, translating with the given material-of-interest.

In some embodiments, an importance of attaching one or more monitoring-sensor-tags 120 with the given material-of-interest, may be that the at least one sensor of a given monitoring-sensor-tag 120 may then convey state information from readings of that at least one given sensor. That is, by using the monitoring-sensor-tags 120 attached to the given material-of-interest, information (e.g., various states) of the given material-of-interest may be monitored and/or tracked. In some embodiments, such monitoring and/or tracking may be accomplished with using radio waves as opposed to ionizing imaging radiation like x-rays; which may provide for increased safety to patients 1328 when the given material-of-interest is associated with a given patient 1328. Additionally, because of this, more frequent monitoring and/or tracking of the given material-of-interest may be utilized, resulting in increased efficacy and minimization of problems that may arise to due to infrequent monitoring, as there may be minimal need to minimize patient 1328 exposure to ionizing imaging radiation since embodiments of the present invention may communicate over radio waves between monitoring-sensor-tags 120 and various readers 100.

For example, and without limiting the scope of the present invention, in some embodiments, such state information of the given material-of-interest that may be monitored and/or tracked by using one or more monitoring-sensor-tags 120 attached to the given material-of-interest may be one or more of: structural integrity of a current state of the material-of-interest; structural integrity changes of the material-of-interest; pressure received at the material-of-interest; force received at the material-of-interest; stress received at the material-of-interest; torsion received at the material-of-interest; deformation received at the material-of-interest; temperature at some portion of the material-of-interest; positional changes of a given monitoring-sensor-tag 120 attached to the material-of-interest with respect to position of another monitoring-sensor-tag 120 attached to the material-of-interest, wherein the given monitoring-sensor-tag 120 and the other monitoring-sensor-tag are 120 selected from the one or more monitoring-sensor-tags 120 attached to the material-of-interest; or positional changes of at least one monitoring-sensor-tag 120 attached to the material-of-interest with respect to time, wherein the at least one monitoring-sensor-tag 120 is selected from the one or more monitoring-sensor-tags 120.

Figure 2A:
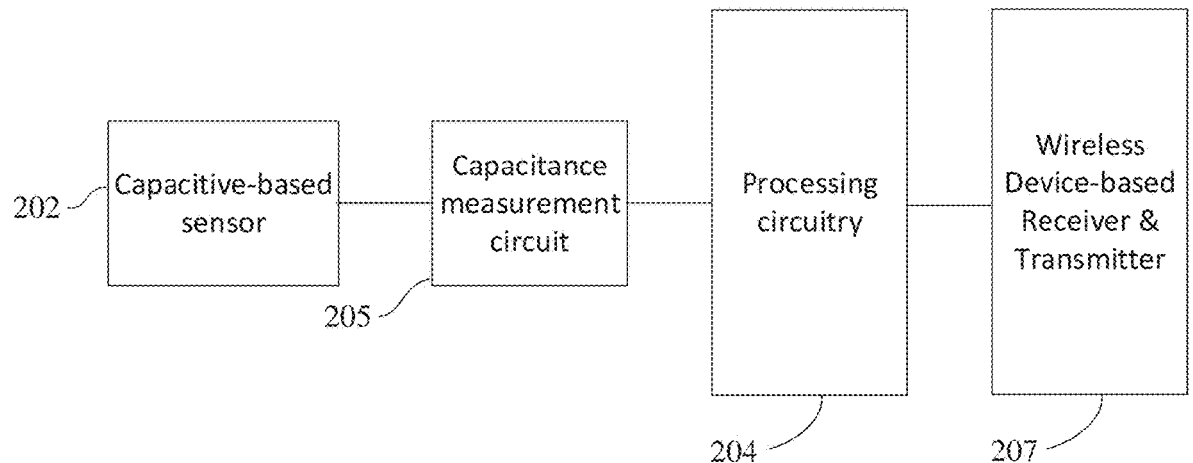
FIG. 2A may depict a schematic block diagram of a monitoring-sensor-tag comprising a capacitive-based sensor.

FIG. 2A may depict a schematic block diagram of monitoring-sensor-tag 120 comprising a capacitive-based sensor 202. In some embodiments, a given monitoring-sensor-tag 120 may comprise wireless-receiver-and-transmitter 207, processing circuitry 204, capacitance measurement circuit 205, and capacitive-based sensor 202. In some embodiments, processing circuitry 204 may be in communication with capacitance measurement circuit 205. In some embodiments, processing circuitry 204 may be in communication with wireless-receiver-and-transmitter 207. In some embodiments, capacitance measurement circuit 205 may be in communication with capacitive-based sensor 202.

In some embodiments, capacitance measurement circuit 205 may measure the capacitance of capacitive-based sensor 202 to quantify a current state reading of material-of-interest that monitoring-sensor-tag 120 may be attached to. In some embodiments, processing circuitry 204 may control capacitance measurement circuit 205 and process the one or more readings (the obtained results) for radio-frequency transmission (or for other electromagnetic transmission). In some embodiments, wireless-receiver-and-transmitter 207 may transmit the one or more readings (the obtained results) to reader 100. In some embodiments, wireless-receiver-and-transmitter 207 may receive instructions from reader 100 using electromagnetic (EM) waves; such as, but not limited to radio wavelength electromagnetic (EM) waves. See e.g., FIG. 2A.

In some embodiments, at least one antenna 130 (of monitoring-sensor-tag 120) may comprise wireless-receiver-and-transmitter 207. In some embodiments, at least one electric circuit 140 (of monitoring-sensor-tag 120) may comprise processing circuitry 204. In some embodiments, at least one electric circuit 140 (of monitoring-sensor-tag 120) may comprise processing circuitry 204 and capacitance measurement circuit 205. In some embodiments, at least one electric circuit 140 (of monitoring-sensor-tag 120) may comprise processing circuitry 204, capacitance measurement circuit 205, and capacitive-based sensor 202.

Figure 2B:
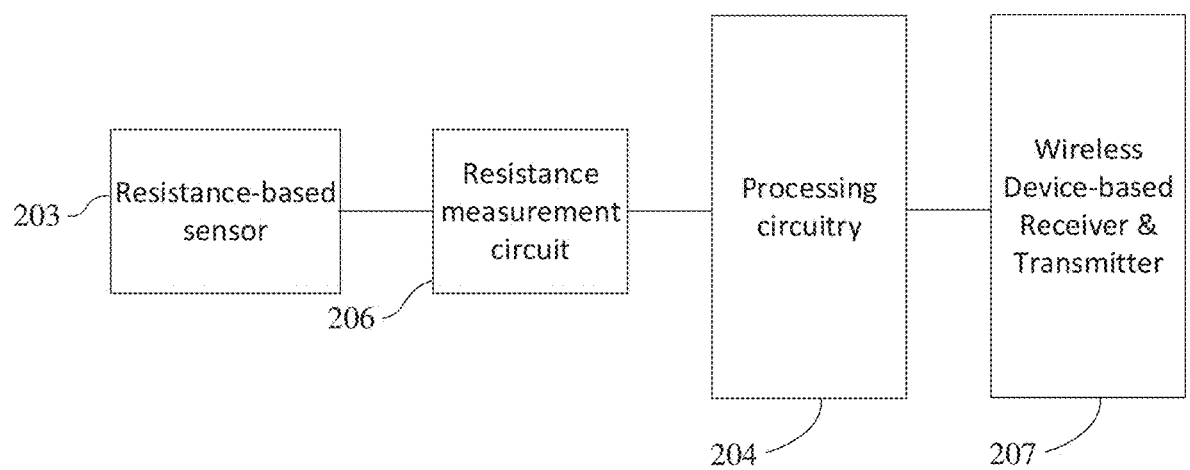
FIG. 2B may depict a schematic block diagram of a monitoring-sensor-tag comprising a resistance-based sensor.

FIG. 2B may depict a schematic block diagram of monitoring-sensor-tag 120 comprising a resistance-based sensor 203. In some embodiments, a given monitoring-sensor-tag 120 may comprise wireless-receiver-and-transmitter 207, processing circuitry 204, resistance measurement circuit 206, and resistance-based sensor 203. In some embodiments, processing circuitry 204 may be in communication with resistance measurement circuit 206. In some embodiments, processing circuitry 204 may be in communication with wireless-receiver-and-transmitter 207. In some embodiments, resistance measurement circuit 206 may be in communication with resistance-based sensor 203.

In some embodiments, resistance measurement circuit 206 may measure the resistance of resistance-based sensor 203 to quantify a current state reading of material-of-interest that monitoring-sensor-tag 120 may be attached to. In some embodiments, processing circuitry 204 may control resistance measurement circuit 206 and process the one or more readings (the obtained results) for radio-frequency transmission (or for other electromagnetic transmission). In some embodiments, wireless-receiver-and-transmitter 207 may transmit the one or more readings (the obtained results) to reader 100. In some embodiments, wireless-receiver-and-transmitter 207 may receive instructions from reader 100 using electromagnetic (EM) waves; such as, but not limited to radio wavelength electromagnetic (EM) waves. See e.g., FIG. 2B.

In some embodiments, at least one antenna 130 (of monitoring-sensor-tag 120) may comprise wireless-receiver-and-transmitter 207. In some embodiments, at least one electric circuit 140 (of monitoring-sensor-tag 120) may comprise processing circuitry 204. In some embodiments, at least one electric circuit 140 (of monitoring-sensor-tag 120) may comprise processing circuitry 204 and resistance measurement circuit 206. In some embodiments, at least one electric circuit 140 (of monitoring-sensor-tag 120) may comprise processing circuitry 204, resistance measurement circuit 206, and resistance-based sensor 203.

Figure 2C:
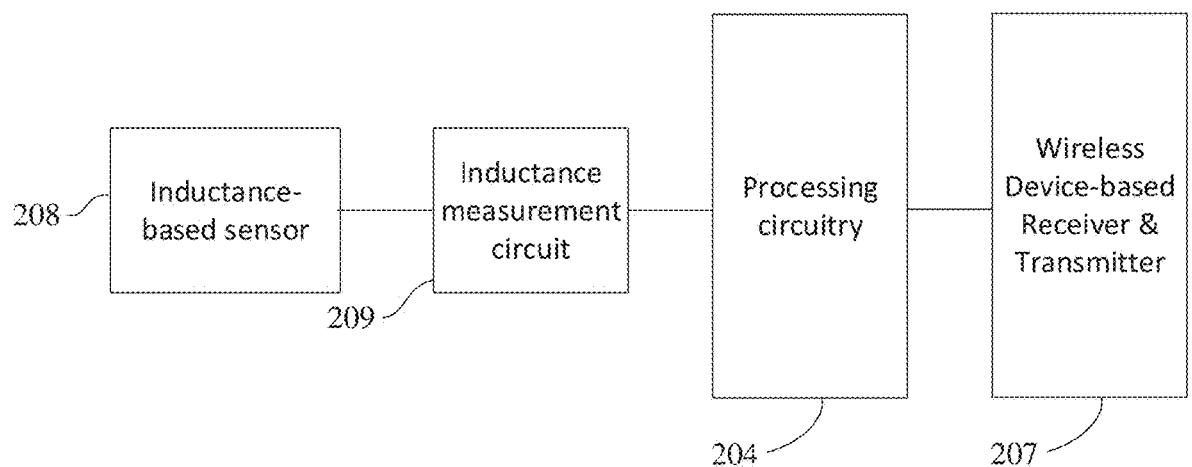
FIG. 2C may depict a schematic block diagram of a monitoring-sensor-tag comprising an inductance-based sensor.

FIG. 2C may depict a schematic block diagram of monitoring-sensor-tag 120 comprising an inductance-based-sensor 208. In some embodiments, a given monitoring-sensor-tag 120 may comprise wireless-receiver-and-transmitter 207, processing circuitry 204, inductance measurement circuit 209, and inductance-based-sensor 208. In some embodiments, processing circuitry 204 may be in communication with inductance measurement circuit 209. In some embodiments, processing circuitry 204 may be in communication with wireless-receiver-and-transmitter 207. In some embodiments, inductance measurement circuit 209 may be in communication with inductance-based-sensor 208.

In some embodiments, inductance measurement circuit 209 may measure the inductance of inductance-based-sensor 208 to quantify a current state reading of material-of-interest that monitoring-sensor-tag 120 may be attached to. In some embodiments, processing circuitry 204 may control inductance measurement circuit 209 and process the one or more readings (the obtained results) for radio-frequency transmission (or for other electromagnetic transmission). In some embodiments, wireless-receiver-and-transmitter 207 may transmit the one or more readings (the obtained results) to reader 100. In some embodiments, wireless-receiver-and-transmitter 207 may receive instructions from reader 100 using electromagnetic (EM) waves; such as, but not limited to radio wavelength electromagnetic (EM) waves. See e.g., FIG. 2C.

In some embodiments, at least one antenna 130 (of monitoring-sensor-tag 120) may comprise wireless-receiver-and-transmitter 207. In some embodiments, at least one electric circuit 140 (of monitoring-sensor-tag 120) may comprise processing circuitry 204. In some embodiments, at least one electric circuit 140 (of monitoring-sensor-tag 120) may comprise processing circuitry 204 and inductance measurement circuit 209. In some embodiments, at least one electric circuit 140 (of monitoring-sensor-tag 120) may comprise processing circuitry 204, inductance measurement circuit 209, and inductance-based-sensor 208.

Figure 2D:
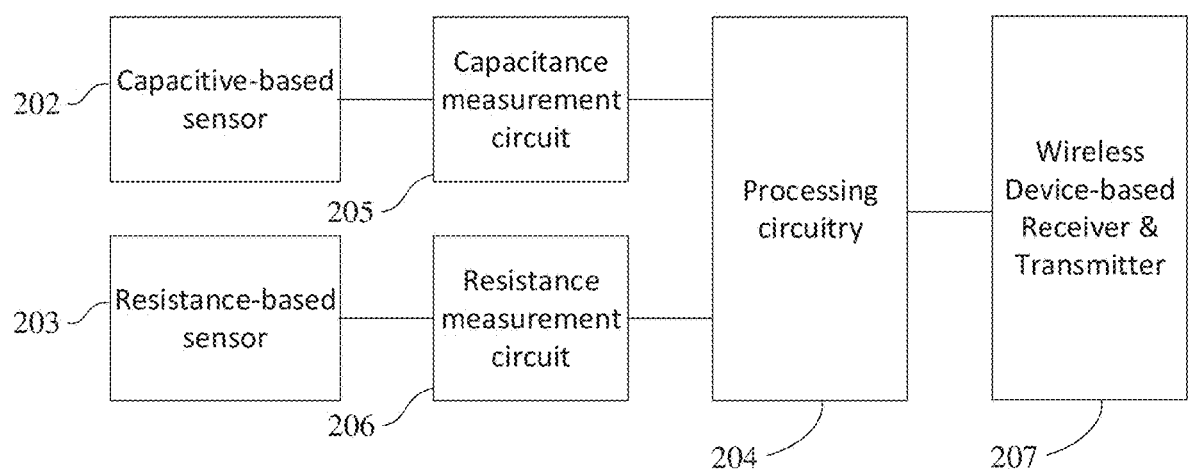
FIG. 2D may depict a schematic block diagram of a monitoring-sensor-tag comprising a capacitive-based sensor and a resistance-based-sensor.

FIG. 2D may depict a schematic block diagram of a monitoring-sensor-tag comprising a capacitive-based sensor 202 and a resistance-based-sensor 203. In some embodiments, a given monitoring-sensor-tag 120 may comprise wireless-receiver-and-transmitter 207, processing circuitry 204, capacitance measurement circuit 205, capacitive-based sensor 202, resistance measurement circuit 206, and resistance-based sensor 203. In some embodiments, processing circuitry 204 may be in communication with capacitance measurement circuit 205. In some embodiments, processing circuitry 204 may be in communication with resistance measurement circuit 206. In some embodiments, processing circuitry 204 may be in communication with wireless-receiver-and-transmitter 207. In some embodiments, capacitance measurement circuit 205 may be in communication with capacitive-based sensor 202. In some embodiments, resistance measurement circuit 206 may be in communication with resistance-based sensor 203.

In some embodiments, capacitance measurement circuit 205 may measure the capacitance of capacitive-based sensor 202 to quantify a current state reading of material-of-interest that monitoring-sensor-tag 120 may be attached to. In some embodiments, resistance measurement circuit 206 may measure the resistance of resistance-based sensor 203 to quantify another current state reading of material-of-interest that monitoring-sensor-tag 120 may be attached to. In some embodiments, processing circuitry 204 may control capacitance measurement circuit 205 and may control resistance measurement circuit 206 and process the one or more readings (the obtained results) for radio-frequency transmission (or for other electromagnetic transmission). In some embodiments, wireless-receiver-and-transmitter 207 may transmit the one or more readings (the obtained results) to reader 100. In some embodiments, wireless-receiver-and-transmitter 207 may receive instructions from reader 100 using electromagnetic (EM) waves; such as, but not limited to radio wavelength electromagnetic (EM) waves. See e.g., FIG. 2D.

In some embodiments, at least one antenna 130 (of monitoring-sensor-tag 120) may comprise wireless-receiver-and-transmitter 207. In some embodiments, at least one electric circuit 140 (of monitoring-sensor-tag 120) may comprise processing circuitry 204. In some embodiments, at least one electric circuit 140 (of monitoring-sensor-tag 120) may comprise processing circuitry 204, capacitance measurement circuit 205, and resistance measurement circuit 206. In some embodiments, at least one electric circuit 140 (of monitoring-sensor-tag 120) may comprise processing circuitry 204, capacitance measurement circuit 205, capacitive-based sensor 202, resistance measurement circuit 206, and resistance-based sensor 203.

Figure 2E:
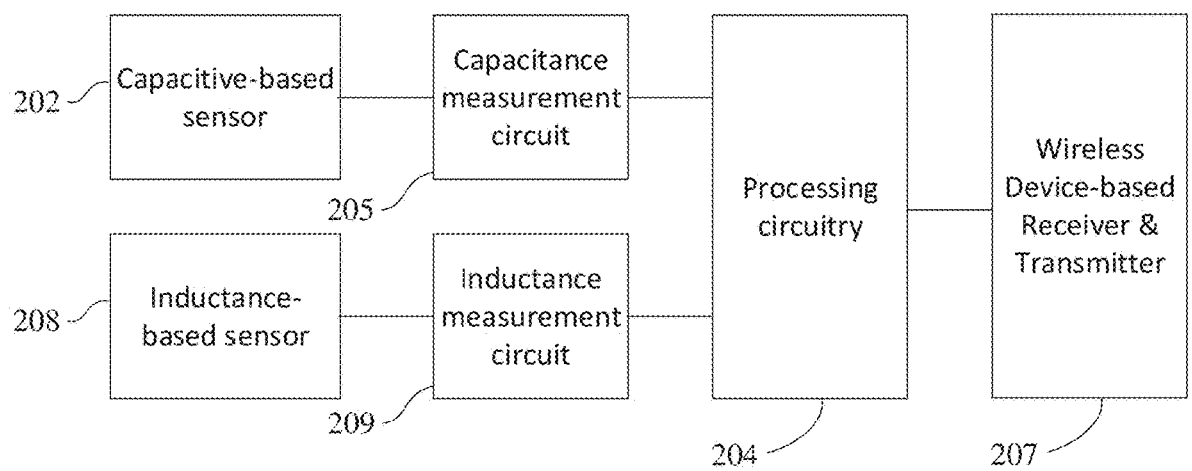
FIG. 2E may depict a schematic block diagram of a monitoring-sensor-tag comprising a capacitive-based sensor and an inductance-based-sensor.

FIG. 2E may depict a schematic block diagram of a monitoring-sensor-tag comprising a capacitive-based sensor 202 and an inductance-based-sensor 208. In some embodiments, a given monitoring-sensor-tag 120 may comprise wireless-receiver-and-transmitter 207, processing circuitry 204, capacitance measurement circuit 205, capacitive-based sensor 202, inductance measurement circuit 209, and inductance-based-sensor 208. In some embodiments, processing circuitry 204 may be in communication with capacitance measurement circuit 205. In some embodiments, processing circuitry 204 may be in communication with inductance measurement circuit 209. In some embodiments, processing circuitry 204 may be in communication with wireless-receiver-and-transmitter 207. In some embodiments, capacitance measurement circuit 205 may be in communication with capacitive-based sensor 202. In some embodiments, inductance measurement circuit 209 may be in communication with inductance-based-sensor 208.

In some embodiments, capacitance measurement circuit 205 may measure the capacitance of capacitive-based sensor 202 to quantify a current state reading of material-of-interest that monitoring-sensor-tag 120 may be attached to. In some embodiments, inductance measurement circuit 209 may measure the inductance of inductance-based-sensor 208 to quantify another current state reading of material-of-interest that monitoring-sensor-tag 120 may be attached to. In some embodiments, processing circuitry 204 may control capacitance measurement circuit 205 and may control inductance measurement circuit 209 and process the one or more readings (the obtained results) for radio-frequency transmission (or for other electromagnetic transmission). In some embodiments, wireless-receiver-and-transmitter 207 may transmit the one or more readings (the obtained results) to reader 100. In some embodiments, wireless-receiver-and-transmitter 207 may receive instructions from reader 100 using electromagnetic (EM) waves; such as, but not limited to radio wavelength electromagnetic (EM) waves. See e.g., FIG. 2E.

In some embodiments, at least one antenna 130 (of monitoring-sensor-tag 120) may comprise wireless-receiver-and-transmitter 207. In some embodiments, at least one electric circuit 140 (of monitoring-sensor-tag 120) may comprise processing circuitry 204. In some embodiments, at least one electric circuit 140 (of monitoring-sensor-tag 120) may comprise processing circuitry 204, capacitance measurement circuit 205, and inductance measurement circuit 209. In some embodiments, at least one electric circuit 140 (of monitoring-sensor-tag 120) may comprise processing circuitry 204, capacitance measurement circuit 205, capacitive-based sensor 202, inductance measurement circuit 209, and inductance-based-sensor 208.

Figure 2F:
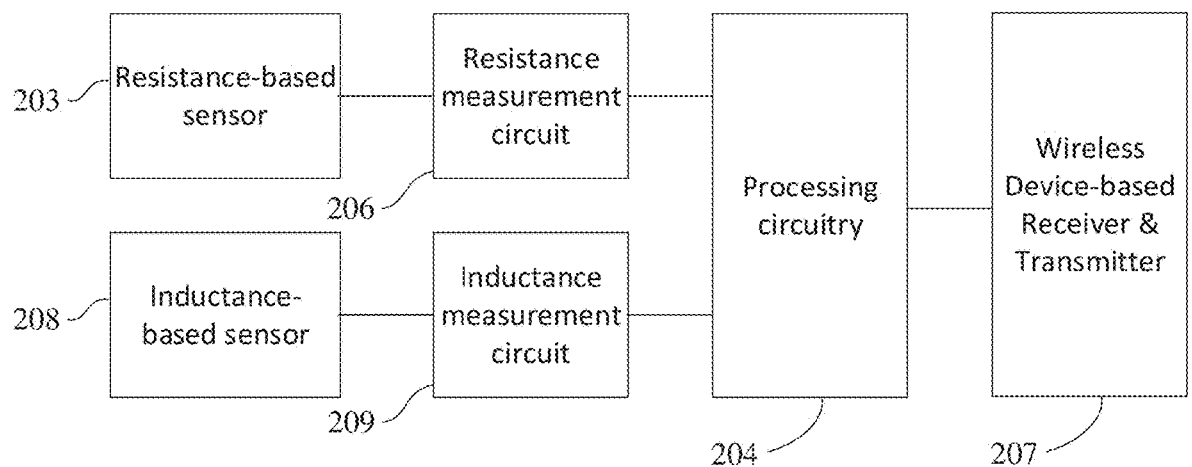
FIG. 2F may depict a schematic block diagram of a monitoring-sensor-tag comprising a resistance-based sensor and an inductance-based-sensor.

FIG. 2F may depict a schematic block diagram of a monitoring-sensor-tag comprising a resistance-based sensor 203 and an inductance-based-sensor 208.

In some embodiments, a given monitoring-sensor-tag 120 may comprise wireless-receiver-and-transmitter 207, processing circuitry 204, resistance measurement circuit 206, resistance-based sensor 203, inductance measurement circuit 209, and inductance-based-sensor 208. In some embodiments, processing circuitry 204 may be in communication with resistance measurement circuit 206. In some embodiments, processing circuitry 204 may be in communication with inductance measurement circuit 209. In some embodiments, processing circuitry 204 may be in communication with wireless-receiver-and-transmitter 207. In some embodiments, resistance measurement circuit 206 may be in communication with resistance-based sensor 203. In some embodiments, inductance measurement circuit 209 may be in communication with inductance-based-sensor 208.

In some embodiments, resistance measurement circuit 206 may measure the resistance of resistance-based sensor 203 to quantify a current state reading of material-of-interest that monitoring-sensor-tag 120 may be attached to. In some embodiments, inductance measurement circuit 209 may measure the inductance of inductance-based-sensor 208 to quantify another current state reading of material-of-interest that monitoring-sensor-tag 120 may be attached to. In some embodiments, processing circuitry 204 may control resistance measurement circuit 206 and may control inductance measurement circuit 209 and may process the one or more readings (the obtained results) for radio-frequency transmission (or for other electromagnetic transmission). In some embodiments, wireless-receiver-and-transmitter 207 may transmit the one or more readings (the obtained results) to reader 100. In some embodiments, wireless-receiver-and-transmitter 207 may receive instructions from reader 100 using electromagnetic (EM) waves; such as, but not limited to radio wavelength electromagnetic (EM) waves. See e.g., FIG. 2F.

In some embodiments, at least one antenna 130 (of monitoring-sensor-tag 120) may comprise wireless-receiver-and-transmitter 207. In some embodiments, at least one electric circuit 140 (of monitoring-sensor-tag 120) may comprise processing circuitry 204. In some embodiments, at least one electric circuit 140 (of monitoring-sensor-tag 120) may comprise processing circuitry 204, resistance measurement circuit 206, and inductance measurement circuit 209. In some embodiments, at least one electric circuit 140 (of monitoring-sensor-tag 120) may comprise processing circuitry 204, resistance measurement circuit 206, resistance-based sensor 203, inductance measurement circuit 209, and inductance-based-sensor 208.

Figure 2G:
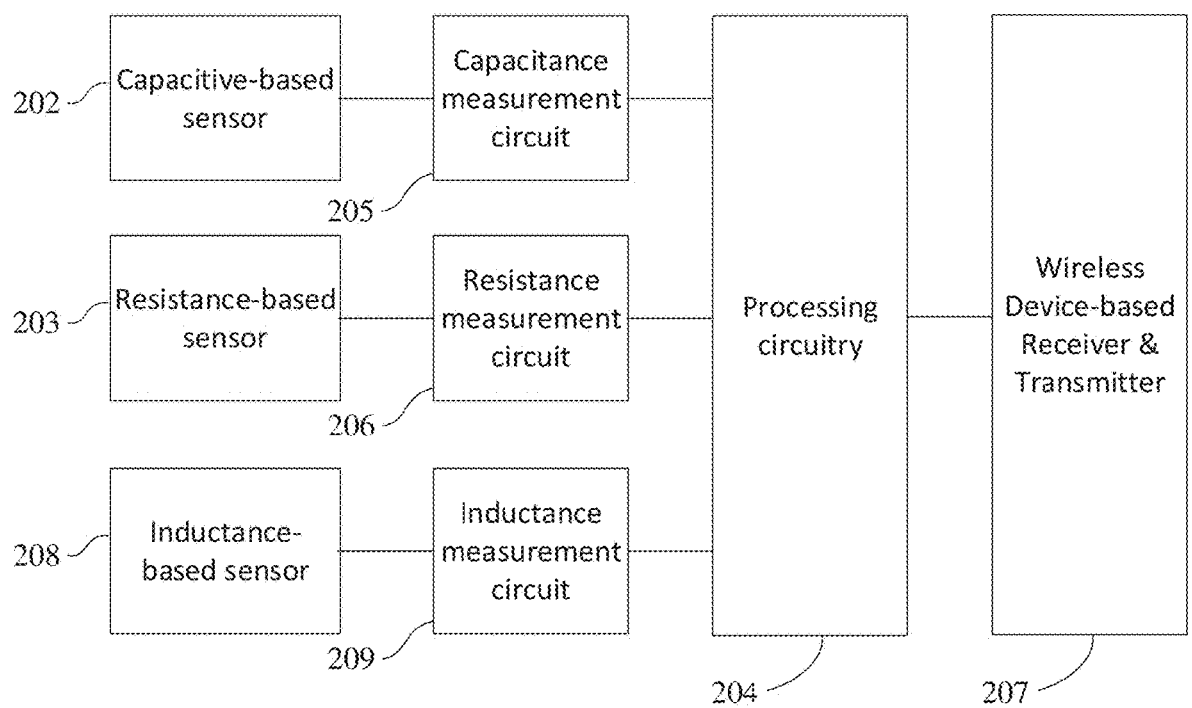
FIG. 2G may depict a schematic block diagram of a monitoring-sensor-tag comprising a capacitive-based sensor, a resistance-based sensor, and an inductance-based-sensor.

FIG. 2G may depict a schematic block diagram of a monitoring-sensor-tag comprising a capacitive-based sensor 202, a resistance-based sensor 203, and an inductance-based-sensor 208.

In some embodiments, a given monitoring-sensor-tag 120 may comprise wireless-receiver-and-transmitter 207, processing circuitry 204, capacitance measurement circuit 205, capacitive-based sensor 202, resistance measurement circuit 206, resistance-based sensor 203, inductance measurement circuit 209, and inductance-based-sensor 208. In some embodiments, processing circuitry 204 may be in communication with capacitance measurement circuit 205. In some embodiments, processing circuitry 204 may be in communication with resistance measurement circuit 206. In some embodiments, processing circuitry 204 may be in communication with inductance measurement circuit 209. In some embodiments, processing circuitry 204 may be in communication with wireless-receiver-and-transmitter 207. In some embodiments, capacitance measurement circuit 205 may be in communication with capacitive-based sensor 202. In some embodiments, resistance measurement circuit 206 may be in communication with resistance-based sensor 203. In some embodiments, inductance measurement circuit 209 may be in communication with inductance-based-sensor 208.

In some embodiments, capacitance measurement circuit 205 may measure the capacitance of capacitive-based sensor 202 to quantify a current state reading of material-of-interest that monitoring-sensor-tag 120 may be attached to. In some embodiments, resistance measurement circuit 206 may measure the resistance of resistance-based sensor 203 to quantify another current state reading of material-of-interest that monitoring-sensor-tag 120 may be attached to. In some embodiments, inductance measurement circuit 209 may measure the inductance of inductance-based-sensor 208 to quantify yet another current state reading of material-of-interest that monitoring-sensor-tag 120 may be attached to. In some embodiments, processing circuitry 204 may control capacitance measurement circuit 205, may control resistance measurement circuit 206, and may control inductance measurement circuit 209. In some embodiments, processing circuitry 204 may process the one or more readings (i.e., the obtained results) for radio-frequency transmission (or for other electromagnetic transmission). In some embodiments, wireless-receiver-and-transmitter 207 may transmit the one or more readings (the obtained results) to reader 100. In some embodiments, wireless-receiver-and-transmitter 207 may receive instructions from reader 100 using electromagnetic (EM) waves; such as, but not limited to radio wavelength electromagnetic (EM) waves. See e.g., FIG. 2G.

In some embodiments, at least one antenna 130 (of monitoring-sensor-tag 120) may comprise wireless-receiver-and-transmitter 207. In some embodiments, at least one electric circuit 140 (of monitoring-sensor-tag 120) may comprise processing circuitry 204. In some embodiments, at least one electric circuit 140 (of monitoring-sensor-tag 120) may comprise processing circuitry 204, capacitance measurement circuit 205, resistance measurement circuit 206, and inductance measurement circuit 209. In some embodiments, at least one electric circuit 140 (of monitoring-sensor-tag 120) may comprise processing circuitry 204, capacitance measurement circuit 205, capacitive-based sensor 202, resistance measurement circuit 206, resistance-based sensor 203, inductance measurement circuit 209, and inductance-based-sensor 208.

As noted above in the FIG. 1B discussion of monitoring-sensor-tag 120, monitoring-sensor-tag 120 may comprise the at least one sensor. In some embodiments, the at least one sensor may be selected from one or more of: capacitive-based sensor 202, resistance-based sensor 203, and/or inductance-based-sensor 208. See e.g., FIG. 2A through and including FIG. 2G.

As noted above in the FIG. 1B discussion of monitoring-sensor-tag 120, at least one electric circuit 140 (of monitoring-sensor-tag 120) may comprise the at least one sensor. In some embodiments, the at least one sensor may be selected from one or more of: capacitive-based sensor 202, resistance-based sensor 203, and/or inductance-based-sensor 208. See e.g., FIG. 2A through and including FIG. 2G.

Figure 10A:
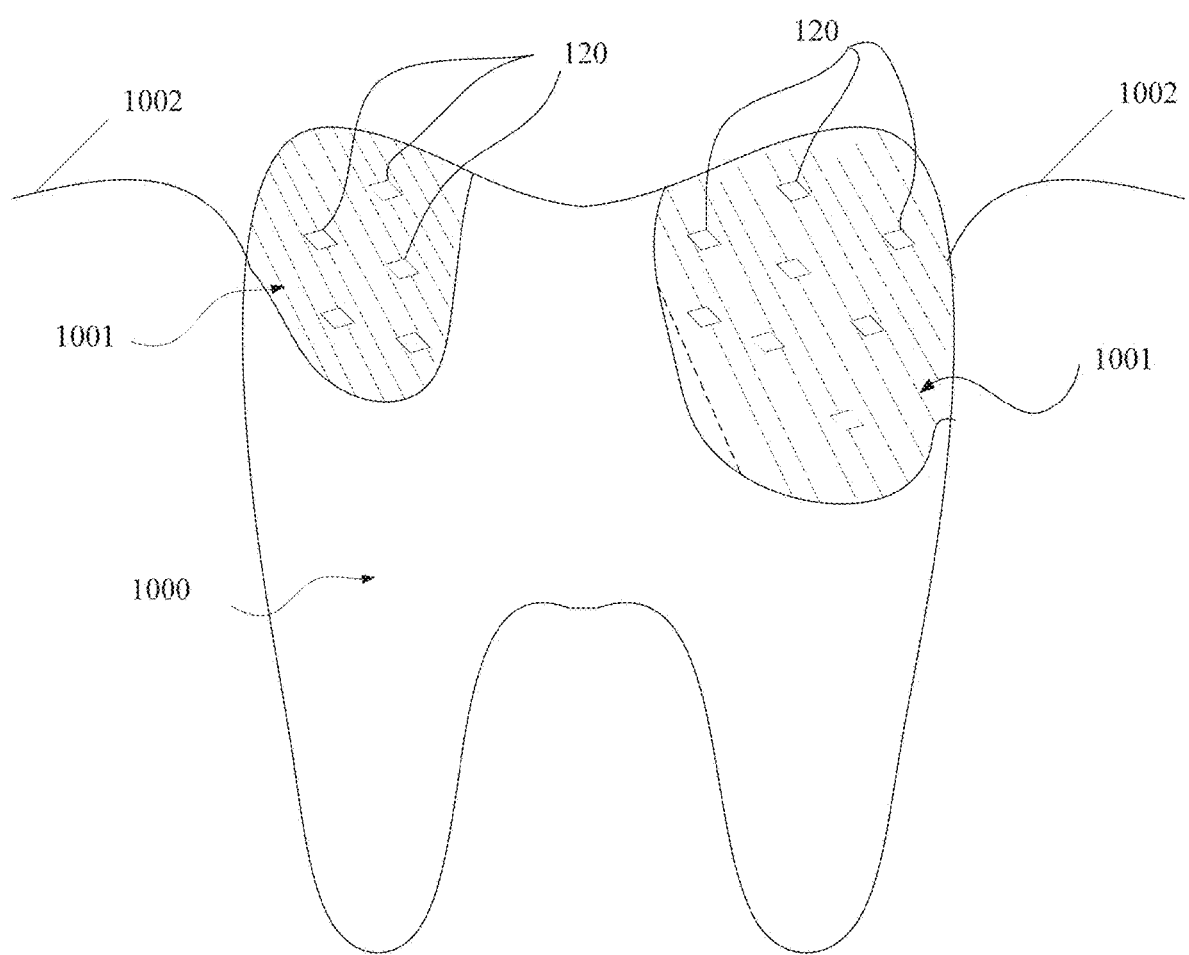
FIG. 10A may be a diagram of a patient's tooth with one or more monitoring-sensor-tags placed in dental-filling as a material-of-interest, in accordance with some embodiments of the present invention.
Figure 10B:
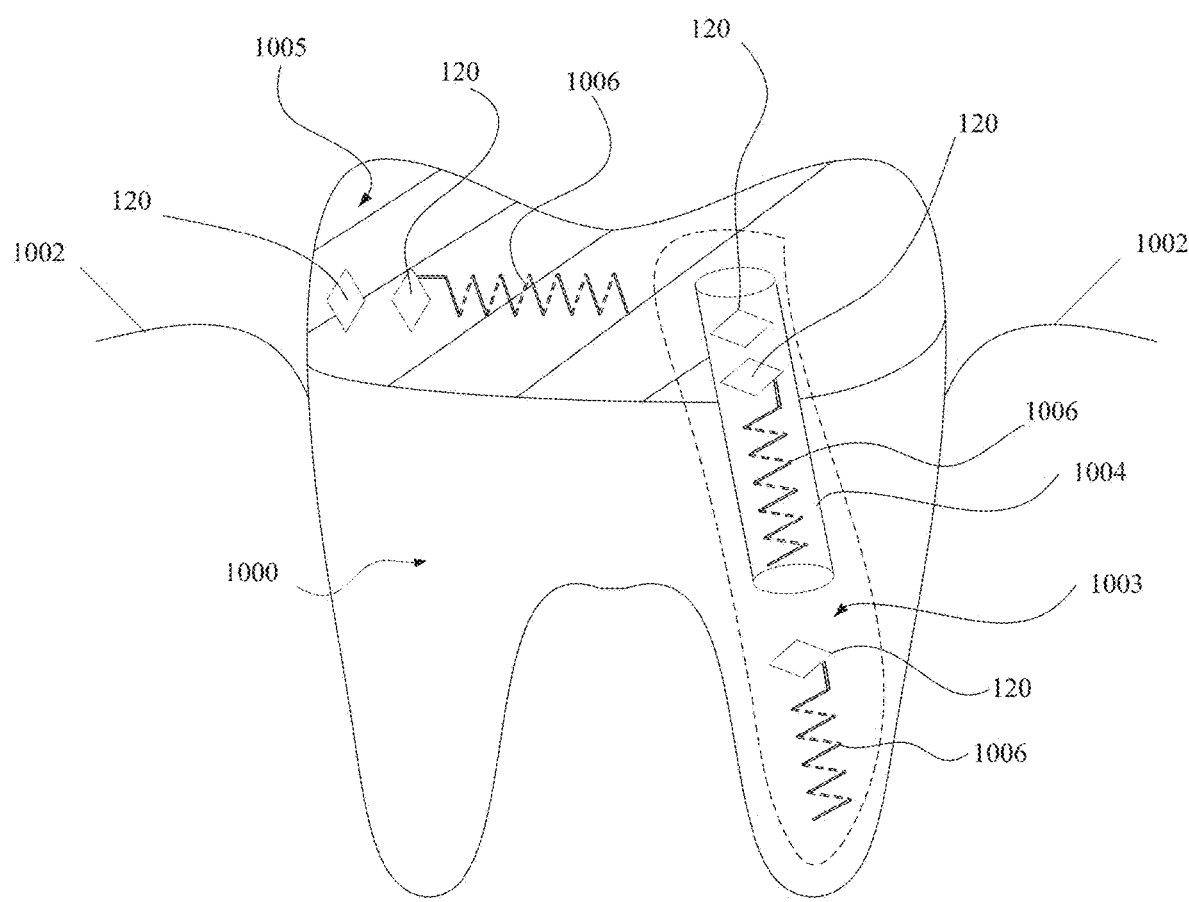
FIG. 10B may be a diagram of a patient's tooth with one or more monitoring-sensor-tags placed in: a root-canal-cavity, in a root-canal-post, and/or in a dental-crown; in accordance with some embodiments of the present invention.
Figure 10C:
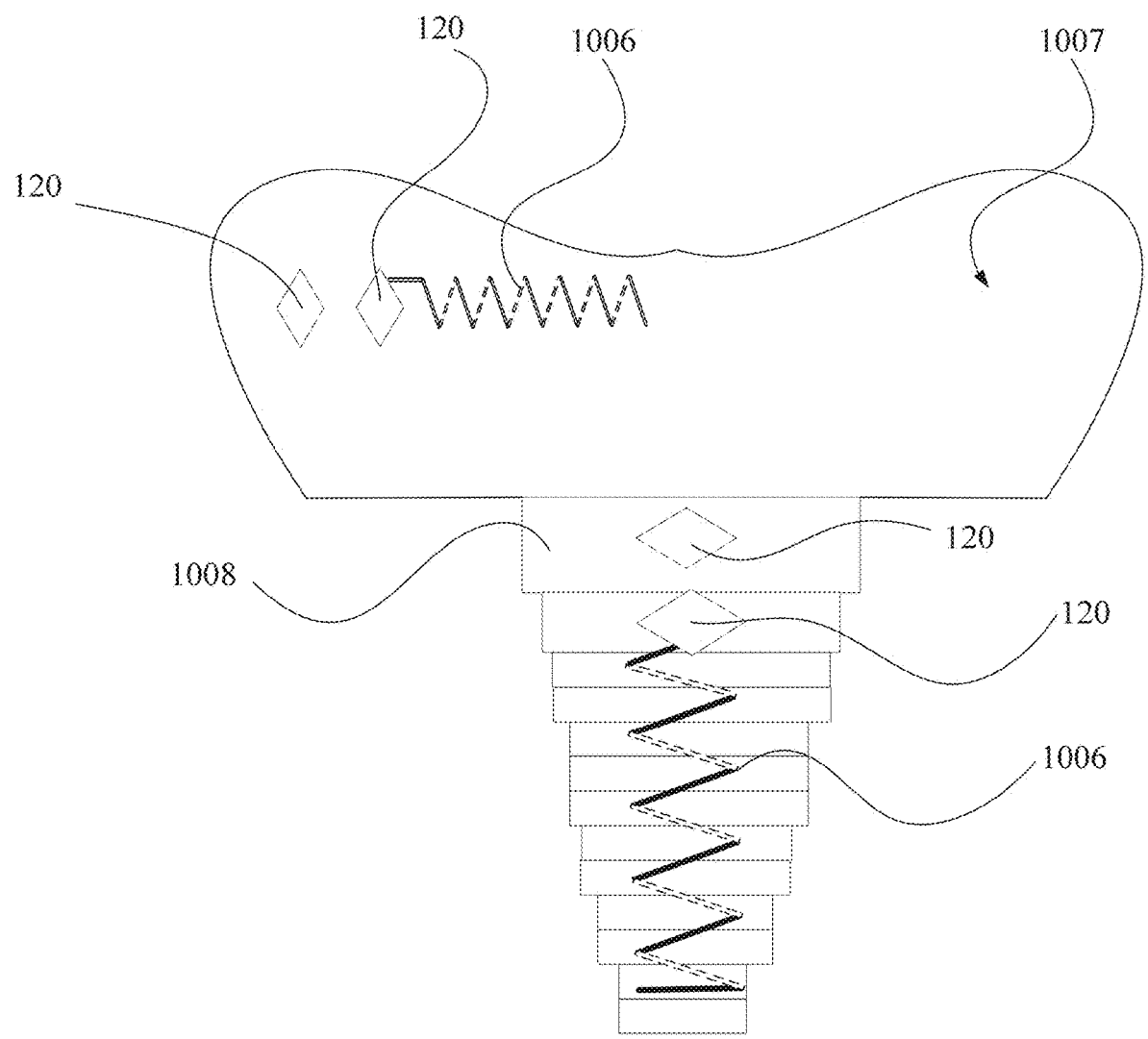
FIG. 10C may be a diagram of a patient's tooth dental-implant with one or more monitoring-sensor-tags, in accordance with some embodiments of the present invention.
Figure 10D:
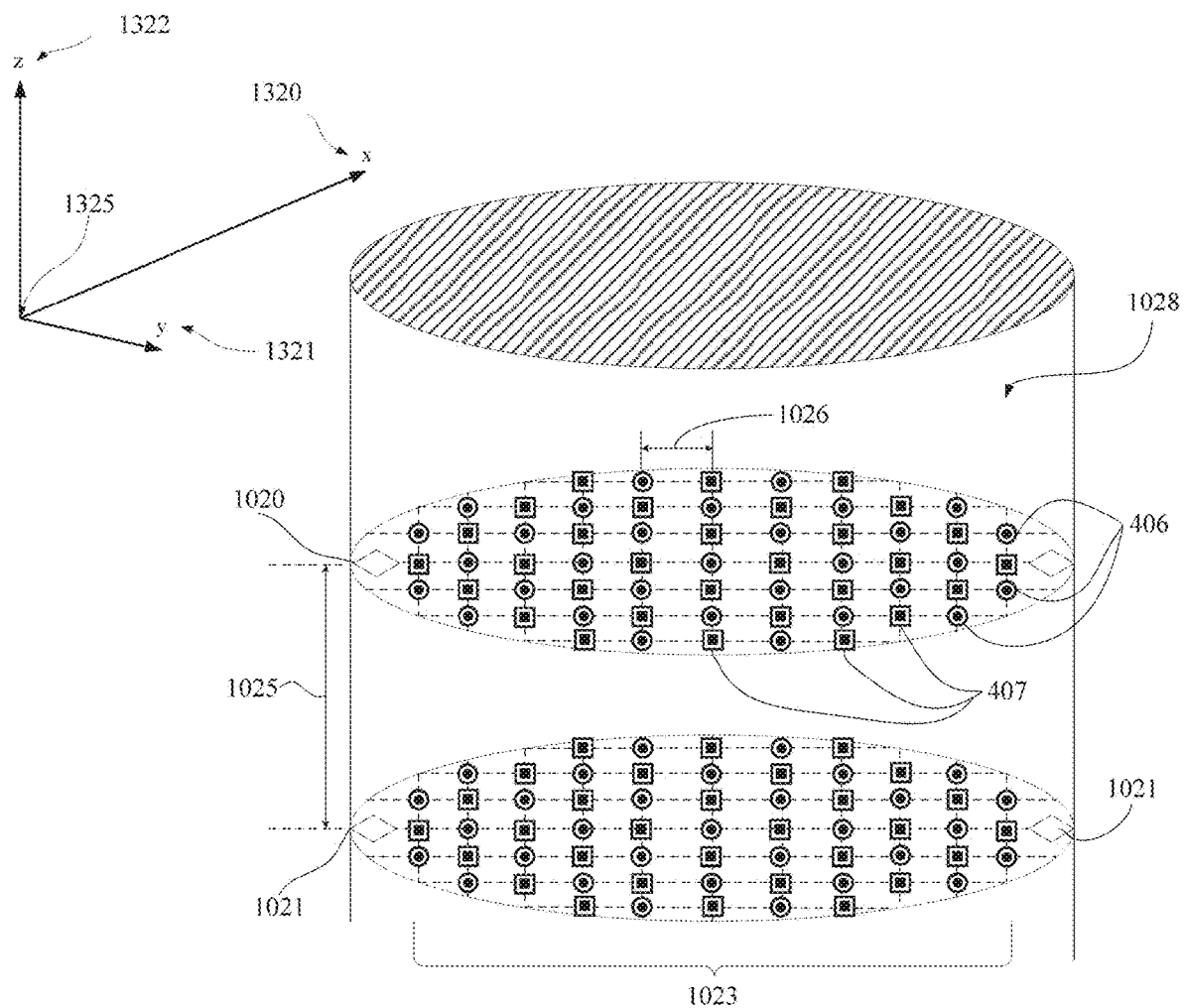
FIG. 10D may be a diagram of a first-sensor-tag and a second-sensor-tag arranged in a material-of-interest with an initial predetermined spacing between the first-sensor-tag and the second-sensor-tag in this material-of-interest.

In some embodiments, at least one electric circuit 140 (of monitoring-sensor-tag 120) may be attached to and in communication with the at least one sensor, such as, but not limited to: spiral-formed-electric-conductor 703 (see e.g., FIG. 7C); standalone-strain-sensor 1006 (see e.g., FIG. 10B, FIG. 10C, and FIG. 18); and lattice-of-sensors 1023 (see e.g., FIG. 10D).

In some embodiments, the one or more readings taken from the at least one sensor may be readings of one or more of: inductance from one or more inductance-based-sensors 208; capacitance from one or more capacitive-based sensors 202; and/or resistance from one or more resistance-based sensors 203. See e.g., FIG. 2A through and including FIG. 2G. In some embodiments, such one or more readings of current values, over time, of one or more of inductance, capacitance, or resistance may determine changes in such properties. In some embodiments, initial current value readings may function as baseline readings that future current value readings may be monitored against to determine changes.

In some embodiments, these one or more readings may provide status information to determine one or more of: structural integrity of a current state of the material-of-interest; structural integrity changes of the material-of-interest; pressure received at the material-of-interest; force received at the material-of-interest; stress received at the material-of-interest; torsion received at the material-of-interest; deformation received at the material-of-interest; temperature at some portion of the material-of-interest; positional changes of a given monitoring-sensor-tag 120 attached to the material-of-interest with respect to position of another monitoring-sensor-tag 120 attached to the material-of-interest, wherein the given monitoring-sensor-tag 120 and the other monitoring-sensor-tag are 120 selected from the one or more monitoring-sensor-tags 120 attached to the material-of-interest; or positional changes of at least one monitoring-sensor-tag 120 attached to the material-of-interest with respect to time, wherein the at least one monitoringsensor-tag 120 is selected from the one or more monitoring-sensor-tags 120. In some embodiments, readings from one or more of capacitive-based sensor 202, resistance-based sensor 203, and/or inductance-based-sensor 208 may yield such current status information as noted above.

In some embodiments, structural integrity changes of the material-of-interest may comprise monitoring for liquid penetration into the given material-of-interest. In some embodiments, liquid as used herein may comprise viscous fluids, slurries, and/or slow flow films. In some embodiments, liquid as used herein may comprise viscous fluids, slurries, and/or slow flow films that may harden and/or become cured into a hardened state (with no to minimal flow). In some embodiments, structural integrity changes of the material-of-interest may comprise monitoring for liquid penetration to the at least one sensors (e.g., 202 and/or 203) located within the given material-of-interest. For example, and without limiting the scope of the present invention, the at least one sensors (e.g., 202, 203, and/or 1006) may monitor for liquid penetration into filling 1001, see e.g., FIG. 10A; for liquid penetration beneath dental-crowns 1005, see e.g., FIG. 10B; for liquid penetration into root-canal-cavity 1003, see e.g., FIG. 10B; or monitor for liquid penetration into other materials-of-interest. Such liquid penetration may indicate an increased likelihood of infection and/or of structural integrity failures and/or detachment of the given material-of-interest (e.g., detachment of: dental-filling 1001, dental-crown 1005, root-canal-post 1004, and/or dental-implant 1007). In some embodiments, such at least one sensors (e.g., 202, 203, and/or 1006) may monitor for liquid penetration at the at least one sensors (e.g., 202, 203, and/or 1006), in at least some portion of the given material-of-interest, and/or within hollow space within the given material-of-interest. In some embodiments, such at least one sensors (e.g., 202, 203, and/or 1006) may monitor for liquid penetration without the at least one sensors (e.g., 202, 203, and/or 1006) coming in physical contact with the liquid.

It should be appreciated by those of ordinary skill in the relevant art that capacitive-based sensor 202 and capacitance measurement circuits 205 may be used to implement configurations depicted in FIG. 2A, FIG. 2D, FIG. 2E, and/or FIG. 2G to quantify, measure, track, monitor, and/or analyze various states and changes in states of materials-of-interest with one or more monitoring-sensor-tag 120 processing the one or more reading originating from such capacitive-based sensor 202.

Figure 3:
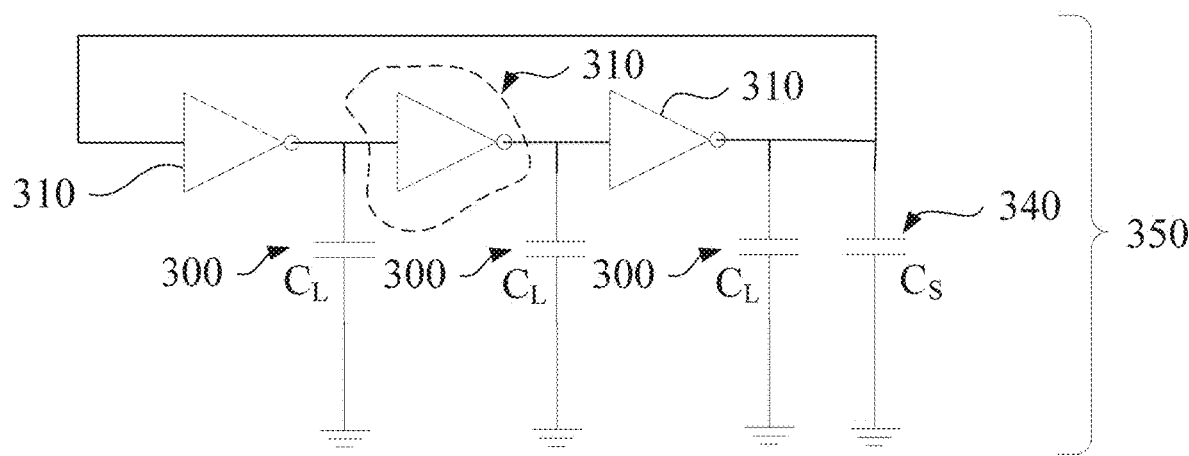
FIG. 3 may be a circuit diagram of a ring oscillator implementing a capacitance measurement circuit.

FIG. 3 may be a circuit diagram of a ring oscillator 350 implementing a capacitance measurement circuit 205 with capacitive-based sensor 202. In some embodiments, capacitance measurement circuit 205 with capacitive-based sensor 202 may be carried out via ring oscillator 350. In some embodiments, ring oscillator circuit 350 may measure values of capacitive-based sensor 202, transferring such values of capacitive-based sensor 202 into frequency of oscillations of said ring oscillator 350.

Continuing discussing FIG. 3, in some embodiments, ring oscillator 350 may comprise an odd number of stages. In some embodiments, each such stage may comprise a respective digital invertor 310 and load capacitor 300. In some embodiments, digital invertor 310 may be C-MOS pair 310, which for example may be a combination of p-type and n-type field-effect transistors depicted in FIG. 5B. In some embodiments, ring oscillator 350 may also comprise capacitive-based sensor 340 (located in some embodiments, after a last stage). In some embodiments, an oscillation frequency of ring oscillator circuit 350 man be found using expression (1):

$$F = \frac{1}{2N\tau} \quad (1)$$

where N may be a number of stages and $\tau$ may be a delay of each stage, and where $\tau$ can be expressed as:

$$\tau = \frac{CV_T}{I_t} \quad (2)$$

where C is a capacitance of each stage, $V_T$ is a threshold voltage of a C-MOS pair 310, and $I_t$ is an average charging current of the load capacitor C of each stage. If the capacitance of the capacitive-based sensor 340 changes, the oscillation frequency of ring oscillator circuit 350 may change as well, according to the expressions above.

Figure 4A:
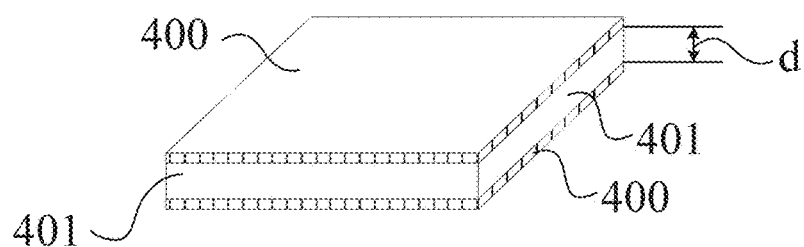
FIG. 4A may be a perspective view of a basic capacitor.
Figure 4B:
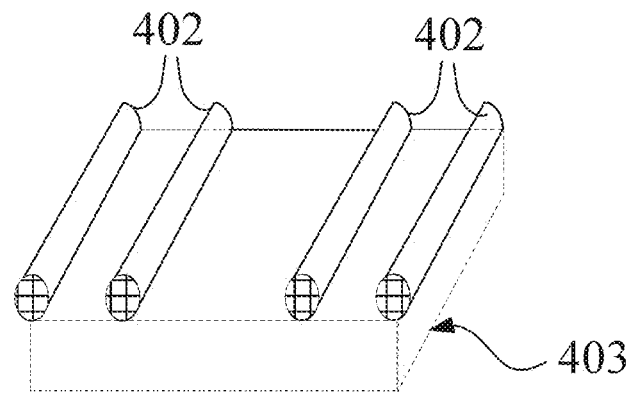
FIG. 4B may be a perspective view of a capacitor with substantially parallel regions of a conductive surface of type "A."
Figure 4C:
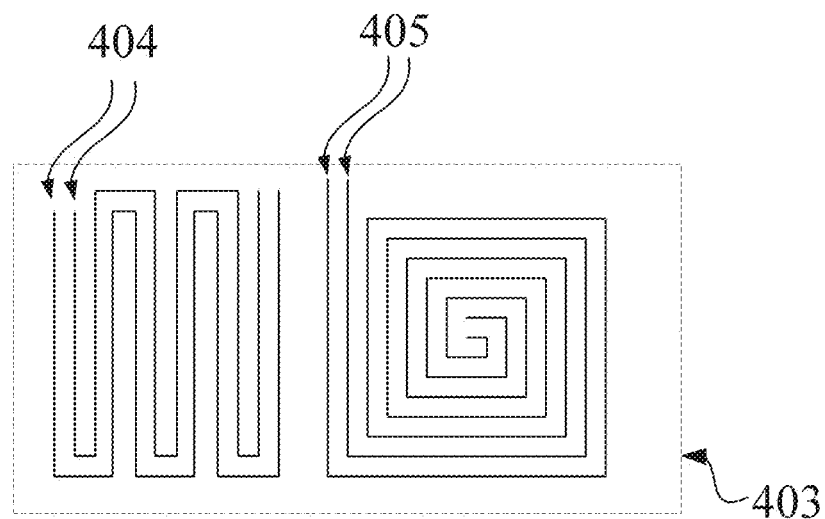
FIG. 4C may be a top view of a capacitor; with substantially parallel regions of a conductive surface of type "B"; and with substantially parallel regions of a conductive surface of type "C."
Figure 4D:
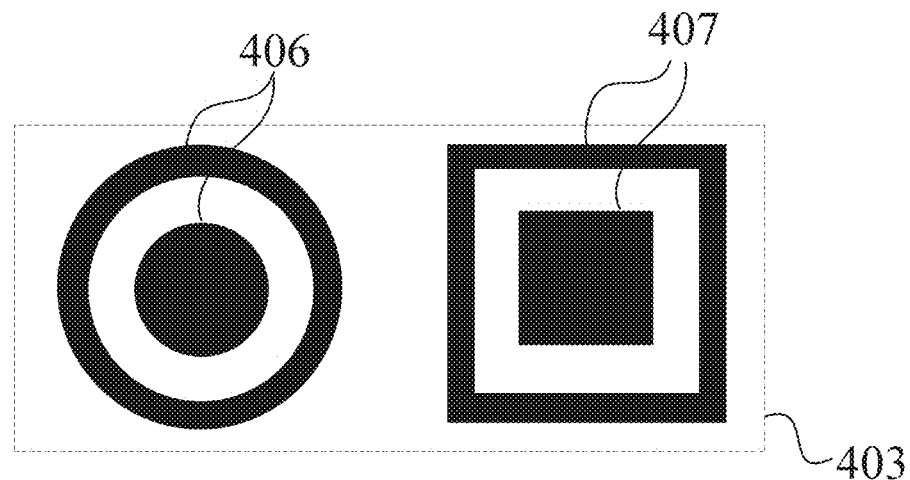
FIG. 4D may be a top view of a capacitor; with regions of a conductive surface of type "D"; and with regions of a conductive surface of type "E."
Figure 4E:
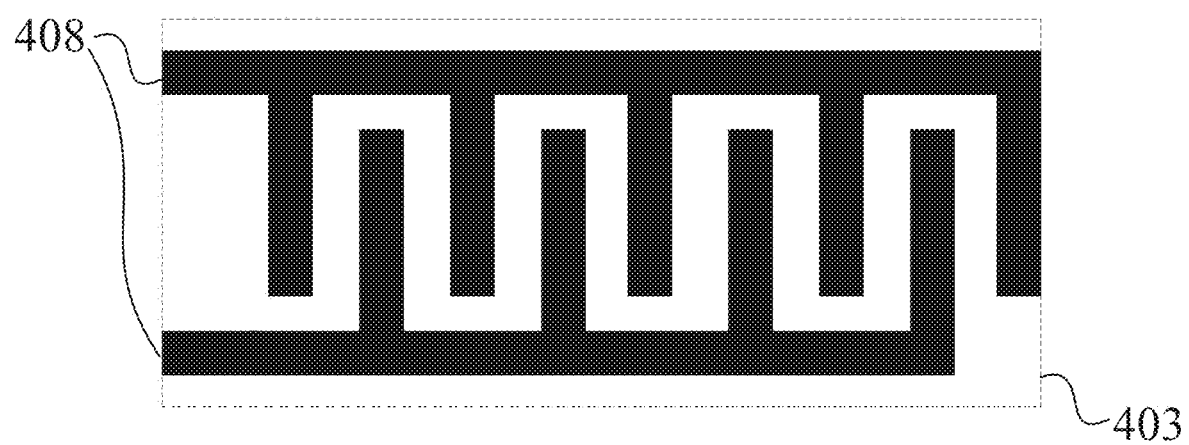
FIG. 4E may be a top view of a capacitor, with regions of a conductive surface of type "F."

FIG. 4A through and including FIG. 4E may depict various capacitors, which may be used as capacitors in at least some of the circuit diagrams shown in the figures. FIG. 4A through and including FIG. 4E may depict various capacitors, which may be used as components in capacitive-based sensors 202.

FIG. 4A may be a perspective view of a basic capacitor. In some embodiments, this basic capacitor may comprise two substantially parallel plates 400 that may be separated by dielectric material 401. In some embodiments, such plates 400 may be separated from each by a distance of d. In some embodiments, plates 400 may be constructed from substantially conductive materials. In some embodiments, the capacitance of this basic capacitor may be found from the following expression (3):

$$C = \frac{\varepsilon_0 \varepsilon_r A}{d} \quad (3)$$

where A is an area of each of the conductive plates 400, d is a width of the dielectric material 401 between the conductive plates 400, $\varepsilon_r$ is the relative permittivity of the dielectric material 401, and $\varepsilon_0 \cong 8.85 \cdot 10^{-12}$ F/m is vacuum permittivity constant.

FIG. 4B may be a perspective view of a capacitor with substantially parallel regions of a conductive surface of type "A" 402 mounted to substrate 403. In some embodiments, substrate 403 may be a dielectric material. In some embodiments, the capacitor of FIG. 4B may comprise two pairs of substantially parallel regions of conductive surface of type "A" 402 mounted to substrate 403. In some embodiments, conductive surface of type "A" 402 may be constructed from electrically conductive materials of construction.

FIG. 4C may be a top view of a capacitor; with substantially parallel regions of a conductive surface of type "B" 404; and with substantially parallel regions of a conductive surface of type "C" 405. In some embodiments, conductive surface of type "B" 404 and conductive surface of type "C" 405 may be mounted to a same substrate 403. In some embodiments, substrate 403 may be a dielectric material. In some embodiments, conductive surface of type "B" 404 and conductive surface of type "C" 405 may be constructed from electrically conductive materials of construction. In some embodiments, conductive surface of type "C" 405 may be arranged in a pair of substantially parallel rows in a spiral fashion with substrate 403 disposed between or/and under such substantially parallel rows; for example, and without limiting the scope of the present invention, arranged as conductive wires in concentric circles on a dielectric substrate.

FIG. 4D may be a top view of a capacitor; with regions of a conductive surface of type "D" 406; and with regions of a conductive surface of type "E" 407. In some embodiments, conductive surface of type "D" 406 and conductive surface of type "E" 407 may be mounted to a same substrate 403. In some embodiments, substrate 403 may be a dielectric material. In some embodiments, conductive surface of type "D" 406 and conductive surface of type "E" 407 may be constructed from electrically conductive materials of construction. In some embodiments, conductive surface of type "D" 406 may be arranged in concentric circles (in a bull's eye fashion) with substrate 403 disposed between such concentric circles. In some embodiments, conductive surface of type "E" 407 may be arranged in concentric squares with substrate 403 disposed between or/and under such concentric squares.

FIG. 4E may be a top view of a capacitor, with regions of a conductive surface of type "F" 408. In some embodiments, the capacitor of FIG. 4E may have regions of conductive surface of type "F" 408 mounted to substrate 403. In some embodiments, substrate 403 may be a dielectric material. In some embodiments, conductive surface of type "F" 408 may be constructed from electrically conductive materials of construction.

FIG. 4B, FIG. 4C, FIG. 4D, and FIG. 4E may depict examples of various capacitors that may be used in some capacitive-based sensors 202 embodiments. Such capacitors may form at least part of capacitive-based sensors 202 that may be the at least one sensor of a given monitoring-sensor-tag 120. In some embodiments, capacitive-based sensors 202 may comprise one or more of: plates 400, conductive surface type "A" 402, conductive surface type "B" 404, conductive surface type "C" 405, conductive surface type "D" 406, conductive surface type "E" 407, and/or conductive surface type "F" 408; placed (e.g., mounted, installed, immersed, implanted, and/or the like) on a dielectric substrate 403 (and/or onto dielectric material 401 in some embodiments).

Continuing discussing FIG. 4B, FIG. 4C, FIG. 4D, and FIG. 4E, in some embodiments, the given material-of-interest that may be the object of analysis, monitoring, and/or tracking may be the dielectric substrate 403. Thus in use, material-of-interest, acting as dielectric substrate 403, may substantially fill in and/or substantially cover one or more of: plates 400, conductive surface type "A" 402, conductive surface type "B" 404, conductive surface type "C" 405, conductive surface type "D" 406, conductive surface type "E" 407, and/or conductive surface type "F" 408. Use of such capacitors in capacitive-based sensor 202 may permit monitoring and/or detection of structural defects in the material-of-interest (such as, but not limited to, cracks or changes in structure of material-of-interest). Because changes in structure of the material-of-interest acting as the dielectric substrate 403 may change the relative permittivity $\varepsilon_r$, which, in turn, may change the capacitance of capacitive-based sensor 202 in communication with capacitance measurement circuit 205.

For example, and without limiting the scope of the present invention, a change in the relative permittivity $\varepsilon_r$ of material-of-interest due to a structural change may be detected (registered) by capacitive-based sensor 340 in ring oscillator 350, which may be one possible implementation of capacitance measurement circuit 205 with capacitive-based sensor 202. That is, this change may register as a change in the frequency of ring oscillator 350. Such frequency changes may be measured, monitored, tracked, and/or analyzed to provide strong indications of structural defects and/or of structural changes in the given material-of-interest. For example, and without limiting the scope of the present invention, the relative permittivity of concrete is approximately 4.5 times higher than the relative permittivity of air. Accordingly, any appearance of a crack in the concrete, that may permit air ingress, may then alter the capacitance of the implanted monitoring-sensor-tag 120 into the given material-of-interest, which in this example may be a section of concrete. A same concept may be applied to liquid ingress into structural defects and/or structural changes of other materials-of-interest, such as, but not limited to, dental-filling 1001.

Capacitive-based, resistance-based, inductance-based or other types of sensors as part of a given monitoring-sensor-tag 120, that may be implanted to (i.e., attached to) the given material-of-interest, may also be used to measure temperature of the analyzed given material-of-interest, according to various embodiments of the present invention.

Figure 5A:
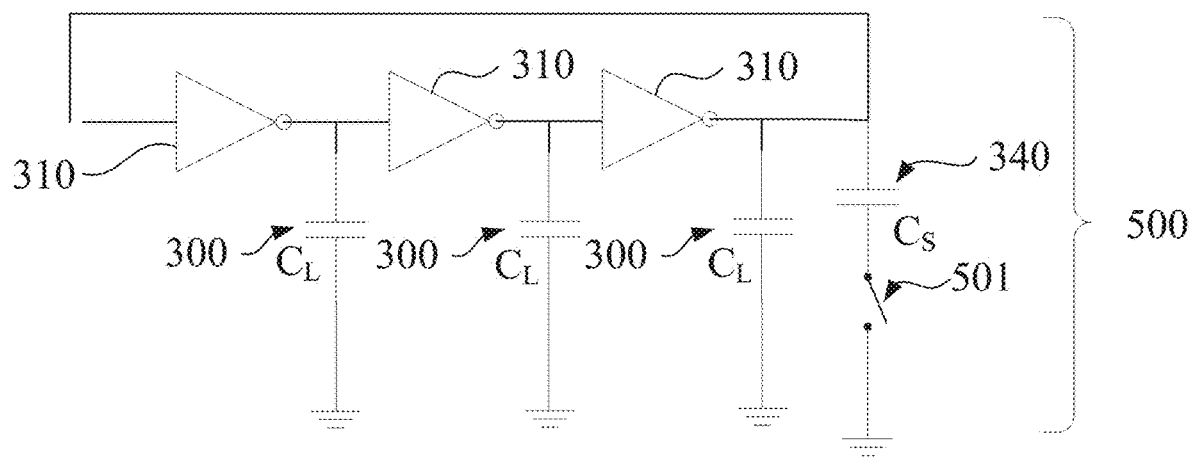
FIG. 5A may be a circuit diagram of a ring oscillator implementing a capacitance measurement circuit.

FIG. 5A may be a circuit diagram of a ring oscillator 500 implementing a capacitance measurement circuit 205 with capacitive-based sensor 202. In some embodiments, capacitance measurement circuit 205 with capacitive-based sensor 202 may be carried out via ring oscillator 500. In some embodiments, ring oscillator circuit 500 may measure values of capacitive-based sensor 202, transferring such values of capacitive-based sensor 202 into frequency of oscillations of said ring oscillator 500. In some embodiments, ring oscillator 500 may be used to monitor, track, and/or analyze temperature changes to the given material-of-interest where ring oscillator 500 may be implanted to (i.e., attached to).

Continuing discussing FIG. 5A, in some embodiments, ring oscillator 500 may comprises an odd number of stages. In some embodiments, each such stage may comprise a respective digital invertor 310 and load capacitor 300. In some embodiments, digital invertor 310 may be C-MOS pair 310. In some embodiments, ring oscillator 500 may also comprise capacitive-based sensor 340 (located in some embodiments, after a last stage) and a switch 501 in series with capacitive-based sensor 340.

Figure 5B:
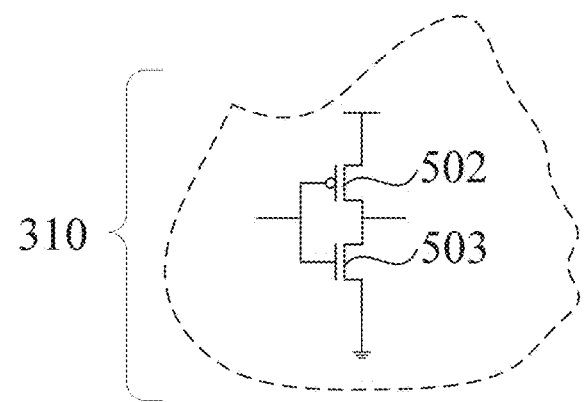
FIG. 5B may be a circuit diagram of a C-MOS pair digital invertor.

FIG. 5B may be a circuit diagram of C-MOS pair 310 (digital invertor 310). In some embodiments, C-MOS pair 310 (digital invertor 310) may comprise P-MOS transistor 502 and N-MOS transistor 503.

Continuing discussing FIG. 5A and FIG. 5B, in some embodiments, ring oscillator 500 may comprise switch 501. In some embodiments, switch 501 may connect or disconnect capacitive-based sensor 340 from ring oscillator 500. Accordingly, the oscillation frequency of ring oscillator 500 may depend on an ambient temperature of the surrounding material-of-interest. Current I flowing through P-MOS transistor 502 and N-MOS transistor 503, forming digital invertor 310, may affect a delay of each stage, depending on the ambient temperature of the surrounding material-of-interest. In this manner, the ring oscillator 500, with the switchable capacitive-based sensor 340, may function as a temperature sensor for the monitored given material-of-interest. With switch 501 in a disconnected state, capacitive-based sensor 340 may not influence the oscillation frequency of ring oscillator 500; therefore the oscillation frequency of ring oscillator 500 may correlate with the ambient temperature of the surrounding material-of-interest.

It should be appreciated by those of ordinary skill in the relevant art that resistance-based sensors 203 and resistance measurement circuits 206 may be used to implement configurations depicted in FIG. 2B, FIG. 2D, FIG. 2F, and/or FIG. 2G to quantify, measure, track, monitor, and/or analyze various states and changes in states of materials-of-interest with one or more monitoring-sensor-tag 120 processing the one or more reading originating from such resistance-based sensors 203.

Figure 6:
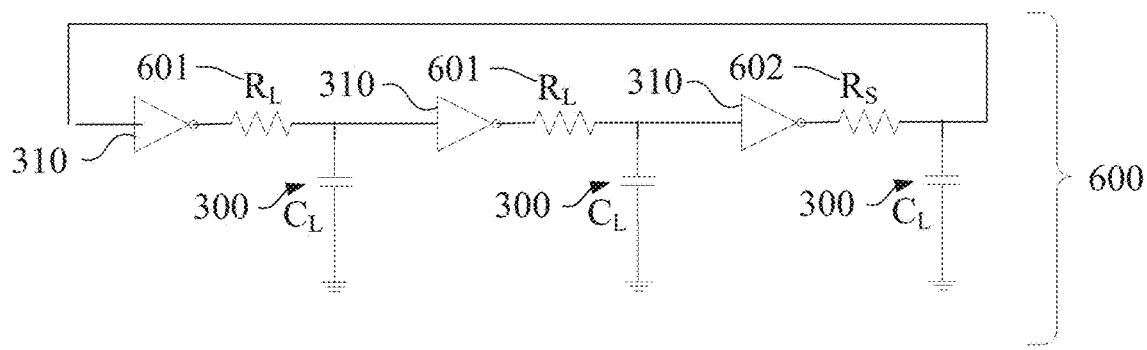
FIG. 6 may be a circuit diagram of a ring oscillator implementing a resistance measurement circuit.

FIG. 6 may be a circuit diagram of a ring oscillator 600 implementing a resistance measurement circuit 206 with resistance-based sensor 203. In some embodiments, ring oscillator 600 may be used to sense, measure, monitor, track, and/or analyze strains, force, torsion, and/or pressure in portions of material-of-interest with monitoring-sensor-tag 120; wherein the at least one sensor (of monitoring-sensor-tag 120) may comprise ring oscillator 600. In the embodiment implemented and depicted in FIG. 6, ring oscillator 600 (e.g., implemented as resistance measurement circuit 206 with resistance-based sensor 203) may comprise resistance-based sensor 203, an example of a strain-influenced resistor 602; wherein monitoring-sensor-tag 120 may comprise ring oscillator 600 and the at least one sensor (of monitoring-sensor-tag 120) may comprise a strain-influenced resistor 602. Thus, ring oscillator 600 may be used to sense, measure, monitor, track, and/or analyze deformations, structural defects, and/or structural changes in material-of-interest.

Continuing discussing FIG. 6, in some embodiments, ring oscillator circuit 600 may comprise an odd number of stages. In some embodiments, each such stage may comprise digital invertor 310 and an "RC pair." In some embodiments, each such RC pair (except a final stage) may comprise a load capacitor 300 and a load resistor 601. In some embodiments, a final stage RC pair may comprise a load capacitor 300 and a strain-influenced resistor 602. In some embodiments, an oscillation frequency F of ring oscillator 600 may be determined from the expression (4):

$$F = \frac{1}{2N\tau} = \frac{1}{2N \cdot f(RC, V_t)} \quad (4)$$

where N may be a number of stages, τ may be a delay of each stage, f (RC,$V_t$) may be a function of the RC value of each stage, and of the threshold voltage of CMOS invertor (digital invertor 310) $V_t$. In some embodiments, strain-influenced resistor 602 (denoted as $R_S$ in FIG. 6) may be a strain-influenced resistor. In some embodiments, ring oscillator 600 may be a component of the least one sensor of monitoring-sensor-tag 120 that may be attached to (i.e., implanted, immersed, and/or the like) to the given material-of-interest. And changes (e.g., strains, forces, torsion, pressure, structural changes, deformations, and/or the like) in the given material-of-interest may then translate into changes in the oscillation frequency F that ring oscillator 600 may be sensing, measuring, monitoring, tracking, and/or analyzing.

Figure 7A:
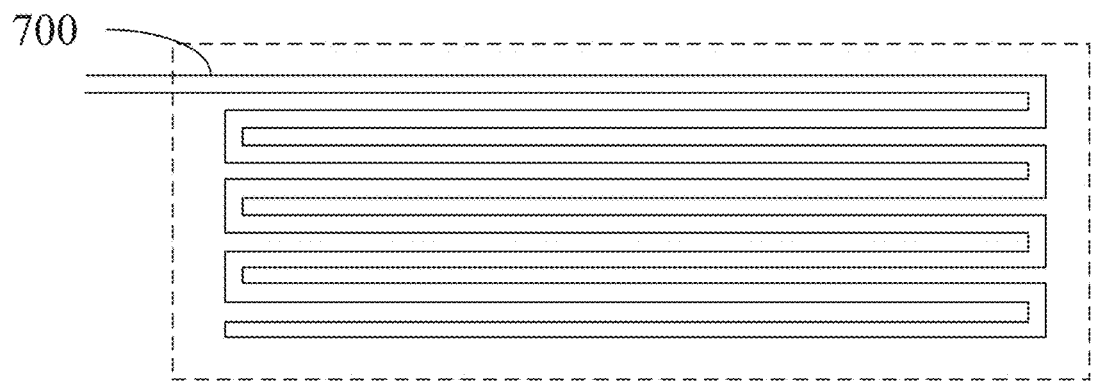
FIG. 7A may be a top view of an example of a stress sensor used in some embodiments of the present invention.

FIG. 7A may be a top view of an example of a stress sensor used in some embodiments of the present invention. In some embodiments, such a stress sensor may be the at least one sensor of monitoring-sensor-tag 120. In some embodiments, the stress sensor depicted in FIG. 7A may be strain-influenced resistor 700. In some embodiments, strain-influenced resistor 700 may be a part of an implementation of ring oscillator 600, strain-influenced resistor 602; thus strain-influenced resistor 700 may be a type of resistance-based sensor 203 used to sense, measure, monitor, track, and/or analyze changes (e.g., strains, forces, torsion, pressure, structural changes, deformations, and/or the like) in the given material-of-interest by such changes to the material-of-interest may translate into changes in the oscillation frequency F that ring oscillator 600 may be sensing, measuring, monitoring, tracking, and/or analyzing.

Figure 7B:
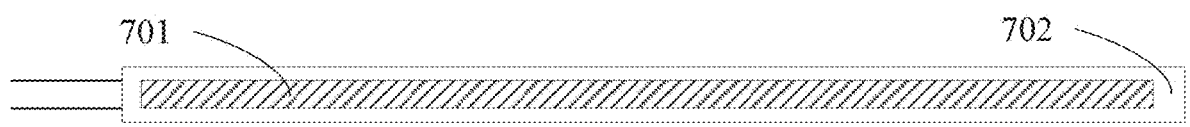
FIG. 7B may be a top view of an example of a stress sensor used in some embodiments of the present invention.

FIG. 7B may be a top view of an example of a stress sensor used in some embodiments of the present invention. In some embodiments, such a stress sensor may be the at least one sensor of monitoring-sensor-tag 120. In some embodiments, this stress sensor depicted in FIG. 7B may be an example of a resistance-based sensor 203. In some embodiments, this stress sensor depicted in FIG. 7B may comprise thin-film-coating 701 and substrate 702. In some embodiments, thin-film-coating 701 may be an electrically resistive compound. When monitoring-sensor-tag 120 with the stress sensor shown in FIG. 7B may be attached to (e.g., implanted, immersed, touching, and/or the like) the given material-of-interest, changes (e.g., strains, forces, torsion, pressure, structural changes, deformations, and/or the like) in the given material-of-interest may translate into changes in the resistance of thin-film-coating 701 which may be registered, sensed, measured, monitored, tracked, and/or analyzed by resistance-based sensor 203. In some embodiments, substrate 702 may be a flexible non-conductive material upon which the thin-film-coating 701 may be attached or set upon. Physical forces acting on and causing various changes such as, but not limited to, possible fracturing, cracking, bending, twisting, excessive pressure, abnormal temperature, and/or the like, of substrate 702 may also change monitorable conductive qualities of thin-film coating 701.

Figure 7C:
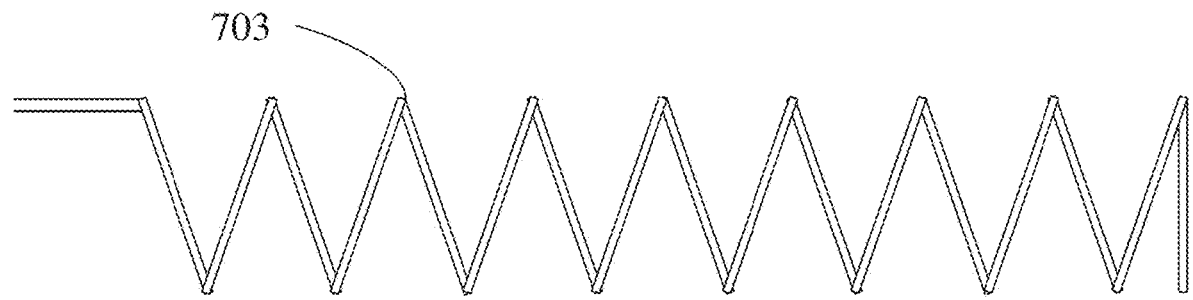
FIG. 7C may be a top view of an example of a stress sensor used in some embodiments of the present invention.

FIG. 7C may be a top view of an example of a stress sensor used in some embodiments of the present invention. In some embodiments, such a stress sensor may be the at least one sensor of monitoring-sensor-tag 120. In some embodiments, this stress sensor depicted in FIG. 7B may be an example of a resistance-based sensor 203. In some embodiments, the stress sensor depicted in FIG. 7C may be spiral-formed-electric-conductor 703. In some embodiments, spiral-formed-electric-conductor 703 may be a type of resistance-based sensor 203. In some embodiments, spiral-formed-electric-conductor 703 may be substantially spiral shaped. When monitoring-sensor-tag 120 with the stress sensor (e.g., spiral-formed-electric-conductor 703) shown in FIG. 7C may be attached to (e.g., implanted, immersed, touching, and/or the like) the given material-of-interest, changes (e.g., strains, forces, torsion, pressure, structural changes, deformations, and/or the like) in the given material-of-interest may translate into changes in the resistance of spiral-formed-electric-conductor 703 which may be registered, sensed, measured, monitored, tracked, and/or analyzed by resistance-based sensor 203.

Figure 8:
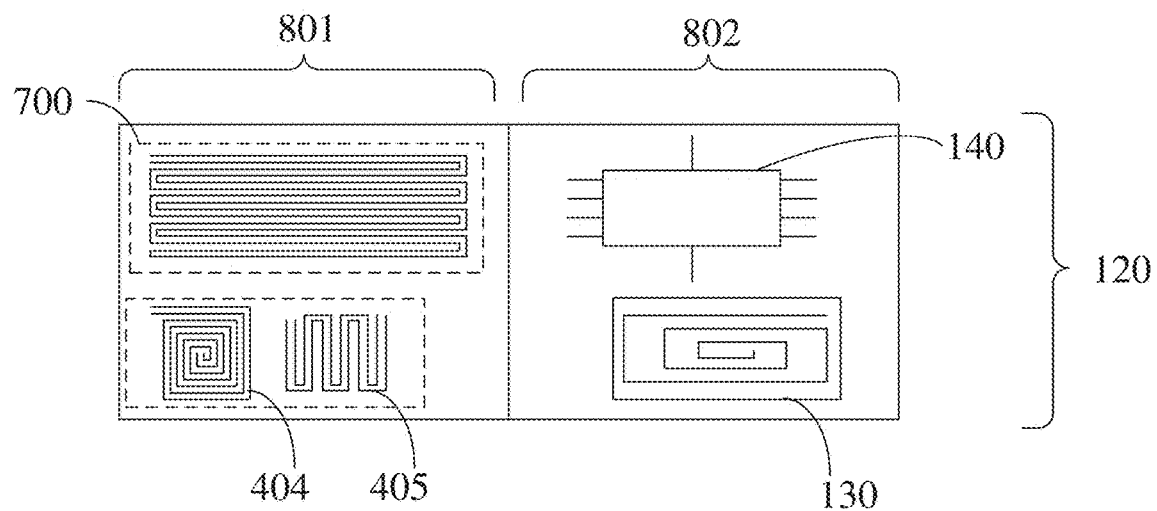
FIG. 8 may be a diagrammatical top view of a monitoring-sensor-tag's structure and components, as used in some embodiments of the present invention.

FIG. 8 may be a diagrammatical top view of a monitoring-sensor-tag's 120 structure and components, as used in some embodiments of the present invention. In some embodiments, a given monitoring-sensor-tag 120 may be divided functionally and/or structurally into sensor-portion 801 and processing-portion 802. While sensor-portion 801 and processing-portion 802 may be shown as distinct portions in FIG. 8, in some embodiments, sensor-portion 801 and processing-portion 802 may overlap. In some embodiments, sensor-portion 801 may comprise the at least one sensor. In some embodiments, processing-portion 802 may comprise at least one antenna 130 and at least one electric circuit 140; wherein at least one electric circuit 140 and at least one antenna 130 may be in communication with each other. In some embodiments, at least one electric circuit 140 may be in communication with sensor-portion 801.

In some embodiments, at least one electric circuit 140 may be in communication with sensor-portion with the at least one sensor. In some embodiments, at least one electric circuit 140 may comprise processing circuitry 204. In some embodiments, at least one electric circuit 140 may comprise processing circuitry 204 and may further comprise one or more of capacitive measurement circuit 205, resistance measurement circuit 206, and/or inductance measurement circuit 209.

Continuing discussing FIG. 8, as shown in FIG. 8 the at least one sensor of sensor-portion 801 may comprise three distinct sensors: conductive surface type "B" 404, conductive surface type "C" 405, and strain-influenced resistor 700 (which may be a part [component] of an implementation of ring oscillator 600). See e.g., FIG. 4C, FIG. 6, and FIG. 7A; as well as their respective discussions above. Continuing discussing FIG. 8, in some embodiments, strain-influenced resistor 700 may be strain influenced sensor. In some embodiments, conductive surface type "B" 404 and conductive surface type "C" 405 may function as compound integrity sensors that may allow for structural integrity analysis of the given material-of-interest where the given sensor may be implanted. In some embodiments, these three distinct sensors may be in communication with at least one electric circuit 140. In some embodiments, at least one electric circuit 140 may provide control logic for controlling these three distinct sensors. In some embodiments, at least one electric circuit 140 may provide control logic for controlling these three distinct sensors by taking one or more readings from these three distinct sensors and instructing at least one antenna 130 in the transmission of such one or more readings for pickup by one or more readers 100.

Continuing discussing FIG. 8, while three distinct sensors may be shown in FIG. 8, it is expressly contemplated the at least one sensor of sensor-portion 801 may comprise one or more of the sensors discussed and shown in the accompanying figures.

Continuing discussing FIG. 8, in some embodiments, sensor-portion 801 and processing-portion 802 may be manufactured as single and distinct articles of manufacture, that once assembled may be in communication with each other. In some embodiments, sensor-portion 801 and processing-portion 802 may be manufactured by printing as single and distinct articles of manufacture, that once assembled may be in communication with each other.

Continuing discussing FIG. 8, in some embodiments, sensor-portion 801 and processing-portion 802 may be manufactured as a single integrated article of manufacture. In some embodiments, sensor-portion 801 and processing-portion 802 may be printed as a single integrated article of manufacture.

Figure 9:
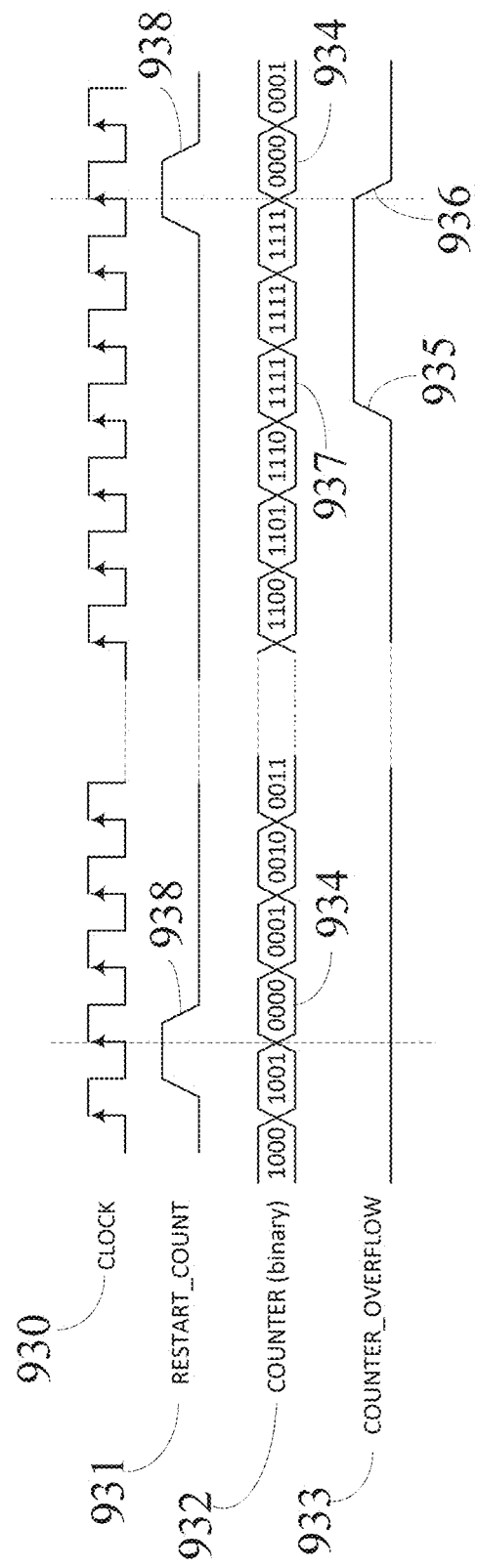
FIG. 9 may be a diagram of control and status signals, in accordance with some embodiments of the present invention.

As noted above, in some embodiments, upon at least one antenna 130 receiving electromagnetic (EM) radiation of a predetermined characteristic as an input from at least one antenna 110 of reader 100, this input may cause at least one electric circuit 140 to take one or more readings from the at least one sensor and to then transmit such one or more readings using at least one antenna 130. FIG. 9 may be a diagram of control and status signals, in accordance with some embodiments of the present invention. In some embodiments, electric circuit 140 (or processing circuitry 204 in some embodiments) may be executing the functions shown in FIG. 9.

Continuing discussing FIG. 9, in some embodiments, electric circuit 140 and/or processing circuitry 204 may be event-driven (or input-driven) and digital CLOCK 930 may implement events which condition time and orchestrate the functionality of electric circuit 140 and/or processing circuitry 204. In some embodiments, CLOCK 930 may be digital clock. In some embodiments, CLOCK 930 may be a binary clock. In some embodiments, RESTART_COUNT signal 931 may change to binary value 1 for at least one CLOCK 930 cycle by electric circuit 140 (or processing circuitry 204 in some embodiments) receiving respective instruction(s) from reader 100, as indicated at Pulse of RESTART_COUNT signal 938. That is, Pulse of RESTART_COUNT signal 938 may be a response to at least one antenna 130 receiving electromagnetic (EM) radiation of a predetermined characteristic as an input from at least one antenna 110 of reader 100, where this input may then cause at least one electric circuit 140 to take the one or more readings from the at least one sensor. In some embodiments, a RESTART_COUNT signal 931 may trigger resetting of a COUNTER 932. In some embodiments, COUNTER 932 may store values from the at least one sensor; such as, the one or more readings. In some embodiments, COUNTER 932 may store values of a number of ring oscillator (e.g., ring oscillator 350 or ring oscillator 600) oscillations. In some embodiments, COUNTER 932 may be a digital register. In some embodiments, COUNTER 932 may be a binary counter. In some embodiments, COUNTER 932 may represent a state of a digital ripple counter, input of which may be connected to the last stage of ring oscillator (e.g., ring oscillator 350 or ring oscillator 600). In some embodiments, COUNTER 932 may have its value set to a zero value, as indicated at zero value 934; which may be triggered by Pulse of RESTART_COUNT signal 938 that may in turn trigger RESTART_COUNT signal 931, which may in turn result in zero value 934 for COUNTER 932. In some embodiments, if COUNTER 932 may reach a maximal value 937, then a COUNTER_OVERFLOW signal 933 may be triggered; wherein this COUNTER_OVERFLOW signal 933 changes its binary value from 0 to 1, as indicated at "0-to-1 transition of Pulse of Counter Overflow signal 935." In that case, COUNTER_OVERFLOW signal 933 may stay at binary value 1 until a next change of RESTART_COUNT signal 931 from binary value 0 to 1 for at least one CLOCK 930 cycle, as indicated at "1-to-0 transition of Pulse of Counter Overflow signal 936."

Optionally, in some embodiments, a value Y, stored in a divider register, may advance COUNTER 932 to the next value every Y CLOCK 930 cycles. That may prevent COUNTER 932 reaching its maximal value 937 too soon.

FIG. 10A may be a diagram of a patient 1328 tooth 1000 with one or more monitoring-sensor-tags 120 placed in a dental-filling 1001 as a material-of-interest, in accordance with some embodiments of the present invention. FIG. 10A may depict a schematic diagram of tooth 1000. Tooth 1000 may comprise one or more dental-fillings 1001. FIG. 10A may also depict gum 1002, so as to schematically indicate a gum 1002 line in relation to tooth 1000 (for demonstration purposes).

In FIG. 10A, dental-filling(s) 1001 may be the material-of-interest. For example, and without limiting the scope of the present invention, dental-fillings 1001 may be selected from filling materials used in the practice of dentistry, such as, but not limited to "fill" cavities and/or to "seal" undesirable surface geometry on teeth 1000. For example, and without limiting the scope of the present invention, dental-fillings 1001 may be selected from one or more of: composite resins; glass ionomer cements; resin-ionomer cements; porcelain (and/or ceramics); porcelain fused to a metal; and/or the like.

Continuing discussing FIG. 10A, in some embodiments, one or more monitoring-sensor-tags 120 may be attached to, located on, located in, immersed, implanted, and/or the like in the one or more dental-fillings 1001 of tooth 1000. Note, characteristics (e.g., one or more readings) of such one or more monitoring-sensor-tags 120 placement with respect to one or more dental-fillings 1001 may change over time as the given one or more dental-fillings 1001 may cure and/or harden. In some embodiments, placement of one or more monitoring-sensor-tags 120 with respect to one or more dental-fillings 1001 may be random. In some embodiments, placement of one or more monitoring-sensor-tags 120 with respect to one or more dental-fillings 1001 may be substantially uniform. In some embodiments, placement of one or more monitoring-sensor-tags 120 with respect to one or more dental-fillings 1001 may be approximately uniform. In some embodiments, placement of one given monitoring-sensor-tags 120 (e.g., a first-sensor-tag 1020) with respect to another different monitoring-sensor-tags 120 (e.g., a second-sensor-tag 1021) may be specified (e.g., at a fixed distance such as at an initial predetermined spacing 1025) within the given material-of-interest, such as dental-filling 1001 (see e.g., FIG. 10D discussed below). Thus, placement of such one or more monitoring-sensor-tag 120 with respect to one or more dental-fillings 1001 may be used to obtain various information about one or more dental-fillings 1001 and may do so in a non-invasive manner and in a manner that does not require use of ionizing imaging radiation.

FIG. 10B may be a diagram of a patient 1328 tooth 1000 with one or more monitoring-sensor-tags 120 placed in: a root-canal-cavity 1003, in a root-canal-post 1004, and/or in a dental-crown 1005; in accordance with some embodiments of the present invention. In FIG. 10B the material-of-interest may be selected from one or more of: root-canal-cavity 1003, root-canal-post 1004, dental-crown 1005, and/or the like. In some embodiments, one or more monitoring-sensor-tags 120 may be attached to, located on, located in, immersed, implanted, and/or the like in the root-canal-cavity 1003, the root-canal-post 1004, and/or the dental-crown 1005. In some embodiments, one or more monitoring-sensor-tags 120 may further comprise a standalone-strain-sensor 1006. In some embodiments, standalone-strain-sensor 1006 may be an external sensor structure attached to a given monitoring-sensor-tag 120. In some embodiments, standalone-strain-sensor 1006 may be a strain-influenced resistor 700 or a spiral-formed-electric-conductor 703. In some embodiments, standalone-strain-sensor 1006 may be capacitive-based sensor 202 or a resistance-based sensor 203. In some embodiments, standalone-strain-sensor 1006 may be in communication with one or more of: electric circuit 140, processing circuitry 204, capacitance measurement circuit 205, and/or resistance measurement circuit 206.

FIG. 10C may be a diagram of a patient 1328 tooth dental-implant 1007 with one or more monitoring-sensor-tags 120, in accordance with some embodiments of the present invention. In some embodiments, dental-implant 1007, which may be an artificial tooth, may comprise implant-post 1008; wherein implant-post 1008 may be anchored to patient 1328. In FIG. 10C, the material-of-interest may be dental-implant 1007 and/or implant-post 1008. In some embodiments, one or more monitoring-sensor-tags 120 may be attached to, located on, located in, immersed, implanted, and/or the like in the dental-implant 1007 and/or in the implant-post 1008. In some embodiments, one or more monitoring-sensor-tags 120 may further comprise a standalone-strain-sensor 1006. In some embodiments, standalone-strain-sensor 1006 may be an external sensor structure attached to a given monitoring-sensor-tag 120. In some embodiments, standalone-strain-sensor 1006 may be a strain-influenced resistor 700 or a spiral-formed-electric-conductor 703. In some embodiments, standalone-strain-sensor 1006 may be capacitive-based sensor 202 or a resistance-based sensor 203. In some embodiments, standalone-strain-sensor 1006 may be in communication with one or more of: electric circuit 140, processing circuitry 204, capacitance measurement circuit 205, and/or resistance measurement circuit 206.

FIG. 10D may be a diagram of a first-sensor-tag 1020 and a second-sensor-tag 1021 arranged in a material-of-interest with an initial predetermined spacing 1025 between the first-sensor-tag 1020 and the second-sensor-tag 1021 in the material-of-interest 1028. Note, in some embodiments, material-of-interest 1028 shown in FIG. 10D may be any material-of-interest noted herein. For example, and without limiting the scope of the present invention, in some embodiments, material-of-interest 1028 may be selected from one or more of: dental-filling 1001, root-canal-cavity 1003, root-canal-post 1004, dental-crown 1005, dental-implant 1007, implant-post 1008, an article implantable within a body of an organism (e.g., where the organism is patient 1328), the article attachable to the body of the organism, specific tissue of the organism, and/or a construction member.

Continuing discussing FIG. 10D, in some embodiments, each of first-sensor-tag 1020 and/or of second-sensor-tag 1021 may comprise a lattice-of-sensors 1023 (e.g., 202, 203, 406, 407, 700, 703, and/or 1006); wherein each respective lattice-of-sensors 1023 may be separated from each other lattice-of-sensors 1023 by initial predetermined spacing 1025. And in some embodiments, sensors within a given lattice (e.g., lattice-of-sensors 1023) may be separated by sensor-spacing 1026. Because initial predetermined spacing 1025 may be known, then positional locations of the other one or more monitoring-sensor-tags 120 may be determined. Likewise, because initial predetermined spacing 1026 may be known, then positional locations of the sensors within a given lattice (e.g., lattice-of-sensors 1023) may be determined. In some embodiments, each lattice-of-sensors 1023 (e.g., of each first-sensor-tag 1020 and/or of second-sensor-tag 1021) may comprise a plurality of sensors (e.g., 202, 203, 406, 407, 700, 703, and/or 1006); wherein this plurality of sensors may be attached to the given sensor-tag, such as first-sensor-tag 1020 and/or second-sensor-tag 1021. In some embodiments, each such sensor-tag (e.g., first-sensor-tag 1020 and/or second-sensor-tag 1021) may comprise their own electric circuit 140 (or processing circuitry 204). In some embodiments, the plurality of sensors (e.g., 202, 203, 406, 407, 700, 703, and/or 1006) of each lattice-of-sensors 1023 may be in communication with such an electric circuit 140 (or processing circuitry 204) but located outside of such an electric circuit 140. See e.g., FIG. 10D. In some embodiments, first-sensor-tag 1020 and second-sensor-tag 1021 may be types of monitoring-sensor-tags 120 with initial predetermined spacing 1025 known between them. Also in some embodiments, there may be a plurality of first-sensor-tag 1020 and a plurality of second-sensor-tag 1021.

In some embodiments, a given lattice-of-sensors 1023 may be arranged in a one dimensional, two dimensional, or three dimensional configuration. In some embodiments, a given lattice-of-sensors 1023 may be arranged in mesh configuration. In some embodiments, a given lattice-of-sensors 1023 may be arranged in lattice configuration.

Note, initial predetermined spacing 1025 may change over time. For example, as the given material-of-interest 1028 may cure and/or harden, initial predetermined spacing 1025 may alter. In some embodiments, initial predetermined spacing 1025 may be calibrated before and after such curing and/or hardening of material-of-interest 1028.

Note, FIG. 10D may also depict a known coordinate system and known origin 1325 (i.e., origin 1325 of chosen coordinate system). Origin 1325 and a chosen coordinate system may be further discussed in the FIG. 13A discussion below.

Figure 11A:
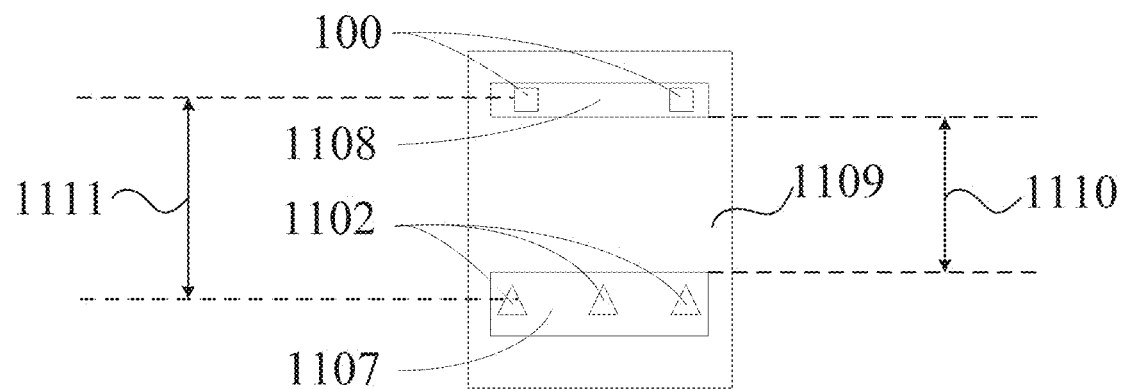
FIG. 11A may be a diagrammatical top view of a reader-and-calibration-member, in accordance with some embodiments of the present invention.

FIG. 11A may be a diagrammatical top view (or a side view in some embodiments) of a reader-and-calibration-member 1109, in accordance with some embodiments of the present invention. In some embodiments, reader-and-calibration-member 1109 may comprise one or more readers 100. In some embodiments, reader-and-calibration-member 1109 may comprise one or more reference-sensor-tags 1102. In some embodiments, reader-and-calibration-member 1109 may comprise a reader-housing-member 1108. In some embodiments, reader-and-calibration-member 1109 may comprise a reference-housing-member 1107. In some embodiments, reader-and-calibration-member 1109 may comprise one or more of: reader-housing-member 1108, reader 100, reference-housing-member 1107, and reference-sensor-tags 1102. In some embodiments, reader-and-calibration-member 1109 may house reader-housing-member 1108 and reference-housing-member 1107. In some embodiments, reader-housing-member 1108 may house one or more readers 100. In some embodiments, reference-housing-member 1107 may house one or more reference-sensor-tags 1102. In some embodiments, reader-and-calibration-member 1109 may be a structural member. In some embodiments, reader-housing-member 1108 may be a structural member. In some embodiments, reference-housing-member 1107 may be a structural member. In some embodiments, reader-and-calibration-member 1109 may be rigid to semi-rigid. In some embodiments, reader-housing-member 1108 may be rigid to semi-rigid. In some embodiments, reference-housing-member 1107 may be rigid to semi-rigid. In some embodiments reader-housing-member 1108 may be separated from reference-housing-member 1107 by a member-separation-distance 1110. In some embodiments, a given reader 100 may be separated from a given reference-sensor-tag 1102 by a reader-tag-separation-distance 1111. In some embodiments, member-separation-distance 1110 and/or reader-tag-separation-distance 1111 may be known (predetermined) and fixed distances. In some embodiments, member-separation-distance 1110 and/or reader-tag-separation-distance 1111 may be changed to a number of different known distances.

In some embodiments, a given reference-sensor-tag 1102 may be a wireless sensor tag. In some embodiments, a given reference-sensor-tag 1102 may be one or more of: a RFID (radio frequency identification) sensor tag; a NFC (near field communication) sensor tag; a backscatter sensor tag; and/or magnetic inductive activated sensor tag.

Continuing discussing FIG. 11A, in some embodiments, a given reference-sensor-tag 1102 may be structurally the same or substantially the same as a given monitoring-sensor-tag 120, except that reference-sensor-tags 1102 are not attached to the given material-of-interest. Rather, in some embodiments, reference-sensor-tags 1102 may be attached to reader-and-calibration-member 1109, reference-housing-member 1107, and/or fixed with respect to a given set of at least one antennas 110 of readers 100. Thus, for the structures of reference-sensor-tags 1102, refer back to disclosed and discussed structures for monitoring-sensor-tags 120. That is, in some embodiments, each reference-sensor-tag 1102 may comprise at least one second-electric-circuit (which may be structurally the same or substantially the same to electric circuit 140 or processing circuitry 204). In some embodiments, each reference-sensor-tag 1102 may comprise at least one second-sensor (which may be structurally the same or substantially the same to various sensors discussed and disclosed herein, such as, but not limited to capacitive-based sensor 202 and/or resistance-based sensor 203). In some embodiments, each reference-sensor-tag 1102 may comprise at least one fourth-antenna (which may be structurally the same or substantially the same to at least one antenna 130). In some embodiments, the at least one fourth-antenna may be in communication with the at least one second-electric-circuit. In some embodiments, the at least one second-electric-circuit may be in communication with the at least one second-sensor. In some embodiments, when at least one fourth-antenna may receive electromagnetic (EM) signaling (e.g., radio waves from at least one antenna 110 of a given reader 100), then the at least one second-electric-circuit may take (or cause to be taken) one or more "calibration-readings" from the at least one second-sensor and then the at least one second-electric-circuit may cause transmission of such one or more calibration-readings using the at least one fourth-antenna, back to the at least one antenna 110 of that given reader 100.

Note, in terms of terminology nomenclature, when the term "fourth-antenna" may be used (which may be an antenna of a reference-sensor-tags 1102), then antenna 130 may be a "first-antenna," and antenna 110 may be a "second-antenna," and a "third-antenna" may be an antenna of position-reference-tag 1203 to be discussed below in a FIG. 12 discussion below.

Continuing discussing FIG. 11A, in some embodiments, each reader 100 (of reader-and-calibration-member 1109) may comprise at least one antenna 110. In some embodiments, each reference-sensor-tag 1102 may be fixed to each at least one antenna 110 of reader 100. In some embodiments, each reference-sensor-tag 1102 may be fixed to each at least one antenna 110 of reader 100 at predetermined distance(s). In some embodiments, a minimum of such predetermined distance may be substantially reader-tag-separation-distance 1111 or approximated by reader-tag-separation-distance 1111. In some embodiments, each reference-sensor-tag 1102 may comprise the at least one fourth-antenna. In some embodiments, each at least one fourth-antenna may be fixed with respect to each at least one antenna 110 of each reader of each reader-and-calibration-member 1109.

Figure 11B:
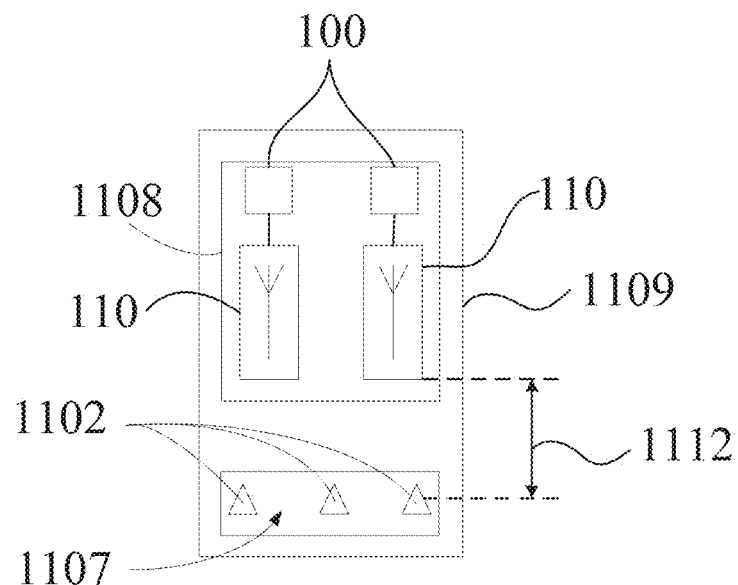
FIG. 11B may be a diagrammatical top view of a reader-and-calibration-member, in accordance with some embodiments of the present invention.

FIG. 11B may be a diagrammatical top view of a reader-and-calibration-member 1109, in accordance with some embodiments of the present invention. Reader-and-calibration-member 1109 shown in FIG. 11B, as compared against FIG. 11A discussed above, may depict additional detail, in that in FIG. 11B the at least one antennas 110 of each reader 100 of reader-and-calibration-member 1109 may be shown. In FIG. 11B, reader-antenna-tag-separation-distance 1112 may be depicted. In some embodiments, reader-antenna-tag-separation-distance 1112 may be a predetermined and fixed distance between a given at least one antenna 110 and a given reference-sensor-tag 1102. In some embodiments, reader-antenna-tag-separation-distance 1112 may be a predetermined and fixed distance between a given at least one antenna 110 and a given at least one fourth-antenna of a given reference-sensor-tag 1102. In some embodiments, each at least one antenna 110 of each reader 100 (of reader-and-calibration-member 1109) may be fixed with respect to each reference-sensor-tags 1102. In some embodiments, reader-antenna-tag-separation-distance 1112 may be changed to a number of different known distances.

Figure 11C:
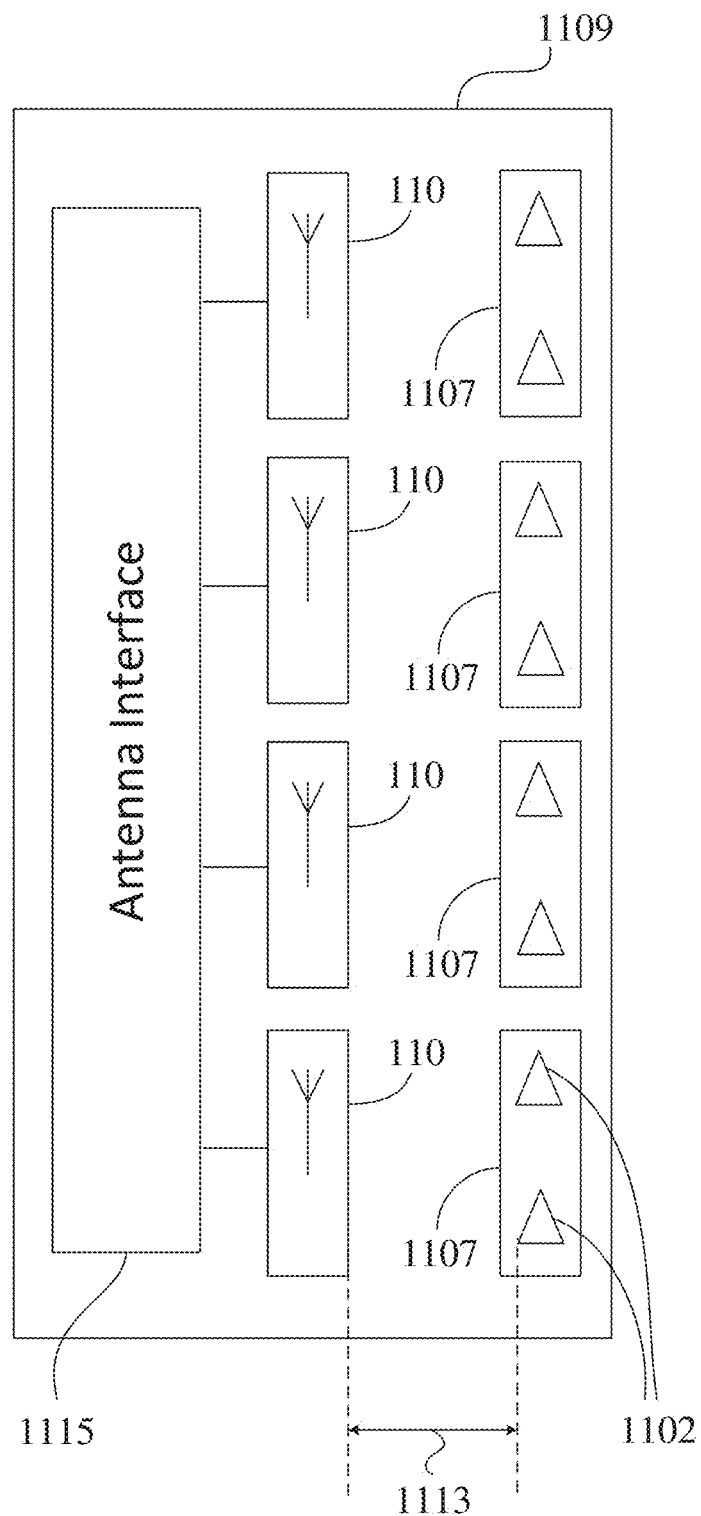
FIG. 11C may be a diagrammatical top view of a reader-and-calibration-member with an antenna interface, in accordance with some embodiments of the present invention.

FIG. 11C may be a diagrammatical top view of a reader-and-calibration-member 1109 with an antenna-interface 1115, in accordance with some embodiments of the present invention. Reader-and-calibration-member 1109 shown in FIG. 11C, as compared against FIG. 11A discussed above, may depict additional detail, in that in FIG. 11C the at least one antennas 110 of each reader 100 of reader-and-calibration-member 1109 may be shown. In FIG. 11C, reader-antenna-tag-separation-distance 1113 may be depicted. In some embodiments, reader-antenna-tag-separation-distance 1113 may be a predetermined and fixed distance between a given at least one antenna 110 and a given reference-sensor-tag 1102. In some embodiments, reader-antenna-tag-separation-distance 1113 may be a predetermined and fixed distance between a given at least one antenna 110 and a given at least one fourth-antenna of a given reference-sensor-tag 1102. In some embodiments, each at least one antenna 110 of each reader 100 (of reader-and-calibration-member 1109) may be fixed with respect to each reference-sensor-tags 1102.

Reader-and-calibration-member 1109 shown in FIG. 11C, as compared against FIG. 11B discussed above, may depict additional detail, in that in FIG. 11C antenna-interface 1115 may be shown. In some embodiments, a given reader 100 may comprise antenna-interface 1115 and at least one antenna 110. In some embodiments, antenna-interface 1115 may be in communication with each at least one antenna 110 for that given reader 100. In some embodiments, antenna-interface 1115 may be hardware block. In some embodiments, antenna-interface 1115 may facilitate communications between at least one antenna 110 and one or more of: a control circuit and/or a processor 1801 (or processing module) (see e.g., FIG. 18). Continuing discussing FIG. 11C, in some embodiments, antenna-interface 1115 may function in communication routing and/or function as a duplex. In some embodiments, antenna-interface 1115 may translate data and/or commands from the control circuit and/or processor 1801 (or processing module) into signals for transmission via at least one antenna 110. In some embodiments, antenna-interface 1115 may translate signals received via at least one antenna 110 into data (e.g., the one or more readings and/or the one or more calibration-readings) and/or commands destined for the control circuit and/or for processor 1801 (or processing module).

With respect to FIG. 11A, FIG. 11B, and/or FIG. 11C, in a given reader-and-calibration-member 1109, locations of all included reference-sensor-tags 1102 relative to all included readers 100 and all included at least one antennas 110, may be known parameters, or may be mathematically determined, thus allowing a calibration process to increase precision of the one or more readings from monitoring-sensor-tag 120 attached to a given material-of-interest.

Note in some embodiments, disclosed structures and functions for a given reader-and-calibration-member 1109 may apply to a given reader 100. That is, in some embodiments, a given reader 100 may be the given reader-and-calibration-member 1109.

Figure 12:
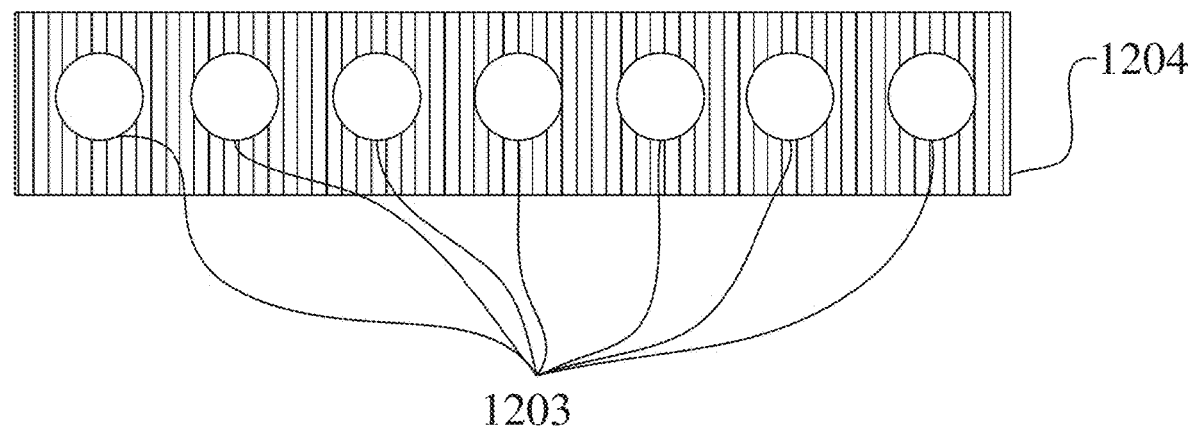
FIG. 12 may be a diagrammatical side view (or a top view) of a position-reference-member, in accordance with the present invention.

FIG. 12 may be a diagrammatical side view (or a top view or a bottom view, in some embodiments) of a position-reference-member 1204, in accordance with the present invention. In some embodiments, position-reference-member 1204 may be a structural member. In some embodiments, position-reference-member 1204 may be rigid to semi-rigid. In some embodiments, during use, position-reference-member 1204 may be fixed with respect to patient 1328. In some embodiments, position-reference-member 1204 may comprise one or more position-reference-tags 1203. In some embodiments, position-reference-member 1204 may house one or more position-reference-tags 1203. In some embodiments, one or more position-reference-tags 1203 located on position-reference-member 1204 may be arranged in known and/or predetermined positions (i.e., configurations and/or patterns). For example, and without limiting the scope of the present invention, as shown in FIG. 12, the position-reference-tags 1203 may be arranged in a substantially linear (straight) arrangement in (on) position-reference-member 1204. The position-reference-tags 1203 may also be arranged in an arbitrary arrangement in (on) position-reference-member 1204.

In some embodiments, a given position-reference-tag 1203 may be a wireless sensor tag. In some embodiments, a given position-reference-tag 1203 may be one or more of: a RFID (radio frequency identification) sensor tag; a NFC (near field communication) sensor tag; a backscatter sensor tag; and/or a magnetic inductive activated sensor tag.

Continuing discussing FIG. 12, in some embodiments, a given position-reference-tag 1203 may be structurally the same or substantially the same as a given monitoring-sensor-tag 120, except that position-reference-tags 1203 are not attached to the given material-of-interest. And in some embodiments, position-reference-tags 1203 may not comprise a sensor. Rather, in some embodiments, position-reference-tags 1203 may be attached to position-reference-member 1204. Thus for the structures of position-reference-tags 1203 refer back to disclosed and discussed structures for monitoring-sensor-tags 120. That is, in some embodiments, each position-reference-tag 1203 may comprise their own electric-circuit (which may be structurally the same or substantially the same to electric circuit 140, but without elements to handle processing from a sensor). In some embodiments, each position-reference-tag 1203 may comprise at least one third-antenna (which may be structurally the same or substantially the same to at least one antenna 130). In some embodiments, the at least one third-antenna may be in communication with its own electric-circuit. In some embodiments, when at least one third-antenna may receive electromagnetic (EM) signaling (e.g., radio waves from at least one antenna 110 of a given reader 100), then the electric-circuit of position-reference-tag 1203 may cause transmission of "calibration-signals" from the at least one third-antenna to be transmitted back to the at least one antenna 110 of that given reader 100.

Note, in terms of terminology nomenclature, when the term "fourth-antenna" may be used (which may be an antenna of a reference-sensor-tags 1102), then antenna 130 may be a "first-antenna," and antenna 110 may be the "second-antenna," and the "third-antenna" may be the antenna of position-reference-tag 1203.

Also note, any antenna disclosed herein, in some embodiments, may be selected from one or more of: monostatic, bistatic, or multistatic. Further note, any antenna disclosed herein, in some embodiments, may be selected from one or more of: only for receiving, only for transmitting, or for both receiving and transmitting. And further note, receiving and/or transmitting may comprise signals for communication purposes, but also signals for energy transmission, harvesting, and usage.

Continuing discussing FIG. 12, in some embodiments, positions (locations) of position-reference-tags 1203 may be known with respect to a given origin (e.g., origin 1325 of FIG. 13A and FIG. 13C) and/or a given coordinate system (e.g., a three-dimensional coordinate system, a Cartesian coordinate system, a radial coordinate system, or other well-known coordinate system). Because positions (locations) of position-reference-tags 1203 may be known, positions (locations) of reader(s) 100 may be determined relative to the position-reference-tags 1203 associated with the position-reference-member 1204. Because positions (locations) of position-reference-tags 1203 may be known, positions (locations) of antennas 110 of reader(s) 100 may be determined relative to the position-reference-tags 1203 associated with the position-reference-member 1204. The positions (locations) of readers 100 (or their antennas 110) may then be specified relative to a chosen three-dimensional coordinate system. See e.g., FIG. 13A and FIG. 13C.

Figure 13A:
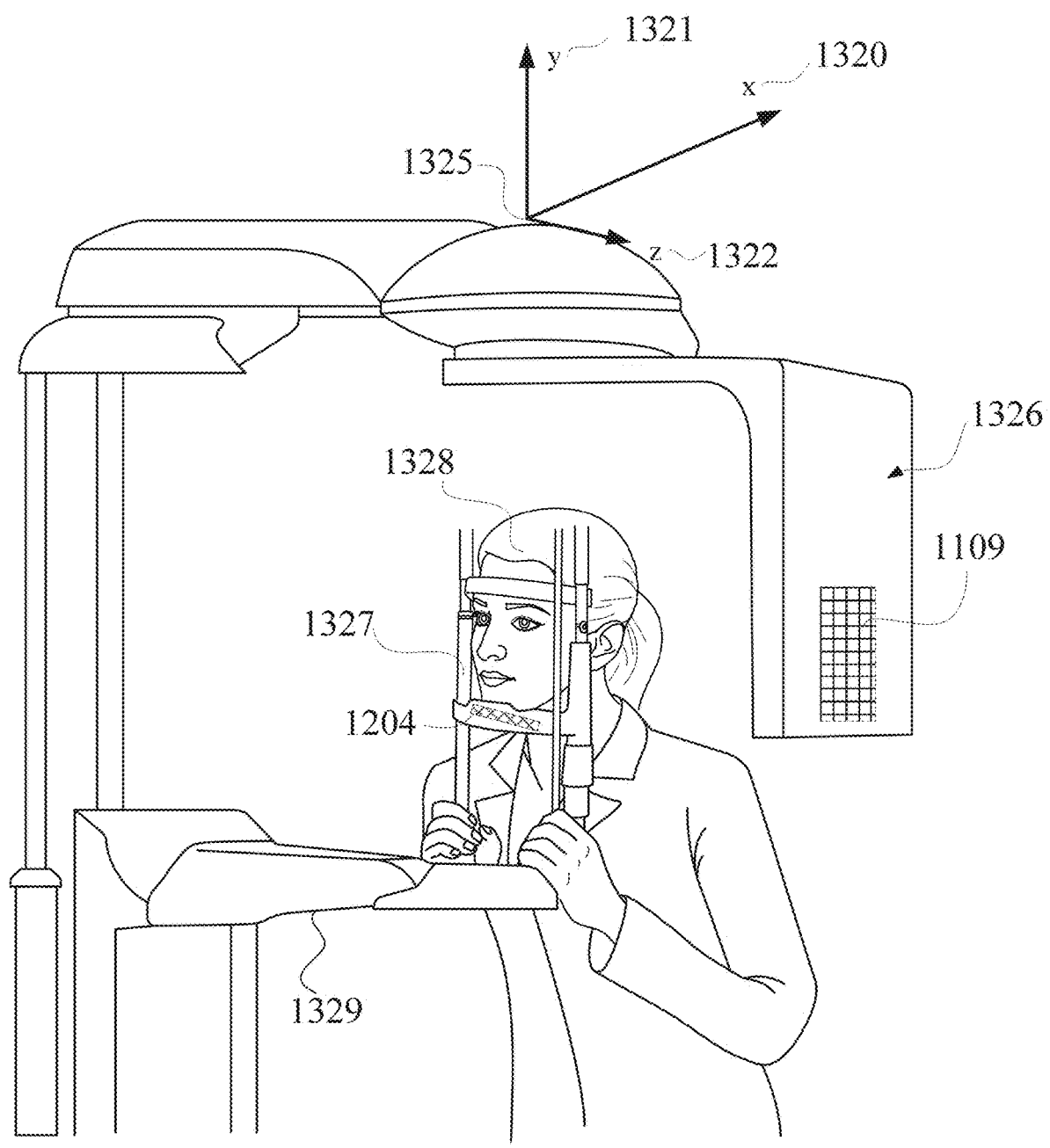
FIG. 13A may depict a system for non-invasive monitoring of a material-of-interest with one or more monitoring-sensor-tags that may be in and/or on a patient; wherein the system comprises a translating-scan-member that may translate along a predetermined path of motion.

FIG. 13A may depict a system for non-invasive monitoring of a material-of-interest with one or more monitoring-sensor-tags 120 that may be in and/or on patient 1328; wherein the system comprises a translating-scan-member 1326 that may translate along a predetermined path of motion.

In some embodiments, FIG. 13A may depict a three-dimensional Cartesian coordinate system chosen to determine three-dimensional coordinates of a plurality of position-reference-tags 1203 affixed to position-reference-member 1204, relative to which the positions (locations) of readers 100 may then be determined. In some embodiments, three dimensional coordinates of at least some of the plurality of position-reference-tags 1203 may be specified relative to the chosen Cartesian coordinate system defined by known origin 1325, Imaginary x-axis 1320, Imaginary y-axis 1321, and Imaginary z-axis 1322. Positions (locations) of reference-sensor-tags 1102 affixed to reader-and-calibration-member 1109 and the positions of the monitoring-sensor-tag 120 may also be specified relative to the chosen coordinate system.

Continuing discussing FIG. 13A, in some embodiments, translating-scan-member 1326 may comprise reader-and-calibration-member 1109. In some embodiments, reader-and-calibration-member 1109 may be attached to translating-scan-member 1326. In some embodiments, reader-and-calibration-member 1109 may comprise one or more reference-sensor-tags 1102. In some embodiments, reader-and-calibration-member 1109 may comprise one or more readers 100. In some embodiments, reference-sensor-tags 1102, readers 100, and/or antenna-interface 1115 (where antenna-interface 1115 may be in electrical communication with the readers 100) may be in electrical communication with translating-scan-member 1326. In some embodiments, translating-scan-member 1326 may be in electrical communication with a processor 1801.

Continuing discussing FIG. 13A, in some embodiments, the one or more monitoring-sensor-tags 120 may be located on or in the given material-of-interest, which may be on or in patient 1328. In some embodiments, the material-of-interest, may be on or in a head of patient 1328. In some embodiments, the material-of-interest, may be on or in a mouth of patient 1328. In some embodiments, the material-of-interest, may be on or in: tooth 1000, dental-filling 1001, gum 1002, root-canal-cavity 1003, root-canal-post 1004, dental-crown 1005, dental-implant 1007, and/or implant-post 1008 of patient 1328. Note in some embodiments, at least some of the one or more monitoring-sensor-tags 120 utilized in the system shown in FIG. 13A may comprise one or more standalone-strain-sensor 1006. See e.g., FIG. 18 which may be applied to the system shown in FIG. 13A.

Continuing discussing FIG. 13A, in some embodiments, the system may comprise patient-fixation-member 1327. In some embodiments, patient-fixation-member 1327 may removably support at least a portion of patient 1328. In some embodiments, patient-fixation-member 1327 may be a structural member. In some embodiments, patient-fixation-member 1327 may be substantially rigid to semi-rigid, not including any portions with padding. In some embodiments, patient-fixation-member 1327 may be supported structurally by support 1329. In some embodiments, support 1329 may attach to patient-fixation-member 1327. In some embodiments, support 1329 may be a structural member. In some embodiments, support 1329 may be a rigid to semi-rigid. In some embodiments, patient-fixation-member 1327 may removably support the at least the portion of patient 1328 such that the supported portion of patient 1328 may be held relatively (sufficiently) fixed (with respect to origin 1325) during scanning, when translating-scan-member 1326 may be translating and travelling along the predetermined path of motion and the readers 100 (of reader-and-calibration-member 1109) may be scanning. In some embodiments, patient 1328 may breathe normally and blink normally, as a scanning frequency may be comparatively faster that such normal motions of patient 1328 may not adversely affect processing of received readings and transmissions from monitoring-sensor-tag 120 and/or from position-reference-tags 1203. In some embodiments, patient-fixation-member 1327 may comprise a chin rest to removably support a chin of patient 1328. In some embodiments, patient-fixation-member 1327 may comprise position-reference-member 1204; and position-reference-member 1204 may comprise one or more position-reference-tags 1203. In some embodiments, position-reference-member 1204 may be attached to patient-fixation-member 1327. In some embodiments, position-reference-member 1204 may be attached to patient-fixation-member 1327 at the chin rest. During scanning, position-reference-member 1204 may be fixed with respect to origin 1325 and the chosen coordinate system. During scanning, the one or more position-reference-tags 1203 of position-reference-member 1204 may be fixed with respect to origin 1325 and the chosen coordinate system. Recall, in some embodiments, position-reference-member 1204 may house the one or more position-reference-tags 1203.

Continuing discussing FIG. 13A, in some embodiments, the predetermined path of motion of translating-scan-member 1326 may translate substantially around patient-fixation-member 1327, which may be removably supporting the at least the portion of patient 1328. In some embodiments, this predetermined path of motion may be curved, sinuous, arcing, ellipsoidal, circular, semi-circular, and/or the like. In some embodiments, translating-scan-member 1326 may be a rotating-scan-member.

Figure 13B:
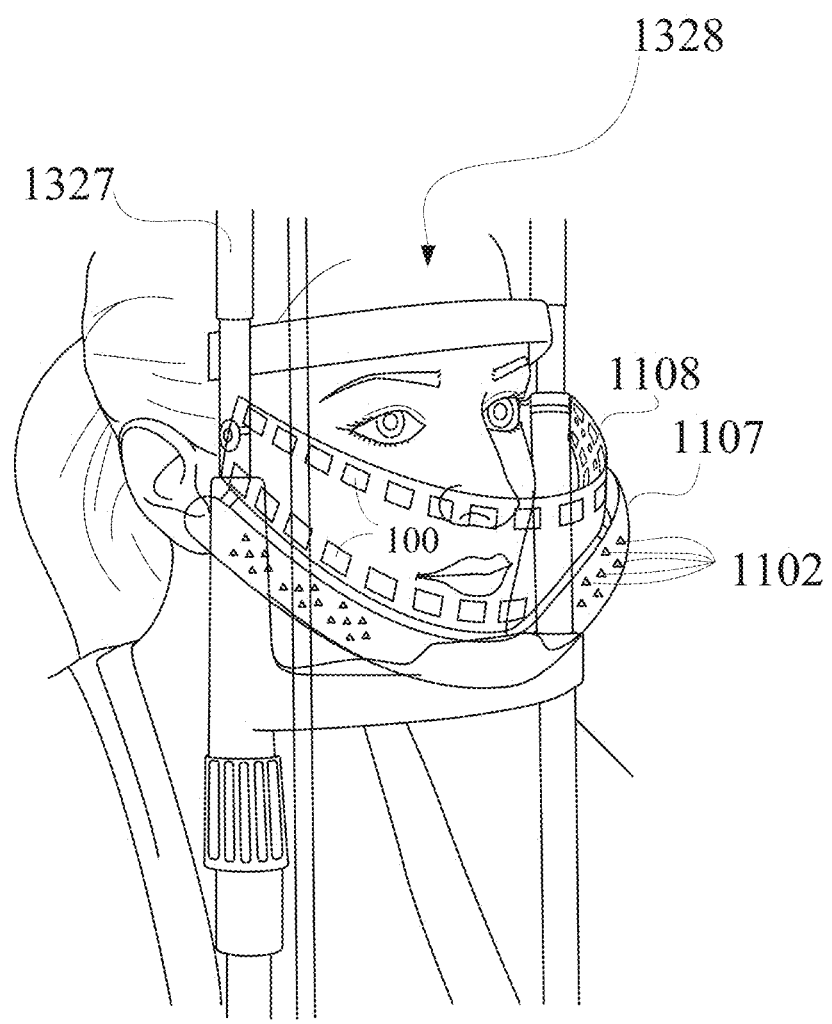
FIG. 13B may depict a system for non-invasive monitoring of a material-of-interest with one or more monitoring-sensor-tags that may be in and/or on a patient; wherein the system comprise a reader-housing-member with one or more readers that may communicate with the one or monitoring-sensor-tags.
Figure 13C:
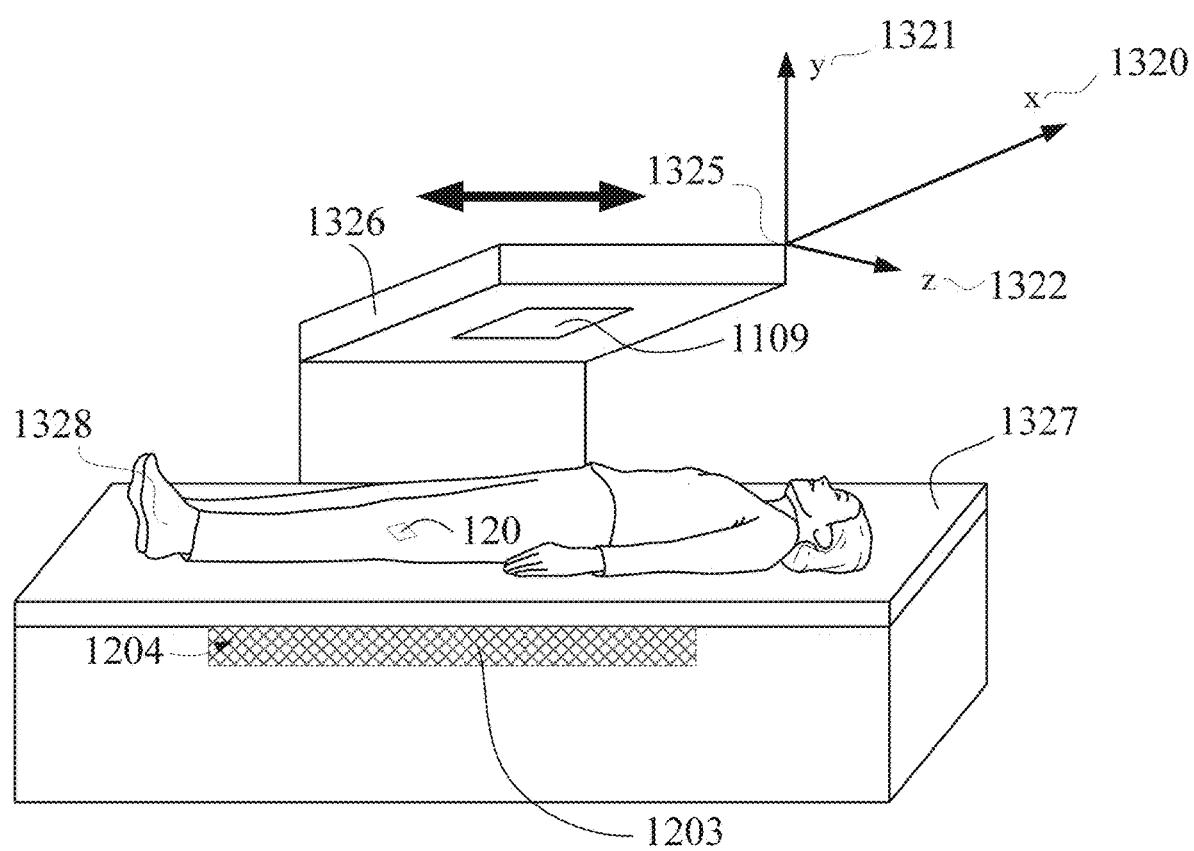
FIG. 13C may depict a system for non-invasive monitoring of a material-of-interest with one or more monitoring-sensor-tags that may be in and/or on a patient; wherein the system comprises a translating-scan-member that may translate along a predetermined path of motion.

FIG. 13B may depict a system for non-invasive monitoring of a material-of-interest with one or more monitoring-sensor-tags 120 that may be in and/or on patient 1328; wherein the system comprise a reader-housing-member 1108 with one or more readers 100 that may communicate with the one or monitoring-sensor-tags 120. The system shown in FIG. 13B may differ fundamentally from the system shown in FIG. 13A, by the system in FIG. 13B not utilizing a translating-scan-member 1326; that is, scanning in the system in FIG. 13B, may be accomplished without translation mechanics; that is, the scanning in the system of FIG. 13B may be accomplished statically (fixedly).

Continuing discussing FIG. 13B, in some embodiments, the one or more monitoring-sensor-tags 120 may be located on or in the given material-of-interest, which may be on or in patient 1328. In some embodiments, the material-of-interest, may be on or in a head of patient 1328. In some embodiments, the material-of-interest, may be on or in a mouth of patient 1328. In some embodiments, the material-of-interest, may be on or in: tooth 1000, dental-filling 1001, gum 1002, root-canal-cavity 1003, root-canal-post 1004, dental-crown 1005, dental-implant 1007, and/or implant-post 1008 of patient 1328. Note in some embodiments, at least some of the one or more monitoring-sensor-tags 120 utilized in the system shown in FIG. 13B may comprise one or more standalone-strain-sensor 1006. See e.g., FIG. 18 which may be applied to the system shown in FIG. 13B.

Continuing discussing FIG. 13B, in some embodiments, the system may comprise patient-fixation-member 1327. In some embodiments, patient-fixation-member 1327 may removably supports at least a portion of patient 1328. In some embodiments, patient-fixation-member 1327 may be a structural member. In some embodiments, patient-fixation-member 1327 may be substantially rigid to semi-rigid, not including any portions with padding. In some embodiments, patient-fixation-member 1327 may be supported structurally by support 1329 (not shown in FIG. 13B). In some embodiments, support 1329 may attach to patient-fixation-member 1327. In some embodiments, support 1329 may be a structural member. In some embodiments, support 1329 may be a rigid to semi-rigid. In some embodiments, patient-fixation-member 1327 may removably supports the at least the portion of patient 1328 such that the supported portion of patient 1328 may be held relatively (sufficiently) fixed (with respect to origin 1325) during scanning, when readers 100 and/or reference-sensor-tags 1102 may be wirelessly transmitting and/or wirelessly receiving transmissions. In some embodiments, patient 1328 may breathe normally and blink normally, as a scanning frequency may be comparatively faster that such normal motions of patient 1328 may not adversely affect processing of received readings and transmissions from monitoring-sensor-tag 120 and/or from reference-sensor-tags 1102. In some embodiments, patient-fixation-member 1327 may comprise a chin rest to removably support a chin of patient 1328. In some embodiments, patient-fixation-member 1327 may comprise reader-housing-member 1108; and reader-housing-member 1108 may comprise one or more readers 100. In some embodiments, reader-housing-member 1108 may be attached to patient-fixation-member 1327. In some embodiments, reader-housing-member 1108 may be attached to patient-fixation-member 1327 at the chin rest (now shown in FIG. 13B). In some embodiments, reader-housing-member 1108 may be at least partially curved so as to arrange readers 100 at least partially around target regions to be scanned, i.e., the material(s)-of-interest with the one or more monitoring-sensor-tags 120 to be scanned. In some embodiments, arrangement of readers 100, via geometry of reader-housing-member 1108 may also locate at least some readers 100 above and below the material(s)-of-interest with the one or more monitoring-sensor-tags 120 to be scanned.

Continuing discussing FIG. 13B, in some embodiments, patient-fixation-member 1327 may comprise reference-housing-member 1107; and reference-housing-member 1107 may comprise one or more reference-sensor-tags 1102. In some embodiments, reference-housing-member 1107 may be attached to patient-fixation-member 1327. In some embodiments, reference-housing-member 1107 may be attached to patient-fixation-member 1327 at the chin rest. In some embodiments, reference-housing-member 1107 may be at least partially curved so as to arrange reference-sensor-tags 1102 at least partially around target regions to be scanned, i.e., the material(s)-of-interest with the one or more monitoring-sensor-tags 120 to be scanned by readers 100. In some embodiments, arrangement of reference-sensor-tags 1102, via geometry of reference-housing-member 1107 may also locate at least some reference-sensor-tags 1102 above and/or below the material(s)-of-interest with the one or more monitoring-sensor-tags 120 to be scanned. In some embodiments, reference-housing-member 1107 may be substantially parallel with reader-housing-member 1108. In some embodiments, reference-housing-member 1107 may be located below, above, or both below and above reader-housing-member 1108. During scanning, readers 100 and/or reference-sensor-tags 1102 may be fixed with respect to patient-fixation-member 1327. Recall, in some embodiments, positions (locations) of reference-sensor-tags 1102 may be known or mathematically determined (derived).

FIG. 13C may depict a system for non-invasive monitoring of a material-of-interest with one or more monitoring-sensor-tags 120 that may be in and/or on patient 1328; wherein the system comprises a translating-scan-member 1326 that may translate along a predetermined path of motion. The system shown in FIG. 13C may be more akin to the system of FIG. 13A, in that both systems may utilize a type of translating-scan-member 1326 but with different predetermined paths of motion. In some embodiments, translating-scan-member 1326 of FIG. 13C may be a reciprocating translating member, wherein the predetermined path may be substantially linear (straight). Also, the patient-fixation-member 1327 utilized in the system of FIG. 13C may also be structurally different from the patient-fixation-member 1327 shown in FIG. 13A. In some embodiments, patient-fixation-member 1327 of FIG. 13C may be a platform for supporting up to all of patient 1328 upon such a platform. In some embodiments, patient 1328 may lay (in various positions) upon this platform embodiment of patient-fixation-member 1327. In some embodiments, the predetermined path may have a length that substantially matches a length of this platform embodiment of patient-fixation-member 1327. In some embodiments, the predetermined path may have a width that substantially matches a width of this platform embodiment of patient-fixation-member 1327; in which case, translating-scan-member 1326 may also translate in a side to side motion as well as reciprocating along the length of the predetermined path. Or in some embodiments, a width of reader-and-calibration-member 1109 may be sufficient wide to accommodate scanning the width of this platform embodiment of patient-fixation-member 1327.

Continuing discussing FIG. 13C, the material(s)-of-interest with the one or more monitoring-sensor-tags 120 may be located on or in patient 1328. In some embodiments, the material(s)-of-interest with the one or more monitoring-sensor-tag 120 may be located anywhere on or in patient 1328. In some embodiments, the material(s)-of-interest with the one or more monitoring-sensor-tag 120 need not be constrained to a head region (nor to a mouth region) of patient 1328. For example, and without limiting the scope of the present invention, as shown in FIG. 13C, the material-of-interest with the one or more monitoring-sensor-tags 120 may be located in (or on) a left leg region of patient 1328. Note in some embodiments, at least some of the one or more monitoring-sensor-tags 120 utilized in the system shown in FIG. 13C may comprise one or more standalone-strain-sensor 1006. See e.g., FIG. 18 which may be applied to the system shown in FIG. 13C.

Figure 14A:
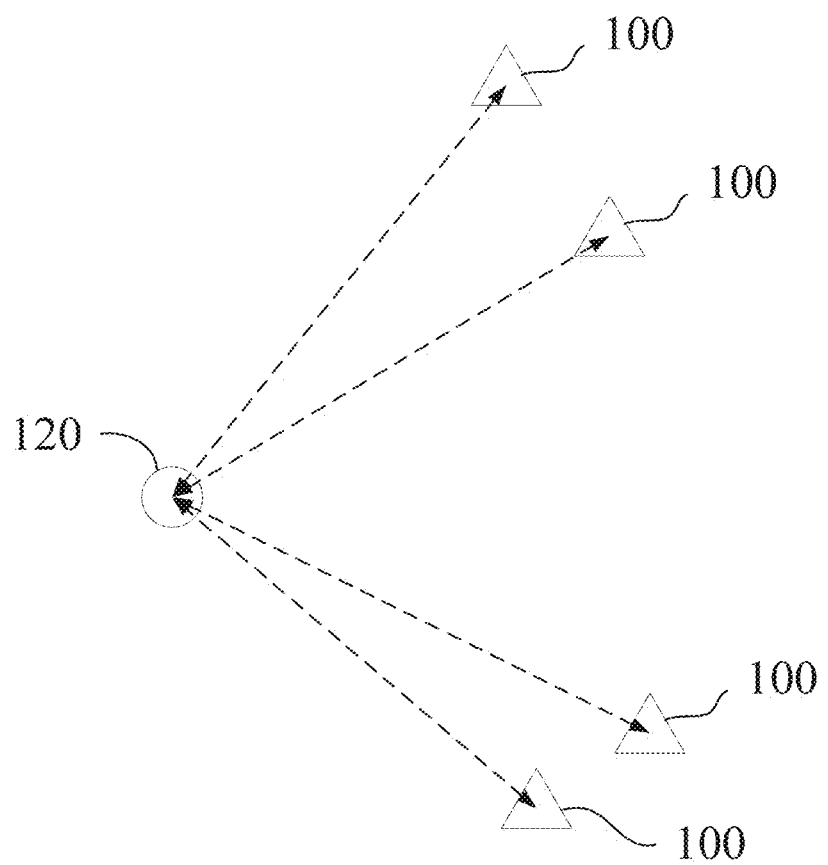
FIG. 14A may be a schematic view of a single monitoring-sensor-tag and a plurality of readers that may communicate (wirelessly) with the single monitoring-sensor-tag.

FIG. 14A may be a schematic view of a single monitoring-sensor-tag 120 and a plurality of readers 100 that may communicate (wirelessly) with the single monitoring-sensor-tag 120. Thus, the arrangement of FIG. 14A may be applicable to the system of FIG. 13B. Knowing the positions (locations) of the readers 100, then a position (location) of the single monitoring-sensor-tag 120 may be determined. Prior to such position (location) determination, the single monitoring-sensor-tag 120 may have unknown coordinates (e.g., x, y, and z in a Cartesian coordinate system). Whereas, in some embodiments, the readers 100 may have known (or determinable) coordinates relative to the chosen coordinate system, which may include a known origin. A process (method) for determining the coordinates of the single monitoring-sensor-tag 120 may be utilized to determine position (location) of all such monitoring-sensor-tags 120 in use in a given system. And thus, positions (locations) corresponding to the readings from sensors (e.g., 202, 203, 1006, and/or the like) of the given monitoring-sensor-tags 120 may be determined and analyzed, with respect to the given material-of-interest that is associated with the monitoring-sensor-tags 120.

Figure 14B:
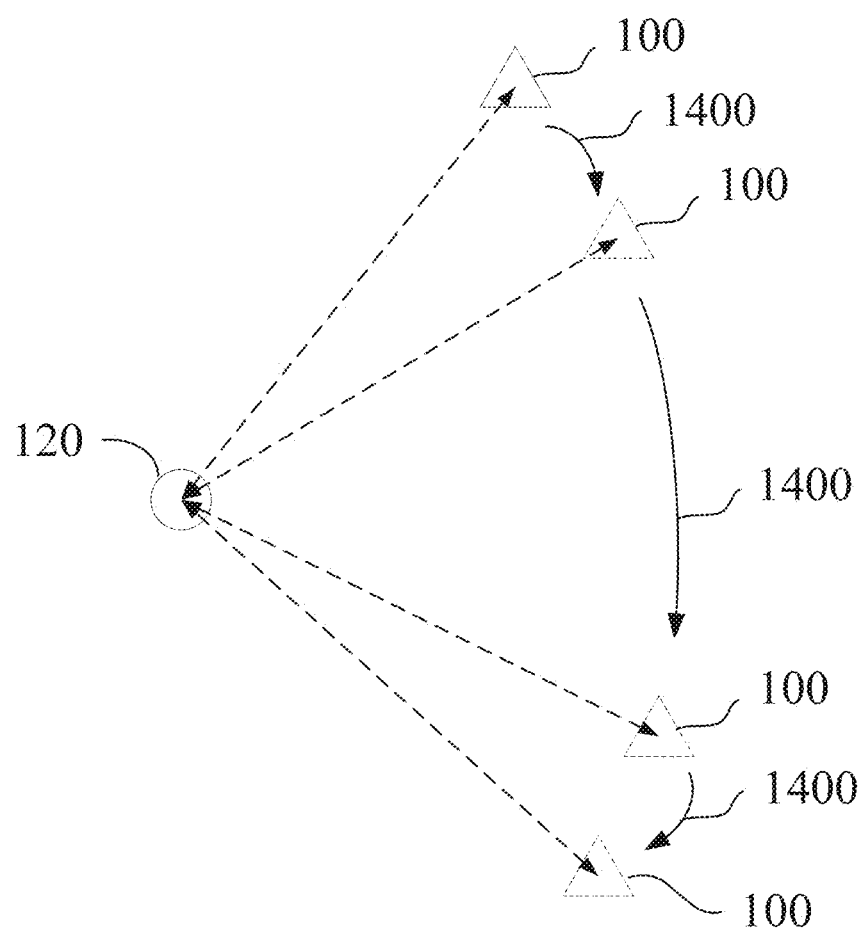
FIG. 14B may be a schematic view of a single monitoring-sensor-tag and a single reader; wherein the single reader may translate with respect to the single monitoring-sensor-tag; and wherein the single reader and the single monitoring-sensor-tag may be in wireless communication.

FIG. 14B may be a schematic view of a single monitoring-sensor-tag 120 and a single reader 100; wherein the single reader 100 may translate (in direction-of-motion 1400) with respect to the single monitoring-sensor-tag 120; and wherein the single reader 100 and the single monitoring-sensor-tag 120 may be in wireless communication. Thus, the arrangement of FIG. 14B may be applicable to the system of FIG. 13A (and/or the system of FIG. 13C).

In some embodiments, knowing the positions (locations) of the single reader 100 as a function of time, a position (location) of the single monitoring-sensor-tag 120 (which may be fixed during scanning) may be determined. Prior to such position (location) determination, the single monitoring-sensor-tag 120 may have unknown coordinates (e.g., x, y, and z in a Cartesian coordinate system). Whereas, in some embodiments, the translating single reader 100 may have known (or determinable) coordinates relative to the chosen coordinate system and as a function of time, which may include a known origin or known starting position at a starting time. A process (method) for determining the coordinates of the single monitoring-sensor-tag 120 may be utilized to determine position (location) of all such monitoring-sensor-tags 120 in use in a given system. And thus, positions (locations) corresponding to the readings from sensors (e.g., 202, 203, 1006, and/or the like) of the given monitoring-sensor-tags 120 may be determined and analyzed, with respect to the given material-of-interest that is associated with the monitoring-sensor-tags 120.

Determining positions (locations) of any given monitoring-sensor-tag 120, and/or determination of any given reader 100, may involve well-known local position systems (LPS) techniques; that may utilize one or more of the following mathematical techniques: triangulation, trilateration, multilateration, combinations thereof, and/or the like. Additionally, such information may be utilized in such positional calculations: known reference points (e.g., origin 1325 and/or known locations of position-reference-tags 1203); direct paths (line of sight or LoS); angle of incidence (or angle of arrival or AoA); phase difference of arrival (PDoA); received signal strength indicator (RSSI); time of arrival (ToA); time of flight (ToF); and/or time difference of arrival (TDoA).

For example, the following discussion presents one method for determining position (location) information of a given monitoring-sensor-tag 120 according to the configuration of FIG. 14A. Let us stipulate that reader 100 number i has coordinates $(x_i, y_i, z_i)$. The actual distance (range) between the given monitoring-sensor-tag 120 $n,m$ with coordinates $\bar{x}=[x\ y\ z]$ and reader 100 number i is $r_{(m,n),i}$. The distance measured between the given monitoring-sensor-tag 120 $n,m$ and reader 100 number i is $h_{(m,n),i}$. The range measurement error is assumed to be a random variable $w_{(m,n),i}$ with variance $\sigma_{(m,n),i}^2$. $h_{(m,n),i}$ can be expressed as follows:

$$h_{(m,n),i} = r_{(m,n),i} + w_{(m,n),i} \quad (5)$$

Let us assume that the number (quantity) of readers 100 used to determine position (location) of the given monitoring-sensor-tag 120 $n,m$ is s. The distance (range) between the given monitoring-sensor-tag 120 $n,m$ and reader 100 number i, denoted as $r_{(m,n),i}$ may be expressed as:

$$r_{(n,m),i} = \sqrt{(x_i-x)^2 + (y_i-y)^2 + (z_i-z)^2}\ i=1,2,\ldots,s \quad (6)$$

We can therefore express the measured distance between the given monitoring-sensor-tag 120 $n,m$ and reader 100 number i as:

$$h_{(m,n),i} = \sqrt{(x_i-x)^2 + (y_i-y)^2 + (z_i-z)^2} + w_{(m,n),i} \quad (7)$$

In vector form, the vector $\bar{r}_{(n,m)}(\bar{x})$ of distances (ranges) between the given monitoring-sensor-tag 120 $n,m$ with coordinates $\bar{x}=[x\ y\ z]$ and the readers 100 where number i may be 1, 2, 3, ..., s is:

$$\bar{r}_{(n,m)}(\bar{x}) = \begin{bmatrix} \sqrt{(x_1-x)^2 + (y_1-y)^2 + (z_1-z)^2} \\ \sqrt{(x_2-x)^2 + (y_2-y)^2 + (z_2-z)^2} \\ \vdots \\ \sqrt{(x_s-x)^2 + (y_s-y)^2 + (z_s-z)^2} \end{bmatrix} \quad (8)$$

In vector form, the vector $\bar{h}_{(n,m)}$ of measured distances between the given monitoring-sensor-tag 120 $n,m$ and the readers 100 where number i may be 1, 2, 3, ..., s is:

$$\bar{h}_{(n,m)} = [h_{(m,n),1}\ h_{(m,n),2}\ \ldots\ h_{(m,n),s}]^T \quad (9)$$

where T is a symbol for a vector or a matrix transpose.

In vector form, the vector $\bar{w}_{(n,m)}$ of measurement errors of the distances between the given monitoring-sensor-tag 120 $n,m$ and the readers 100 where number i may be 1, 2, 3, ..., s is:

$$\bar{w}_{(n,m)} = [w_{(m,n),1}\ w_{(m,n),2}\ \ldots\ w_{(m,n),s}]^T \quad (10)$$

We may express equation (5) in vector form, expressing the vector of distance measurements $\bar{h}_{(n,m)}$ as follows:

$$\bar{h}_{(n,m)}(\bar{x}) = \bar{r}_{(n,m)}(\bar{x}) + \bar{w}_{(n,m)} \quad (11)$$

$$\bar{h}_{(n,m)}(\bar{x}) = \begin{bmatrix} \sqrt{(x_1-x)^2 + (y_1-y)^2 + (z_1-z)^2} \\ \sqrt{(x_2-x)^2 + (y_2-y)^2 + (z_2-z)^2} \\ \vdots \\ \sqrt{(x_s-x)^2 + (y_s-y)^2 + (z_s-z)^2} \end{bmatrix} + \bar{w}_{(n,m)} \quad (12)$$

We need to estimate location coordinate $\bar{x}=[x\ y\ z]^T$ for each monitoring-sensor-tag 120 $n,m$ given the vector of distance measurements $\bar{h}_{(n,m)}$ between the given monitoring-sensor-tag 120 $n,m$ and the readers 100 where i may be 1, 2, 3, ..., s.

Alternatively (or in addition to), in conformity with the arrangement shown in FIG. 14B, a single moving reader 100 number i may be used to obtain a series of coordinates ($x_i$, $y_i$, $z_i$) of this reader 100 number i, assuming the movement of this reader 100 number i may be controlled and its coordinates known, and as a function of time.

There are numerous well-known methods (techniques and/or algorithms) to estimate $\bar{x}$ in equation (11). Based on the results of a calibration process described below, one may optionally use Nonlinear Least Squares (NLS) or Maximum Likelihood (ML) estimators among other available optimization techniques.

An optional Nonlinear Least Squares (NLS) approach minimizes the least squares cost function derived from equation (7). It is a widely used and well-known method, that is discussed below. Based on equation (7) one may denote the NLS cost function $C(\bar{x})$ of the given monitoring-sensor-tag 120 $n,m$ position estimate $x=[x\ y\ z]^T$ as:

$$C(\bar{x}) = \sum_{i=1}^{s} \left(h_{(m,n),i} - \sqrt{(x_i - x)^2 + (y_i - y)^2 + (z_i - z)^2}\right)^2 = \quad (13)$$

$$(\bar{h} - \bar{r}(\bar{x}))^T (\bar{h} - r(\bar{x}))$$

where:

($x_i$, $y_i$, $z_i$) are coordinates of Reader 100 number i, where i may be 1, 2, ..., s; and $h_{(m,n),i}$ the measured distance between the given monitoring-sensor-tag 120 $n,m$ and reader 100 number i.

The NLS position estimate $\hat{x}$ will correspond to the smallest value of the cost function $C(\bar{x})$:

$$\hat{x} = \arg\min_{\bar{x}} C(\bar{x}) \quad (14)$$

Levenberg-Marquardt Algorithm (LMA), Newton-Raphson Algorithm (NRA), Gauss-Newton Algorithm (GNA) are some methods widely used for solving optimization problem in equation (14).

An optional Maximum Likelihood (ML) approach is a widely used and well-known method for solving non-linear equations by means of maximizing the Probability Density Function (PDF) of the function in question.

A probability density function $\rho(\bar{h}_{(n,m)})$ for the vector of measured distances $\bar{h}_{(m,n)}$ from equation (11) may be expressed as:

$$\rho(\bar{h}_{(n,m)}) = \frac{1}{(2\pi)^{\frac{s}{2}}|R|^{\frac{1}{2}}} \exp\left(-\frac{1}{2}(\bar{h}_{(n,m)} - \bar{r}_{(n,m)})^T R^{-1}(\bar{h}_{(n,m)} - \bar{r}_{(n,m)})\right) \quad (15)$$

where R is the covariance matrix of $\bar{h}_{(n,m)}$ wherein R may be defined as:

$$R = E\{(\bar{h}_{(n,m)} - \bar{r}_{(n,m)})(\bar{h}_{(n,m)} - \bar{r}_{(n,m)})^T\} = \text{diag}(\sigma_1^2, \sigma_2^2, \ldots, \sigma_s^2) \quad (16)$$

where $\sigma_i^2$ of is the variance of the range measurement error $w_{(m,n),i}$ from above equation (6). $R^{-1}$ is matrix inverse of the matrix R and $|R|$ is determinant of matrix R Maximization of the probability density function $\rho(\bar{h}_{(n,m)})$ of the vector of measured distances $\bar{h}_{(n,m)}$ in equation (12) may be expressed as the following minimization problem:

$$\hat{x} = \arg\min_{\bar{x}} C(\bar{x}) \quad (17)$$

where $C(\bar{x})$ is a cost function of the position estimate $\bar{x}=[x\ y\ z]^T$ of the given monitoring-sensor-tag 120 $n,m$ expressed as:

$$C(\bar{x}) = (\bar{h}_{(n,m)} - \bar{r}_{(n,m)})^T R^{-1}(\bar{h}_{(n,m)} - \bar{r}_{(n,m)}) = \quad (18)$$

$$\sum_{i=1}^{s} \frac{\left(h_{(m,n),i} - \sqrt{(x_i - x)^2 + (y_i - y)^2 + (z_i - z)^2}\right)}{\sigma_i^2}$$

where:

($x_i$, $y_i$, $z_i$) are coordinates of Reader 100 number i, wherein number i may be 1, 2, ..., s;

$h_{(m,n),i}$ is the measured distance between the given monitoring-sensor-tag 120 $n,m$ and reader 100 number i; and $\bar{x}=[x\ y\ z]^T$ is the position estimate of the given monitoring-sensor-tag 120 $n,m$.

Levenberg-Marquardt Algorithm (LMA), Newton-Raphson Algorithm (NRA), Gauss-Newton Algorithm (GNA) are some methods widely used for solving optimization problem in equation (17).

Linear approaches for initial coordinate estimate. Many approaches have been used to convert non-linear equations (12) copied below:

$$\bar{h}_{(n,m)}(\bar{x}) = \begin{bmatrix} \sqrt{(x_1 - x)^2 + (y_1 - y)^2 + (z_1 - z)^2} \\ \sqrt{(x_2 - x)^2 + (y_2 - y)^2 + (z_2 - z)^2} \\ \vdots \\ \sqrt{(x_s - x)^2 + (y_s - y)^2 + (z_s - z)^2} \end{bmatrix} + \bar{w}_{(n,m)} \quad (12)$$

to set of linear equations, direct solution of which may provide a start point for an optimization process employed for finding the coordinates of the given monitoring-sensor-tag 120 $n,m$ in above equations (14) and (17). Some embodiments may employ widely described and well-known Linear Least Squares (LLS) and Weighted Linear Least Squares (WLLS) approaches in order to convert non-linear equation (12) into a linear forma; and then to find $\bar{x}=[x\ y\ z]^T$ which is used as a start point for subsequent optimization processes in determining coordinates of the given monitoring-sensor-tag 120 $n,m$.

Figure 15:
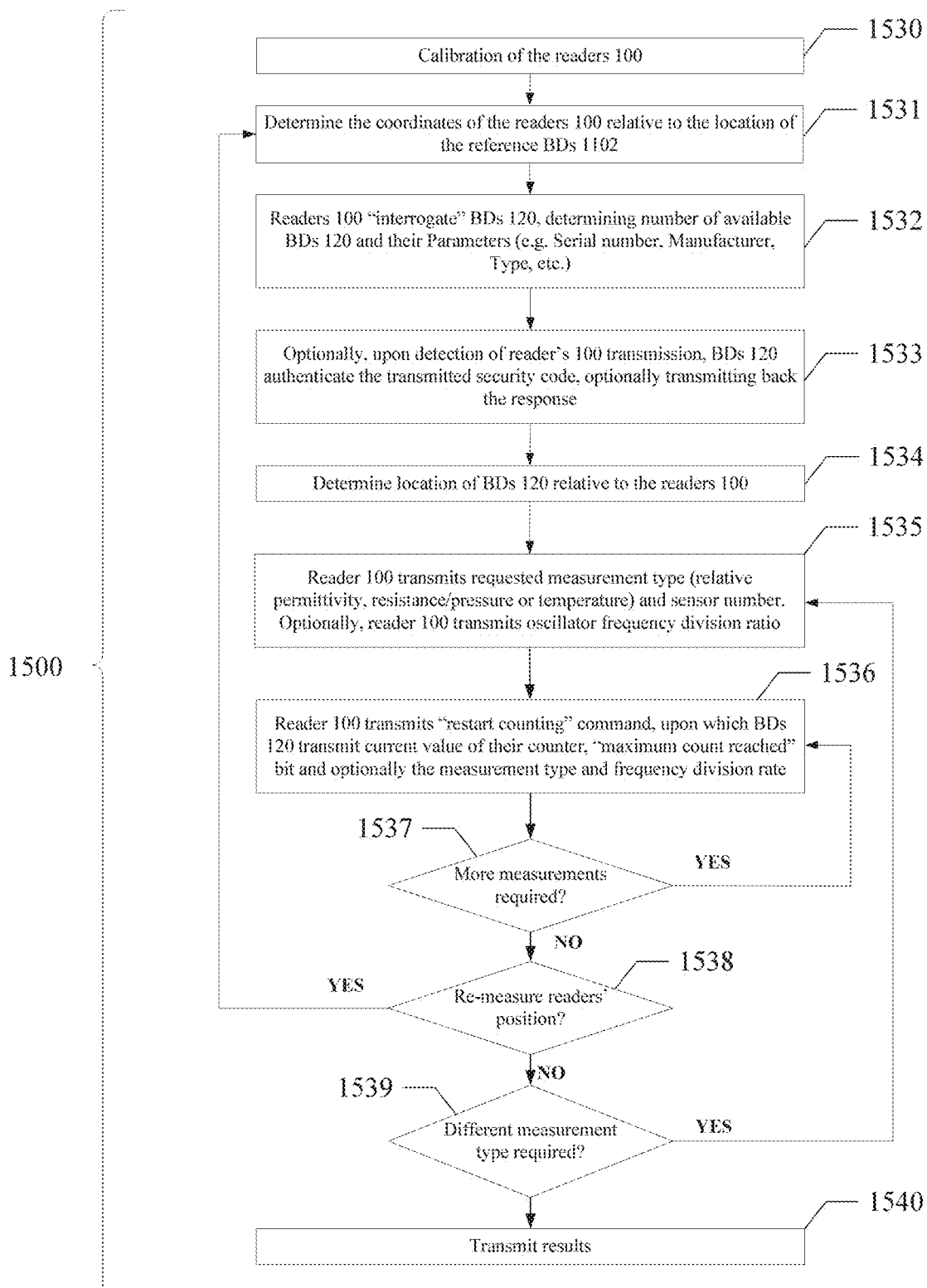
FIG. 15 may depict a flow diagram illustrating steps in a method for non-invasive monitoring of a material-of-interest with one or more monitoring-sensor tag using one or more readers.

FIG. 15 may depict a flow diagram illustrating steps in a method 1500 for non-invasive monitoring of a material-of-interest with one or more monitoring-sensor tag 120 using one or more readers 100.

Continuing discussing FIG. 15, in some embodiments method 1500 may comprise step 1530; wherein step 1530 may be a step of calibrating readers 100 that are to be used. That is in some embodiments, method 1500 may begin with step 1530 of calibrating the readers 100. Reader 100 calibration in step 1530 may involve wireless communication between readers 100 and reference-sensor-tags 1102. Recall, in some embodiments, reference-sensor-tags 1102 may have known locations (positions, coordinates). In some embodiments, reference-sensor-tags 1102 may comprise stress (deformation) sensor resistors (such as 700 and/or 703) with known parameters. In some embodiments, reference-sensor-tags 1102 may comprise capacitor-based relative permittivity sensors (such as 402, 404, 405, 406, 407, and/or 408) with known parameters. In some embodiments, reference-sensor-tags 1102 may comprise one or more of: stress (deformation) sensor resistors (such as 700 and/or 703); and/or capacitor-based relative permittivity sensors (such as 402, 404, 405, 406, 407, and/or 408) with known parameters. Such sensors of reference-sensor-tags 1102 may provide the one or more "calibration-readings" back to readers 100; which may then provide for various reference (or foundational) qualities to assist in calibrating readers 100. In some embodiments, reference-sensor-tags 1102 sensors may also sense local (ambient) temperature to aid in temperature calibration while the local (ambient) temperature in vicinity of said sensors is known.

Continuing discussing FIG. 15, in some embodiments, method 1500 may comprise step 1531. In some embodiments, successful conclusion of step 1530 may then transition into step 1531. In some embodiments, step 1531 may be a step of determining a location (i.e., position and/or coordinates) of the one or more readers 100. Step 1531 may be accomplished by wireless communication between readers 100 and reference-sensor-tags 1102, wherein locations of reference-sensor-tags 1102 may be known and thus locations of readers 100 may be determined relative to these known locations of reference-sensor-tags 1102.

Continuing discussing FIG. 15, in some embodiments, method 1500 may comprise step 1532. In some embodiments, successful conclusion of step 1531 may then transition into step 1532. In some embodiments, step 1532 may be a step of reader 100 interrogation of the one or more monitoring-sensor-tags 120 that are associated with the material-of-interest. In some embodiments, in this interrogation step 1532, a number (quantity) of available one or more monitoring-sensor-tags 120 may be transmitted back to the readers 100 and determined. In some embodiments, in this interrogation step 1532, "additional information" of the one or more monitoring-sensor-tags 120 may be transmitted back to the readers 100 and determined. In some embodiments, this "additional information" may comprise one or more of: identification information for a given monitoring-sensor-tag 120 that is transmitting (e.g., an ID for each monitoring-sensor-tag 120 that is transmitting); model number for the given monitoring-sensor-tag 120 that is transmitting; serial number for the given monitoring-sensor-tag 120 that is transmitting; manufacturer of the given monitoring-sensor-tag 120 that is transmitting; year of manufacture of the given monitoring-sensor-tag 120 that is transmitting; or a request for a security code associated with that given monitoring-sensor-tag 120 that is transmitting; a public security key; a cyclic redundancy check code for the given monitoring-sensor-tag 120 that is transmitting; a parity check code for the given monitoring-sensor-tag 120 that is transmitting; and receipt of a disable instruction for the given monitoring-sensor-tag 120 that is transmitting; wherein the given monitoring-sensor-tag 120 that is transmitting is selected from the one or more monitoring-sensor-tags 120.

The cyclic redundancy check code and/or the parity check code for the given monitoring-sensor-tag 120 that may be transmitting may be known approaches to generate additional data based on the transmitted information. That additional data, once received by the readers 100 and further analyzed by a processor 1801 (see e.g., FIG. 18) may be used to validate correct transmission of said transmitted information.

The model number for the given monitoring-sensor-tag 120 that may be transmitting; the serial number for the given monitoring-sensor-tag 120 that may be transmitting; and/or the manufacturer of the given monitoring-sensor-tag 120 may be information used for identifying the type of the given monitoring-sensor-tag 120 to be used in subsequent steps including but not limited to calibration.

Continuing discussing FIG. 15, in some embodiments, step 1532 may progress into step 1534 or into step 1533. In some embodiments, method 1500 may comprise step 1533.

In some embodiments, step 1533 may be an authentication step, to ensure that only authorized readers 100 (and not some other RFID type of reading/scanning device) may be accessing the one or more monitoring-sensor-tags 120. For example, and without limiting the scope of the present invention, in some embodiments, the one or more monitoring-sensor-tags 120 may not transmit useful information, such as the one or more readings, unless the given monitoring-sensor-tag 120 first receives a proper security code (e.g., password) from the given reader 100. In some embodiments, the given monitoring-sensor-tag 120 may transmit a request for this security code to the readers 100. In some embodiments, the given monitoring-sensor-tag 120 may transmit its public security key in addition for the request for the said security code to the readers 100. In some embodiments, where step 1533 is required in method 1500, successful completion of the authentication step 1533 may then transition into step 1534.

Some applications of method 1500 may not include step 1533, in which case, step 1532 may transition into step 1534.

Continuing discussing FIG. 15, in some embodiments, method 1500 may comprise step 1534. In some embodiments, step 1534 may follow step 1532 or may follow step 1533. In some embodiments, step 1534 may be a step of determining locations (positions and/or coordinates) of the one or more monitoring-sensor-tags 120. Such location determination may proceed via LPS (local positioning systems) techniques as discussed above in the FIG. 14A and FIG. 14B discussion.

Continuing discussing FIG. 15, in some embodiments, method 1500 may comprise step 1535. In some embodiments, step 1535 may follow step 1534. In some embodiments, step 1535 may be a step of the reader 100 instructing (i.e., commanding and/or requesting) the one more monitoring-sensor-tags 120. In some embodiments, such instructions from the readers 100 may initiate a process in the one or more monitoring-sensor-tags 120 such that the given monitoring-sensor-tag 120 may generate the one or more readings from their one or more sensors and then transmit the resulting one or more readings back to the readers 100 via the antennas 130 of the given monitoring-sensor-tag 120. For example, and without limiting the scope of the present invention, the readers 100 may request a specific measurement type to provide information (one or more readings) that may correlate with specific state information of the given material-of-interest that may be monitored and/or tracked by using one or more monitoring-sensor-tags 120 attached to (associated with) the given material-of-interest. Recall the one or more readings from the sensors of the one or more monitoring-sensor-tags 120 may yield state information such as, but not limited to: structural integrity of a current state of the material-of-interest; structural integrity changes of the material-of-interest; pressure received at the material-of-interest; force received at the material-of-interest; stress received at the material-of-interest; torsion received at the material-of-interest; deformation received at the material-of-interest; temperature at some portion of the material-of-interest; positional changes of a given monitoring-sensor-tag 120 attached to the material-of-interest with respect to position of another monitoring-sensor-tag 120 attached to the material-of-interest, wherein the given monitoring-sensor-tag 120 and the other monitoring-sensor-tag are 120 selected from the one or more monitoring-sensor-tags 120 attached to the material-of-interest; or positional changes of at least one monitoring-sensor-tag 120 attached to the material-of-interest with respect to time, wherein the at least one monitoring-sensor-tag 120 is selected from the one or more monitoring-sensor-tags 120. For example, and without limiting the scope of the present invention, the readers 100 may request a specific measurement type from a specific sensor type. For example, and without limiting the scope of the present invention, the readers 100 may request one or more readings from specific sensors, wherein the specific sensors may be identified by a sensor-specific-ID (e.g., a unique sensor number for that specific sensor). In some embodiments, the sensor-specific-ID (sensor number) may serve to choose a specific sensor from a number of sensors of a given monitoring-sensor-tag 120. For example, and without limiting the scope of the present invention, as shown in FIG. 8, a number of different sensors may exist for a given monitoring-sensor-tag 120. For example, and without limiting the scope of the present invention, the readers 100 may transmit an oscillator frequency division ratio to the given monitoring-sensor-tag 120. For example, and without limiting the scope of the present invention, sensors (of monitoring-sensor-tags 120) may belong to different ring oscillator circuits; and such different ring oscillator circuits may be selected sequentially or in parallel. That is, any given independent ring oscillators in a given monitoring-sensor-tag 120 may be engaged either sequentially or in parallel.

Continuing discussing FIG. 15, in some embodiments, method 1500 may comprise step 1536. In some embodiments, step 1536 may follow step 1535. Alternatively, in some embodiments, step 1536 may be a sub-step of step 1535. In some embodiments, step 1536 may be a step of the readers 100 transmitting the "restart counting" command to the one or more monitoring-sensor-tags 120. Recall RESTART_COUNT signal 931 of FIG. 9 and the FIG. 9 discussion above. A monitoring-sensor-tag 120 receiving RESTART_COUNT signal 931 may then cause that monitoring-sensor-tag 120 to transmit one or more of the following: their current value of their counter; "maximum count reached" bit; the measurement type (sensor type); the sensor-specific-ID; the sensor's one or more readings; and/or frequency division rate.

Continuing discussing FIG. 15, in some embodiments, method 1500 may comprise step 1537. In some embodiments, step 1537 may follow step 1536. In some embodiments, step 1537 may be a step of determining if additional measurements to be taken from the sensors of the one or more monitoring-sensor-tags 120. If yes, then method 1500 may progress back to step 1536. If no, then method 1500 may progress to step 1538. In some embodiments, criteria for evaluating step 1537 may comprise, but may not be limited to, either achieving the predetermined mathematical variance of the series of obtained measurements or reaching a pre-defined maximal number of measurements.

Continuing discussing FIG. 15, in some embodiments, method 1500 may comprise step 1538. In some embodiments, step 1538 may follow a "no" outcome of step 1537. In some embodiments, step 1538 may be a step of determining if the reader 100 locations are to be re-determined per step 1531. If yes, then method 1500 may progress back to step 1531. If no, then method 1500 may progress to step 1539. In some embodiments, criteria for evaluating step 1538 may be defined by the settings provided by the user, matching the type of environment in which the specific embodiment is used. For example, in the case of a static set of readers as related to patient 1328, like the one depicted in FIG. 13B, step 1538 may not be required. In case of a system, like the one shown in FIG. 13C, comprising a translating-scan-member 1326 that may translate along a predetermined path of motion, step 1538 may be performed either each time or at predetermined time intervals to ensure that the location of the translating-scan-member 1326 is determined correctly.

Continuing discussing FIG. 15, in some embodiments, method 1500 may comprise step 1539. In some embodiments, step 1539 may follow a "no" outcome of step 1538. In some embodiments, step 1539 may be a step of determining if different measurement types are be taken from the sensors of the one or more monitoring-sensor-tags 120. If yes, then method 1500 may progress back to step 1535. If no, then method 1500 may progress to step 1540. In some embodiments, criteria for evaluating step 1539 may be provided by the settings in the specific embodiment. For example, if monitoring-sensor-tags 120 of different types are used (e.g., measuring stress, temperature, humidity, liquid penetration, etc.) step 1539 may determine that additional measurement types have to be performed.

Continuing discussing FIG. 15, in some embodiments, method 1500 may comprise step 1540. In some embodiments, step 1540 may follow a "no" outcome of step 1539. In some embodiments, step 1540 may be a step of readers 100 transmitting "received monitoring-sensor-tag 120 transmissions." In some embodiments, the received monitoring-sensor-tag 120 transmissions may comprise one or more of the following: the one or more readings; the sensor-specific-ID; the additional information; and/or any other information and/or data transmitted from antennas 130 of the one or more monitoring-sensor-tags 120. In some embodiments, the readers 100 may transmit this "received monitoring-sensor-tag 120 transmissions" to processor 1801 (see e.g., FIG. 18) for processing and analysis. In some embodiments, the readers 100 may transmit this "received monitoring-sensor-tag 120 transmissions" to memory 1803, where processor 1801 (see e.g., FIG. 18) may then access for processing and analysis. In some embodiments, the readers 100 may transmit this "received monitoring-sensor-tag 120 transmissions" to antenna-interface 1115; wherein antenna-interface 1115 may route (transmit) to memory 1803, where processor 1801 (see e.g., FIG. 18) may then access for processing and analysis. In some embodiments, the readers 100 may transmit this "received monitoring-sensor-tag 120 transmissions" to antenna-interface 1115; wherein antenna-interface 1115 may route (transmit) to processor 1801 (see e.g., FIG. 18) which may then access the said "received monitoring-sensor-tag 120 transmissions" for processing and analysis. In some embodiments, the readers 100 may pre-process some of "received monitoring-sensor-tag 120 transmissions" via an electric circuit of the reader 100 prior to transmission to: antenna-interface 1115, memory 1803, or processor 1801.

Overall broadly speaking, calibration may mean adjusting precision based on known facts (i.e., known data and/or known information). For example, positioning a reference tag at a known distance before start of using a device may permit fine-tuning of the system. For example, it may be known what electromagnetic (EM) wave phase delay should be at a distance of 1 m (i.e., one meter). The extra phase which may be measured may be due to phase distortion, introduced by tag, antenna, reader 100, cable and; may be filtered out (accounted for) thanks to a calibration process.

It is natural that in the specific system 1800 there may be a need for more than one calibration method based on the type of monitoring-sensor-tags 120, readers 100, antennas 110 as well as other elements of the system 1800. Below, for example, may describe one such possible calibration method 1600. In some embodiments, FIG. 16 may depict a flow diagram illustrating a method 1600 for calibrating the system 1800 (see FIG. 18) based on one or more reference-sensor-tags 1102. In some embodiments, FIG. 16 may depict a flow diagram illustrating a method 1600 for calibrating one or more readers 100. In some embodiments, step 1530 of method 1500 shown in FIG. 15 may be method 1600. That is, in some embodiments, method 1600 shown in FIG. 16 may depict how step 1530 may proceed. In some embodiments, method 1600 may comprise steps: step 1680, step 1681, step 1682, and step 1683.

Figure 16:
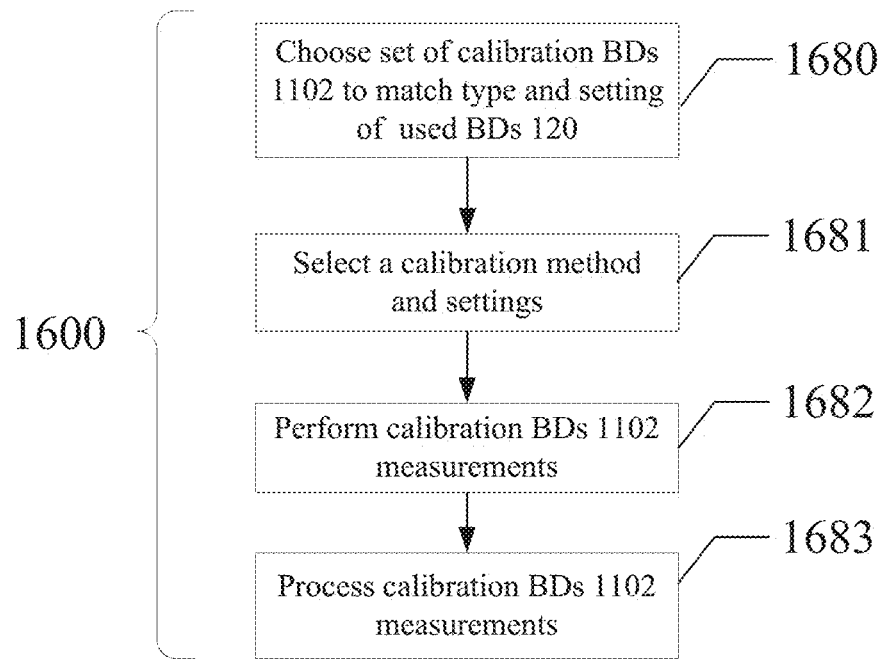
FIG. 16 may depict a flow diagram illustrating a method for calibrating a system (shown in FIG. 18) based on one or more reference-sensor-tags.

Discussing FIG. 16, in some embodiments, step 1680 may choose a set of reference-sensor-tags 1102 to match a type and an environmental setting of used (or to be used) monitoring-sensor-tags 120. As noted below, in order to filter out possible measurement distortions from the measurements and to fine-tune the system 1800, the type of the reference-sensor-tags 1102 needs to match or to be as close as possible to the type of monitoring-sensor-tag 120.

Continuing discussing FIG. 16, in some embodiments, step 1681 may be a stage at which a calibration method and its settings are chosen based on the specific system 1800 in place, and based on the user-provided options and preferences. For example, and without limiting the scope of the present invention, a specific range of the reader 100 frequencies may be selected, reader 100 transmitting power may be adjusted, reader 100 transmitting mode can be selected, among other settings, during step 1681.

Determining range, using one of the techniques above, such as phase difference of arrival (PDoA), is based on measuring the phase difference of arrival $\varphi$ of the electromagnetic (EM) wave emitted by reader 100, wirelessly (e.g., backscattered) by a given monitoring-sensor-tag 120, and received by reader 100, according to the configuration of FIG. 14A, as an example.

Continuing discussing FIG. 16, in some embodiments, step 1682 may perform phase measurements of monitoring-sensor-tags 120. For each reader 100 number $\alpha_j$ take N measurements of the phase $\varphi(f_s)_k^{\alpha_j, c_i}$ (where k=1 . . . N) between $\alpha_j$ and each reference-sensor-tag 1102 number $c_i$ allocated to reader 100 number $\alpha_j$ in the software settings. The said phase measurements may be taken at a number of different frequencies $f_s$ where s=1 . . . M.

In some embodiments, instead of performing a predefined number N of phase measurements, a number of phase measurements may be limited by the number at which the mathematical variance of $\varphi(f_s)_k^{\alpha_j, c_i}$ falls below a predetermined value for each pair $\alpha_j$, $c_i$ and each frequency $f_s$ where s=1 . . . M.

In some embodiments, the phase difference of arrival $\varphi$ between the electromagnetic (EM) wave emitted by reader 100, wirelessly (e.g., backscattered) by a given monitoring-sensor-tag 120, and received by reader 100, according to the configuration of FIG. 14A may be expressed as:

$$\varphi(f_s)_k^{\alpha_j, c_i} = \varphi_{wave} + \varphi_{reader} + \varphi_{tag}$$

Where:
$\varphi_{wave}$ is the phase difference due to the propagation of the emitted electromagnetic (EM) wave; $\varphi_{reader}$ is the phase difference introduced by but not limited to reader 100, antenna 110, and cables connecting reader 100 and antenna 110; and $\varphi_{tag}$ is the phase difference introduced by a given monitoring-sensor-tag 120.

Continuing discussing FIG. 16, in some embodiments, step 1683 calibration of reference-sensor-tags 1102 measurements may be processed as follows:

For each reader 100 number $\alpha_j$ and each reference-sensor-tag 1102 number $c_i$ allocated to the reader 100, calculate:

Mean $\bar{\varphi}(f_s)_k^{\alpha_j, c_i}$ of the phase measurements $\varphi(f_s)_k^{\alpha_j, c_i}$ between $\alpha_j$ and $c_i$, k=1 . . . N for each frequency $f_s$ where s=1 . . . M;

Difference $\varphi_{delta}(f_s)_k^{\alpha_j, c_i}$ between the calculated phase $\varphi_{wave}(f_s)_k^{\alpha_j, c_i}$ and $\bar{\varphi}(f_s)_k^{\alpha_j, c_i}$ where:

$$\varphi_{delta}(f_s)_k^{\alpha_j, c_i} = \varphi_{wave}(f_s)_k^{\alpha_j, c_i} - \bar{\varphi}(f_s)_k^{\alpha_j, c_i} \tag{20}$$

where $\varphi_{wave}(f_s)_k^{\alpha_j, c_i}$ the phase difference, due to the propagation of the emitted electromagnetic (EM) wave, mentioned above, is calculated as:

$$\varphi_{wave}(f_s)^{\alpha_j, c_i} = \left(\frac{4\pi r_{j,i} f_s}{c}\right) \mod 2\pi$$

where c is the speed of light constant, mod is modulo (remainder) function, and as $r_{j,i}$ is the known distance (range) from reader 100 number $\alpha_j$ and reference-sensor-tag 1102 number $c_i$.

Thus, the correction $\varphi_{delta}(f_s)_k^{\alpha_j, c_i}$ to be applied to the reported phase $\varphi(f_s)_k^{\alpha_j, c_i}$ has been calculated.

Figure 17:
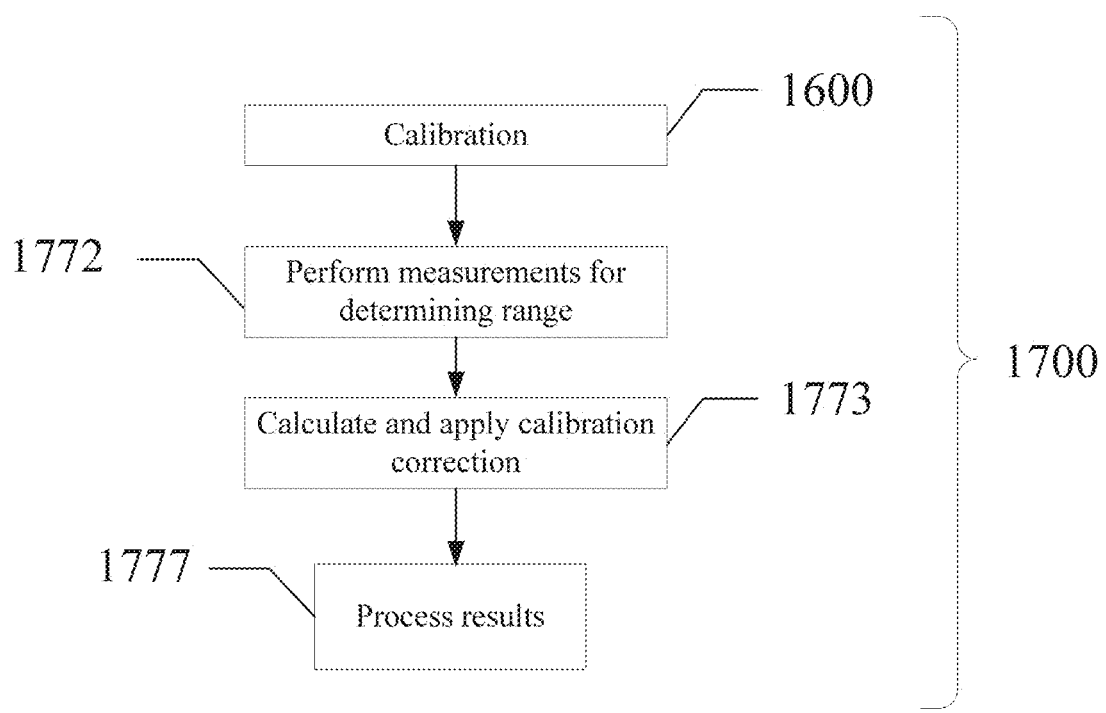
FIG. 17 may depict a flow diagram for determining location of one or more monitoring-sensor-tags associated with a material-of-interest.

FIG. 17 may depict a flow diagram for determining location of one or more monitoring-sensor-tags 120 associated with (e.g., attached to) the given material-of-interest. FIG. 17 may depict method 1700. In some embodiments, method 1700 may be a method for determining location of one or more monitoring-sensor-tags 120 associated with (e.g., attached to) the given material-of-interest. In some embodiments, method 1700 may provide additional details of step 1534 from FIG. 15.

For example, and without limiting the scope of the present invention, method 1700 may be employed to determine locations of one or more monitoring-sensor-tags 120 located in or on: dental-filling 1001 (FIG. 10A); root-canal-cavity 1003 (FIG. 10B); root-canal-post 1004 (FIG. 10B); dental-crown 1005 (FIG. 10B); dental-implant 1007 (FIG. 10C); implant-post 1008 (FIG. 10C); and/or the like.

For example, and without limiting the scope of the present invention, method 1700 may be employed to determine locations of one or more monitoring-sensor-tags 120 located in or on the given material-of-interest in the systems of FIG. 13A, FIG. 13B, or FIG. 13C.

In some embodiments, method 1700 may comprise method 1600, step 1772, step 1773, and step 1777. See e.g., FIG. 17.

Continuing discussing FIG. 17, in some embodiments, method 1700 may comprise method 1600 as discussed above, which may be a calibration method. In some embodiments, method 1700 may begin with method 1600.

Continuing discussing FIG. 17, in some embodiments, method 1700 may comprise step 1772. In some embodiments, successful calibration under method 1600 may then transition into step 1772. In some embodiments, step 1772 may be a step of obtaining measurements for determining ranges (distance) of the one or more monitoring-sensor tags 120 between readers 100. As mentioned before, one of well-known techniques for location and range (distance) measurement may include phase difference of arrival (PDoA); received signal strength indicator (RSSI); time of arrival (ToA); time of flight (ToF); and/or time difference of arrival (TDoA). For example, for the phase difference of arrival (PDoA) technique, the measurements may include phase difference of arrival. In some embodiments, such range measuring may be between each operational monitoring-sensor tag 120 selected from the one or more monitoring-sensor tags 120; and from a predetermined number (quantity) of operational readers 100. In some embodiments, the predetermined number (quantity) of operational readers 100 may be selected by a user engaging with software settings; wherein the software may be non-transitorily stored in memory 1803. In some embodiments, the predetermined number (quantity) of operational readers 100 may be those readers 100 closest to the given monitoring-sensor-tag 120. In some embodiments, the predetermined number (quantity) of operational readers 100 may be readers 100 determined under method 1600. In some embodiments of step 1772, measurements for determining of the range (distance) between each monitoring-sensor-tag 120 to each reader 100 from the group of readers 100 allocated to the given monitoring-sensor-tag 120 may be performed. In some embodiments, measurements of phase difference of arrival (PDoA) $\varphi(f_s)_k^{\alpha_j,s_u}$ from each monitoring-sensor-tag 120 number $s_u$ to each reader 100 number $\alpha_j$ in its vicinity may be performed. In some embodiments, "in its vicinity" may be dependent upon a frequency (or a wavelength) of wireless communication utilized by antennas 110 and/or antennas 130 for a given application (for a given use). For example, and without limiting the scope of the present invention, when radio waves may be used by antennas 110 and/or antennas 130, then "in its vicinity" may be selected from the group of 1 mm (millimeter) to 50 meters or less. In some embodiments, for each reader 100 number $\alpha_j$ step 1772 may take M measurements of phase difference of arrival (PDoA) $\varphi(f_s)_k^{\alpha_j,s_u}$ (where k=1 . . . M) between reader 100 number $\alpha_j$ and each monitoring-sensor-tag 120 number $s_u$ allocated to reader 100 number $\alpha_j$. The said phase measurements may be taken at a number of different frequencies $f_s$ where s=1 . . . L. In some embodiments, as noted above, allocation of readers 100 to monitoring-sensor-tags 120 may be predetermined and/or set by a user engaging with the software setting of the software.

Continuing discussing FIG. 17 and step 1772 in particular, in some embodiments, the above range phase difference of arrival (PDoA) $\varphi(f_s)_k^{\alpha_j,s_u}$ measurements may be processed by calculating a mean and a variance for each of the frequencies $f_s$ where s=1 . . . L. For example, and without limiting the scope of the present invention, for each reader 100 number $\alpha_j$ and each monitoring-sensor-tag 120 number $s_u$ allocated to that reader 100, calculate for each of the frequencies $f_s$ where s=1 . . . L:

- Mean $\overline{\varphi}(f_s)_k^{\alpha_j,s_u}$ of the phase measurements $\varphi(f_s)_k^{\alpha_j,s_u}$ between $\alpha_j$ and $s_u$, k=1 . . . M; and
- Variance $\sigma^2(\varphi(f)_k^{\alpha_j,s_u})$ of the phase measurements $\varphi(f_s)_k^{\alpha_j,s_u}$ between $\alpha_j$ and $s_u$, k=1 . . . M.

Continuing discussing FIG. 17, in some embodiments, method 1700 may comprise step 1773. In some embodiments, step 1773 may follow step 1772. In some embodiments, step 1773 may be a step of applying calibration-based corrections (adjustments) to the measurements and/or calculations of step 1772. For example, and without limiting the scope of the present invention, if monitoring-sensor-tags 120 locations have not been determined (calculated), then step 1773 may apply correction $\varphi_{delta}(f_s)_k^{\alpha_j,c_i}$ calculated in equation (20) during described calibration process of method 1600, to the phase $\overline{\varphi}(f_s)_k^{\alpha_j,s_u}$ calculated above, such a corrected phase may be:

$$\varphi_{corrected}(f_s)_k^{\alpha_j,s_u} = \overline{\varphi}(f_s)_k^{\alpha_j,s_u} + \varphi_{delta}(f_s)_k^{\alpha_j,c_i} \quad (21)$$

wherein the reference-sensor-tags 1102 number $c_i$ in equation (21) may be the one closest to reader 100 number $\alpha_j$. In some embodiments, the reference-sensor-tags 1102 number $c_i$ in equation (21) may be the one closest in type to monitoring-sensor-tag 120 number $s_u$ In some embodiments, reader 100 may emit electromagnetic (EM) waves at a number of pre-set frequencies $f_s$. It is well known and shown that it is possible to range estimate (distance) $h_k^{\alpha_j,s_u}$ between each reader 100 number $\alpha_j$ and each monitoring-sensor-tag 120 number $s_u$ by:

$$h^{\alpha_j,s_u} = \frac{c}{4\pi} \frac{\Delta \varphi^{\alpha_j,s_u}}{\Delta f^{\alpha_j,s_u}} \quad (22)$$

where $\Delta\ddot{o}_k^{\alpha_j,s_u}$ is a phase difference between two values of phase $\varphi_{corrected}(f_s)_k^{\alpha_j,s_u}$ corresponding to two different frequencies from the set of frequencies $f_s$, and $\Delta f_k^{\alpha_j,s_u}$ is the difference between the said two different frequencies. In some embodiments, equation (22) is used to calculate the range estimate (distance) $h_k^{\alpha_j,s_u}$ between each reader 100 number $\alpha_j$ and each monitoring-sensor-tag 120 number $s_u$. Continuing discussing FIG. 17, in some embodiments, method 1700 may comprise step 1777. In some embodiments, step 1777 may follow step 1773. In some embodiments, step 1777 may be a step of (non-transitory) saving determined (calculated) locations for the one or more monitoring-sensor-tags 120 to memory 1803.

Figure 18:
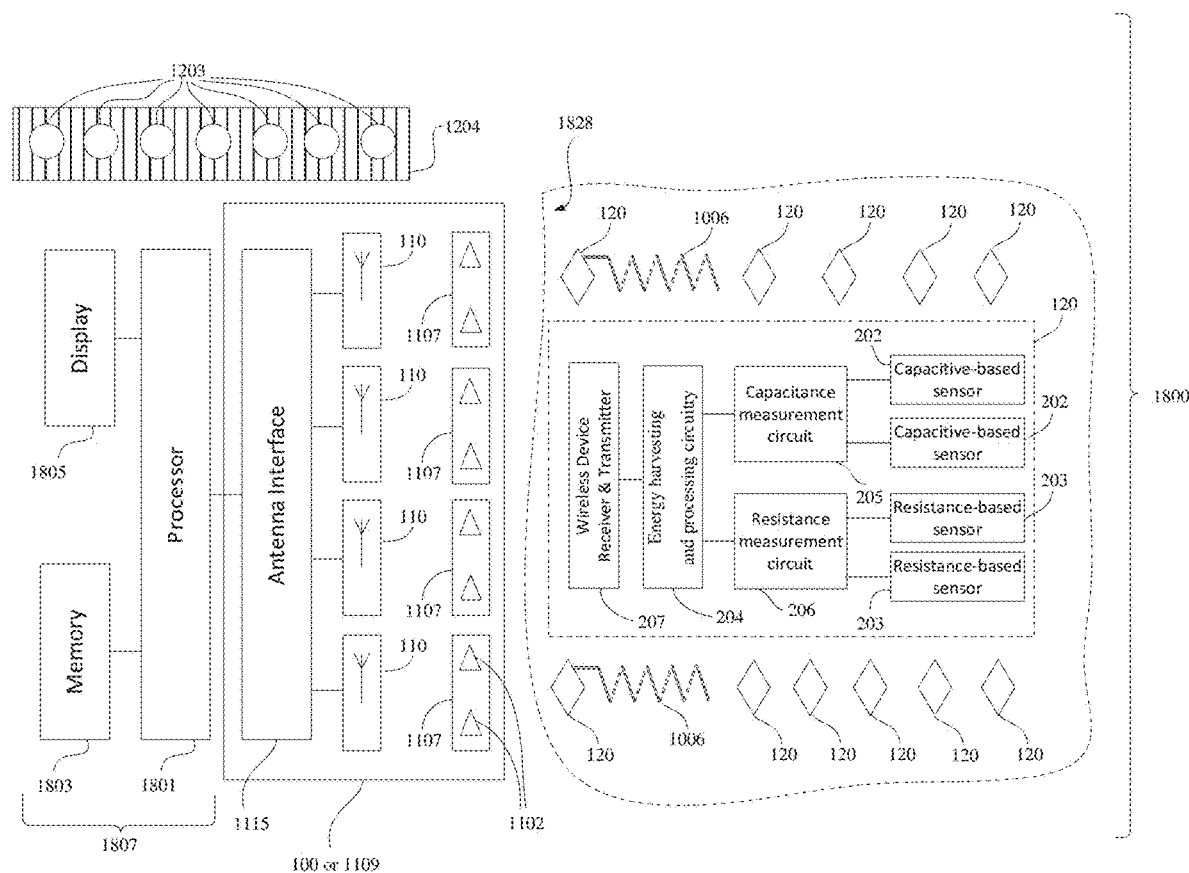
FIG. 18 may depict a block diagram of a device, a reader, a processor, memory, a display, a position-reference-member, and a material-of-interest with one or more monitoring-sensor-tags.

Note, in some embodiments, calculations carried out in methods 1500, 1600, and/or 1700 may be carried out by processor 1801 (see e.g., FIG. 18).

FIG. 18 may depict a block diagram of reader 100 (or of reader-and-calibration-member 1109), processor 1801, memory 1803, a display 1805, a position-reference-member 1204, and a material-of-interest 1828 with one or more monitoring-sensor-tags 120. In some embodiments, FIG. 18 may depict a system 1800 for non-invasive monitoring of material-of-interest 1828 with one or more monitoring-sensor tag 120 using one or more readers 100 (or using at least one reader-and-calibration-member 1109 with one or more readers 100).

Continuing discussing FIG. 18, in some embodiments, system 1800 may comprise one or more monitoring-sensor-tags 120 and one or more readers 100. In some embodiments, the one or more readers 100 and the one or more monitoring-sensor-tags 120 may be in wireless communications with each other.

Continuing discussing FIG. 18, the one or more monitoring-sensor-tags 120 may be as discussed previously above for monitoring-sensor-tags 120. For example, and without limiting the scope of the present invention, the one or more monitoring-sensor-tags 120 may be "attached to" material-of-interest 1828, wherein "attached to" has been described above.

Continuing discussing FIG. 18, the one or more readers 100 may be as discussed previously above for readers 100. In some embodiments, each of the one or more readers 100 may comprise one or more second-antennas 110; whereas a term of "first-antennas 130" may be antennas of the one or more monitoring-sensor-tags 120. In some embodiments, the one or more readers 100 using their one or more second-antennas 110 may transmits electromagnetic (EM) radiation (e.g., radio waves) of a predetermined characteristic. Such a transmission may be directed to the one or more monitoring-sensor-tags 120, specifically to their first-antennas 130. Such that first-antennas 130 (of the one or more monitoring-sensor-tags 120) may receive this electromagnetic (EM) radiation of the predetermined characteristic as an input. In some embodiments, this input may cause the at least one electric circuit 140 (of the one or more monitoring-sensor-tags 120) to take the one or more readings from the at least one sensor (e.g., 202 and/or 203); and to then transmit the one or more readings using the first-antennas 130 back to the one or more second-antennas 110 of the one or more readers 100. In some embodiments, at least one of the second-antennas 110 selected from the one or more second-antennas 110 then receives the one or more readings; and the one or more readers 100 or a device 1807 in communication with the one or more readers 100 may then use the one or more readings to determine a "current state" (as them term has been discussed previously) of material-of-interest 1828.

In some embodiments, material-of-interest 1828 shown in FIG. 18 may be representative of any materials-of-interest discussed previously herein, such as, but not limited to: dental-filling 1001; root-canal-post 1004; dental-crown 1005; an article implantable within a body of an organism; the article attachable to the body of the organism; specific tissue of the organism; and/or the construction member. As noted, in some embodiments, the article may be selected from: a medical device; a tissue graft; a bone graft; an artificial tissue; a bolus with time-release medication; and/or a medication. As noted, in some embodiments, the medical device may be dental-implant 1007 and/or implant-post 1008. As noted, in some embodiments, the organism may be a human, such as patient 1328. As noted, in some embodiments, the tissue may be tooth 1000, gum 1002, and/or root-canal-cavity 1003 and/or any other tissue of the organism.

Continuing discussing FIG. 18, in some embodiments, system 1800 may further comprise device 1807 that may be in communication with the one or more readers 100 and that may then use the one or more readings to determine a current state of material-of-interest 1828. In some embodiments, this device 1807 may comprise processor 1801 and memory 1803. In some embodiments, device 1807 may be a computing device and/or a computer. In some embodiments, processor 1801 may be in communication with the one or more second-antennas 110. In some embodiments, disposed between processor 1801 and the one or more second-antennas 110 may be antenna-interface 1115, as that component has been discussed previously. In some embodiments, antenna-interface 1115 may be in communication with both the one or more second-antennas 110 and processor 1801. In some embodiments, memory 1803 may be in communication with processor 1801. In some embodiments, memory 1803 may be in communication with processor 1801 as well as with antenna-interface 1115 and/or the one or more second-antennas 110. In some embodiments, non-transitorily stored in memory 1803 may be code (i.e., the software) for instructing processor 1801 how to interpret the current state by processing the one or more readings received at the at least one of the second-antennas 110 selected from the one or more second-antennas 110. In some embodiments, data; information, the one or more readings; measurement results; calculation results; the "additional information"; and/or the like may be non-transitorily stored in memory 1803.

Note, in some embodiments, instead of a separate device 1807 as noted above, each reader 100 may itself comprise antenna-interface 1115, processor 1801, and memory 1803. Whereas, in other embodiments, device 1807 may be integrated with the one or more readers 100.

In some embodiments, memory 1803 may store (hold) information on a volatile or non-volatile medium, and may be fixed and/or removable. In some embodiments, memory 1803 may include a tangible computer readable and computer writable non-volatile recording medium, on which signals are stored that define a computer program (i.e., the code or the software) or information to be used by the computer program. The recording medium may, for example, be hard drive, disk memory, flash memory, and/or any other article(s) of manufacture usable to record and store information (in a non-transitory fashion). In some embodiments, in operation, processor 1801 may cause(s) data (such as, but not limited to, information, the one or more readings; measurement results; calculation results; the "additional information"; and/or the like) to be read from the nonvolatile recording medium into a volatile memory (e.g., a random access memory, or RAM) that may allow for more efficient (i.e., faster) access to the information by processor 1801 as compared against the nonvolatile recording medium. Memory 1803 may be located in device 1807 and in communication with processor 1801. See e.g., FIG. 18. In some embodiments, processor 1801 may manipulate(s) the data and/or information within integrated circuit memory (e.g., RAM) and may then copy the data to the nonvolatile recording medium (e.g., memory 1803) after processing may be completed. A variety of mechanisms are known for managing data movement between the nonvolatile recording medium and the integrated circuit memory element, and the invention is not limited to any mechanism, whether now known or later developed. The invention is also not limited to a particular processing unit (e.g., processor 1801) or storage unit (e.g., memory 1803).

Continuing discussing FIG. 18, in some embodiments of system 1800 the one or more second-antennas 110 may have known (or determinable) positional locations. As previously discussed, locations of the one or more readers 100 (or locations of the second-antennas 110) may be determined via wireless communications between the one or more readers 100 (via their one or more second-antennas 110) and one or more reference-sensor-tags 1102 (via their at least one fourth-antennas). And/or as previously discussed, locations of the one or more readers 100 (or locations of the second-antennas 110) may be determined via wireless communications between the one or more readers 100 (via their one or more second-antennas 110) and one or more position-reference-tag 1203 (via their at least one third-antennas). That is in some embodiments, system 1800 may further comprise one or more reference-sensor-tags 1102 and/or system 1800 may further comprise one or more position-reference-tag 1203. See e.g., FIG. 18. As discussed previously, reference-sensor-tags 1102 may be housed in reference-housing-member 1107. As discussed previously, reference-sensor-tags 1102 may be fixed with respect to second-antennas 110; even in embodiments where the second-antennas 110 may be translating with respect to origin 1325 (e.g., the systems of FIG. 13A and of FIG. 13C) (because the reader-and-calibration-member 1109 housing the second-antennas 110 may be translating together as a unit). As previously discussed, in some embodiments, position-reference-tags 1203 may be housed in position-reference-member 1204. As previously discussed, in some embodiments, position-reference-tags 1203 and position-reference-member 1204 may be stationary; i.e., fixed with respect to an origin 1325; even when second-antennas 110 may be translating as shown in FIG. 13A and in FIG. 13C (because the reader-and-calibration-member 1109 housing the second-antennas 110 may be translating while position-reference-member 1204 remains stationary). Note, in some embodiments of system 1800, position-reference-member 1204 (with position-reference-tags 1203) may be optional or not included. In any event, because locations (positions) of second-antennas 110 (or readers 100) may be determinable and thus known; then processor 1801 running the code (i.e., the software or the computer program) non-transitorily stored in memory 1803 may be instructed by that code, using these known positional locations of the one or more second-antennas 110 and using communications from the first-antennas 130, may then determine (calculate) positional locations of the one or more monitoring-sensor-tags 120.

Continuing discussing FIG. 18, in some embodiments, reader 100 may comprise the one or more second-antennas 110; one or more reference-sensor-tags 1102; and antenna-interface 1115. In some embodiments, the one or more reference-sensor-tags 1102 may be fixed relative to the one or more second-antennas 110. In some embodiments, reader 100 may comprise one or more reference-housing-member 1107; wherein each reference-housing-member 1107 may comprise the one or more reference-sensor-tags 1102. Thus, reader 100 may function as reader-and-calibration-member 1109; which is why reader 100 in FIG. 18 is also noted as reader-and-calibration-member 1109. In some embodiments, one or more second-antennas 110 may have known (or determinable) positional locations relative to: a known origin (e.g., origin 1325), known reference-sensor-tags 1102 locations, and/or known position-reference-tag 1203 locations.

In some embodiments, one or more readers 100 may be disposed within reader-and-calibration-member 1109 and the one or more second-antennas 110 may have known positional locations relative to: a known origin (e.g., origin 1325), known reference-sensor-tags 1102 locations, and/or known position-reference-tag 1203 locations. See e.g., FIG. 11A, FIG. 11B, and FIG. 18.

Figure 19A:
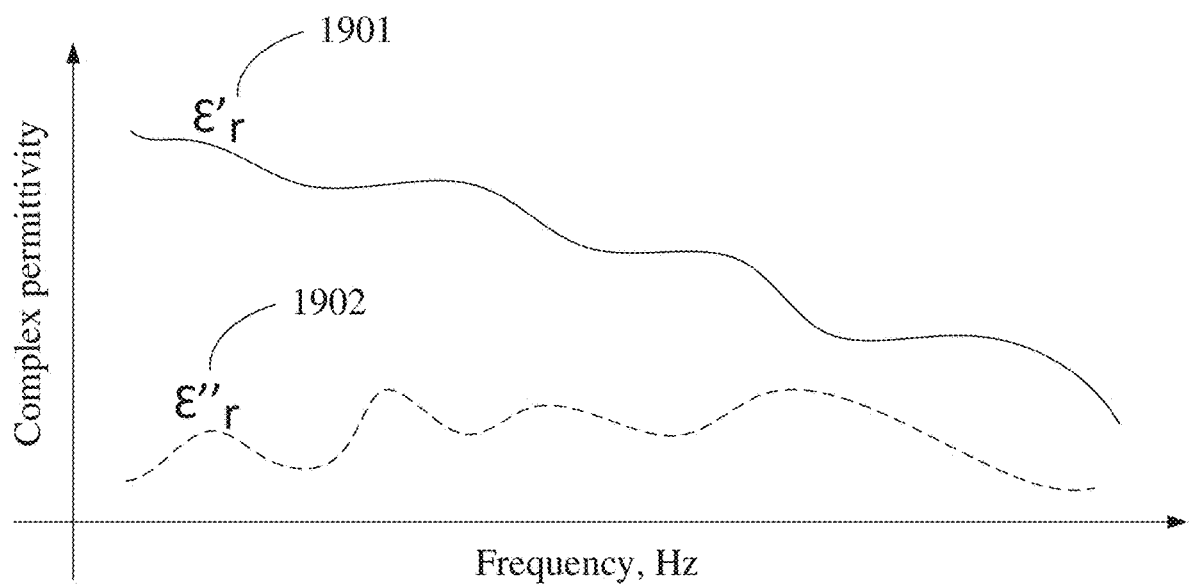
FIG. 19A may depict a graph showing a physical relationship between complex permittivity and changes in frequency.

FIG. 19A may show, in general, how complex permittivity of a given material (including biologic materials) may vary according to changes in frequency. FIG. 19A may show two graphs depicting real and imaginary parts $\varepsilon_r'$ and $\varepsilon_r''$, respectively, of complex permittivity $\overline{\varepsilon}_r$, as a function of alternating current (AC) frequency. In FIG. 19A, real and imaginary parts $\varepsilon_r'$ and $\varepsilon_r''$, respectively, of complex permittivity $\overline{\varepsilon}_r$ may be denoted on the vertical axis; while the frequency may be denoted on the horizontal axis. In FIG. 19A, the real part, $\varepsilon_r'$, may also be denoted by reference numeral 1901. In FIG. 19A, the imaginary part, $\varepsilon_r''$, may also be denoted by reference numeral 1902.

The complex permittivity $\overline{\varepsilon}_r$, which may be referred to as a complex dielectric constant, may be expressed as:

$$\overline{\varepsilon}_r = \varepsilon_r' - \varepsilon_r'' \tag{23}$$

where $\varepsilon_r'$ is a "real" permittivity, $\varepsilon_r''$ is an imaginary permittivity, and j is an imaginary unit.

FIG. 19A demonstrates that in some embodiments, to measure complex permittivity of a given material, then frequency may need to be varied.

It should be noted that the "real" permittivity $\varepsilon_r'$, a real part of complex permittivity $\overline{\varepsilon}_r$, may be referred to as the relative permittivity of the dielectric material $\varepsilon_r$.

Figure 19B:
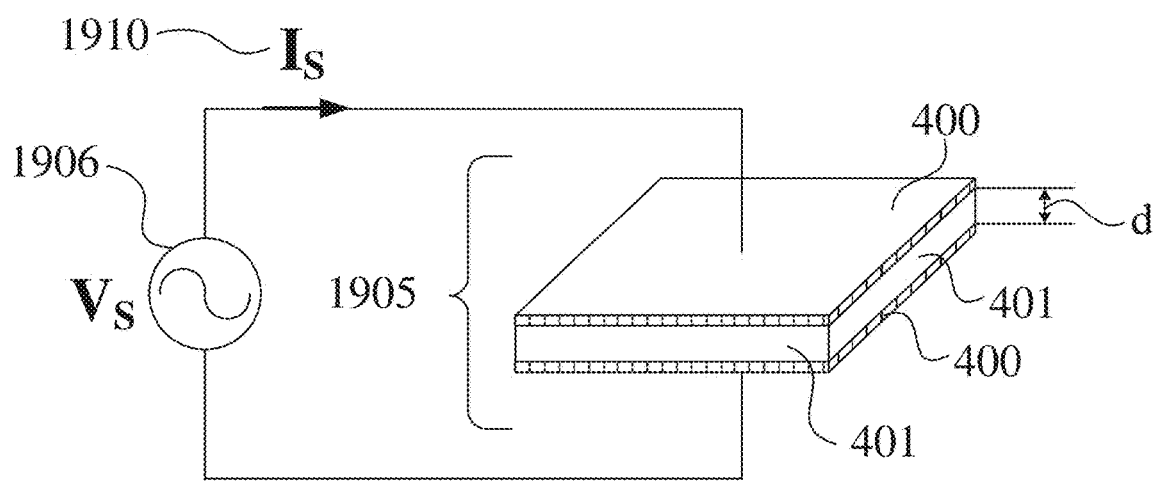
FIG. 19B may depict a perspective view of a capacitor connected to an alternating current (AC) voltage source.

FIG. 19B may be a perspective view of a capacitor 1905 connected to an alternating current (AC) voltage source 1906. Current 1910 may thus flow via capacitor 1905. In some embodiments, this capacitor 1905 may comprise two substantially parallel plates 400 that may be separated by dielectric material 401. In some embodiments, such plates 400 may be separated from each other by a distance of d. In some embodiments, plates 400 may be constructed from substantially conductive materials.

It should be appreciated by those of ordinary skill in the relevant art that one may find current 1910 flowing via capacitor 1905 by:

$$I_s = \frac{V_s}{Z} \tag{24}$$

where $V_s$ is a complex representation of the voltage of the alternating current (AC) voltage source 1906, $I_s$ is a complex representation of current 1910 flowing via capacitor 1905, and Z is complex impedance of capacitor 1905.

Figure 19C:
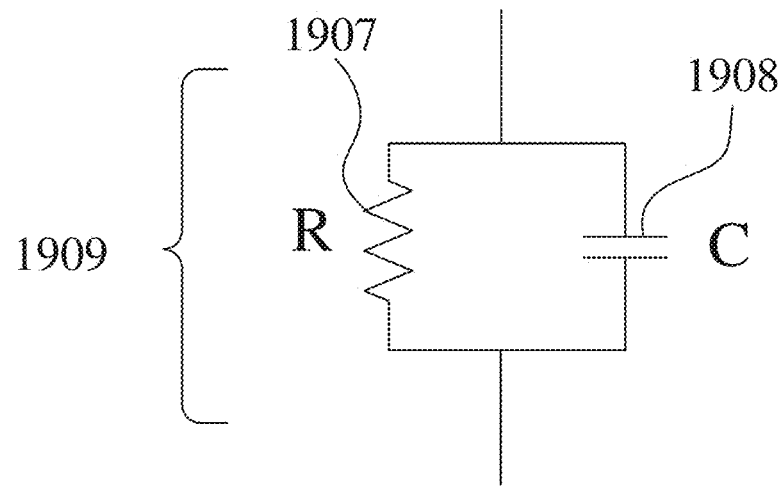
FIG. 19C may depict a schematic view of a capacitor representative circuit.

It should be appreciated by those of ordinary skill in the relevant art that capacitor 1905 may be represented by a number of representative circuits. FIG. 19C may depict a schematic view of a possible capacitor representative circuit 1909 of capacitor 1905 from FIG. 19B. Capacitor representative circuit 1909 may comprise of an ideal resistor 1907 and an ideal capacitor 1908, connected in parallel, see e.g., FIG. 19C.

Figure 19D:
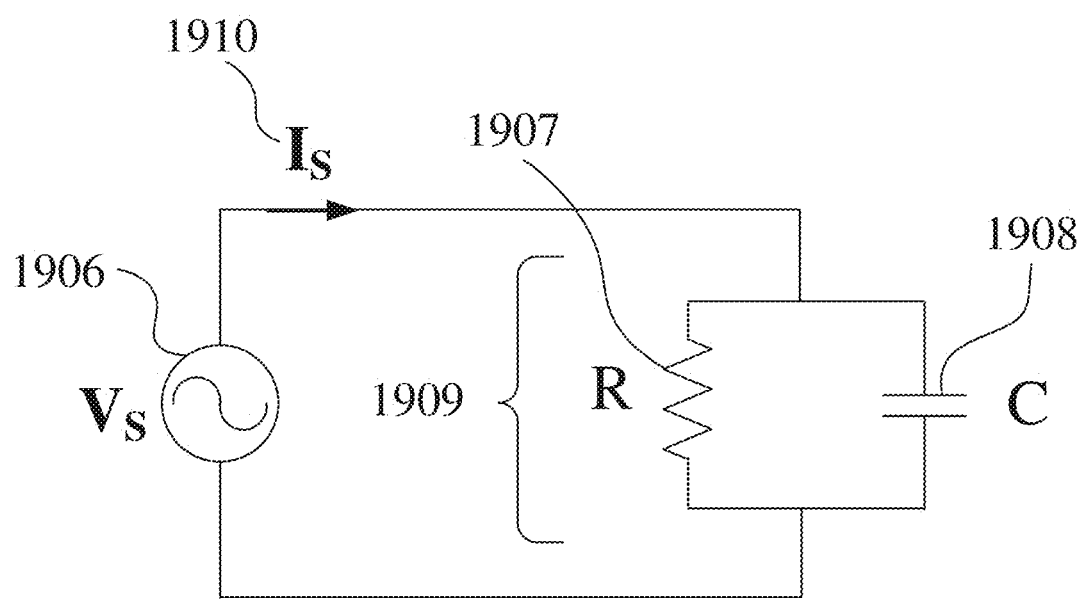
FIG. 19D may depict a schematic view of a capacitor representative circuit connected to an alternating current (AC) voltage source.

FIG. 19D may depict a schematic view of capacitor representative circuit 1909, connected to the alternating current (AC) voltage source 1906.

Complex admittance Y of the capacitor 1905 may be expressed as:

$$Y = \frac{1}{Z} = \frac{j\omega A \varepsilon_0 \overline{\varepsilon}_r}{d} = \frac{j\omega A \varepsilon_0 (\varepsilon_r' - j\varepsilon_r'')}{d} = \frac{j\omega A \varepsilon_0 \varepsilon_r'}{d} + \frac{\omega A \varepsilon_0 \varepsilon_r''}{d} \tag{25}$$

$$Y = \frac{1}{Z} = G + jB = j\omega C + \frac{1}{R} \tag{26}$$

where Z is complex impedance of capacitor 1905, G and B are conductance and susceptance, respectively of capacitor 1905, ω is the angular frequency of the alternating current (AC) voltage source 1906, A is an area of each of the conductive plates 400, d is a width of the dielectric material 401 between the conductive plates 400, $\varepsilon_0 \approx 8.85 \cdot 10^{-12}$ F/m is vacuum permittivity constant, C is the capacitance of the ideal capacitor 1908 and R is the resistance of the ideal resistor 1907.

Based on equations (25) and (26) one may express real and imaginary parts $\varepsilon_r'$ and $\varepsilon_r''$, respectively, via real and imaginary components G and B, respectively, of the complex admittance Y:

$$\varepsilon_r' = \frac{Bd}{\omega A \varepsilon_0} \tag{27}$$

$$\varepsilon_r'' = \frac{Gd}{\omega A \varepsilon_0} \tag{28}$$

Based on equations (25) and (26) one may express real and imaginary parts $\varepsilon_r'$ and $\varepsilon_r''$, respectively, via components C and R, respectively, of the possible representative circuit 1909 of capacitor 1905:

$$\varepsilon_r' = \frac{Cd}{A \varepsilon_0} \tag{29}$$

$$\varepsilon_r'' = \frac{d}{\omega A \varepsilon_0 R} \tag{30}$$

Thus, FIG. 19B, FIG. 19C, and FIG. 19D may show how relatively simple circuits may be employed so that complex permittivity of a given material may be measured. FIG. 19B, FIG. 19C, and FIG. 19D may demonstrate relationships between complex permittivity of a given material and the parameters of the electric elements, such as capacitors comprising the given material. FIG. 19B, FIG. 19C, and FIG. 19D may also demonstrate how complex permittivity of a given material may be expressed via measuring parameters of the electric circuits comprising said capacitor.

Figure 19E:
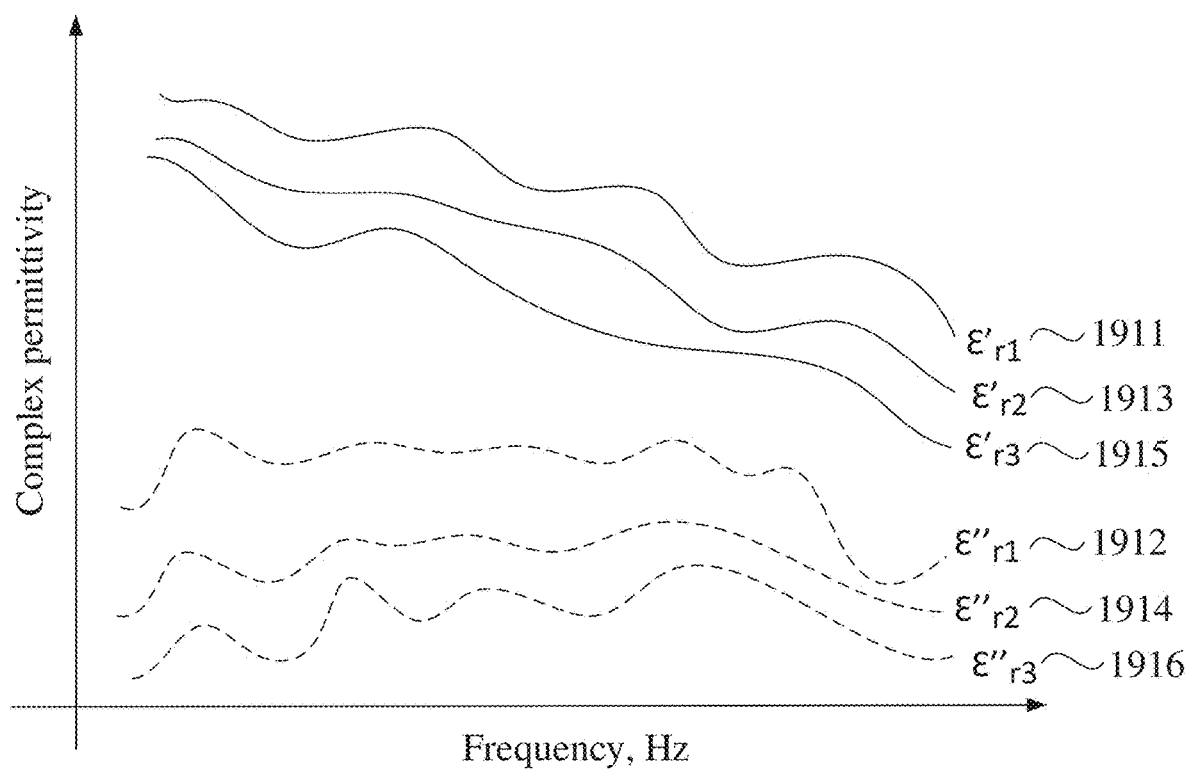
FIG. 19E may show how complex permittivity of a given material (including biologic materials) may vary according to changes in excitation source(s), as well as changes in frequency.

FIG. 19E may show, in general, how complex permittivity of a given material (including biologic materials) may vary according to changes in excitation source as well as changes in frequency. Excitation sources (inputs) may be selected from one or more of: visible light, infrared (IR) light, ultraviolet (UV) light, electromagnetic (EM) radiation, ultrasonic sound, temperature, pH, and/or the like—of predetermined characteristics (e.g., predetermined frequency, wavelength, temperature, etc.). The pairs of complex permittivity values $[\epsilon'_{r1}, \epsilon''_{r1}]$, $[\epsilon'_{r1}, \epsilon''_{r1}]$, $[\epsilon'_{r1}, \epsilon''_{r1}]$ shown in FIG. 19E may depict changes in complex permittivity of the same material under different excitation conditions. For example the graphs 1911, 1912 in FIG. 19E correspond to the pairs $[E'_{r1}, \epsilon''_{r1}]$ may be obtained without excitation sources. The graphs 1913, 1914 in FIG. 19E correspond to the pairs $[\epsilon_2, \epsilon''_{r2}]$ may be obtained when exposing a given material under test with infrared (IR) light of predetermined frequency. While, the graphs 1915, 1916 in FIG. 19E correspond to the pairs $[\epsilon'_{r3}, \epsilon''_{r3}]$ may be obtained when applying infrared (IR) light of yet another frequency to that same given material. A significance of using various predetermined excitation sources, of predetermined characteristics, may be in obtaining a more specific response or a more complete response, which could be then used to identify various conditions of the given material under test better rather than without using excitation sources.

Figure 19F:
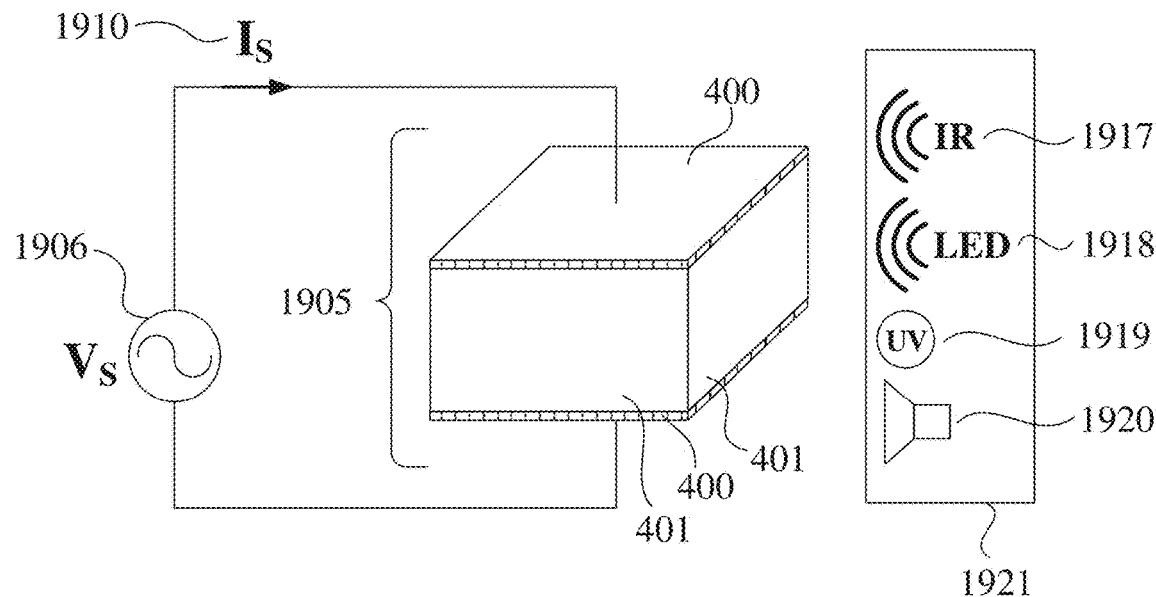
FIG. 19F may be a view of a capacitor connected to an alternating current (AC) voltage source, wherein a dielectric material, disposed between opposing capacitor plates of the capacitor, may be exposed to one or more types of excitation sources, of predetermined characteristics.

FIG. 19F may be a view of a capacitor 1905 connected to an alternating current (AC) voltage source 1906, wherein dielectric material 401, disposed between opposing capacitor plates 400 of capacitor 1905, may be exposed to one or more types of excitation sources, of predetermined characteristics. Current 1910 may flow via capacitor 1905. In some embodiments, this capacitor 1905 may comprise two substantially parallel plates 400 that may be separated by dielectric material 401. In some embodiments, plates 400 may be constructed from substantially conductive materials. In some embodiments dielectric material 401 may be subjected to external excitation sources including, but not limited to, infrared (IR) light source 1917, LED light source 1918, ultraviolet (UV) light source 1919, and/or sonic or ultrasonic sound source 1920—all of predetermined characteristics. As is conventional, LED may be one or more light emitting diodes. LED light source 1919 may emit visible light, IR light, UV light, and/or the like. And 1921 in FIG. 19F may be array-of-excitation-sources 1921 which may house one or more of: IR light source 1917, LED light source 1918, UV light source 1919, and/or sonic or ultrasonic sound source 1920. In some embodiments, in application, dielectric material 401 may be material-of-interest 2201 and/or implant 2431.

Figure 20A:
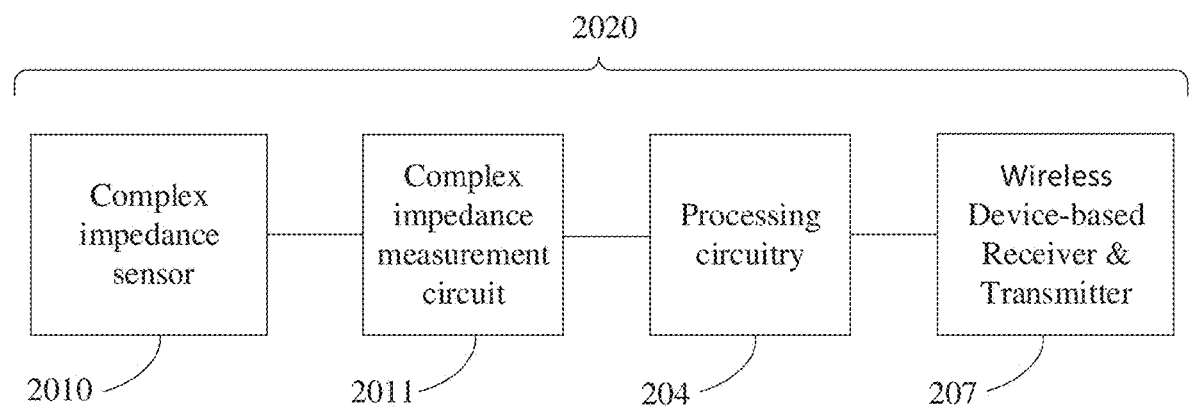
FIG. 20A may depict a schematic view of a complex-monitoring-sensor-tag.

FIG. 20A may depict a schematic block diagram of complex-monitoring-sensor-tag 2020 comprising a complex-impedance-sensor 2010. In some embodiments, any given monitoring-sensor-tag 120 may be replaced with a given complex-monitoring-sensor-tag 2020. In some embodiments, a given complex-monitoring-sensor-tag 2020 may comprise wireless-receiver-and-transmitter 207, processing circuitry 204, complex-impedance-measurement-circuit 2011, and complex-impedance-sensor 2010. In some embodiments, processing circuitry 204 may be in communication with complex-impedance-measurement-circuit 2011. In some embodiments, processing circuitry 204 may be in communication with wireless-receiver-and-transmitter 207. In some embodiments, complex-impedance-measurement-circuit 2011 may be in communication with complex-impedance-sensor 2010.

In some embodiments, complex-impedance-measurement-circuit 2011 may measure the complex impedance of complex-impedance-sensor 2010 to quantify a current state reading of material-of-interest (such as material-of-interest 2201 or of implant 2431) that complex-monitoring-sensor-tag 2020 may be attached to. In some embodiments, complex-impedance-measurement-circuit 2011 may interpret, calculate, and/or measure inputs received at the complex impedance of complex-impedance-sensor 2010 to quantify a current state reading of material-of-interest (such as material-of-interest 2201 or of implant 2431) that complex-monitoring-sensor-tag 2020 may be attached to. In some embodiments, processing circuitry 204 may control complex-impedance-measurement-circuit 2011 and process the one or more readings (the obtained results) received by complex-impedance-sensor 2010, for radio-frequency transmission (or for other electromagnetic transmission); e.g., via wireless-receiver-and-transmitter 207. In some embodiments, wireless-receiver-and-transmitter 207 may transmit the one or more readings (the obtained results) to reader 100. In some embodiments, wireless-receiver-and-transmitter 207 may receive instructions from reader 100 using electromagnetic (EM) waves; such as, but not limited to radio wavelength electromagnetic (EM) waves. See e.g., FIG. 20A.

In some embodiments, monitoring-sensor-tag 120 shown in FIG. 1B may be complex-monitoring-sensor-tag 2020. In such embodiments, complex-monitoring-sensor-tag 2020 may comprise at least one antenna 130 and at least one electric circuit 140; which may be in communication with each other. In some such embodiments, at least one antenna 130 (of complex-monitoring-sensor-tag 2020) may comprise wireless-receiver-and-transmitter 207. In some embodiments, at least one electric circuit 140 (of complex-monitoring-sensor-tag 2020) may comprise processing circuitry 204. In some embodiments, at least one electric circuit 140 (of complex-monitoring-sensor-tag 2020) may comprise processing circuitry 204 and complex-impedance-measurement-circuit 2011. In some embodiments, at least one electric circuit 140 (of complex-monitoring-sensor-tag 2020) may comprise processing circuitry 204, complex-impedance-measurement-circuit 2011, and complex-impedance-sensor 2010. See e.g., FIG. 20A, FIG. 20B, FIG. 25A, FIG. 25B, FIG. 25C, FIG. 25D, and FIG. 1B.

Figure 20B:
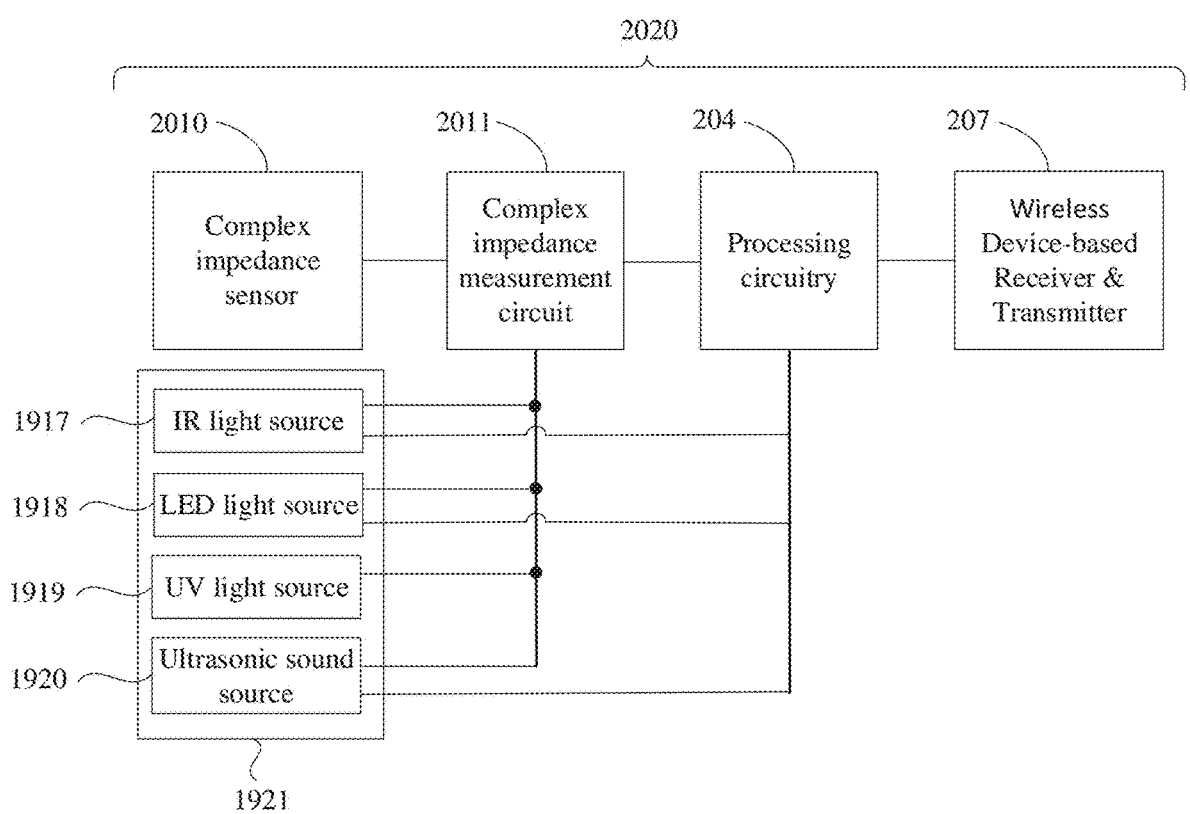
FIG. 20B may depict a schematic block diagram of a complex-monitoring-sensor-tag, similar to that as shown in FIG. 20A, but wherein in FIG. 20B, the complex-monitoring-sensor-tag may further comprise an array-of-excitation-sources, that may comprise one or more excitation sources.

FIG. 20B may depict a schematic block diagram of complex-monitoring-sensor-tag 2020 comprising a complex-impedance-sensor 2010, similar to that as shown in FIG. 20A, but wherein in FIG. 20B, complex-monitoring-sensor-tag 2020 may further comprise array-of-excitation-sources 1921. In some embodiments array-of-excitation-sources 1921 may comprise and/or house one or more: IR light source 1917, LED light source 1918, UV light source 1919, and/or a sonic or ultrasonic sound source 1920; wherein such sources of external excitation emit of a predetermined characteristic (e.g., predetermined frequency/ wavelength). In some embodiments, the one or more external excitation sources of array-of-excitation-sources 1921 may be in electrical communication with one or more of complex-impedance-measurement-circuit 2011 and/or processing circuitry 204. In some embodiments, the one or more external excitation sources of array-of-excitation-sources 1921 may be controlled by one or more of complex-impedance-measurement-circuit 2011 and/or processing circuitry 204. See e.g., FIG. 20B.

In some embodiments, wireless-receiver-and-transmitter 207 may be known as the "at least one antenna" and/or as the "at least one different antenna." In some embodiments, the at least one antenna may be a given wireless-receiver-and-transmitter 207. In some embodiments, the at least one different antenna may be a given wireless-receiver-and-transmitter 207. In some embodiments, the at least one antenna, the at least one different antenna, and/or wireless-receiver-and-transmitter 207 may be a type of excitation source, emitting electromagnetic (EM) radiation (e.g., radio waves) of a predetermined frequency.

In some embodiments, the at least one electric circuit may be processing circuitry 204 and/or complex-impedance-measurement-circuit 2011. In some embodiments, the at least one different electric circuit may be processing circuitry 204 and/or complex-impedance-measurement-circuit 2011.

In some embodiments, the at least one sensor may be a given complex-impedance-sensor 2010. In some embodiments, the at least one different sensor may be a given complex-impedance-sensor 2010.

Figure 21A:
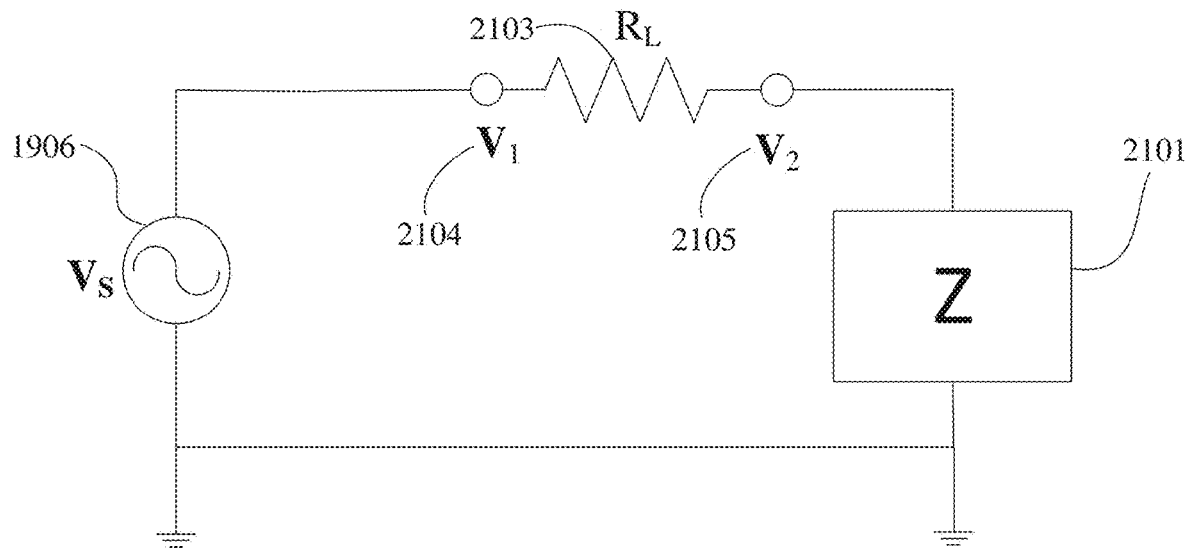
FIG. 21A may depict a schematic view of an example of measuring complex impedance using an alternating AC voltage source.

FIG. 21A may depict a schematic block diagram of a resistor 2103 with resistance $R_L$ and a load 2101 with complex impedance Z connected serially to the alternating current (AC) voltage source 1906. It should be appreciated by those of ordinary skill in the relevant art that one may find the value of the complex impedance Z by:

$$Z = R_L \frac{V_2}{V_1 - V_2} \tag{31}$$

where $V_1$ is a complex representation of the voltage of the alternating current (AC) voltage source 1906 measured at point 2104 and $V_2$ is a complex representation of the voltage across the load 2101 measured at point 2105. In some embodiments, point 2104 and point 2105 may be disposed at opposite sides of resistor 2103. Thus, FIG. 21A may depict a circuit where complex impedance may be determined.

Figure 21B:
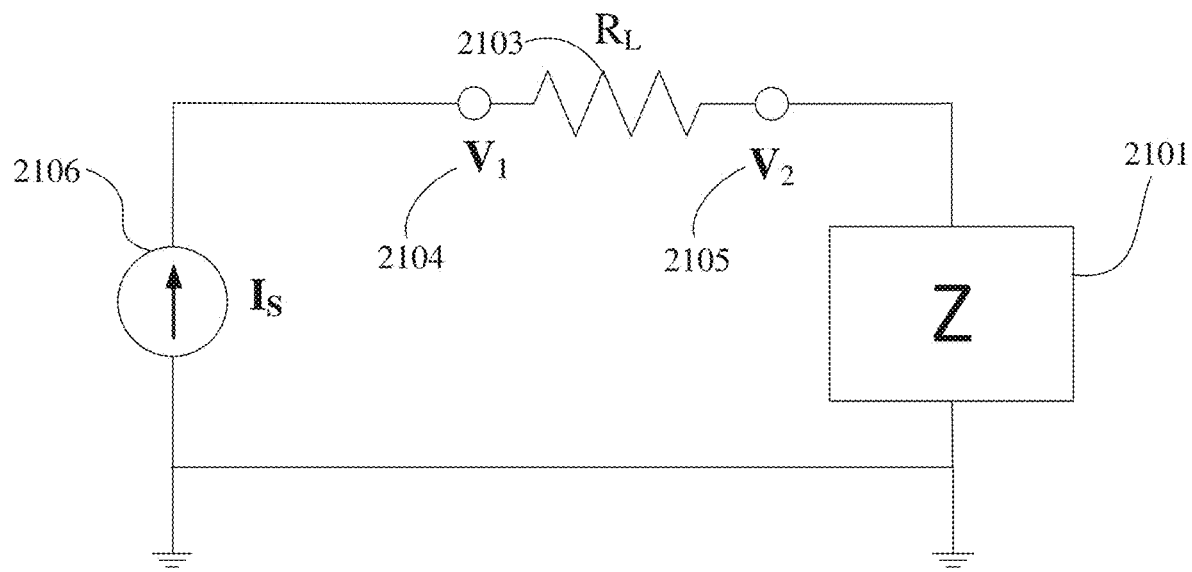
FIG. 21B may depict a schematic view of an example of measuring complex impedance using an alternating AC current source.

FIG. 21B may depict a schematic block diagram of resistor 2103 with resistance $R_L$ and with load 2101 with complex impedance Z connected serially to an alternating current (AC) current source 2106. The value of the complex impedance Z may be determined using equation (31) noted above. Thus, FIG. 21B may depict a circuit where complex impedance may be determined.

Basic techniques for measuring complex impedance or complex permittivity may be understood in the relevant art. See e.g., J. Walworth, "Measuring complex impedances at actual operating levels," Electronics, 47(15), pp. 117-118, 1974; and see also R. H. Johnson, N. M. Pothecary, M. P. Robinson, A. W. Preece and C. J. Railton, "Simple non-invasive measurement of complex permittivity," in Electronics Letters, vol. 29, no. 15, pp. 1360-1361, 22 Jul. 1993.

Figure 22A:
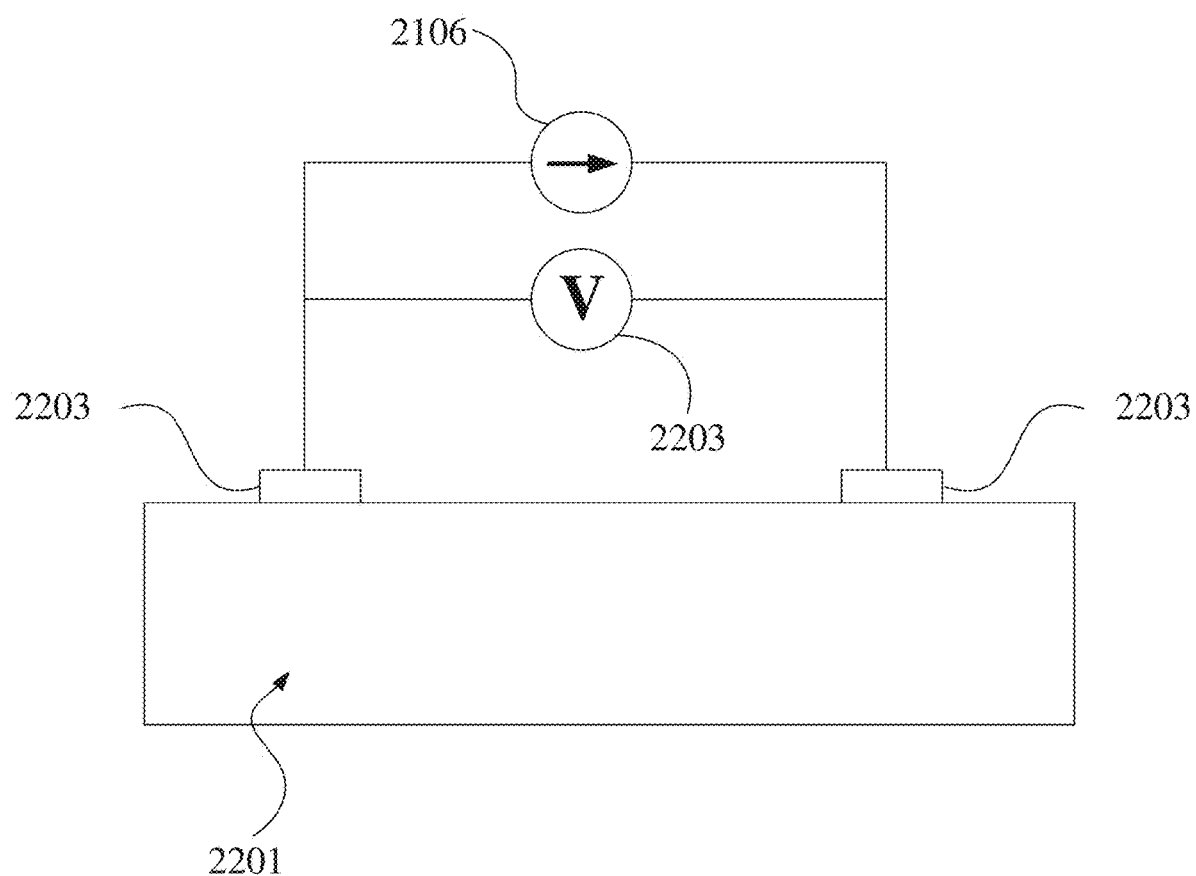
FIG. 22A may depict a schematic view of an example of a two electrode electrochemical impedance spectroscopy (EIS) application.

FIG. 22A may depict a schematic view of an example of a two electrode electrochemical impedance spectroscopy (EIS) application. FIG. 22A may depict a schematic block diagram of a two-electrode complex impedance measuring technique using alternating current (AC) current source 2106 and two electrodes 2203 attached to material-of-interest 2201. Voltage meter 2205 measures complex voltage across the two electrodes 2203. In some embodiments, material-of-interest 2201 may be at least a portion of tissue (e.g., skin) or a cell of patient 1328.

Figure 22B:
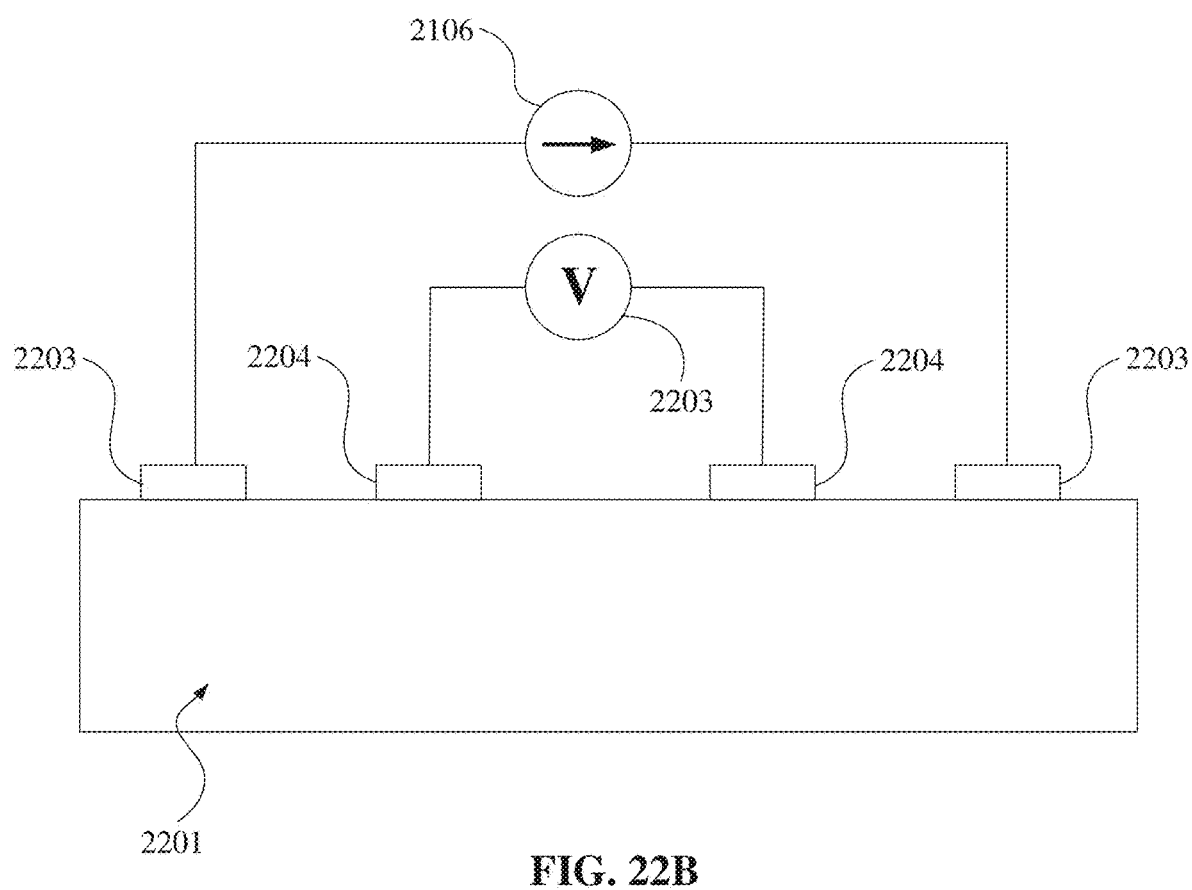
FIG. 22B may depict a schematic view of an example of a four electrode electrochemical impedance spectroscopy (EIS) application.

FIG. 22B may depict a schematic view of an example of a four electrode electrochemical impedance spectroscopy (EIS) application. FIG. 22B may depict a schematic block diagram of a four-electrode complex impedance measuring technique using alternating current (AC) current source 2106, two electrodes 2203 attached to the material-of-interest 2201, and another two electrodes 2204 attached to the material-of-interest 2201. Voltage meter 2205 measures complex voltage across the two electrodes 2204.

Basic techniques for measuring impedance using two or four electrodes may be understood in the relevant art. See e.g., Millard, S. G. "Reinforced concrete resistivity measurement techniques," In: Proceedings of Institution of Civil Engineers, Part 2: Research and Theory, pp. 91:71-88, 1991.

Figure 23A:
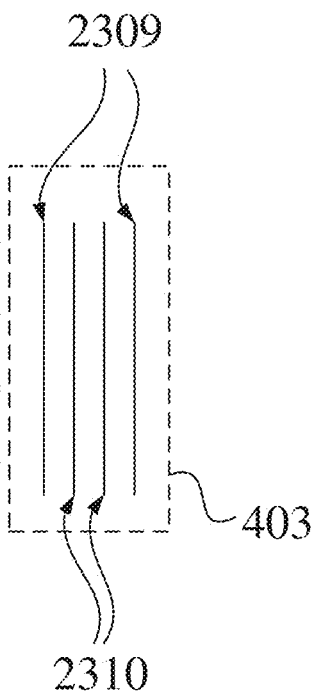
FIG. 23A may depict a schematic view of an example of a four terminal (electrode) portion of a complex impedance sensor.

FIG. 23A may be a top view of a four-terminal probe; with substantially parallel regions of a conductive surface of type "G" 2309 and 2310. In some embodiments, conductive surface of type "G" 2309 and 2310 may be mounted to the substrate 403. In some embodiments, substrate 403 may be a dielectric material. In some embodiments, conductive surface of type "G" 2309 and 2310 may be constructed from electrically conductive materials of construction. In some embodiments, conductive surface of type "G" 2309 and 2310 may be arranged in pairs of substantially parallel rows in a spiral fashion with substrate 403 disposed between or/and under such substantially parallel rows; for example, and without limiting the scope of the present invention, arranged as conductive wires in concentric circles on a dielectric substrate.

In some embodiments, FIG. 23A may depict at least a portion of a four terminal complex impedance measuring sensor. In some embodiments, FIG. 23A may be at least a portion of complex-impedance-sensor 2010.

Figure 23B:
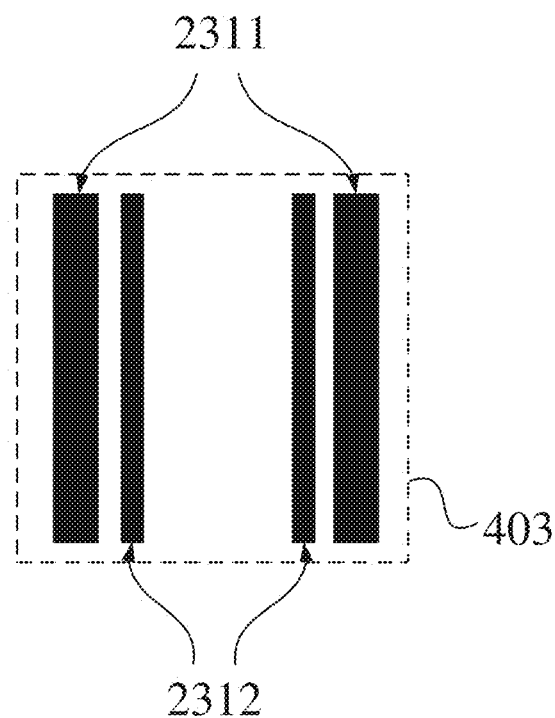
FIG. 23B may depict a schematic view of an example of a four terminal (electrode) portion of a complex impedance sensor.

FIG. 23B may be a top view of a four-terminal probe; with substantially parallel regions of a conductive surface of type "H" 2311 and 2312. In some embodiments, conductive surface of type "H" 2311 and 2312 may be mounted to the substrate 403. In some embodiments, substrate 403 may be a dielectric material. In some embodiments, conductive surface of type "H" 2311 and 2312 may be constructed from electrically conductive materials of construction. In some embodiments, conductive surface of type "H" 2311 and 2312 may be arranged in pairs of substantially parallel rows in a spiral fashion with substrate 403 disposed between or/and under such substantially parallel rows; for example, and without limiting the scope of the present invention, arranged as conductive wires in concentric circles on a dielectric substrate.

In some embodiments, FIG. 23B may depict at least a portion of a four terminal complex impedance measuring sensor. In some embodiments, FIG. 23B may be at least a portion of complex-impedance-sensor 2010.

Figure 23C:
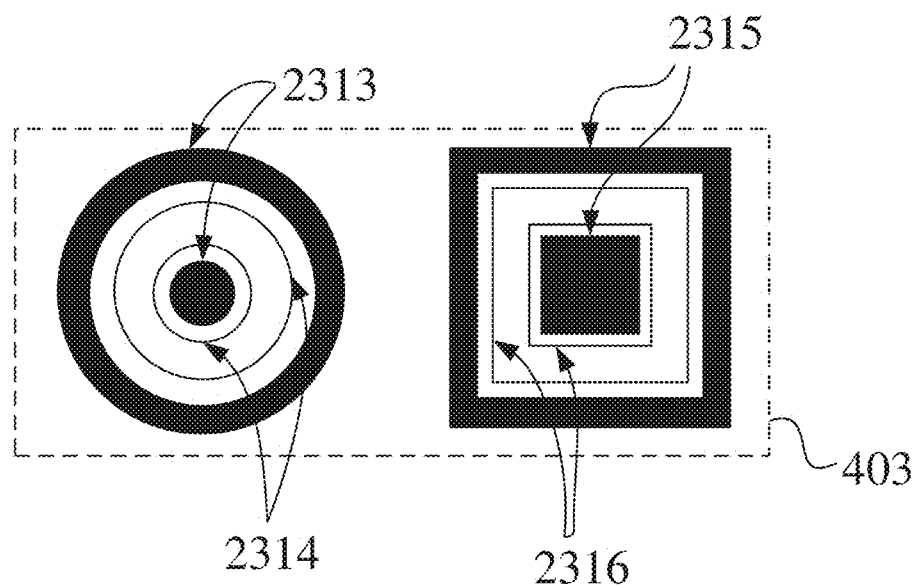
FIG. 23C may depict a schematic view of an example of a four terminal (electrode) portion of a complex impedance sensor.

FIG. 23C may be a top view of two four-terminal probes; with regions of a conductive surface of type "I" 2313 and 2314; and with regions of a conductive surface of type "J" 2315 and 2316. In some embodiments, conductive surface of type "I" 2313 and 2314 and conductive surface of type "J" 2315 and 2316 may each be mounted to a same substrate 403. In some embodiments, substrate 403 may be a dielectric material. In some embodiments, conductive surface of type "I" 2313 and 2314 and conductive surface of type "J" 2315 and 2316 may be constructed from electrically conductive materials of construction. In some embodiments, conductive surface of type "I" 2313 and 2314 may be arranged in concentric circles (e.g., in a bull's eye fashion) with substrate 403 disposed between such concentric circles. In some embodiments, conductive surface of type "J" 2315 and 2316 may be arranged in concentric squares with substrate 403 disposed between or/and under such concentric squares.

In some embodiments, FIG. 23C may depict at least a portion of a four terminal complex impedance measuring sensor. In some embodiments, FIG. 23C may be at least a portion of complex-impedance-sensor 2010.

Figure 23D:
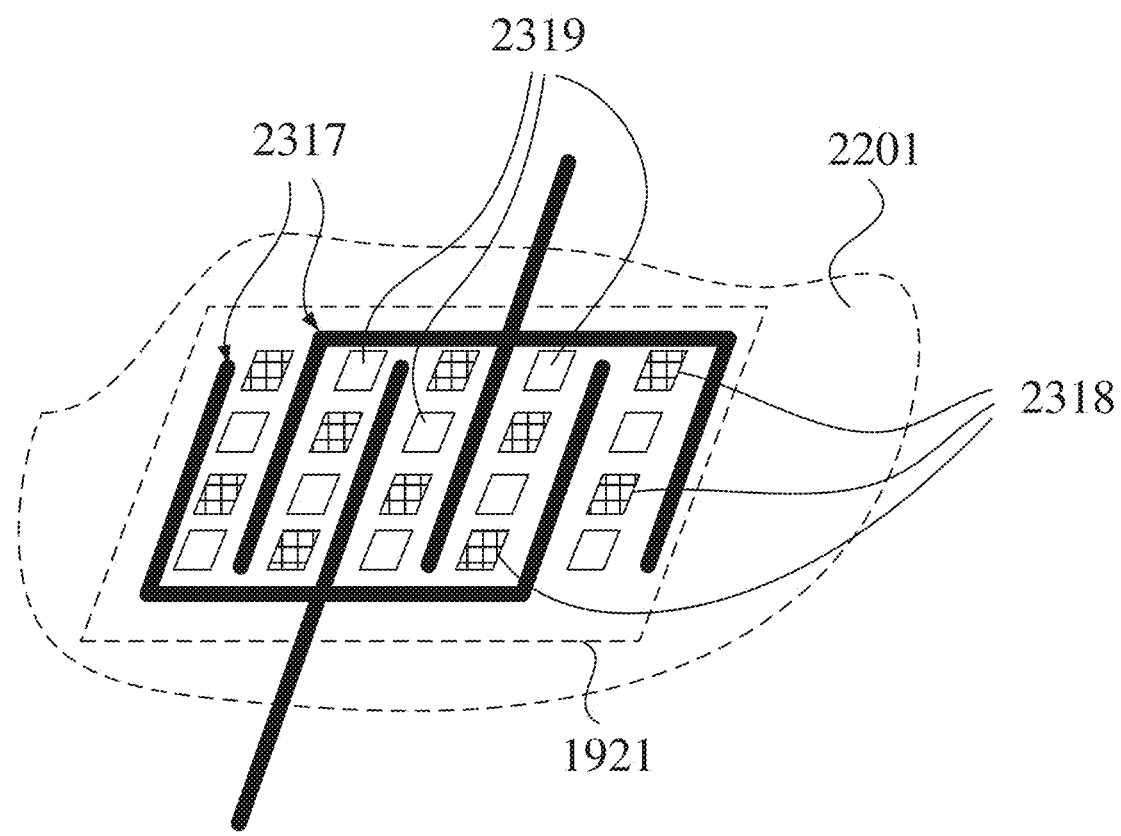
FIG. 23D may be a view of two different opposed terminal probes; of regions of a conductive surface of type "K" mounted to a given material-of-interest, with different IR lights sources disposed between the probes and capable of emitting different IR light to the given material-of-interest.

FIG. 23D may be a view of two different opposed terminal probes; of regions of a conductive surface of type "K" 2317 mounted to material-of-interest 2201. In some embodiments, conductive surface of type "K" 2317 may be constructed from electrically conductive materials of construction. In some embodiments a plurality of infrared (IR) light sources of type "A" 2318 and/or a plurality of infrared (IR) light sources of type "B" 2319 may be affixed in the vicinity (e.g., within a predetermined distance in some embodiments) of the two different opposed terminal probes; of regions of a conductive surface of type "K" 2317 in order to expose material-of-interest 2201 to external excitation source, such as, but not limited to, infrared (IR) light. In some embodiments the plurality of infrared (IR) light sources of type "A" 2318 or the plurality of infrared (IR) light sources of type "B" 2319 may be of a predetermined frequency (e.g., monochromatic). In some embodiments, the plurality of infrared (IR) light sources of type "A" 2318 or the plurality of infrared (IR) light sources of type "B" 2319 may be of coherent emission type. In some embodiments, a plurality of infrared (IR) light source of type "B" 2319 may be present to expose material-of-interest 2201 to external excitation source of a different type or characteristic from infrared (IR) light source of type "A" 2318. For example, and without limiting the scope of the present invention, such as an IR light source of a different frequency than the IR light source of type "A" 2318. In some embodiments, the plurality of infrared (IR) light source of type "B" 2319 may be visible light sources, ultraviolet (UV) light sources, and/or ultrasonic (or sonic) sound sources.

In some embodiments, the plurality of infrared (IR) light sources of type "A" 2318 or/and the plurality of infrared (IR) light sources of type "B" 2319 may be part of the array-of-excitation-sources 1921.

It can be appreciated by one skilled in the art that the plurality of infrared (IR) light sources of type "A" 2318, the plurality of infrared (IR) light sources of type "B" 2319, visible light sources, ultraviolet light sources, or ultrasonic sound sources should be powered by an electric energy source.

Figure 24A:
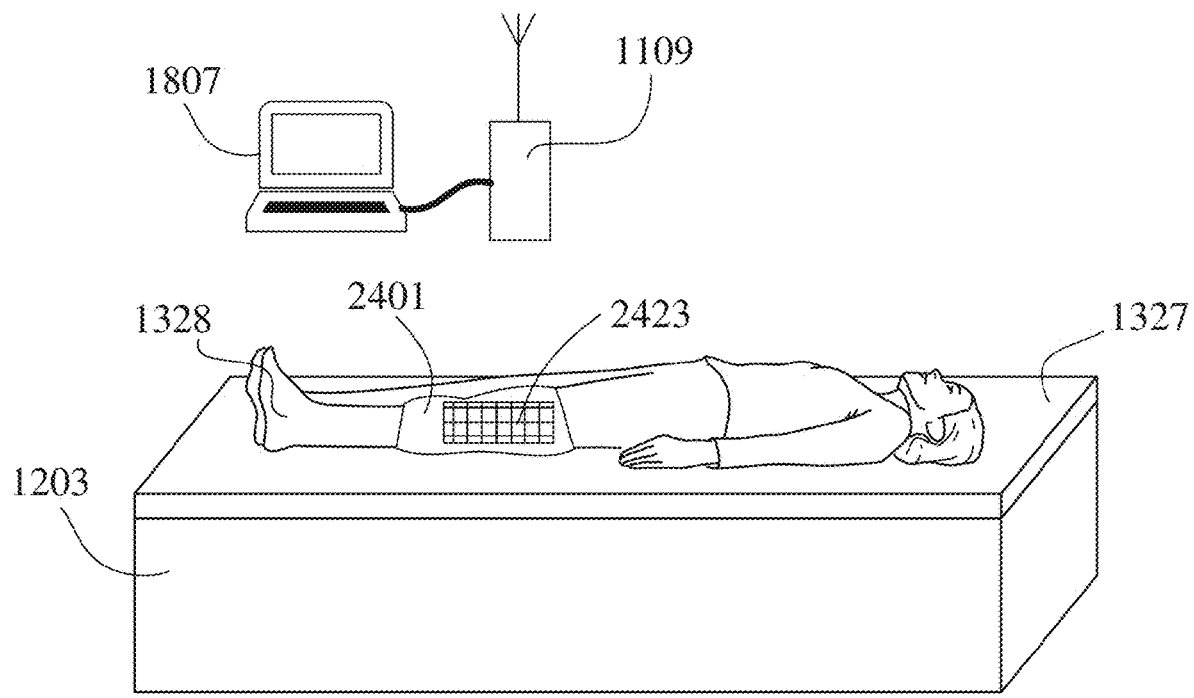
FIG. 24A may depict a system for monitoring and/or tracking, non-invasively, a state of skin or of tissue, using a cast-or-bandage with lattice-of-sensors that may be in communication with a reader-and-calibration-member and/or with a device (e.g., a mobile computer).

FIG. 24A may depict a system for non-invasive monitoring of a material-of-interest (e.g., material-of-interest 2201, not shown in FIG. 24A) with lattice-of-sensors 2423 that may be in and/or on patient 1328. In some embodiments, reader-and-calibration-member 1109 may be used to interrogate lattice-of-sensors 2423. In some embodiments, lattice-of-sensors 2423 may comprise a plurality of complex-monitoring-sensor-tags 2020 (e.g., first-sensor-tag 2420 and/or second-sensor-tag 2421) and/or a plurality of sensors (e.g., first-sensor-type 2406 and/or second-sensor-type 2407), see FIG. 24B for details of lattice-of-sensors 2423. In some embodiments, material-of-interest 2201 may be on or in patient 1328. In some embodiments, material-of-interest 2201 may be at least a portion of tissue (e.g., skin) or a cell of patient 1328. In some embodiments, lattice-of-sensors 2423 may be located under cast-or-bandage 2401. In some embodiments, lattice-of-sensors 2423 may be on an interior-surface 2402 of cast-or-bandage 2401 (see FIG. 24D for interior-surface 2402 of cast-or-bandage 2401).

In some embodiments, cast-or-bandage 2401 may be: a cast, a bandage, a dressing, gauze, a compression bandage, an elastic bandage, tape, kinesiology tape, KT tape, elastic therapeutic tape, strapping, webbing, a patch, a sling, a splint, or the like.

In some embodiments, lattice-of-sensors 2423 may be in physical contact with at least portions of material-of-interest 2201, and thus lattice-of-sensors 2423 may be used to monitor material-of-interest 2201 for various states of material-of-interest 2201. For example, and without limiting the scope of the present invention, the system and/or configuration shown in FIG. 24A may be used and useful for monitoring healing of wounds and/or of skin of patient 1328; wherein material-of-interest 2201 may a portion of the wound and/or the skin.

For example, and without limiting the scope of the present invention, the system and/or configuration shown in FIG. 24A may be used and useful for monitoring status (state) (e.g., healing or recovery progression) of tissue of interest (e.g., a region of skin) in a burn victim.

For example, and without limiting the scope of the present invention, the system and/or configuration shown in FIG. 24A may be used and useful for monitoring status (state) (e.g., healing or recovery progression) of tissue of interest (e.g., a region of skin) of various skin cancers.

For example, and without limiting the scope of the present invention, the system and/or configuration shown in FIG. 24A may be used and useful for monitoring status (state) (e.g., healing or recovery progression) of tissue of interest (e.g., a region of skin) of various dermatological issues, such as, but not limited to, rashes.

Changes in measured complex impedance of material-of-interest 2201 (e.g., tissue, cells, or a cell), may also indicate problems in patient 1328, such as, but not limited to, infection, decay, dying tissue, and/or the like.

And recall such monitoring and/or tacking via the system and/or configuration of FIG. 24A may be done non-invasively and with minimal to no ionizing radiation.

Continuing discussing FIG. 24A, in some embodiments, reader-and-calibration-member 1109 may be handheld. In some embodiments, reader-and-calibration-member 1109 may be mobile. In some embodiments, reader-and-calibration-member 1109 may be used to interrogate lattice-of-sensors 2423. In some embodiments, reader-and-calibration-member 1109 may provide the necessary electrical power lattice-of-sensors 2423 needs to operate; and this may only occur when reader-and-calibration-member 1109 and lattice-of-sensors 2423 are sufficiently close to each other.

Continuing discussing FIG. 24A, in some embodiments, device 1807 may be selected from: a computer, a personal computer, a desktop computer, a handheld computer, a laptop computer, a tablet computer, a smartphone, a mobile computing device, a computing device, or the like.

Continuing discussing FIG. 24A, in some embodiments, reader-and-calibration-member 1109 and device 1807 may be in communication with each other. In some embodiments, reader-and-calibration-member 1109 and device 1807 may be in wired communication with each other. In some embodiments, reader-and-calibration-member 1109 and device 1807 may be in wireless communication with each other. In some embodiments, reader-and-calibration-member 1109 and device 1807 may be attached to each other. In some embodiments, reader-and-calibration-member 1109 and device 1807 may be flexibly attached to each other. In some embodiments, reader-and-calibration-member 1109 and device 1807 may be in removable connection with each other.

In some embodiments, FIG. 24A may depict a system for non-invasive monitoring of a material-of-interest (e.g., material-of-interest 2201, not shown in FIG. 24A) with one or more complex-monitoring-sensor-tags 2020 that may be in and/or on patient 1328.

In some embodiments, lattice-of-sensors 2423 shown in FIG. 24A may be replaced with lattice-of-sensors 1023 or with monitoring-sensor-tag 120. Compare FIG. 24A against FIG. 13C.

Figure 24B:
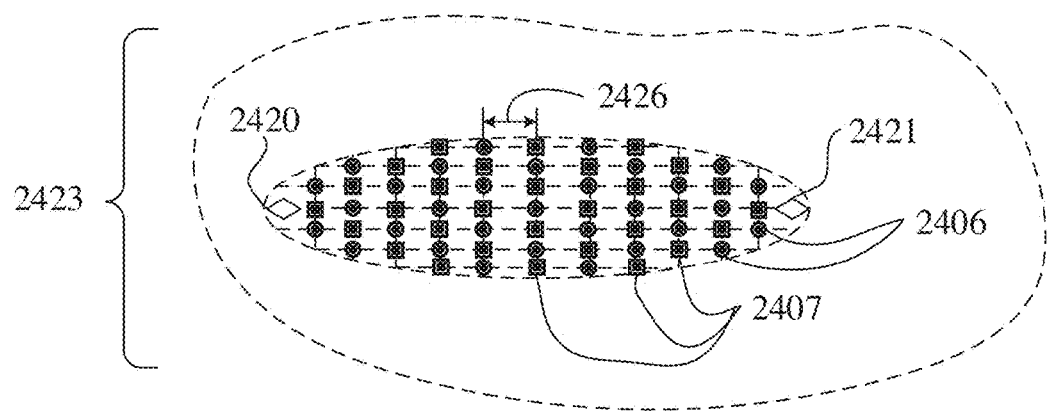
FIG. 24B may depict a schematic view of lattice-of-sensors.

FIG. 24B may depict structural details of a given lattice-of-sensors 2423. In some embodiments, lattice-of-sensors 2423 may be a lattice framework of a plurality of sensor-tags, such as complex-monitoring-sensor-tag 2020 and/or of monitoring-sensor-tag 120. In some embodiments, this plurality of sensor-tags may comprise sensor-spacing 2426; wherein sensor-spacing 2426 may be spacing between two adjacent sensor-tags of lattice-of-sensors 2423. In some embodiments, sensor-spacing 2426 may be predetermined and fixed. In some embodiments, sensor-spacing 2426 may be predetermined, fixed, and substantially equal between various adjacent sensor-tags. In some embodiments, sensor-spacing 2426 may be predetermined, fixed, and may be different distances, but known, between various adjacent sensor-tags.

Continuing discussing FIG. 24B, in some embodiments, lattice-of-sensors 2423 may comprise a first-sensor-tag 2420, a lattice framework of a plurality of sensors, and a second-sensor-tag 2421. In some embodiments, first-sensor-tag 2420 may be a complex-monitoring-sensor-tag 2020 (see e.g., FIG. 20A, FIG. 20, FIG. 25A, FIG. 25B, FIG. 25C, and/or FIG. 25D). Continuing discussing FIG. 24B, in some embodiments, second-sensor-tag 2421 may be another complex-monitoring-sensor-tag 2020 (see e.g., FIG. 20A, FIG. 20, FIG. 25A, FIG. 25B, FIG. 25C, and/or FIG. 25D). Continuing discussing FIG. 24B, in some embodiments, this plurality of sensors may comprise first-sensor-type(s) 2406 and/or second-sensor-type(s) 2407. In some embodiments, first-sensor-type 2406 may be a complex-impedance-sensor 2010. In some embodiments, a given first-sensor-type 2406 may be a complex-impedance-sensor 2010; such as shown in FIG. 22A, FIG. 22B, FIG. 23A, FIG. 23B, FIG. 23C, or FIG. 23D. In some embodiments, second-sensor-type 2407 may be another complex-impedance-sensor 2010. In some embodiments, a given second-sensor-type 2407 may be another complex-impedance-sensor 2010; such as shown in FIG. 22A, FIG. 22B, FIG. 23A, FIG. 23B, FIG. 23C, or FIG. 23D. Continuing discussing FIG. 24B, in some embodiments, first-sensor-type 2406 and second-sensor-type 2407 may be of different types of complex-impedance-sensors 2010 with respect to each other. In some embodiments, first-sensor-type 2406 and/or second-sensor-type 2407 may in communication with first-sensor-tag 2420. In some embodiments, first-sensor-type 2406 and/or second-sensor-type 2407 may in electrical communication with first-sensor-tag 2420. In some embodiments, first-sensor-type 2406 and/or second-sensor-type 2407 may in communication with second-sensor-tag 2421. In some embodiments, first-sensor-type 2406 and/or second-sensor-type 2407 may in electrical communication with second-sensor-tag 2421. In some embodiments, sensor-spacing 2426 may be spacing between adjacent sensors. In some embodiments, sensor-spacing 2426 may be spacing between first-sensor-type 2406 and an adjacent second-sensor-type 2407. In some embodiments, within a given lattice-of-sensors 2423 positions of sensor-tags (e.g., first-sensor-tag 2420 and/or second-sensor-tag 2421) and positions of the plurality of sensors (e.g., first-sensor-type 2406 and/or second-sensor-type 2407) may be fixed with respect to each other. In some embodiments, within a given lattice-of-sensors 2423 positions of sensor-tags (e.g., first-sensor-tag 2420 and/or second-sensor-tag 2421) and positions of the plurality of sensors (e.g., first-sensor-type 2406 and/or second-sensor-type 2407) may be known with respect to each other. See e.g., FIG. 24B. Compare FIG. 24B against FIG. 10D. Compare lattice-of-sensors 2423 against lattice-of-sensors 1023.

Continuing discussing FIG. 24B, in some embodiments, lattice-of-sensors 2423 may comprise first-sensor-tag 2420, and the lattice framework of the plurality of sensors.

Continuing discussing FIG. 24B, in some embodiments, first-sensor-type 2406 may be a complex-monitoring-sensor-tag 2020. In some embodiments, second-sensor-type 2407 may be a complex-monitoring-sensor-tag 2020.

In some embodiments, a given lattice-of-sensors 2423 may be arranged in a one dimensional, two dimensional, or three dimensional configuration. In some embodiments, a given lattice-of-sensors 2423 may be arranged in mesh configuration. In some embodiments, a given lattice-of-sensors 2423 may be arranged in lattice configuration.

In some embodiments, at least a portion of a given lattice-of-sensors 2423 may be substantially covered in a protective covering (e.g., a protective film).

In some embodiments, a system for non-invasive monitoring of tissue (e.g., tissue-of-interest), may comprise at least one lattice-of-sensors (such as lattice-of-sensors 2423 and/or lattice-of-sensors 1023).

In some embodiments, material-of-interest 2201 may be a tissue-of-interest. In some embodiments, material-of-interest 1028 may be a tissue-of-interest. In some embodiments, material-of-interest 1828 may be a tissue-of-interest. In some embodiments, the tissue-of-interest may be tissue from an organism, such as, but not limited to, an organ, a portion of an organ, a bone, a joint, skin, a region of skin, a body part, a portion of a body part, portions thereof, combinations thereof, and/or the like.

In some embodiments, at least a portion of the at least one lattice-of-sensors 2423 may be proximate to the tissue-of-interest. See e.g., FIG. 24A, wherein the tissue-of-interest may be skin or tissue beneath cast-or-bandage 2401. In some embodiments, this proximate distance may be predetermined. In some embodiments, at least a portion of the at least one lattice-of-sensors 2423, with or without a protective covering (layer or film), may be in direct physical contact to the tissue-of-interest; e.g., when the tissue-of-interest may be skin.

In some embodiments, upon the at least one antenna (e.g., a given wireless-receiver-and-transmitter 207) of a given lattice-of-sensors 2423, receiving electromagnetic (EM) radiation of a predetermined characteristic (e.g., from a reader-and-calibration-member 1109 or from a reader 100) as an input, this input may cause the at least one circuit (e.g., processing circuitry 204 and/or complex-impedance-measurement-circuit 2011) to take one or more readings from the at least one sensor of the first-sensor-tag (complex-monitoring-sensor-tag 2020 and/or monitoring-sensor-tag 120) or from at least one sensor (first-sensor-type 2406 and/or 2407) selected from the plurality of sensors; and to then transmit the one or more readings using the at least one antenna; wherein this transmitted one or more readings may be received back at reader-and-calibration-member 1109 or at reader 100.

In some embodiments, the system for non-invasive monitoring of tissue, the at least one lattice-of-sensors 2423 may further comprise second-sensor-tag 2421. In some embodiments, second-sensor-tag 2421 may comprise at least one different electric circuit (e.g., processing circuitry 204 and/or complex-impedance-measurement-circuit 2011) comprising at least one different sensor (e.g., complex-impedance-sensor 2010). In some embodiments, second-sensor-tag 2421 may comprise the at least one different antenna (e.g., which may be a given wireless-receiver-and-transmitter 207) which may be in communication with the at least one different electric circuit. In some embodiments, the plurality of sensors (of lattice-of-sensors 2423) may be in communication with second-sensor-tag 2421; wherein at least a different portion of the plurality of sensors may be physically connected to second-sensor-tag 2421. In some embodiments, upon the at least one different antenna receiving the electromagnetic (EM) radiation of the predetermined characteristic as the input, this input may cause the at least one different circuit to take one or more different readings from the at least one different sensor of the second-sensor-tag 2421 or from at least one sensor selected from the plurality of sensors (such as, first-sensor-type 2406 and/or second-sensor-type 2407); and to then transmit the one or more different readings using the at least one different antenna; back to a reader-and-calibration-member 1109 and/or a reader 100. See e.g., FIG. 24B, FIG. 24A, and FIG. 24C.

In some embodiments, the system for non-invasive monitoring of tissue, the plurality of sensors of lattice-of-sensors 2423 may be disposed between first-sensor-tag 2420 and second-sensor-tag 2421. See e.g., FIG. 24B.

In some embodiments, the system for non-invasive monitoring of tissue, the at least one sensor of the first-sensor-tag 2420, the at least one different sensor of the second-sensor-tag 2421, or the plurality of sensors may be selected from one or more of: a capacitive-based sensor, a resistance-based sensor, an inductance-based sensor, a permittivity based sensor, a complex permittivity based sensor, and/or a complex impedance based sensor.

In some embodiments, the system for non-invasive monitoring of tissue, the one or more readings (e.g., from the at least one sensor of first-sensor-tag 2420 and/or from the plurality of sensors); and/or the one or more different readings (e.g., from the at least one different sensor of second-sensor-tag 2421 and/or from the plurality of sensors) may convey information of one or more of: inductance, capacitance, resistance, permittivity, complex permittivity, or complex impedance. Such information received at a given reader-and-calibration-member 1109 and/or a given reader 100, wherein this received information may then be stored and/or interpreted.

In some embodiments, the system for non-invasive monitoring of tissue, the at least one different circuit of first-sensor-tag 2420 may be given a complex-impedance-measurement-circuit 2011 and/or a given processing circuitry 204.

In some embodiments, the system for non-invasive monitoring of tissue, the at least one different circuit of second-sensor-tag 2421 may be given a complex-impedance-measurement-circuit 2011 and/or a given processing circuitry 204.

Continuing discussing FIG. 24B, in some embodiments, the system for non-invasive monitoring of tissue, each sensor selected from the plurality of sensors (e.g., first-sensor-type 2406 and/or second-sensor-type 2407) of lattice-of-sensors 2423 may comprises its own measurement circuit and its own antenna; which may communicate with reader-and-calibration-member 1109 and/or with reader 100.

In some embodiments, the system for non-invasive monitoring of tissue, the at least one lattice-of-sensors 2423 may further comprise array-of-excitation-sources 1921. In some embodiments, array-of-excitation-sources 1921 may house and/or may comprise one or more excitation sources that may emit energy of a predetermined frequency. In some embodiments, the one or more excitation sources may be IR light source 1917, LED light source 1918, UV light source 1919, and/or sonic or ultrasonic sound source 1920. In some embodiments, the one or more excitation sources of the array-of-excitation-sources 1921 may be in electrical communication with the at least one electric circuit (e.g., processing circuitry 204 and/or complex-impedance-measurement-circuit 2011 of complex-monitoring-sensor-tag 2020 which may be first-sensor-tag 2420). In some embodiments, the one or more excitation sources of the array-of-excitation-sources 1921 may be in electrical communication with the at least one different electric circuit (e.g., processing circuitry 204 and/or complex-impedance-measurement-circuit 2011 of complex-monitoring-sensor-tag 2020 which may be second-sensor-tag 2421). Recall, in some embodiments, lattice-of-sensor 2423 (e.g., FIG. 24B) may comprise first-sensor-tag 2420 and/or second-sensor-tag 2421; and that first-sensor-tag 2420 and/or second-sensor-tag 2421 may be a given complex-monitoring-sensor-tag 2020 as shown in FIG. 20B and/or as shown FIG. 25D, both with a given array-of-excitation-sources 1921.

In some embodiments, the system for non-invasive monitoring of tissue, the input (e.g., from reader-and-calibration-member 1109 and/or from reader 100) may further cause the at least one circuit (e.g., of first-sensor-tag 2420) to cause the one or more excitation sources to emit the energy of the predetermined frequency. In some embodiments, the input (e.g., from reader-and-calibration-member 1109 and/or from reader 100) may further cause the at least one different circuit (e.g., of second-sensor-tag 2421) to cause the one or more excitation sources to emit the energy of the predetermined frequency. In some embodiments, the input (e.g., from reader-and-calibration-member 1109 and/or from reader 100) may power the one or more excitation sources to emit the energy of the predetermined frequency.

Figure 24C:
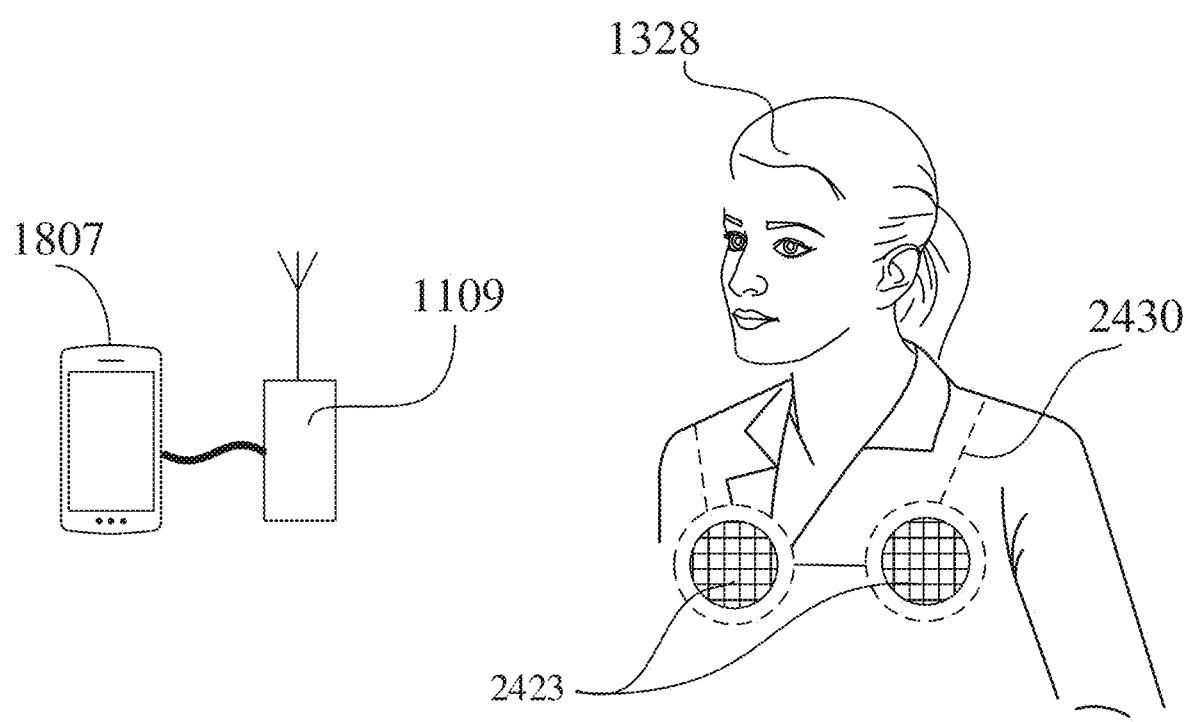
FIG. 24C may depict a system for monitoring and/or tracking, non-invasively, a state of breast skin or of breast tissue, using an article-in-lattice-contact (e.g., a bra) with lattice-of-sensors that may be in communication with a reader-and-calibration-member and/or with a device (e.g., a mobile computer).

FIG. 24C may depict another system for non-invasive monitoring of material-of-interest (e.g., material-of-interest 2201, not shown in FIG. 24C) with lattice-of-sensors 2423 that may be in and/or on patient 1328. In FIG. 24C, reader-and-calibration-member 1109 and device 1807 may be as noted in the above FIG. 24A discussion; and in the earlier discussions of reader-and-calibration-member 1109 and of device 1807. In some embodiments, reader-and-calibration-member 1109 may be used to interrogate lattice-of-sensors 2423. As noted above (see e.g., FIG. 24B), in some embodiments, lattice-of-sensors 2423 may comprise a plurality of complex-monitoring-sensor-tags 2020 (e.g., first-sensor-tag 2420 and/or second-sensor-tag 2421) and/or a plurality of sensors (e.g., first-sensor-type 2406 and/or second-sensor-type 2407). In some embodiments, material-of-interest 2201 may be on or in patient 1328. In some embodiments, material-of-interest 2201 may be at least a portion of tissue (e.g., skin) or a cell of patient 1328. In some embodiments, lattice-of-sensors 2423 may be located under article-in-lattice-contact 2430. In some embodiments, lattice-of-sensors 2423 may be on an interior-surface 2402 of article-in-lattice-contact 2430 (see FIG. 24D for interior-surface 2402 of article-in-lattice-contact 2430).

In some embodiments, article-in-lattice-contact 2430 may be: a bra, a sports bra, a brazier, an undergarment, underwear, an article of clothing, a cast, a bandage, cast-or-bandage 2401, a dressing, gauze, a compression bandage, an elastic bandage, tape, kinesiology tape, elastic therapeutic tape, strapping, webbing, a patch, a sling, a splint, sutures, a medical device, an implant 2431, a breast implant, and/or the like. As a category, article-in-lattice-contact 2430 may be broader and encompass cast-or-bandage 2401. As shown in FIG. 24C, article-in-lattice-contact 2430 may be bra.

Specifically as shown in FIG. 24C, article-in-lattice-contact 2430 may be a bra, wherein lattice-of-sensors 2423 may be disposed on an inside surface of the bra (e.g., interior-surface 2402), such that at least portions of lattice-of-sensors 2423 may be in physical contact with skin of the breasts of patient 1328; wherein complex impedance of the contacted skin may then may be monitored and provide state (status) information of not only such contacted skin, but also of breast tissue beneath such skin; wherein such monitoring may be facilitated by reader-and-calibration-member 1109 interrogating lattice-of-sensors 2423, with results and/or data displayed and/or stored on device 1807. By using such a system and/or configuration breast health may be monitored and/or tracked, non-invasively and with minimal to no ionizing radiation, in real time or near real time. By using such a system and/or configuration breast cancers and/or breast tumors may be monitored and/or tracked, non-invasively and with minimal to no ionizing radiation, in real time or near real.

Similarly, the system and/or configuration shown in FIG. 24C may be adapted such that article-in-lattice-contact 2430 is underwear with lattice-of-sensors 2423 in physical contact with skin of testicles, such that testicle health, testicular tumors, and/or testicular cancers may be monitored and/or tracked, non-invasively and with minimal to no ionizing radiation, in real time or near real time.

In some embodiments, FIG. 24C may depict a system for non-invasive monitoring of a material-of-interest (e.g., material-of-interest 2201, not shown in FIG. 24C) with one or more complex-monitoring-sensor-tags 2020 that may be in and/or on patient 1328.

In some embodiments, FIG. 24C may depict the system for non-invasive monitoring of tissue with one or more complex-monitoring-sensor-tags 2020 that may be in and/or on patient 1328.

In some embodiments, the system for non-invasive monitoring of tissue, the system further may comprise at least one reader-and-calibration-member 1109, see e.g., FIG. 24A and FIG. 24C. In some embodiments, at least one reader-and-calibration-member 1109 may have its own antenna (e.g., antenna 110, see e.g., FIG. 11A, FIG. 11B, and/or FIG. 11C). In some embodiments, the at least one reader-and-calibration-member 1109 may provide the electromagnetic (EM) radiation of the predetermined characteristic as the input. In some embodiments, the at least one reader-and-calibration-member 1109 may be in radio communication with the at least one lattice-of-sensors 2423. See e.g., FIG. 24A and FIG. 24C. In some embodiments, the at least one reader-and-calibration-member 1109 may receive the one or more readings and/or the one or more different readings.

In some embodiments, the system for non-invasive monitoring of tissue, the at least one reader-and-calibration-member 1109 may comprises one or more reference-sensor-tags 1102. See e.g., FIG. 11A, FIG. 11B, and/or FIG. 11C.

In some embodiments, the system for non-invasive monitoring of tissue, the at least one reader-and-calibration-member 1109 may be in communication (wireless or wired communication) with a computing device 1807. In some embodiments, this computing device 1807 may perform one or more of the following with the one or more readings (and/or with the one or more different readings): interprets, displays, and/or stores (e.g., in memory 1803 of device 1807). See e.g., FIG. 24A, FIG. 24C, and FIG. 18.

In some embodiments, the system for non-invasive monitoring of tissue, the system may further comprise computing device 1807. See e.g., FIG. 24A and FIG. 24C. In some embodiments, computing device 1807 may be mobile, as in a smartphone, tablet, laptop, and/or the like.

Figure 24D:
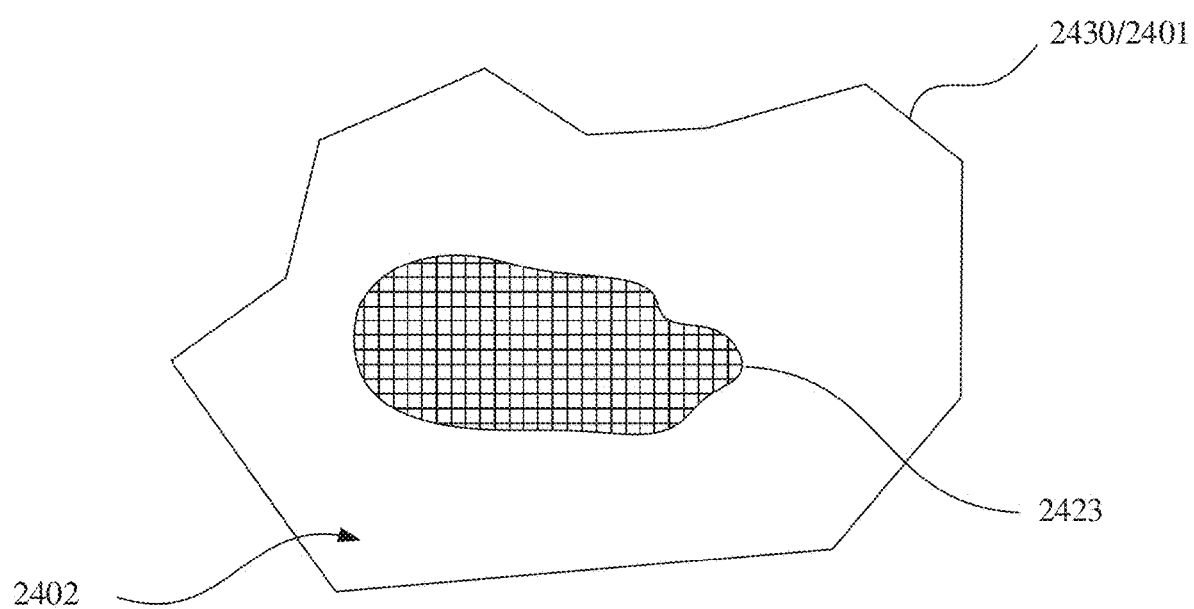
FIG. 24D may depict a portion of an article-in-lattice-contact (e.g., a bra) or a portion of a cast-or-bandage (e.g., a cast or bandage), showing lattice-of-sensors on the interior-surface.

In some embodiments, FIG. 24D may depict a portion of cast-or-bandage 2401. In some embodiments, FIG. 24D may depict an interior-surface 2402 side of cast-or-bandage 2401. In some embodiments, FIG. 24D may show lattice-of-sensors 2423 against interior-surface 2402 of cast-or-bandage 2401. In some embodiments, at least portions of lattice-of-sensors 2423 may in physical contact with portions of interior-surface 2402. In some embodiments, at least portions of lattice-of-sensors 2423 may physically attached to portions of interior-surface 2402. In some embodiments, at least portions of lattice-of-sensors 2423 and portions of interior-surface 2402 may be integral with each other. See e.g., FIG. 24D.

In some embodiments, FIG. 24D may depict a portion of article-in-lattice-contact 2430. In some embodiments, FIG. 24D may depict an interior-surface 2402 side of article-in-lattice-contact 2430. In some embodiments, FIG. 24D may show lattice-of-sensors 2423 against interior-surface 2402 of article-in-lattice-contact 2430. In some embodiments, at least portions of lattice-of-sensors 2423 may in physical contact with portions of interior-surface 2402. In some embodiments, at least portions of lattice-of-sensors 2423 may physically attached to portions of interior-surface 2402. In some embodiments, at least portions of lattice-of-sensors 2423 and portions of interior-surface 2402 may be integral with each other. See e.g., FIG. 24D.

Figure 24E:
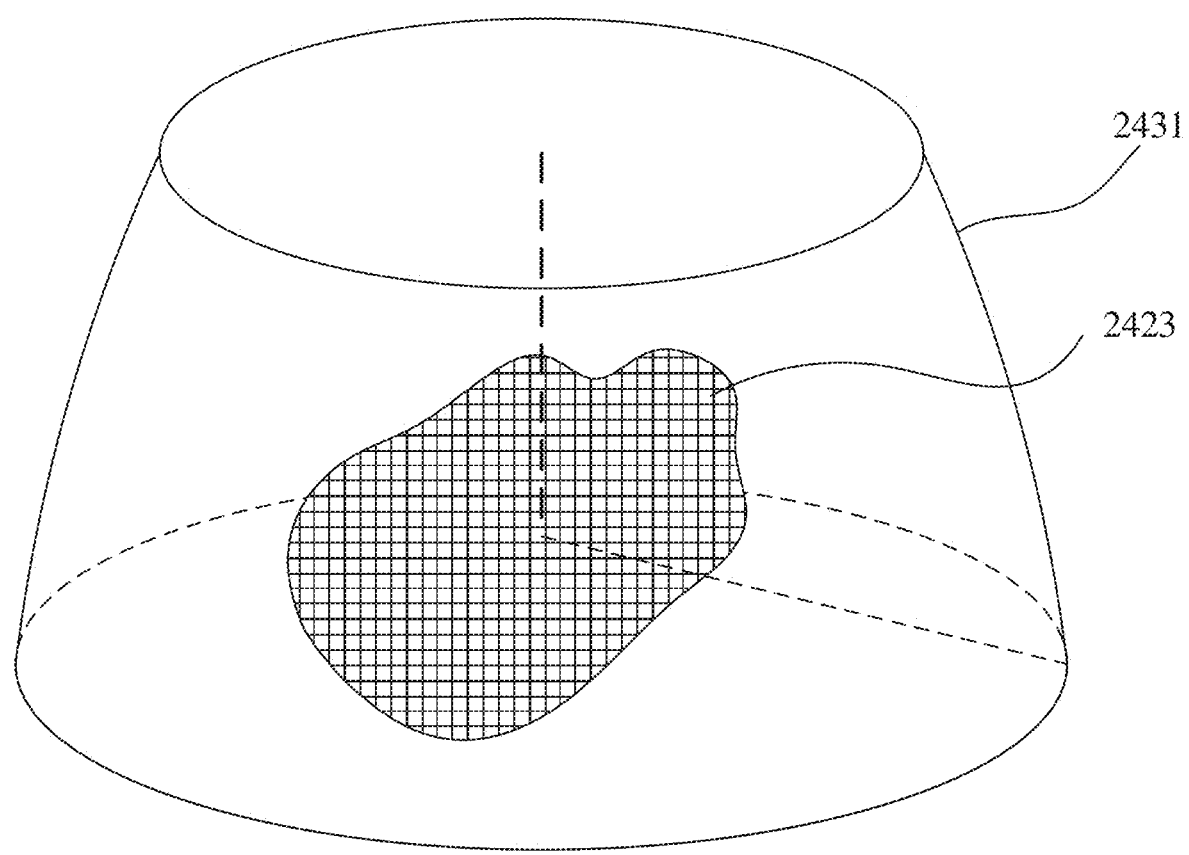
FIG. 24E may depict a diagram showing at least one lattice-of-sensors that may be imbedded within a given implant.

In some embodiments, article-in-lattice-contact 2430 may be a medical device and/or an implant, such as in implant 2431. See e.g., FIG. 24E. FIG. 24E may depict a diagram showing at least one lattice-of-sensors 2423 that may be imbedded within a given implant 2431. For example, and without limiting the scope of the present invention, implant 2431 may be: a breast implant, a medical device, a pump, a medication release bolus, an artificial organ, an artificial bone, an artificial limb, an artificial joint, mesh (e.g., hernia repair mesh), combinations thereof, and/or the like.

Figure 24F:
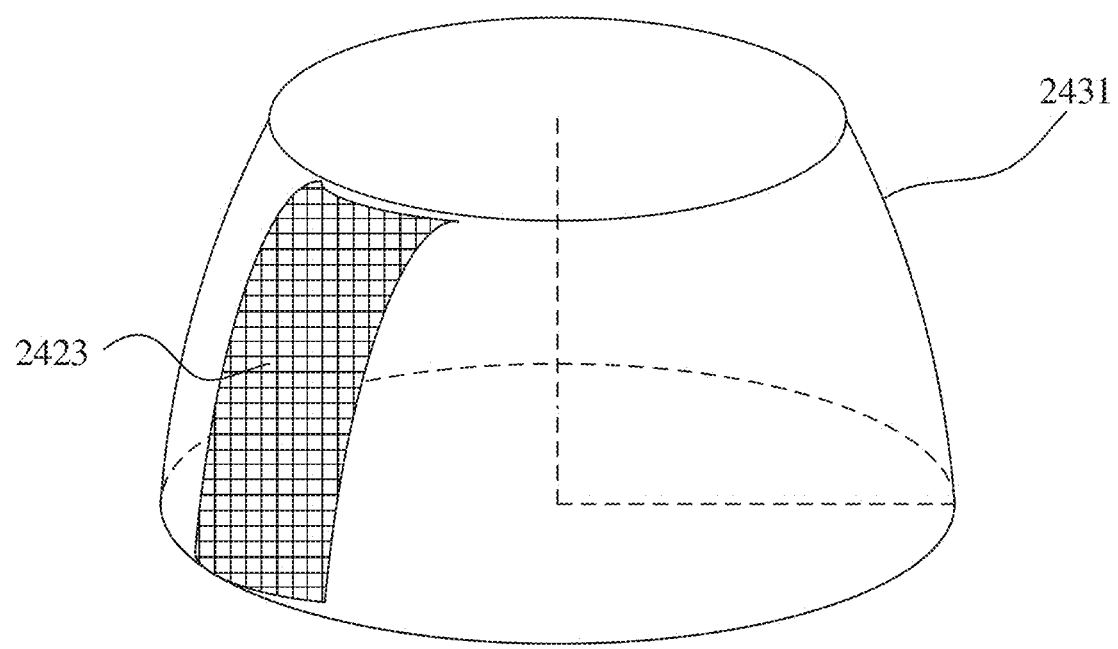
FIG. 24F may depict a diagram showing at least one lattice-of-sensors that may be mounted on (attached to) an external surface of a given implant.

FIG. 24F may depict a diagram showing at least one lattice-of-sensors 2423 that may be mounted on (attached to) an external surface of a given implant 2431.

In some embodiments, at least one lattice-of-sensors 2423 may be partially located on an external surface of implant 2431 and may also be partially located within the implant 2431, i.e., a combination of FIG. 24E and FIG. 24F.

In some embodiments, the system for non-invasive monitoring of tissue, this system may further comprise at least one article-in-lattice-contact 2430. In some embodiments, the at least one lattice-of-sensors 2423 may be attached to the article-in-lattice-contact 2430 such that the at least the portion of the at least one lattice-of-sensors 2423 may be proximate to the tissue-of-interest, when the article-in-lattice-contact 2430 may be removably affixed to a portion of a body. See e.g., FIG. 24A, FIG. 24C, FIG. 24D, FIG. 24E, and FIG. 24F. In some embodiments, implant 2431 may be a type of article-in-lattice-contact 2430.

In some embodiments, the at least one lattice-of-sensors 2423 may be attached to an interior-surface of the articlein-lattice-contact 2430 such that the at least a portion of the at least one lattice-of-sensors 2423 may be proximate to the tissue-of-interest, when the article-in-lattice-contact 2430 may be removably affixed to a portion of a body. See e.g., FIG. 24A, FIG. 24C, and FIG. 24D.

In some embodiments, the system for non-invasive monitoring of tissue, the at least one lattice-of-sensors 2423 may be located within the article-in-lattice-contact 2430 such that the at least a portion of the at least one lattice-of-sensors 2423 may be proximate to the article-in-lattice-contact 2430, when the article-in-lattice-contact 2430 may be removably affixed to a portion of a body. See e.g., FIG. 24E where implant 2431 may be a type of article-in-lattice-contact 2430.

In some embodiments, the system for non-invasive monitoring of tissue, the at least one lattice-of-sensors 2423 may be located on an exterior surface of the article-in-lattice-contact 2430 such that the at least a portion of the at least one lattice-of-sensors 2423 may be proximate to the article-in-lattice-contact 2430 and/or proximate to the tissue-of-interest, when the article-in-lattice-contact 2430 may be removably affixed to a portion of a body. See e.g., FIG. 24F where implant 2431 may be a type of article-in-lattice-contact 2430.

In some embodiments, the system for non-invasive monitoring of tissue, the one or more readings (e.g., from first-sensor-tag 2420 and/or from the plurality of sensors); and/or the one or more different readings (e.g., from second-sensor-tag 2421 and/or from the plurality of sensors) may be transmitted through the at least one article-in-lattice-contact 2430 while the article-in-lattice-contact 2430 may be removably affixed to the portion of the body.

Figure 25A:
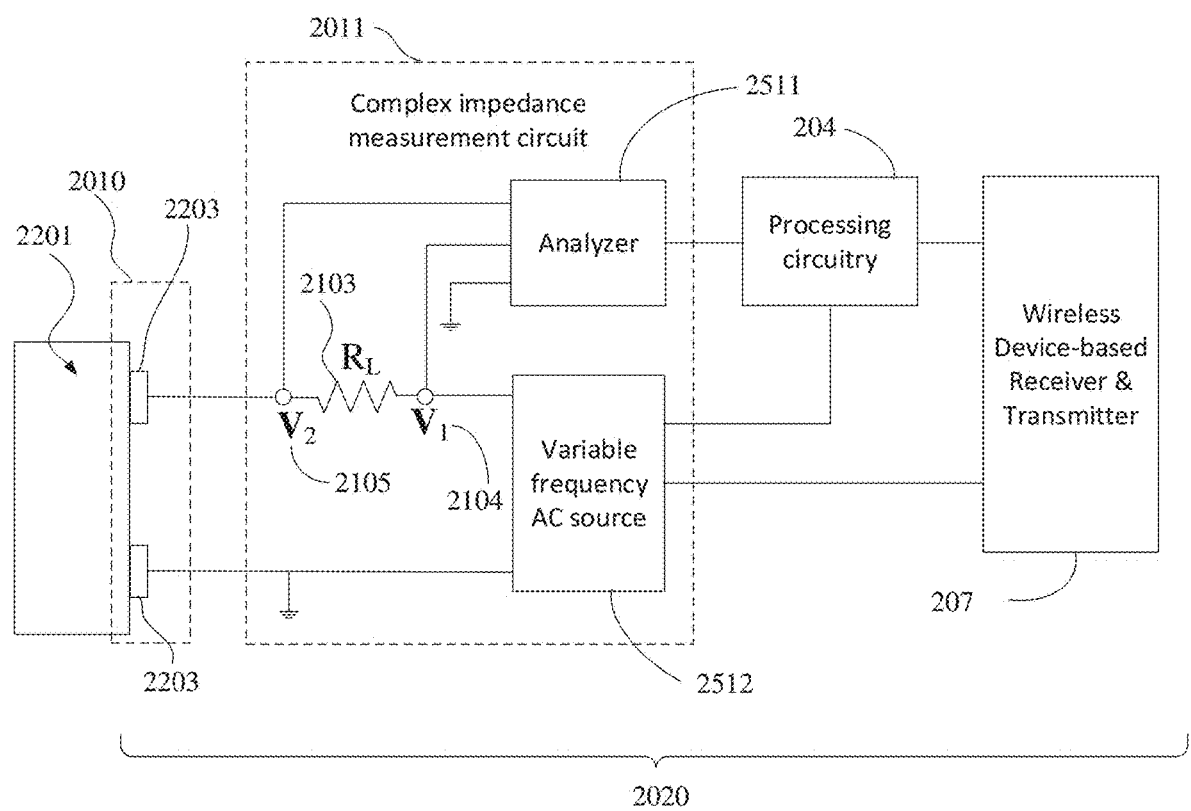
FIG. 25A may depict a schematic view of a complex-monitoring-sensor-tag, showing details of a complex-impedance-measurement-circuit.

FIG. 25A may depict additional details of a given complex-monitoring-sensor-tag 2020, in a schematic block diagram. In some embodiments, complex-monitoring-sensor-tag 2020 may comprise wireless-receiver-and-transmitter 207, processing circuitry 204, complex-impedance-measurement-circuit 2011, and complex-impedance-sensor 2010, see e.g., FIG. 20A. In some embodiments, complex-impedance-sensor 2010 may comprise at least two electrodes 2203, that may be in physical contact with material-of-interest 2201, as shown in FIG. 25A.

Here in FIG. 25A, additional details of complex-impedance-measurement-circuit 2011 may be shown. In some embodiments, complex-impedance-measurement-circuit 2011 may comprise resistor 2103, point 2104, point 2105, analyzer 2511, and variable-frequency-AC-source 2512. In some embodiments, resistor 2103 may be disposed between point 2104 and point 2105. In some embodiments, analyzer 2511 may be in communication with processing circuitry 204, point 2104, and point 2105. In some embodiments, variable-frequency-AC-source 2512 may be in communication with processing circuitry 204, wireless-receiver-and-transmitter 207, point 2104, and an electrode 2203 of complex-impedance-sensor 2010.

In some embodiments, variable-frequency-AC-source 2512 may perform a function of an alternating current (AC) voltage source (e.g., 1906) or of an alternating current (AC) current source (e.g., 2106). In some embodiments, variable-frequency-AC-source 2512 may change its frequency. Therefore, determination of the complex impedance or complex permittivity of material-of-interest 2201 may be done at different frequencies, as may be desirable. In some embodiments, processing circuitry 204 may control variable-frequency-AC-source 2512. In some embodiments, wireless-receiver-and-transmitter 207 may control variable-frequency-AC-source 2512. In some embodiments, both processing circuitry 204 and wireless-receiver-and-transmitter 207 may control variable-frequency-AC-source 2512. In some embodiments, the carrier frequency of wireless-receiver-and-transmitter 207 may be supplied to variable-frequency-AC-source 2512. Techniques for designing and building variable frequency alternating current (AC) sources are well understood in the relevant art and should be appreciated by those of ordinary skill in the relevant art.

Continuing discussing FIG. 24A, in some embodiments, analyzer 2511 may be used to determine the value of the complex impedance or complex permittivity of material-of-interest 2201.

It should be appreciated by those of ordinary skill in the relevant art that one of the ways that one may find the value of the complex impedance Z of material-of-interest 2201 may be in using equation (31) which will be copied below for convenience:

$$Z = R_L \frac{V_2}{V_1 - V_2} \tag{31}$$

where $V_1$ is a complex representation of the voltage at point 2104 and $V_2$ is a complex representation of the voltage at point 2105, and $R_L$ is the known impedance of resistor 2103.

The analyzer 2511 may be connected to point 2104 and point 2105. The known impedance of resistor 2103 may be available in digital or analogue form to analyzer 2511 as well in order to obtain the value of the complex impedance Z of material-of-interest 2201.

Basic techniques for realizing a variant of analyzer 2511 may be understood in the relevant art. See e.g., J. Walworth, "Measuring complex impedances at actual operating levels," Electronics, 47(15), pp. 117-118, 1974.

Figure 25B:
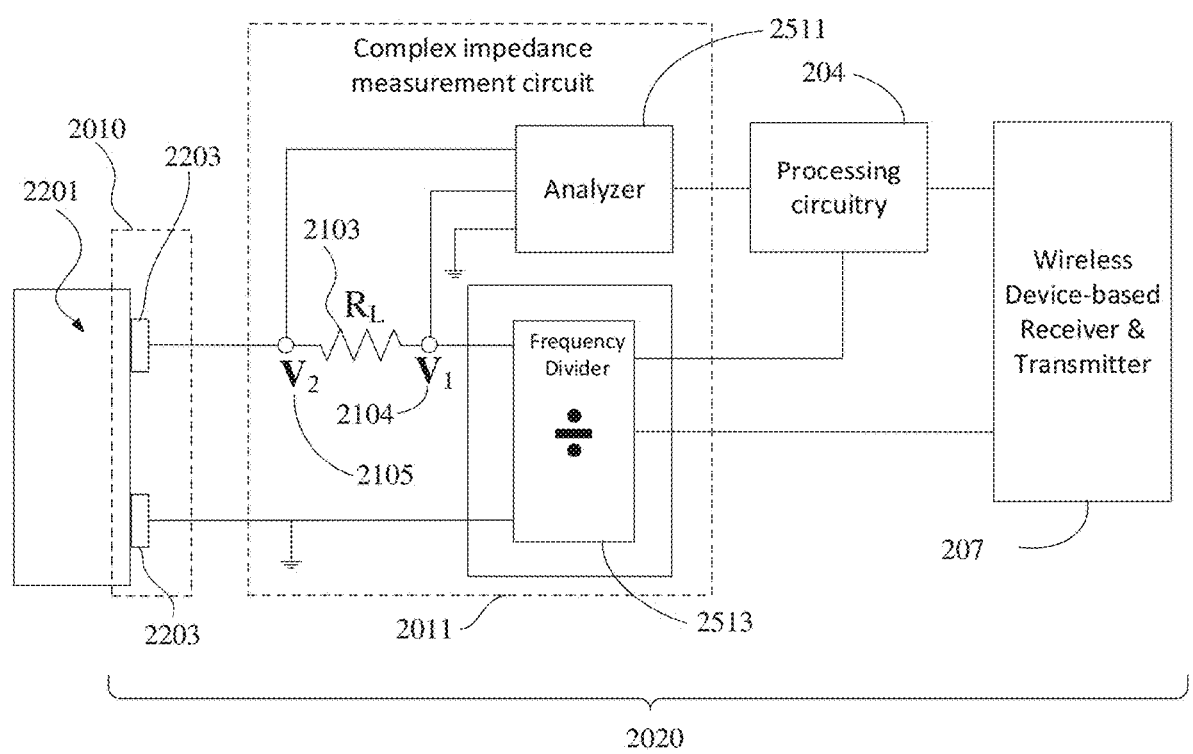
FIG. 25B may depict a schematic view of a complex-monitoring-sensor-tag, showing details of a complex-impedance-measurement-circuit.

FIG. 25B may depict additional details of a given complex-monitoring-sensor-tag 2020, in a schematic block diagram. In some embodiments, complex-monitoring-sensor-tag 2020 may comprise wireless-receiver-and-transmitter 207, processing circuitry 204, complex-impedance-measurement-circuit 2011, and complex-impedance-sensor 2010, see e.g., FIG. 20A. In some embodiments, complex-impedance-sensor 2010 may comprise at least two electrodes 2203, that may be in physical contact with material-of-interest 2201, as shown in FIG. 25B.

Here in FIG. 25B, additional details of complex-impedance-measurement-circuit 2011 may be shown. In some embodiments, complex-impedance-measurement-circuit 2011 may comprise resistor 2103, point 2104, point 2105, analyzer 2511, and frequency-divider 2513. In some embodiments, resistor 2103 may be disposed between point 2104 and point 2105. In some embodiments, analyzer 2511 may be in communication with processing circuitry 204, point 2104, and point 2105. In some embodiments, frequency-divider 2513 may be in communication with processing circuitry 204, wireless-receiver-and-transmitter 207, point 2104, and an electrode 2203 of complex-impedance-sensor 2010.

Continuing discussing FIG. 25B, in some embodiments, frequency-divider 2513 may be programmable. In some embodiments, frequency-divider 2513 may perform a function of controllably reducing the carrier frequency of wireless-receiver-and-transmitter 207, supplied to frequency-divider 2513. Therefore, determination of the complex impedance or complex permittivity of material-of-interest 2201 may be done at different frequencies, as may be desired. In some embodiments, processing circuitry 204 may control frequency-divider 2513. In some embodiments, wireless-receiver-and-transmitter 207 may control frequency-divider 2513. In some embodiments, both processing circuitry 204 and wireless-receiver-and-transmitter 207 may control frequency-divider 2513. As a result, frequency range from zero up to the carrier frequency of wireless-receiver-and-transmitter 207, may be produced by frequency-divider 2513 in order to determine the complex impedance or complex permittivity of material-of-interest 2201 at different frequencies. Techniques for designing programmable frequency dividers are well understood in the relevant art and should be appreciated by those of ordinary skill in the relevant art.

In some embodiments, variable-frequency-AC-source 2512 and/or frequency-divider 2513 may be examples of means-to-supply-variable-frequencies to material-of-interest 2201.

In some embodiments, the system for non-invasive monitoring of tissue, the complex-impedance-measurement-circuit 2011 (which may be a component of the at least one electric circuit of first-sensor-tag 2420) may comprise a variable-frequency-AC-source 2512 that may use a frequency supplied by the at least one antenna (e.g., a wireless-receiver-and-transmitter 207), so that complex impedance may be measured within a predetermined ranges of frequencies. See e.g., FIG. 25A. That is, the complex-monitoring-sensor-tag 2020 shown in FIG. 25A may be first-sensor-tag 2420 of lattice-of-sensors 2423 shown in FIG. 24B.

In some embodiments, the system for non-invasive monitoring of tissue, the complex-impedance-measurement-circuit 2011 (which may be a component of the at least one electric circuit of first-sensor-tag 2420) may comprise a frequency-divider 2513 that may use a frequency supplied by the at least one antenna (e.g., a wireless-receiver-and-transmitter 207), to measure complex impedance within a range of frequencies. See e.g., FIG. 25B. That is, the complex-monitoring-sensor-tag 2020 shown in FIG. 25B may be first-sensor-tag 2420 of lattice-of-sensors 2423 shown in FIG. 24B.

Figure 25C:
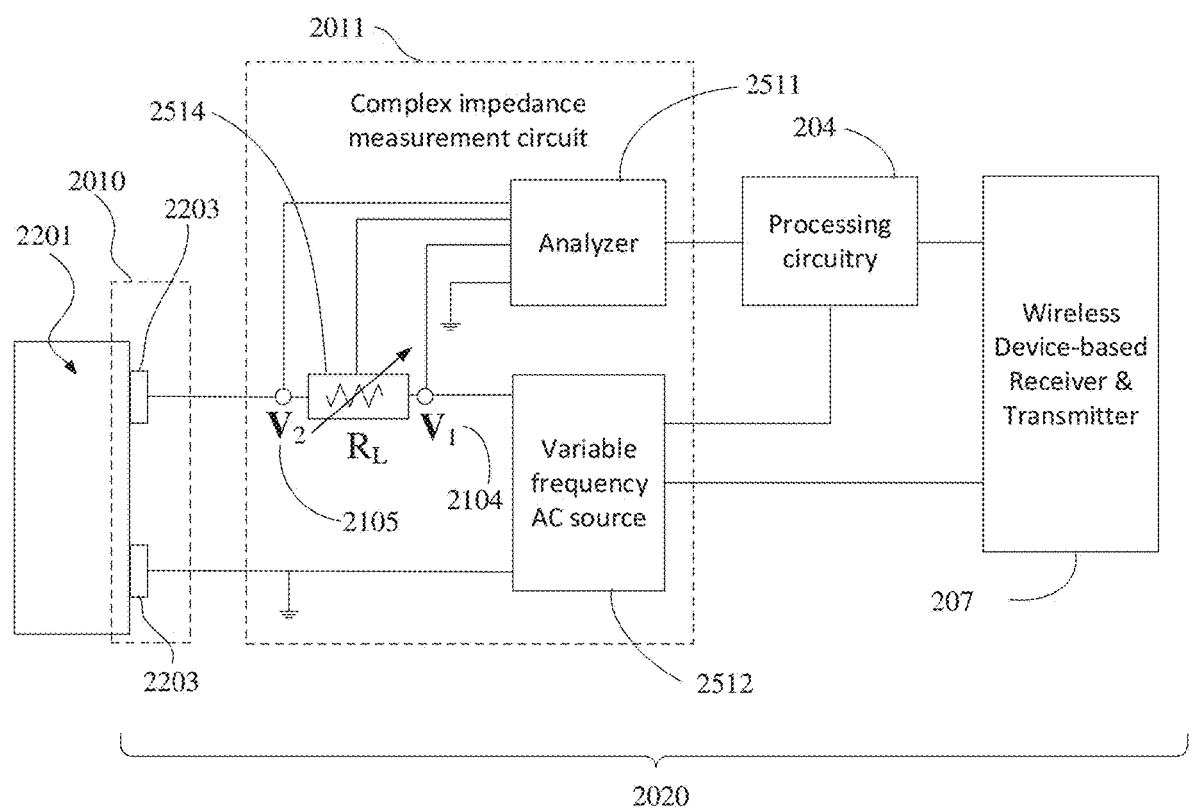
FIG. 25C may depict a schematic view of a complex-monitoring-sensor-tag, showing details of a complex-impedance-measurement-circuit.
Figure 25D:
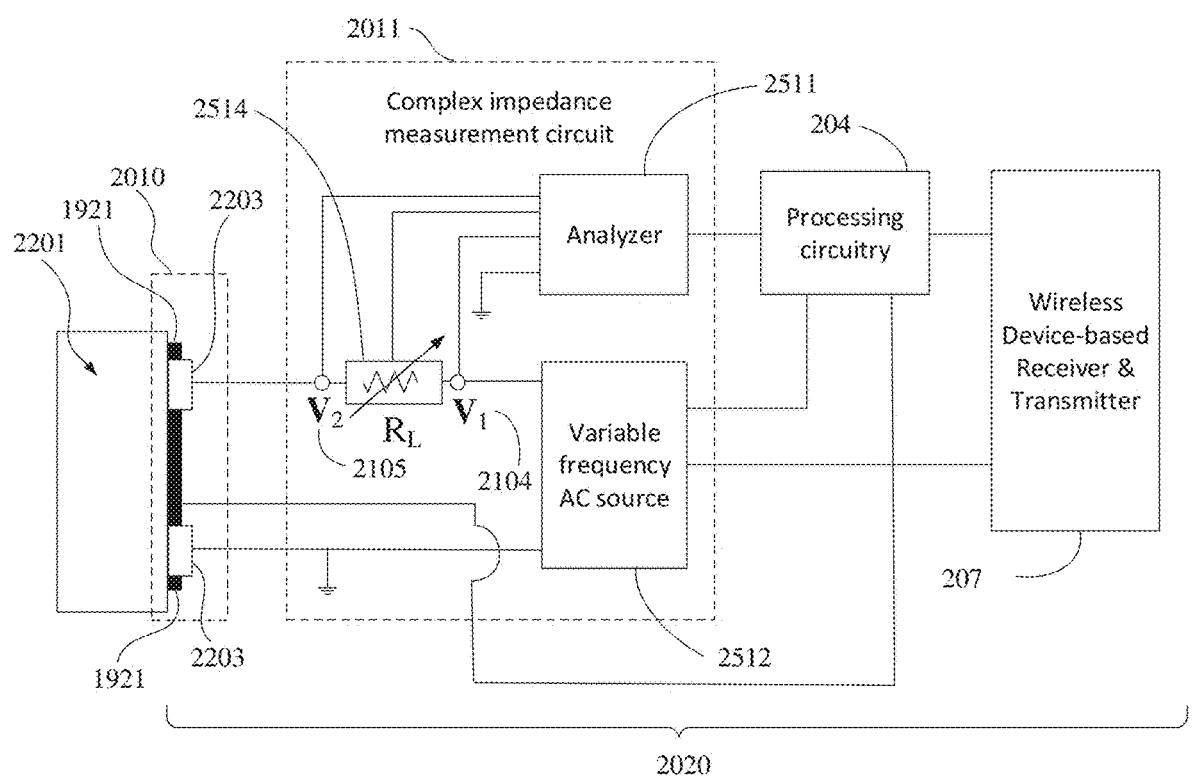
FIG. 25D may depict additional details of the complex-monitoring-sensor-tag of FIG. 20B, in a schematic block diagram.

See e.g., complex-monitoring-sensor-tag 2020 of FIG. 25A, FIG. 25B, FIG. 25C, and/or FIG. 25D. In some embodiments, first-sensor-tag 2420 (see e.g., FIG. 24B) may be a complex-monitoring-sensor-tag 2020 (see e.g., FIG. 20A, FIG. 20B, FIG. 25A, FIG. 25B, FIG. 25C, and FIG. 25D). In some embodiments, the at least one antenna of first-sensor-tag 2420 may be wireless-receiver-and-transmitter 207 of complex-monitoring-sensor-tag 2020.

In some embodiments, the system for non-invasive monitoring of tissue, the complex-impedance-measurement-circuit 2011 (which may be a component of the at least one different electric circuit of second-sensor-tag 2421) may comprise a variable-frequency-AC-source 2512 that may use a frequency supplied by the at least one different antenna (e.g., a wireless-receiver-and-transmitter 207), so that complex impedance may be measured within a predetermined ranges of frequencies. See e.g., FIG. 25A. That is, the complex-monitoring-sensor-tag 2020 shown in FIG. 25A may be second-sensor-tag 2421 of lattice-of-sensors 2423 shown in FIG. 24B.

In some embodiments, the system for non-invasive monitoring of tissue, the complex-impedance-measurement-circuit 2011 (which may be a component of the at least one different electric circuit of second-sensor-tag 2421) may comprise frequency-divider 2513 that may use a frequency supplied by the at least one different antenna (e.g., a wireless-receiver-and-transmitter 207), to measure complex impedance within a range of frequencies. See e.g., FIG. 25B. That is, the complex-monitoring-sensor-tag 2020 shown in FIG. 25B may be second-sensor-tag 2421 of lattice-of-sensors 2423 shown in FIG. 24B.

See e.g., complex-monitoring-sensor-tag 2020 of FIG. 25A, FIG. 25B, FIG. 25C, and/or FIG. 25D. In some embodiments, second-sensor-tag 2421 (see e.g., FIG. 24B) may be a complex-monitoring-sensor-tag 2020 (see e.g., FIG. 20A, FIG. 20B, FIG. 25A, FIG. 25B, FIG. 25C, and FIG. 25D). In some embodiments, the at least one different antenna of second-sensor-tag 2421 may be wireless-receiver-and-transmitter 207 of complex-monitoring-sensor-tag 2020.

FIG. 25C may depict additional details of a given complex-monitoring-sensor-tag 2020, in a schematic block diagram. In some embodiments, complex-monitoring-sensor-tag 2020 may comprise wireless-receiver-and-transmitter 207, processing circuitry 204, complex-impedance-measurement-circuit 2011, and complex-impedance-sensor 2010, see e.g., FIG. 20A. In some embodiments, complex-impedance-sensor 2010 may comprise at least two electrodes 2203, that may be in physical contact with material-of-interest 2201, as shown in FIG. 25C.

Here in FIG. 25C, additional details of complex-impedance-measurement-circuit 2011 may be shown. In some embodiments, complex-impedance-measurement-circuit 2011 may comprise variable resistor 2514, point 2104, point 2105, analyzer 2511, and variable-frequency-AC-source 2512. In some embodiments, variable resistor 2514 may be disposed between point 2104 and point 2105. In some embodiments, analyzer 2511 may be in communication with processing circuitry 204, point 2104, point 2105, and variable resistor 2514. In some embodiments, variable-frequency-AC-source 2512 may be in communication with processing circuitry 204, wireless-receiver-and-transmitter 207, point 2104, and an electrode 2203 of complex-impedance-sensor 2010.

Continuing discussing FIG. 25C, in some embodiments, variable resistor 2514 may be programmable. In some embodiments, analyzer 2511 may perform a function of controlling the impedance of variable resistor 2514. Therefore, determination of the complex impedance or complex permittivity of material-of-interest 2201 may be done at different impedance levels of variable resistor 2514, as may be desired. In some embodiments, processing circuitry 204 may control variable resistor 2514. In some embodiments, analyzer 2511 may control variable resistor 2514. In some embodiments, both processing circuitry 204 and analyzer 2511 may control variable resistor 2514. Techniques for designing variable resistors are well understood in the relevant art and should be appreciated by those of ordinary skill in the relevant art.

FIG. 25D may depict additional details of the complex-monitoring-sensor-tag 2020 of FIG. 20B, in a schematic block diagram. In some embodiments, complex-monitoring-sensor-tag 2020 shown in FIG. 25D may be substantially similar to the complex-monitoring-sensor-tag 2020 shown in FIG. 25C, except in FIG. 25D, complex-monitoring-sensor-tag 2020 may further comprise array-of-excitation-sources 1921. As noted, in some embodiments, array-of-excitation-sources 1921 may house and/or may comprise one or more excitation sources, such as, but not limited to, IR light source 1917, LED light source 1918, UV light source 1919, and/or sonic sound source 1920, as shown in FIG. 20B. Continuing discussing FIG. 25D, in some embodiments, the one or more excitation sources of array-of-excitation-sources 1921 may be in electrical communication with processing circuitry 204. In some embodiments, the one or more excitation sources of array-of-excitation-sources 1921 may be controlled by processing circuitry 204. In some embodiments, processing circuitry may control the one or more excitation sources of array-of-excitation-sources 1921. In some embodiments, processing circuitry 204 may also be known as the "at least one electric circuit" and/or as the "at least one different electric circuit."

Continuing discussing FIG. 25D, in some embodiments, the one or more excitation sources of array-of-excitation-sources 1921 may be proximate (e.g., within a predetermined distance) to material-of-interest 2201; such that at least some of the emitted energy from the one or more excitation sources of array-of-excitation-sources 1921 may be received at material-of-interest 2201, such as at a surface of material-of-interest 2201.

Continuing discussing FIG. 25D, in some embodiments, array-of-excitation-sources 1921 may be attached to, next to, adjacent to, and/or part of complex-impedance-sensor 2010.

In some embodiments, a given array-of-excitation-sources 1921, with the one or more excitation sources, may be incorporated into a given complex-monitoring-sensor-tag 2020 of FIG. 25A, FIG. 25B, and/or FIG. 25C; specifically at least attached to (and/or adjacent to) a given complex-impedance-sensor 2010, in some embodiments.

In some embodiments, the system for non-invasive monitoring of tissue, may be further characterized as a system for non-invasive detection of problems, conditions, and/or substances of interest within tissue-of-interest (e.g., material-of-interest 2201); wherein these problems, conditions, and/or substances may be selected from one or more of: biological cells (e.g., foreign cells, abnormal cells, cancerous cells, etc.), infection, fever, inflammation, antigens, antibodies, foreign substances, tissue conditions, ailments, disease state, and/or the like. Such detection may be a subset of monitoring.

Figure 32:
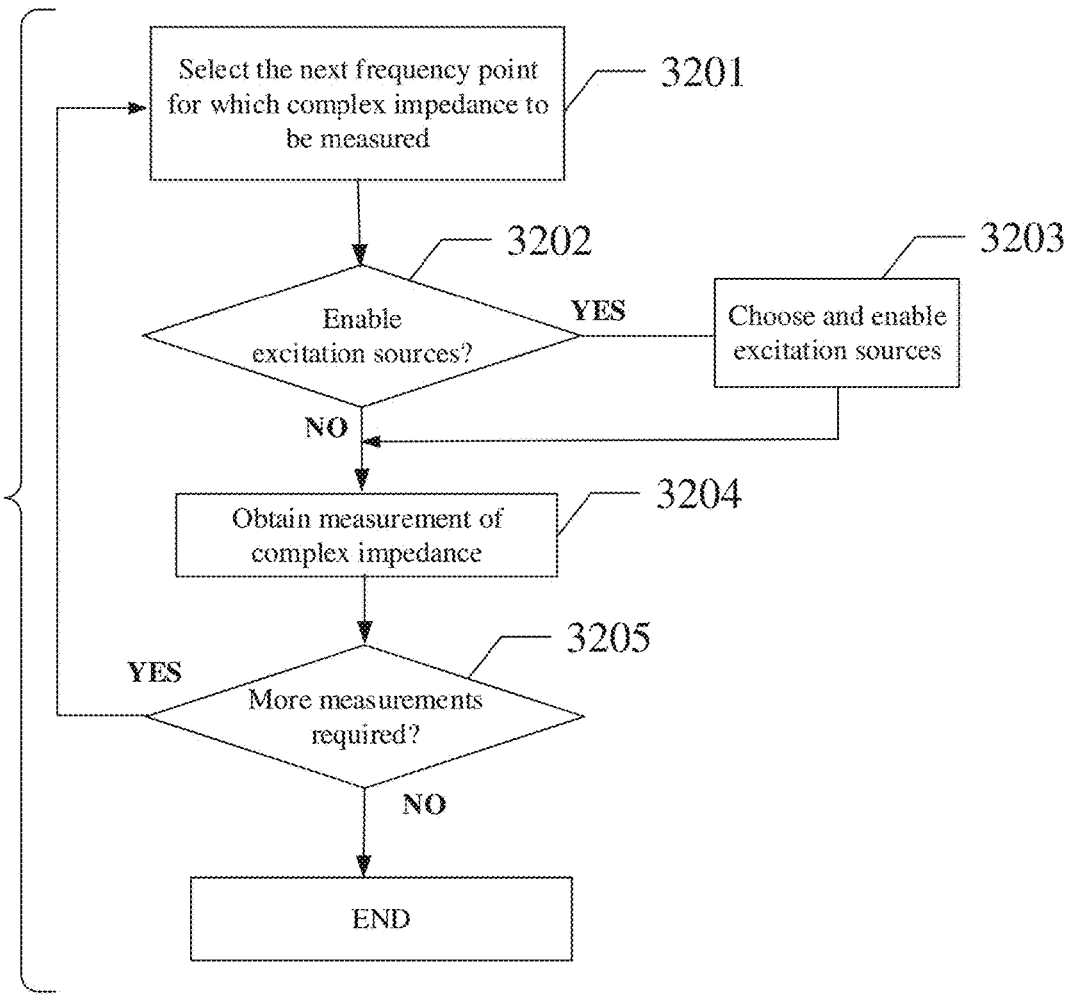
FIG. 32 may depict a flow diagram illustrating steps in a method for non-invasive monitoring of a material-of-interest with one or more complex-monitoring-sensor-tag(s) employing electrochemical impedance spectroscopy (EIS).

FIG. 32 may depict a flow diagram illustrating steps in a method 1535a for monitoring material-of-interest 2201. In some embodiments, one or more complex-monitoring-sensor-tag 2020 may be employing electrochemical impedance spectroscopy (EIS). In some embodiments, method 1500 may comprise step 1535a. In some embodiments, step 1535a may follow step 1534. In some embodiments, step 1535a may be a step of the reader 100 (or the reader-and-calibration-member 1109 or the computing device 1807) instructing (i.e., commanding and/or requesting) the one or more complex-monitoring-sensor-tag 2020.

Continuing discussing FIG. 32, in some embodiments, method 1535a may comprise step 3201; wherein step 3201 may be a step of selecting another (or a first) frequency point for which complex impedance may be measured at. In some embodiments, selecting the next frequency point in step 3201 may involve selecting a value of frequency at which a complex impedance of material-of-interest 2201 has not yet been measured. In some embodiments, selecting the next frequency point in step 3201 may involve selecting a value of frequency at which a complex impedance of material-of-interest 2201 has already been measured but under different options; which may include, but may not be limited to, enabling or not enabling excitation sources or enabling different types or combinations of excitation sources among other options. For such different types of excitation sources, see e.g., array-of-excitation-sources 1921 of FIG. 20B.

As depicted in FIG. 19A, real and imaginary parts $\varepsilon_r'$ and $\varepsilon_r''$, respectively, of complex permittivity $\varepsilon_r$ may be a function of alternating current (AC) frequency and may be determined at predetermined quantity of frequency values $\bar{f} = [f_1, f_2, \ldots, f_N]$ where $\bar{f}$ is a vector of N frequencies $[f_1, f_2, \ldots, f_N]$, at which real and imaginary parts $\varepsilon_r'$ and $\varepsilon_r''$, respectively, of complex permittivity $\bar{\varepsilon}_r$ may be determined.

Using equations (27) and (28) which are copied below for convenience, $$\varepsilon_r' = \frac{Bd}{\omega A \varepsilon_0} \quad (27)$$

$$\varepsilon_r'' = \frac{Gd}{\omega A \varepsilon_0} \quad (28)$$

one may express real and imaginary parts $\varepsilon_r'$ and $\varepsilon_r''$ respectively, of complex permittivity $\bar{\varepsilon}_r$, via real and imaginary components G and B, respectively, of the complex admittance, $$Y = G + jB = \frac{1}{Z}$$

where Z is the complex impedance. The values of complex impedance Z, from which complex permittivity $\bar{\varepsilon}_r$ may be determined, may be measured at N pre-defined frequencies $[f_1, f_2, \ldots, f_N]$.

Therefore, in step 3201 another value of frequency from the vector $[f_1, f_2, \ldots, f_N]$ may be selected for which complex impedance has not yet been measured (or previously measured, but under different options [conditions]).

Continuing discussing FIG. 32, in some embodiments method 1535a may utilize array-of-excitation-sources 1921, with one or more excitation-sources, as described in the discussion of FIG. 19F and in FIG. 20B.

Continuing discussing FIG. 32, in some embodiments, method 1535a may comprise step 3202. In some embodiments, step 3202 may follow step 3201. In some embodiments, step 3202 may be a step of determining if the one or more excitation-sources which may be included in the array-of-excitation-sources 1921 are to be enabled. If yes, then method 1535a may progress to step 3203. If no, then method 1535a may progress to step 3204. In some embodiments, criteria for evaluating step 3202 may comprise, but may not be limited to, predetermined settings.

Continuing discussing FIG. 32, in some embodiments, method 1535a may comprise step 3203. In some embodiments, step 3203 may follow a "yes" outcome of step 3202. In some embodiments, step 3203 may be a step of choosing and enabling one or more excitation-sources which may be included in array-of-excitation-sources 1921.

Note, different materials-of-interest (such as different material-of-interest 2201) may exhibit different complex impedance or complex permittivity values at the same frequencies when subjected to exposure of external excitation-sources.

As noted in the discussion of FIG. 19F and FIG. 20B, array-of-excitation-sources 1921 may comprise one or more of: IR light source 1917, LED light source 1918, UV light source 1919, and/or sonic or ultrasonic sound source 1920. As noted in the discussion of FIG. 23D, array-of-excitation-sources 1921 may comprise the plurality of IR light sources of type "A" 2318 or/and the plurality of infrared (IR) light sources of type "B".

In some embodiments, the plurality of infrared IR light sources of type "A" 2318 and/or the plurality of IR light sources of type "B" 2319 may be of a predetermined frequency (e.g., monochromatic). In some embodiments, the plurality of IR light sources of type "A" 2318 and/or the plurality of IR light sources of type "B" 2319 may be of coherent emission type.

Continuing discussing FIG. 32, in some embodiments, method 1535*a* may comprise step 3204. In some embodiments, step 3204 may follow a "no" outcome of step 3202. In some embodiments, step 3203 may be a step of obtain measurement of complex impedance of material-of-interest 2201 when optionally present excitation-sources, such as array-of-excitation-sources 1921 are not activated and/or not enabled, therefore not influencing characteristics of material-of-interest 2201.

Continuing discussing FIG. 32, in some embodiments, method 1535*a* may comprise step 3205. In some embodiments, step 3205 may follow step 3204. In some embodiments, step 3205 may be a step of determining if more measurements of material-of-interest 2201 are required and/or desired (according to predetermined criteria). If yes, then method 1535 may progress back to step 3201. If no, then method 1535 may progress to completion of method 1535*a*.

In some embodiments, criteria for evaluating step 3205 may comprise, but may not be limited to, enabling or not enabling excitation-sources, using different types or combinations of excitation-sources, performing EIS measurements at different frequency ranges, performing EIS measurements at different values of an alternating current (AC) current source 2106 or different values of an alternating current (AC) voltage source 1906, among other predetermined options.

Continuing discussing method 1535*a* of FIG. 32, in some embodiments the analysis of the material-of-interest 2201 based on the performed measurements may include comparing the obtained measurements of complex impedance or complex permittivity to the previous measurements performed under the same or sufficiently similar conditions such as the choice of type and combination of excitation-sources, frequency range among, other options. Changes in the material-of-interest 2201 that had occurred since the previous measurements may provide a basis for qualitative or quantitative assessment of such changes.

Continuing discussing method 1535*a* of FIG. 32, in some embodiments the analysis of the material-of-interest 2201 based on the performed measurements may include comparing the obtained measurements of complex impedance or complex permittivity to the available reference measurements of the material-of-interest 2201 performed under the same or sufficiently similar conditions such as the choice of type and combination of excitation-sources, frequency range, among other options.

For example, and without limiting the scope of the present invention, in some embodiments, subjecting the material-of-interest 2201 to excitation-source of predefined characteristic, such as IR light of a certain frequency, may yield a characteristic change in the obtained measurements of complex impedance or complex permittivity as compared to the absence of the said excitation-source.

In some embodiments, subjecting the material-of-interest 2201 to excitation-source of predefined characteristic, such as IR light of certain frequency may yield a characteristic measurements of complex impedance or complex permittivity as compared to the reference data.

And such principles are not limited to IR light sources, but may be applied to visible light, UV light, LED light, and/or sound of predetermined characteristics.

Therefore, some embodiments, of the present invention may be used to detect specific problems, conditions, and/or substances of material-of-interest (e.g., 2201, 1028, and/or 1828), such as, but not limited to, biological cells (e.g., foreign cells, abnormal cells, cancerous cells, etc.), infection, fever, inflammation, antigens, antibodies, foreign substances, tissue conditions, ailments, and/or the like. Detection may be a subset of monitoring. For example, and without limiting the scope of the present invention, by virtue of detecting a characteristic measurement(s) of complex impedance or complex permittivity, with or without excitation source or sources, or by virtue of detecting a characteristic change in the obtained measurements of complex impedance or complex permittivity as compared to the measurements of complex impedance or complex permittivity in the absence of the said excitation-source or sources.

Some embodiments of the present invention may also be used to detect specific problems, conditions, and/or substances of material-of-interest (e.g., 2201, 1028, and/or 1828), such as, but not limited to, biological cells (e.g., foreign cells, abnormal cells, cancerous cells, etc.), infection, fever, inflammation, antigens, antibodies, foreign substances, tissue conditions, ailments, and/or the like; by virtue of detecting a characteristic change in the obtained measurement(s) of complex impedance or complex permittivity under influence of excitation source or sources as compared to the measurements of complex impedance or complex permittivity when subjected to the excitation-source or sources of a different nature (including but not limited to the frequency of the IR excitation source for example).

To demonstrate application of the points above, let us assume that the graphs 1911, 1912 of FIG. 19E correspond to vectors of complex permittivity of the material-of-interest 2201 $[\varepsilon'_{r1}, \varepsilon''_{r1}]$ measured at a pre-defined frequency range $[f_1, f_2]$ and obtained without excitation sources.

Let us assume that the graphs 1913, 1914 of FIG. 19E correspond to the vectors of complex permittivity of the material-of-interest 2201 $[\varepsilon'_{r2}, \varepsilon''_{r2}]$ measured at the pre-defined frequency range $[f_1, f_2]$ and obtained when exposing a given material under test (or under monitoring or under observation) with infrared (IR) light of predetermined frequency.

Let us assume that the graphs 1915, 1916 of FIG. 19E correspond to the vectors of complex permittivity of the material-of-interest 2201 $[\varepsilon'_{r3}, \varepsilon''_{r3}]$ measured at the pre-defined frequency range $[f_1, f_2]$ and obtained when applying IR light of yet another frequency to that same given material-of-interest 2201.

The following vectors may be used to identify or detect specific problems, conditions, and/or substances, such as, but not limited to, biological cells (e.g., foreign cells, abnormal cells, cancerous cells, etc.), infection, fever, inflammation, antigens, antibodies, foreign substances, tissue conditions, ailments, and/or the like. The vectors (32), (33), (34), values of which over the frequency range $[f_1, f_2]$ or its sub-ranges will serve to identify or detect specific problems, conditions, and/or substances:

$$[\varepsilon'_{r1}, \varepsilon''_{r1}] \tag{32}$$

$$[\varepsilon'_{r2}, \varepsilon''_{r2}] \tag{33}$$

$$[\varepsilon'_{r3}, \varepsilon''_{r3}] \tag{34}$$

The vectors (35) and (36), values of which over the frequency range $[f_1, f_2]$ or its sub-ranges may serve to identify or detect specific problems, conditions, and/or substances. The vectors (35) and (36) may represent the difference in the vectors of complex permittivity of the material-of-interest 2201 introduced by excitation source(s).

$$[\varepsilon'_{r2}-\varepsilon'_{r1},\varepsilon''_{r2}-\varepsilon'_{r1}] \quad (35)$$

$$[\varepsilon'_{r3}-\varepsilon'_{r1})\varepsilon''_{r3}-\varepsilon'_{r1}] \quad (36)$$

The vectors (37), (38), and (39) values of which over the frequency range $[f_1,f_2]$ or its sub-ranges will serve to identify or detect specific problems, conditions, and/or substances.

$$[\varepsilon'_{r1}-\varepsilon'_{r1\_ref},\varepsilon''_{r1}-\varepsilon'_{r1\_ref}] \quad (37)$$

$$[\varepsilon'_{r2}-\varepsilon'_{r2\_ref},\varepsilon''_{r2}-\varepsilon'_{r2\_ref}] \quad (38)$$

$$[\varepsilon'_{r3}-\varepsilon'_{r3\_ref},\varepsilon''_{r3}-\varepsilon'_{r3\_ref}] \quad (39)$$

where $[\varepsilon'_{r1\_ref}]$, $[\varepsilon''_{r1\_ref}]$, $[\varepsilon'_{r2\_ref}, \varepsilon''_{r2\_ref}]$, $[\varepsilon'_{r3\_ref}, \varepsilon''_{r3\_ref}]$ are reference values of vectors of complex permittivity of the material-of-interest 2201 measured at the pre-defined frequency range $[f_1,f_2]$ at the same or materially (substantially) similar conditions and under the influence of the same excitation sources as the vectors of complex permittivity of the material-of-interest 2201 $[\varepsilon'_{r1}, \varepsilon''_{r1}]$, $[\varepsilon'_{r2}, \varepsilon''_{r2}]$, $[\varepsilon'_{r3}, \varepsilon''_{r3}]$ respectively.

The vectors (37), (38), and (39) may represent the measure of closeness of the measured values of vectors of complex permittivity $[\varepsilon'_{r1}, \varepsilon''_{r1}]$, $[\varepsilon'_{r2}, \varepsilon''_{r2}]$, $[\varepsilon'_{r3}, \varepsilon''_{r3}]$ to the reference values of vectors of complex permittivity $[\varepsilon'_{r1\_ref}]$, $[\varepsilon''_{r1\_ref}]$, $[\varepsilon'_{r2\_ref}, \varepsilon''_{r2\_ref}]$, $[\varepsilon'_{r3\_ref}, \varepsilon''_{r3\_ref}]$, respectively, of the known specific problems, conditions, and/or substances, under the same excitation sources or the lack thereof.

Figure 26:
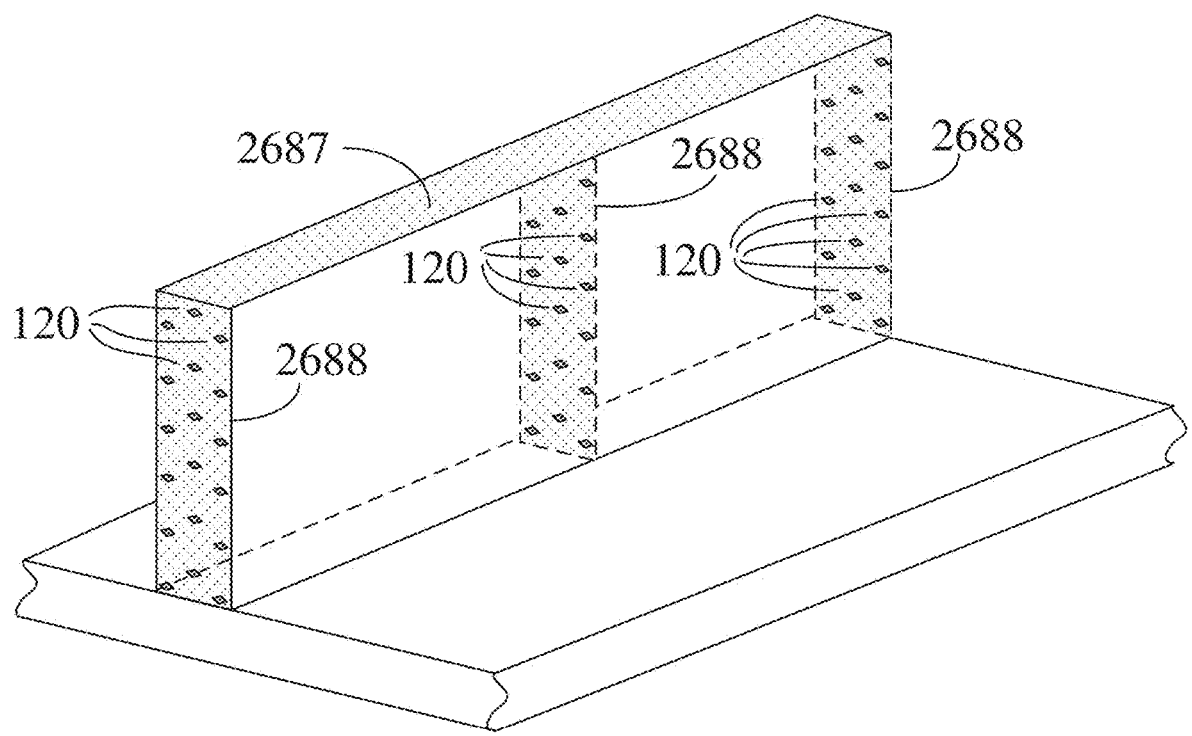
FIG. 26 may depict may depict a perspective view of a portion of a material-of-interest with monitoring-sensor-tags.

FIG. 26 may depict a portion of a material-of-interest 2687, with a plurality of monitoring-sensor-tags 120; wherein the plurality of monitoring-sensor-tags 120 may be on and/or within material-of-interest 2687. In some embodiments, material-of-interest 2687 may be a structural member, an engineering member, and/or a construction member. For example, and without limiting the scope of the present invention, in some embodiments, material-of-interest 2687 may be a portion of concrete, cement, masonry, and/or the like. FIG. 26 may also show sections 2688, which may be sections of material-of-interest 2687. In some embodiments, a given section 2688 may comprise one or more monitoring-sensor-tags 120 distributed within that given section 2688.

Figure 27A:
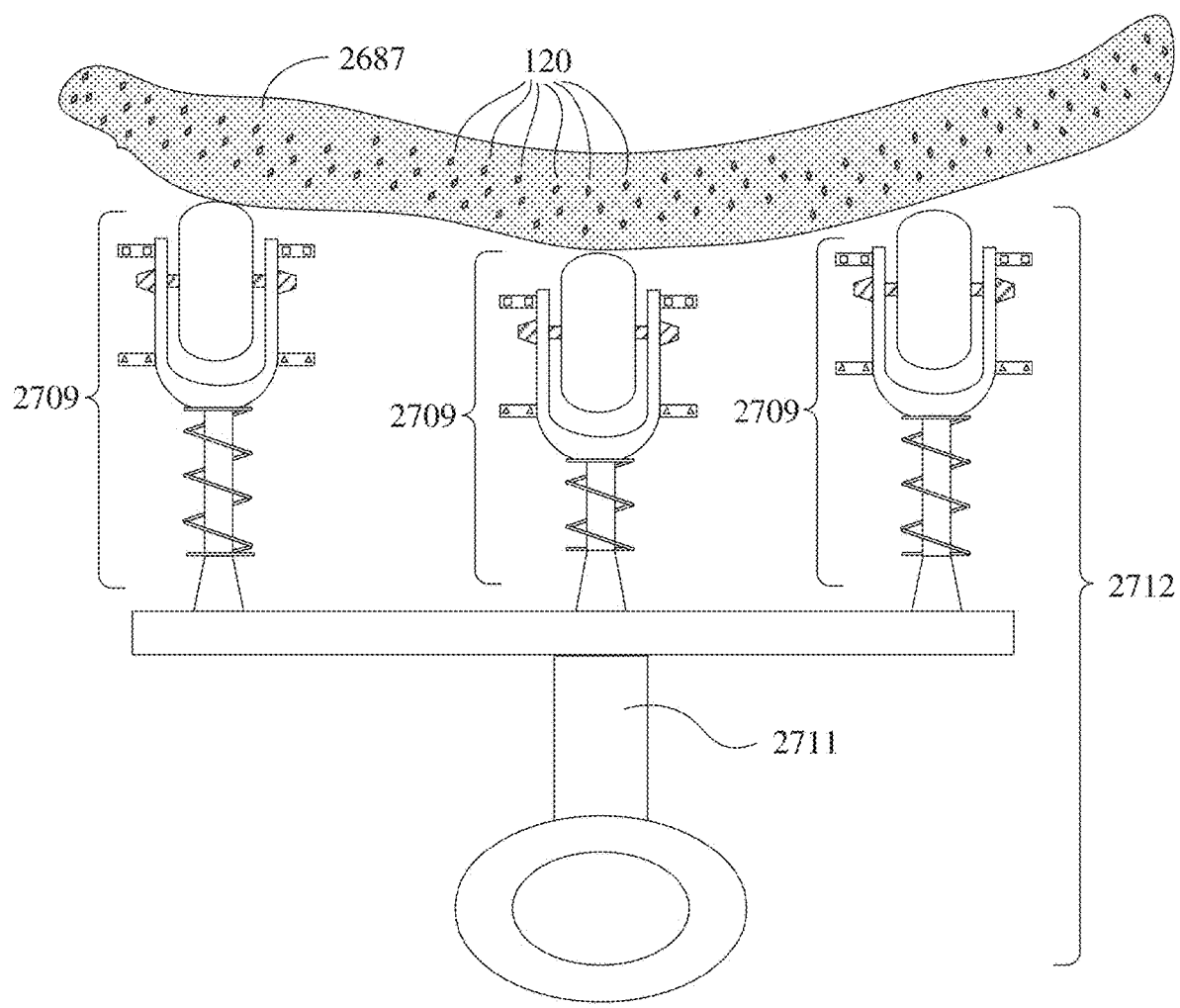
FIG. 27A may depict a top view of an imaging-device rolling along an exterior surface of a material-of-interest.

FIG. 27A may depict an imaging-device 2712 for interrogating (reading) at least some of the plurality of monitoring-sensor-tags 120 that may be on and/or within material-of-interest 2687. In FIG. 27A, a portion of material-of-interest 2687 may be shown with at least some of the plurality of monitoring-sensor-tags 120. In some embodiments, imaging-device 2712 may comprise a frame-member 2711 and one or more reader-assemblys 2709. In some embodiments, the one or more reader-assemblys 2709 may be attached to the frame-member 2711. In some embodiments, the frame-member 2711 may be a structural member. In some embodiments, each given reader-assembly 2709 may comprise necessary electronics for reading (interrogating) monitoring-sensor-tags 120.

Figure 27B:
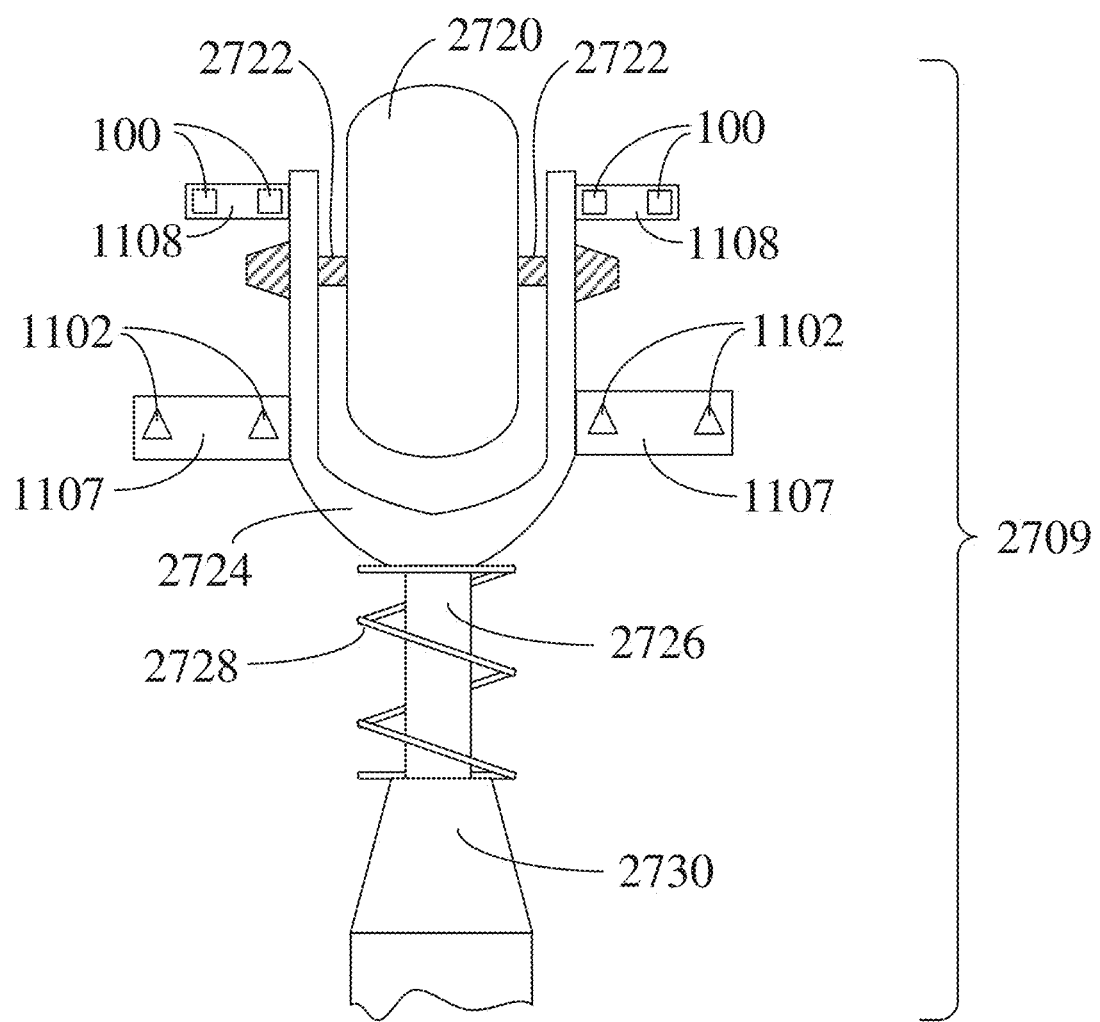
FIG. 27B may depict a top view of a reader-assembly.
Figure 27C:
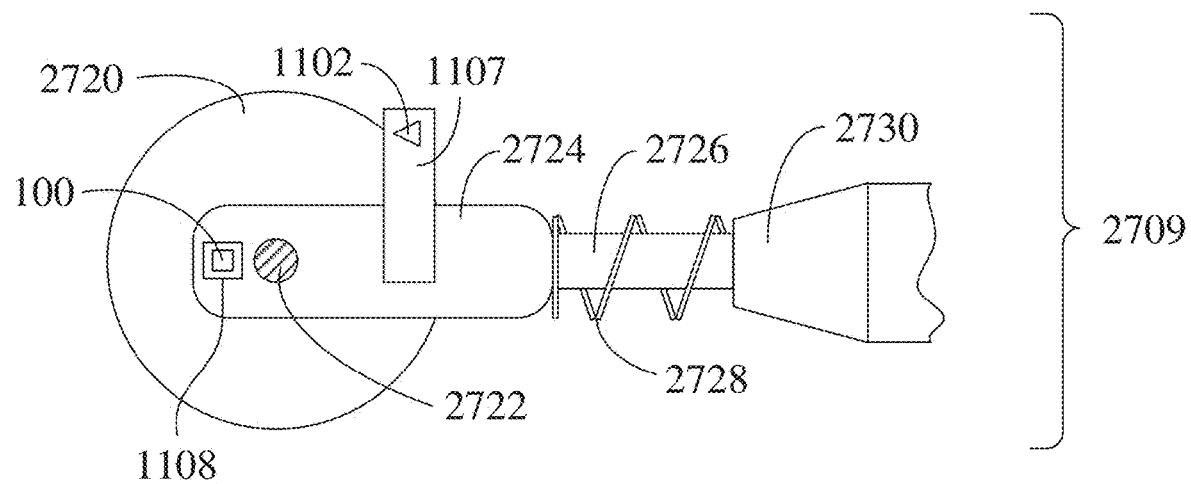
FIG. 27C may depict an orthogonal view (e.g., a side view) of the reader-assembly of FIG. 27B.

FIG. 27B may show a top view of a given reader-assembly 2709 shown in FIG. 27A. FIG. 27C may be an orthogonal view (e.g., a side view) of the reader-assembly 2709 shown in FIG. 27B. FIG. 27B may show a given reader-assembly 2709 that may be used to image (e.g., read) radiation emitted from at least some of the monitoring-sensor-tags 120, that may be located on and/or within material-of-interest 2687. In some embodiments, reference-sensor-tags 1102 may be mounted on reference-housing-member 1107. In some embodiments, reference-housing-member 1107 may be attached to a portion of frame 2724 of the given reader-assembly 2709. In some embodiments, readers 100 may be mounted on reader-housing-member 1108. In some embodiments, reader-housing-member 1108 may be attached to another portion of frame 2724. In some embodiments, both readers 100 and reference-sensor-tags 1102 may be fixedly mounted on the frame 2724 (e.g., at different locations), and thus may be fixed in position relative to each other. It can be appreciated by one skilled in the art that the locations of reference-sensor-tags 1102 relative to readers 100 are known parameters, or can be mathematically determined, thus allowing a calibration process to increase precision of reading monitoring-sensor-tags 120 associated with material-of-interest 2687. See e.g., FIG. 27B and FIG. 27C.

Continuing discussing FIG. 27A, in some embodiments, a wheel 2720 of reader-assembly 2709 may facilitate movement of the frame 2724 across a surface of material-of-interest 2687 as portions of this material-of-interest 2687 may be irradiated by readers 100. In some embodiments, an axle 2722 of wheel 2720 may be in communication with frame 2724, such that wheel 2720 may rotate about axle 2722 and wheel 2720 may translate with frame 2724. In some embodiments, frame 2724 may be attached to handle 2726. In some embodiments, handle 2726 may be telescopic. In some embodiments, handle 2726 may be attached to base 2730. In some embodiments, base 2730 may be attached to frame-member 2711. In some embodiments, handle 2726 may be substantially disposed within a hollow portion of a spring 2728. In some embodiments, wheel 2720 along with handle 2726 (which may be telescopic) with spring 2728 may function to retain reader-assembly 2709 on the surface of material-of-interest 2687, as the given reader-assembly 2709 (or as image-device 2712) translates along the surface of material-of-interest 2687, obtaining readings from the interrogated monitoring-sensor-tags 120 associated with material-of-interest 2687. See e.g., FIG. 27B and FIG. 27C.

Continuing discussing FIG. 27B, in some embodiments, structural components of reader-assembly 2709 may comprise at least one of: reference-housing-member 1107, reader-housing-member 1108, wheel 2720, axle 2722, frame 2724, handle 2726, and/or base 2730. In some embodiments, electronics components of reader-assembly 2709 may comprise at least one of: readers 100, reference-sensor-tags 1102, and/or a power source for readers 100. See e.g., FIG. 27B and FIG. 27C.

Figure 28:
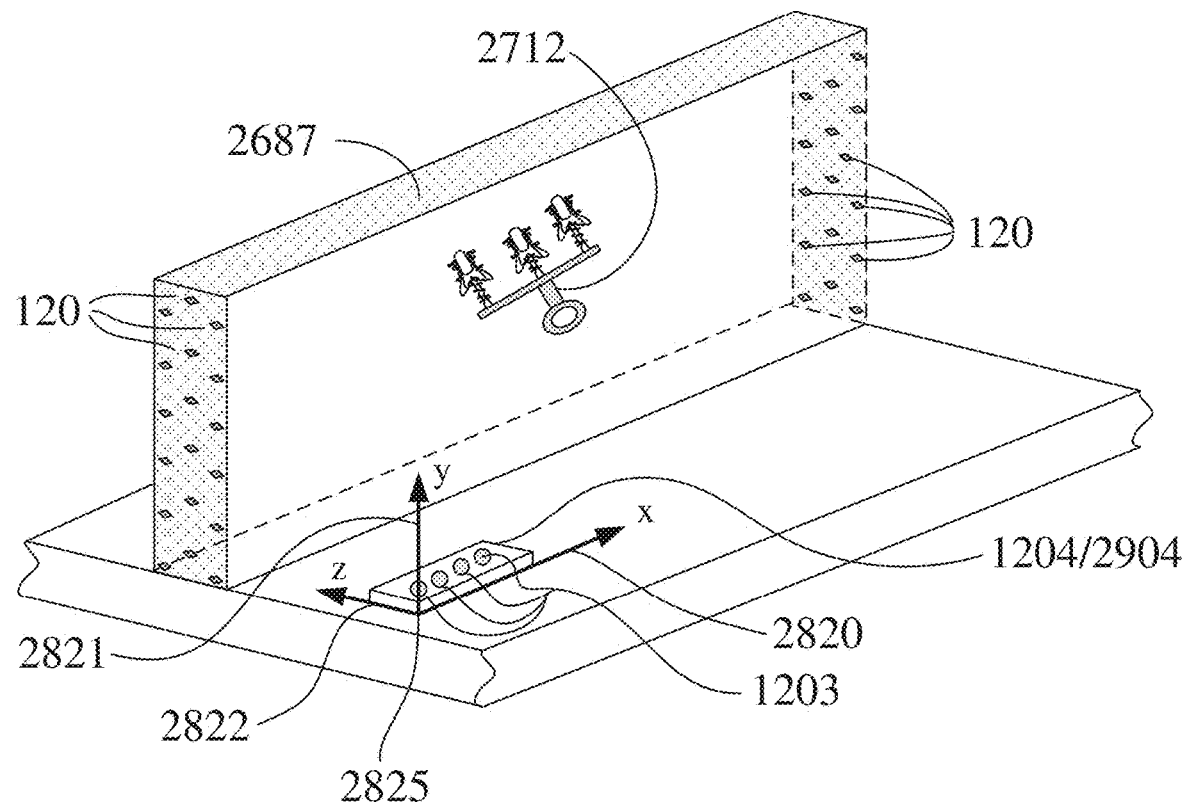
FIG. 28 may depict a perspective view of a portion of a material-of-interest with monitoring-sensor-tags; and may also depict an imaging-device, a position-reference-member, and a predetermined coordinate system.

FIG. 28 may depict a three-dimensional Cartesian coordinate system chosen to determine three-dimensional coordinates of position-reference-tag 1203, relative to which the positions of readers 100 may be determined. Recall, in some embodiments, readers 100 may be located on each reader-assembly 2709; wherein the reader-assemblies 2709 may be components of imaging-device 2712. And recall, imaging-device 2712 may translate along the surface of material-of-interest 2687.

Continuing discussing FIG. 28, in some embodiments, coordinates of position-reference-tag 1203 are specified relative to a chosen (e.g., predetermined) Cartesian coordinate system defined by: an origin 2825, an x-axis 2820, a y-axis 2821, and a z-axis 2822. Locations of reference-sensor-tags 1102 and locations of at least some monitoring-sensor-tags 120 associated with material-of-interest 2687 may be also specified relative to the chosen coordinate system. Recall, in some embodiments, reference-sensor-tags 1102 may be located on each reader-assembly 2709; wherein the reader-assemblies 2709 may be components of imaging-device 2712.

Also note, any such predetermined Cartesian coordinate system as noted herein may be replaced with other coordinate systems, such as but not limited to, radial, cylindrical, or spherical coordinate systems.

Figure 29A:
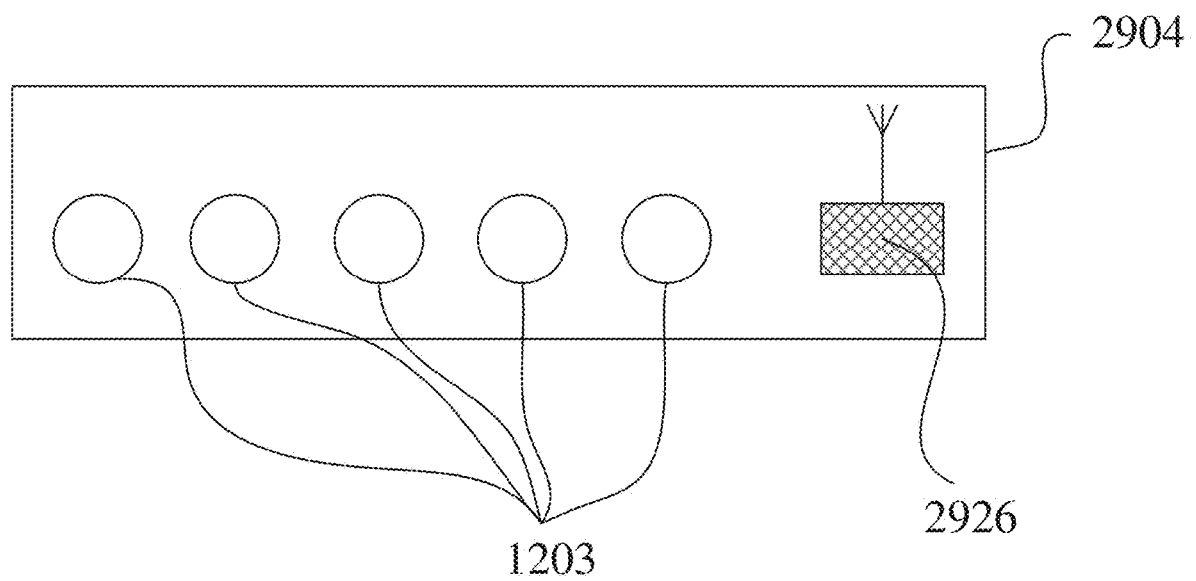
FIG. 29A may depict a schematic view of a position-reference-member with a transmitter.

FIG. 29A may depict an embodiment of a position-reference-member 2904. In some embodiments, a given position-reference-member 2904 may be substantially similar to a given position-reference-member 1204; except the given position-reference-member 2904 may comprise a transmitter 2926. In some embodiments, position-reference-member 2904 may be a housing, an enclosure, and/or a structural member. In some embodiments, one or more position-reference-tag 1203 may be mounted or attached to position-reference-member 2904. In some embodiments, a plurality of position-reference-tag 1203 may be mounted or attached to position-reference-member 2904. In some embodiments, a relationship between position-reference-tags 1203 and position-reference-member 2904 may be fixed.

Continuing discussing FIG. 29A, in some embodiments, transmitter 2926 may be attached to or mounted to position-reference-member 2904. In some embodiments, transmitter 2926 may communicate wirelessly, using various well known wireless communication protocols, such as, but not limited to, cellular communications, radio-based communications, WiFi, RFID, NFC, magnetic inductive communication, and/or the like. In some embodiments, transmitter 2926 may be in wireless communication with readers 100 of reader-assembly 2709 of imaging-device 2712. In some embodiments, transmitter 2926 may be in wireless communication with one or more of: devices 1807, reader-and-calibration-member 1109, servers 3103, remote-computing-devices 3105, WANs 3101 (wide area networks), LANs 3103 (local area networks), and/or the internet 3103. In some embodiments, remote-computing-devices 3105, servers 3103, WANs 3101, LANs 3101, and/or the internet 3101 may be remotely located with respect to transmitter 2926, see e.g., FIG. 31. In some embodiments, transmitter 2926 may be used to wirelessly transmit readings from readers 100. Such readings could denote and/or convey abnormalities and/or structural problems with material-of-interest 2687. Inclusion of transmitter 2926 may facilitate automated, automatic, and/or remote monitoring and/or tracking of material-of-interest 2687.

In some embodiments, a quantity (predetermined) of reader-and-calibration-member 1109 may be affixed to material-of-interest 2687 (see e.g., FIG. 30), in order to provide better precision of location information of readers 100 relative to the position-reference-tags 1203 mounted on or attached to position-reference-member 2904. See e.g., FIG. 29A and FIG. 30.

Figure 29B:
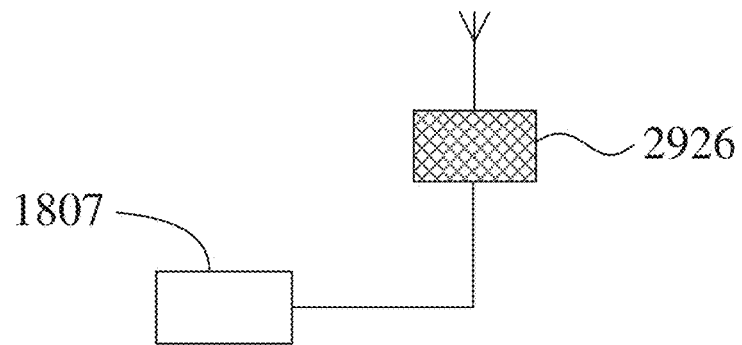
FIG. 29B may depict a schematic view of the transmitter of FIG. 29A connected to a device, such as a computer.

FIG. 29B may depict that transmitter 2926 may be connected to a device 1807, such as a computer. In some embodiments, such a device 1807 may comprise at least processor 1801 and memory 1803. Note, while position-reference-member 2904 may not be shown in FIG. 29B, transmitter 2926 may be associated with position-reference-member 2904 as discussed above in the FIG. 29A discussion.

Figure 30:
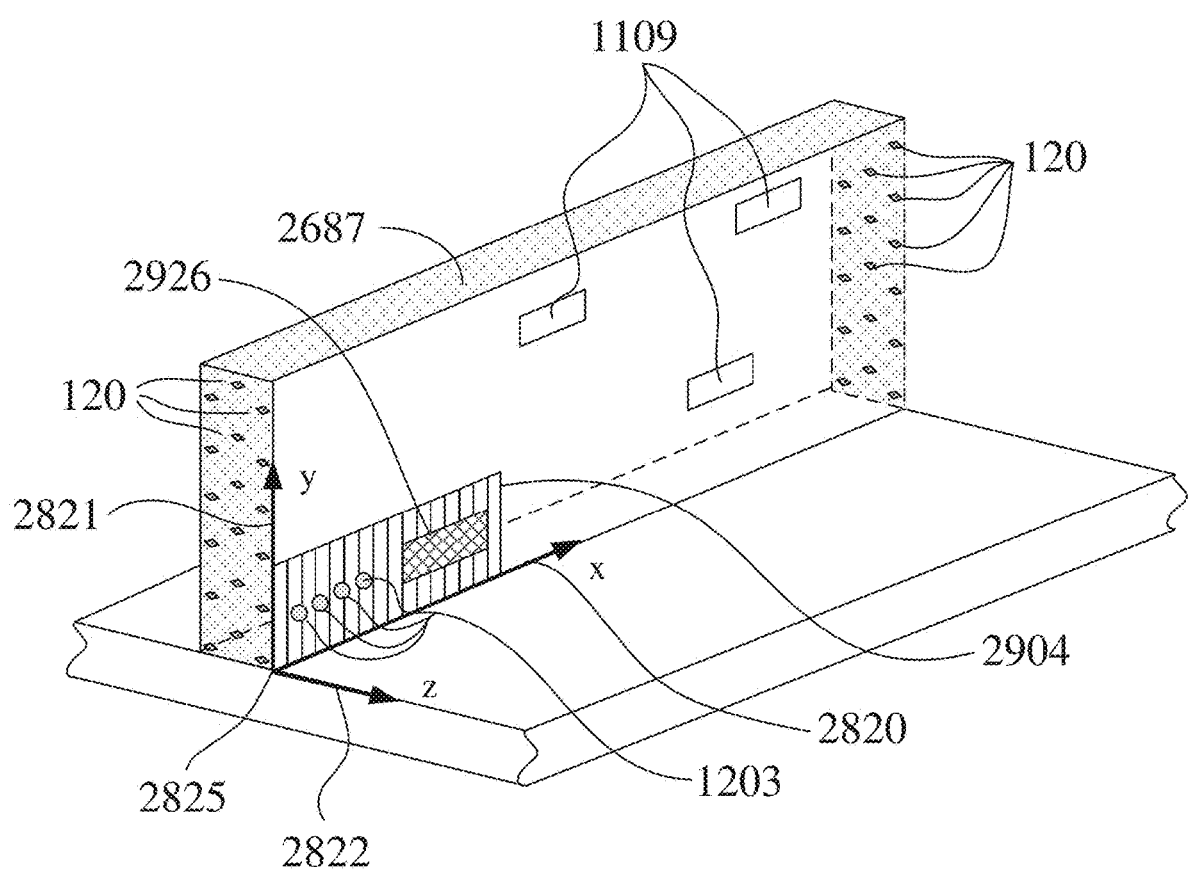
FIG. 30 may depict a perspective view of a portion of a material-of-interest: with reader-and-calibration-members, a position-reference-member, monitoring-sensor-tags, and a predetermined coordinate system.

FIG. 30 may be substantially similar to FIG. 28, except in FIG. 30: (a) one or more reader-and-calibration-member 1109 may be fixedly attached to or mounted to material-of-interest 2687; (b) position-reference-member 2904 (e.g., with transmitter 2926) may be utilized instead of position-reference-member 1204; and/or (c) position-reference-member 2904 may be associated with material-of-interest 2687 instead of a fixed distance from material-of-interest 2687 as shown in FIG. 28. As noted above, fixedly attaching or mounting the one or more reader-and-calibration-member 1109 to material-of-interest 2687 may increase precision of various locations measurements (e.g., determining positions of readers 100, which may then be used to determine positions of monitoring-sensor-tags 120).

Figure 31:
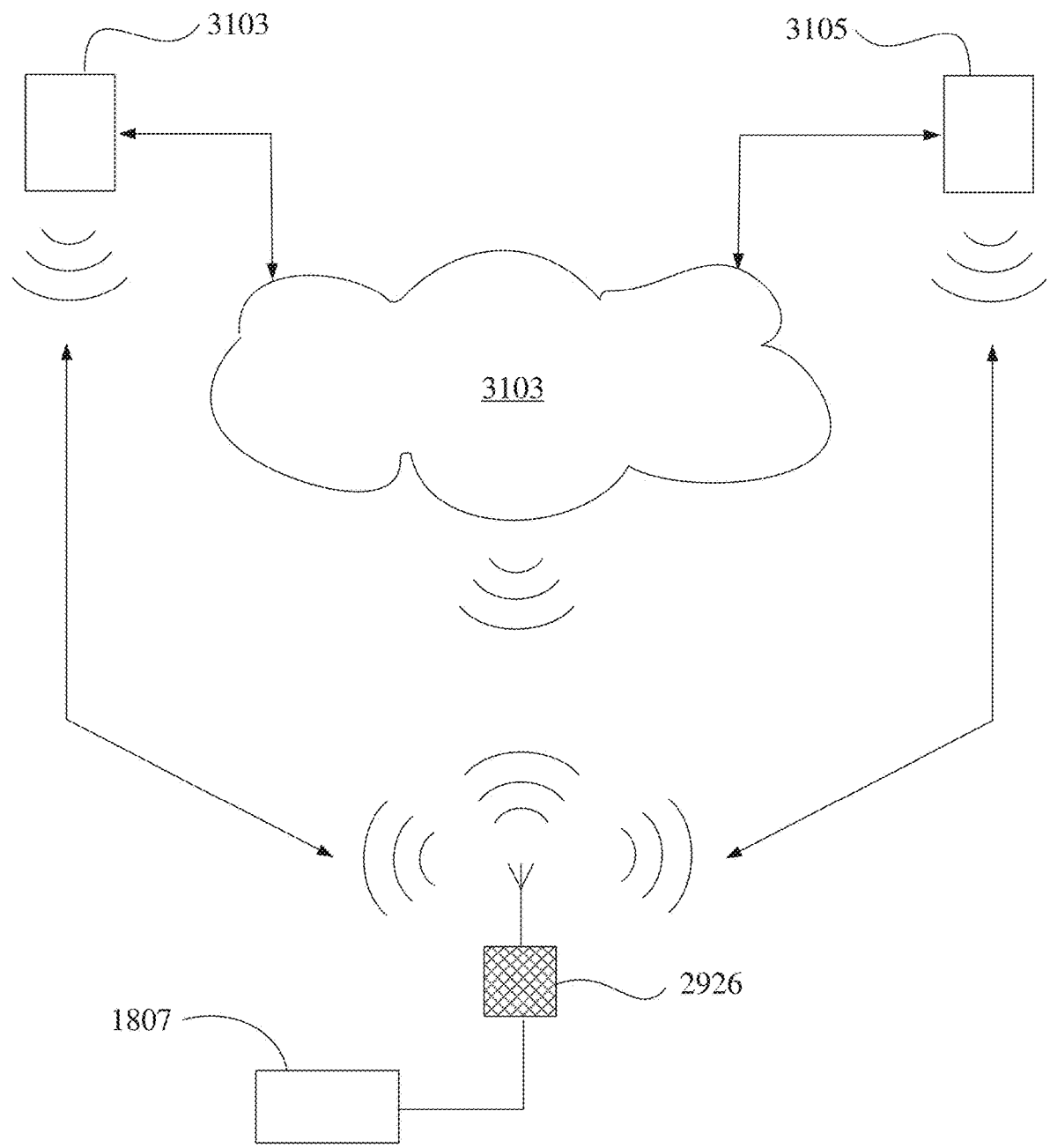
FIG. 31 may depict possible wireless communication pathways for a transmitter.

FIG. 31 may depict possible remote wireless communications of transmitter 2926. Remote-computing-device 3105 may be structurally similar to device 1807, but remotely located with respect to the location of transmitter 2926. In some embodiments, remote-computing-device 3105 may be selected from: a computer, a personal computer, a desktop computer, a handheld computer, a laptop computer, a tablet computer, a smartphone, a mobile computing device, a computing device, or the like. Note, while position-reference-member 2904 may not be shown in FIG. 31, transmitter 2926 may be associated with position-reference-member 2904 as discussed above.

Note, any of the antennas, receives, transmitters, discussed herein and/or shown in the associated drawing figures, as well as, IR light source 1917, LED light source 1918, and/or ultraviolet UV light source 1919, may emit and/or may receive electromagnetic (EM) radiation (e.g., of a predetermined frequency, including a predetermined ranges of frequency), such as, but not limited to: radio waves, UHF, microwaves, magnetic fields, visible light, UV light, IR light. Note, any of the antennas, receives, transmitters, discussed herein and/or shown in the associated drawing figures, may communicate wirelessly, such as, but not limited to, via: NFC (near field communication), RFID (radio frequency ID) communication, backscatter communication, magnetic induction communication, and/or the like.

Monitoring-sensor-tags, systems for utilizing such, and methods of use have been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A system for non-invasive monitoring of tissue, the system comprising:
  at least one lattice-of-sensors; wherein the at least one lattice-of-sensors comprises:
    a first-sensor-tag; wherein the first-sensor-tag comprises,
      at least one electric circuit comprising at least one sensor;
      at least one antenna in communication with the at least one electric circuit;
    a plurality of sensors, not of the at least one sensor of the first-sensor-tag, with an initial predetermined spacing between any two adjacent sensors selected from the plurality of sensors such that the plurality of sensors is arranged in a lattice framework; wherein the plurality of sensors are in electrical communication with the first-sensor-tag; wherein at least a portion of the plurality of sensors are physically connected to the first-sensor-tag; wherein a positional location according to a coordinate system of each sensor selected from the plurality of sensors is fixed and known by the system;

wherein at least a portion of the at least one lattice-of-sensors is proximate to the tissue;

wherein upon the at least one antenna receiving electromagnetic radiation of a predetermined characteristic as an input, this input causes the at least one circuit to take one or more readings from the at least one sensor of the first-sensor-tag or from at least one sensor selected from the plurality of sensors; and to then transmit the one or more readings using the at least one antenna;

wherein the system further comprises at least one reader-and-calibration-member; wherein the at least one reader-and-calibration-member has its own antenna; wherein the at least one reader-and-calibration-member provides the electromagnetic radiation of the predetermined characteristic as the input; wherein the at least one reader-and-calibration-member is in radio communication with the at least one lattice-of-sensors; wherein the at least one reader-and-calibration-member receives the one or more readings;

wherein the at least one reader-and-calibration-member comprises two or more reference-sensor-tags that have a location known by the at least one reader-and-calibration-member.

2. The system according to claim 1, wherein the at least one lattice-of-sensors further comprises a second-sensor-tag; wherein the second-sensor-tag comprises:

at least one different electric circuit comprising at least one different sensor;

at least one different antenna in communication with the at least one different electric circuit;

wherein the plurality of sensors are in communication with the second-sensor-tag; wherein at least a different portion of the plurality of sensors are physically connected to the second-sensor-tag;

wherein upon the at least one different antenna receiving the electromagnetic radiation of the predetermined characteristic as the input, this input causes the at least one different circuit to take one or more different readings from the at least one different sensor of the second-sensor-tag or from at least one sensor selected from the plurality of sensors; and to then transmit the one or more different readings using the at least one different antenna.

3. The system according to claim 2, wherein the plurality of sensors is disposed between the first-sensor-tag and the second-sensor-tag.

4. The system according to claim 2, wherein the at least one sensor of the first-sensor-tag, the at least one different sensor of the second-sensor-tag, or the plurality of sensors are selected from one or more of: a capacitive-based sensor, a resistance-based sensor, an inductance-based sensor, a permittivity based sensor, a complex permittivity based sensor, or a complex impedance based sensor.

5. The system according to claim 2, wherein the one or more different readings convey information of one or more of: inductance, capacitance, resistance, permittivity, complex permittivity, or complex impedance.

6. The system according to claim 2, wherein the at least one different circuit is a complex-impedance-measurement-circuit.

7. The system according to claim 6, wherein the complex-impedance-measurement-circuit comprises a variable frequency alternating current source that uses a frequency supplied by the at least one different antenna or comprises a frequency divider that uses the frequency supplied by the at least one different antenna.

8. The system according to claim 1, wherein the one or more readings convey information of one or more of: inductance, capacitance, resistance, permittivity, complex permittivity, or complex impedance.

9. The system according to claim 1, wherein the at least one circuit is a complex-impedance-measurement-circuit.

10. The system according to claim 9, wherein the complex-impedance-measurement-circuit comprises a variable frequency alternating current source that uses a frequency supplied by the at least one antenna or comprises a frequency divider that uses the frequency supplied by the at least one antenna.

11. The system according to claim 1, wherein the one or more readings are transmitted through at least a portion of the brazier at least one article-in-lattice-contact; wherein the at least one article-in-lattice-contact is configured to be removably attached to a portion of a body of a person; wherein the at least one lattice-of-sensors is attached to the at least one article-in-lattice-contact.

12. The system according to claim 1, wherein the at least one reader-and-calibration-member is in communication with a computing device; wherein the computing device performs one or more of the following with the one or more readings: interprets, displays, or stores.

13. The system according to claim 12, wherein the system further comprises the computing device.

14. The system according to claim 12, wherein the computing device is configured to be mobile for a user.

15. The system according to claim 1, wherein each sensor selected from the plurality of sensors comprises its own measurement circuit and its own antenna.

16. The system according to claim 1, wherein the at least one reader-and-calibration-member calibrates the positional location of each sensor selected from the plurality of sensors.

17. The system according to claim 1, wherein each reference-sensor-tag selected from the two or more reference-sensor-tags is positionally fixed with a known location relative to the at least one reader-and-calibration-member.

18. The system according to claim 1, wherein the plurality of sensors rely on external communications via the at least one antenna of the first-sensor-tag.

19. The system according to claim 1, wherein the system further comprises a second lattice-of-sensors; wherein a distance between the at least one lattice-of-sensors and the second lattice-of-sensors is initially predetermined and known by the system; wherein the at least one lattice-of-sensors and the second lattice-of-sensors are arranged in a three dimensional configuration with respect to each other.

* * * * *